(12) United States Patent
Calderwood et al.

(10) Patent No.: US 8,188,083 B2
(45) Date of Patent: May 29, 2012

(54) TRIAZOLOPYRIDAZINES

(75) Inventors: David J. Calderwood, Framingham, MA (US); Dominique F. Bonafoux, Cambridge, MA (US); Andrew Burchat, Shrewsbury, MA (US); Ping Ding, Acton, MA (US); Kristine E. Frank, Worcester, MA (US); Michael Z. Hoemann, Marlborough, MA (US); Kelly D. Mullen, Charlton, MA (US); Heather M. Davis, Oxford, MA (US)

(73) Assignee: Abbott Laboratories, Abbott Park, IL (US)

( * ) Notice: Subject to any disclaimer, the term of this patent is extended or adjusted under 35 U.S.C. 154(b) by 861 days.

(21) Appl. No.: 12/215,338

(22) Filed: Jun. 26, 2008

(65) Prior Publication Data

US 2009/0270402 A1    Oct. 29, 2009

Related U.S. Application Data

(60) Provisional application No. 60/937,607, filed on Jun. 28, 2007.

(51) Int. Cl.
 *A61K 31/50* (2006.01)
 *C07D 237/26* (2006.01)
(52) U.S. Cl. .................... 514/252.01; 544/235
(58) Field of Classification Search ........... 544/235; 514/252.01
See application file for complete search history.

(56) References Cited

U.S. PATENT DOCUMENTS

| | | | |
|---|---|---|---|
| 4,654,343 A * | 3/1987 | Albright et al. | 514/248 |
| 5,225,414 A | 7/1993 | Henning et al. | |
| 6,610,694 B1 | 8/2003 | Kawano et al. | |
| 6,696,464 B2 | 2/2004 | McClure et al. | |
| 7,173,033 B2 | 2/2007 | Igarashi et al. | |
| 7,268,136 B2 | 9/2007 | Green et al. | |
| 7,884,104 B2 * | 2/2011 | Cox et al. | 514/250 |
| 2004/0176390 A1 | 9/2004 | Blumberg et al. | |
| 2005/0079387 A1 | 4/2005 | Lee et al. | |
| 2005/0096322 A1 * | 5/2005 | Igarashi et al. | 514/248 |
| 2005/0272794 A1 | 12/2005 | Parmee et al. | |
| 2006/0156484 A1 | 7/2006 | Lim | |
| 2006/0173009 A1 * | 8/2006 | Kanoh et al. | 514/248 |
| 2006/0281750 A1 | 12/2006 | Li et al. | |
| 2006/0287323 A1 | 12/2006 | Ewing et al. | |
| 2006/0287324 A1 | 12/2006 | Sun et al. | |
| 2007/0191369 A1 | 8/2007 | Lauffer et al. | |

FOREIGN PATENT DOCUMENTS

| | | |
|---|---|---|
| DE | 4023215 | 1/1992 |
| EP | 0403251 | 12/1990 |
| EP | 0662477 | 7/1995 |
| EP | 1426050 | 6/2004 |
| EP | 1122243 | 9/2004 |
| EP | 1719756 | 11/2006 |
| JP | 2001/48786 | 2/2001 |
| WO | WO 91/19497 | 12/1991 |
| WO | WO 92/10190 | 6/1992 |
| WO | WO 92/10498 | 6/1992 |
| WO | WO 02/14321 | 2/2002 |
| WO | WO 03/031587 | 4/2003 |
| WO | WO 03/076409 | 9/2003 |
| WO | WO 2004/014900 | 2/2004 |
| WO | WO 2004/058769 | 7/2004 |
| WO | WO 2004/072072 | 8/2004 |
| WO | WO 2004/110990 | 12/2004 |
| WO | WO 2005/079735 | 9/2005 |
| WO | WO 2005/080380 | 9/2005 |
| WO | WO 2005/085219 | 9/2005 |
| WO | WO 2006/008556 | 1/2006 |
| WO | WO 2006/039325 | 4/2006 |
| WO | WO 2006/044869 | 4/2006 |
| WO | WO 2007/022385 | 2/2007 |
| WO | WO 2007/024859 | 3/2007 |
| WO | WO 2007/026950 | 3/2007 |
| WO | WO 2007/064797 | 6/2007 |
| WO | WO 2007/075567 | 7/2007 |
| WO | WO 2007/138472 | 12/2007 |
| WO | WO 2008/069500 | 6/2008 |

OTHER PUBLICATIONS

Vippagunta et al., "Crystalline Solids", Adv. Drug Del. Rev., 48 (2001) 3-26.*
Cox et al., Bioorganic & Medicinal Chemistry Letters (2007), 17(16), 4579-4583.*

* cited by examiner

*Primary Examiner* — Paul V. Ward
(74) *Attorney, Agent, or Firm* — Gayle B. O'Brien; Kenneth P. Zwicker

(57) ABSTRACT

The present invention is directed to novel compounds of formula (I)

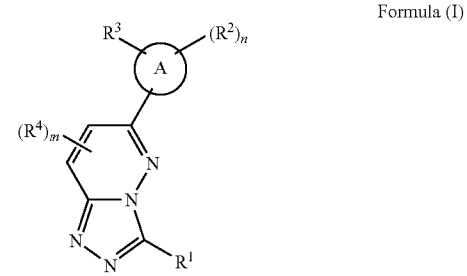

Formula (I)

wherein the variables are defined as herein. The compounds of formula (I) are useful as kinase inhibitors and as such would be useful in treating certain conditions and diseases, especially inflammatory conditions and diseases and proliferative disorders and conditions, for example, cancers.

18 Claims, No Drawings

TRIAZOLOPYRIDAZINES

CROSS REFERENCE TO RELATED APPLICATION

This application is a continuation-in-part and claims priority to U.S. Provisional Application Ser. No. 60/937,607 filed on Jun. 28, 2007, which is incorporated herein in its entirety.

BACKGROUND OF THE INVENTION

Protein phosphorylation, at specific amino acid residues, is important for the regulation of many cellular processes including cell cycle progression and division, signal transduction, and apoptosis. The phosphorylation is usually a transfer reaction of the terminal phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine (S/T) kinases. The phosphorylation reactions, and counteracting phosphatase reactions, on the tyrosine, serine and threonine residues are involved in countless cellular processes that underlie responses to diverse intracellular signals, regulation of cellular functions, and activation or deactivation of cellular processes. A cascade of protein kinases often participate in intracellular signal transduction and are necessary for the realization of cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell. Given the importance and diversity of protein kinase function, it is not surprising that alterations in phosphorylation are associated with many diseases such as cancer, diabetes, inflammation, and hypertension.

The identification of effective small molecules that specifically inhibit protein kinases involved in abnormal or inappropriate cell proliferation, signaling, differentiation, protein production, or metabolism is therefore desirable. In particular, the identification of methods and compounds that specifically inhibit the function of kinases that are involved in immune modulation or proliferative disorders.

The present invention provides novel compounds that inhibit one or more S/T kinase or receptor or non-receptor tyrosine kinase. The compounds of the present invention affect cytokine inhibitory activity.

Cytokine mediated diseases and cytokine inhibition, suppression and antagonism are used in the context of diseases or conditions in which excessive or unregulated production or activity of one or more cytokine occurs. Examples of such cytokines are tumour necrosis factor alpha (TNFα), interleukin-1 (IL-1), interleukin-6 (IL-6) and interleukin-8 (IL-8). There remains a need for compounds which are useful in treating cytokine mediated diseases, and as such, inhibit, suppress or antagonize the production or activity of cytokines such as TNF, IL-1, IL-6 and IL-8.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, *Nature Reviews Drug Discovery* 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation. (see G. Panayi, *N Engl J Med* 2001, 344(12), 907; J. Smolen *Nature Reviews Drug Discovery* 2003, 2, 473 and references cited therein). The four known isoforms of p38 MAP kinase (p38 α, β, γ, δ) each showing different expression levels, tissue distributions and regulation, support the concept that they are involved in the etiology of many diseases.

Many solid tumours increase in mass through proliferation of malignant cells and stromal cells, including endothelial cells. In order for a tumor to grow lager than 2-3 mm in diameter, it must form a vasculature, a process known as angiogenesis. A selective p38 inhibitor has been shown to inhibit angiogenesis (see J. R. Jackson, *J. Pharmacol Exp. Therapeutics*, 1998, 284, 687). Because angiogenesis is a critical component of the mass expansion of solid tumours, the development of new p38 kinase inhibitors for the inhibition of this process represents a promising approach for anti-tumour therapy. The compounds of the present invention are also useful in inhibiting growth of susceptible neoplasms (see R. M. Schultz, *Potential of p38 MAP kinase inhibitors in the treatment of cancer*. In: E. Jucker (editor), *Progress in Drug Research* 2003, 60, 59-92. The term "susceptible neoplasm" used in present application includes human cancers such as malignant melanoma, colorectal carcinoma, gastric carcinoma, breast carcinoma and non-small cell lung carcinoma.

Furthermore, inhibition of p38 kinase may be effective in treatment of certain viral conditions such as influenza (*J. Immunology*, 2000, 164, 3222), rhinovirus (*J. Immunology*, 2000, 165, 5211) and HIV (*Proc. Nat. Acad. Sci.*, 1998, 95, 7422).

In summary, a number of inhibitors of p38 kinase are under active investigation for the treatment of a variety of disorders (Boehm, Adams *Exp. Opin. Ther. Patents* 2000, 10(1), 25-37. There remains a need for treatment in this field for compounds that are cytokine suppressive, i.e compounds that are capable of inhibiting p38 kinase.

SUMMARY OF THE INVENTION

In a first embodiment, the invention provides a compound of formula (I)

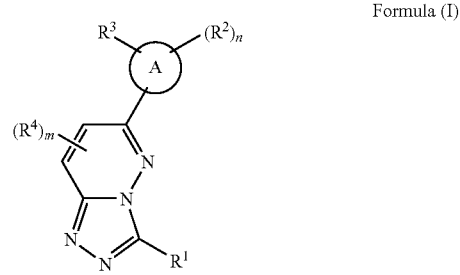

Formula (I)

pharmaceutically acceptable salts thereof, metabolites thereof, isomers thereof, or pro-drugs thereof wherein A is heteroaryl or heterocyclyl;

R$^1$ is —C(O)—(C$_1$-C$_6$) optionally substituted alkyl, —C(O)—O—(C$_1$-C$_6$) optionally substituted alkyl, —NR$^a$R$^b$, —(C$_1$-C$_6$)alkyl-NR$^a$—S(O)$_2$—(C$_1$-C$_6$)alkyl or —(C$_1$-C$_6$)alkyl —NR$^a$—C(O)—(C$_1$-C$_6$)alkyl; or R$^1$ is optionally substituted (C$_1$-C$_6$)alkyl, optionally substituted (C$_2$-C$_6$)alkenyl, optionally substituted (C$_3$-C$_6$)cycloalkyl, optionally substituted aryl or optionally substituted heterocyclyl;

R$^2$ for each occurrence is independently H, OH, oxo, —(CR$^a$R$^b$)$_x$—NR$^a$—C(O)—NR$^a$—(C$_3$-C$_6$)cycloalkyl-phenyl or —(CR$^a$R$^b$)$_x$—NR$^a$R$^b$; or R$^2$ for each occurrence is independently optionally substituted (C$_1$-C$_6$)alkyl, —(CH$_2$)$_x$— optionally substituted aryl, —(CH$_2$)$_x$—(C$_3$-C$_6$) optionally substituted cycloalkyl, —(CH$_2$)$_x$— optionally substituted heteroaryl, or —(CH$_2$)$_x$— optionally substituted heterocyclyl;

wherein R$^2$ can replace hydrogen on either nitrogen or carbon;

R$^3$ is aryl optionally substituted with one or more substituents;

R$^4$ for each occurrence is independently H, OH, halo or optionally substituted (C$_1$-C$_4$)alkyl;

R$^a$ and R$^b$ are independently H or optionally substituted (C$_1$-C$_6$)alkyl;

m is 1 or 2;

n is 0, 1 or 2; and x for each occurrence is independently 0, 1 or 2;

provided the compound is not

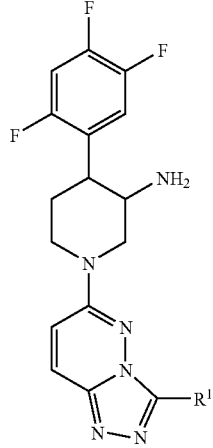

wherein R$^1$ is methyl, ethyl, propyl, isopropyl, t-butyl, cyclopropyl, cyclohexyl, C$_2$F$_5$, CF$_3$, or 4-fluorophenyl;

provided that the compound is not

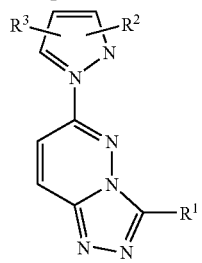

wherein R$^1$ is CF$_3$, CH$_3$, NH$_2$ or phenyl optionally substituted with Br or F;

R$^2$ is H or CH$_3$; and R$^3$ is phenyl optionally substituted with F;

provided the compound is not

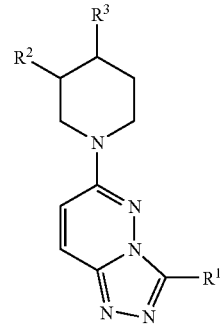

wherein R$^1$ is or phenyl substituted with F;

R$^2$ is CN or NH$_2$; and R$^3$ is phenyl optionally substituted with three F;

provided the compound is not

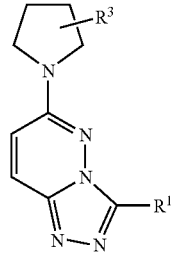

wherein R$^1$ is CF$_3$, CH$_3$ or phenyl optionally substituted with F; and

R$^3$ is phenyl optionally substituted with CH$_3$, F or two OCH$_3$;

provided the compound is not

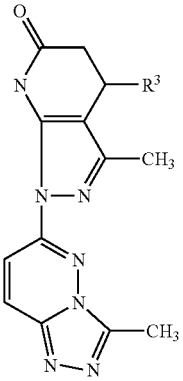

wherein R$^3$ is phenyl substituted with three OCH$_3$ or phenyl substituted with two OCH$_3$ and one OH;

provided the compound is not

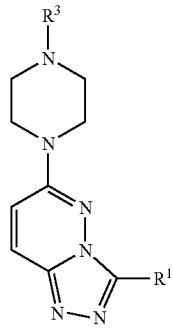

wherein $R^1$ is $CH_3$, $CF_3$, —$CH_2CH_2OH$ or phenyl optionally substituted with B, Cl or F; and $R^3$ is phenyl optionally substituted with $OCH_3$, $CF_3$, F, isopropyl, Cl or one or two $CH_3$; or $R^1$ is phenyl substituted with four F and one $CF_3$; and provided the compound is not

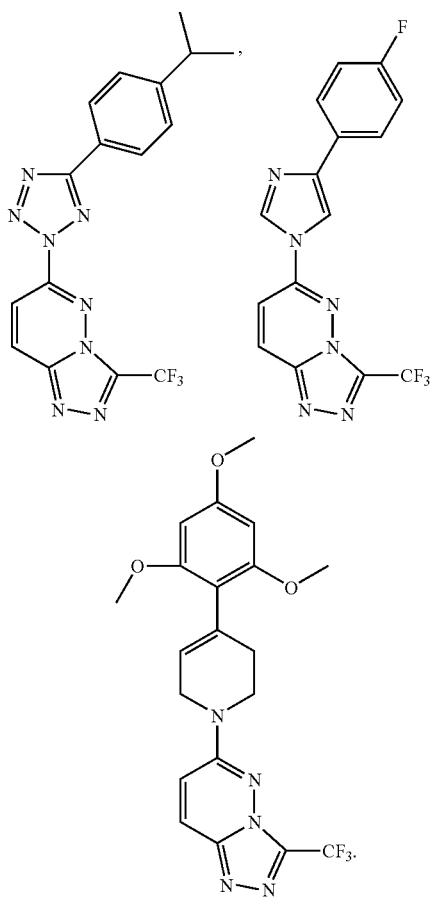

In a second embodiment, the invention provides a compound according to the first embodiment wherein A is

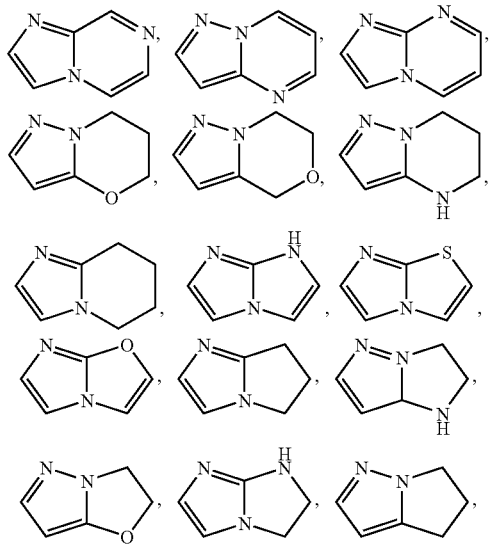

-continued

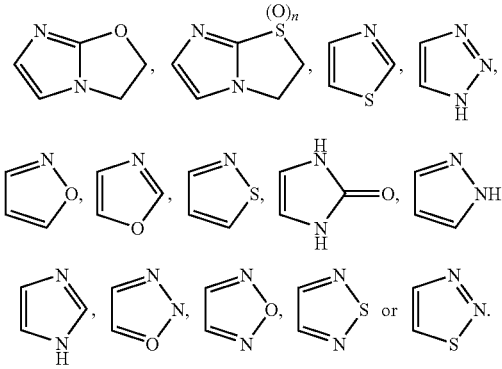

In a third embodiment, the invention provides a compound according to any of the foregoing embodiments wherein

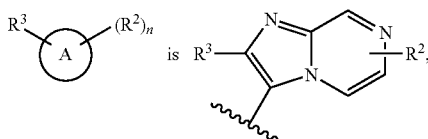

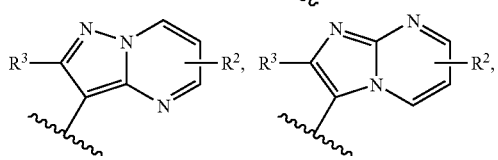

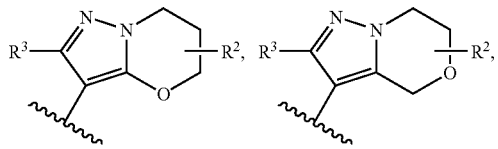

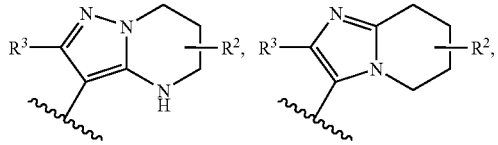

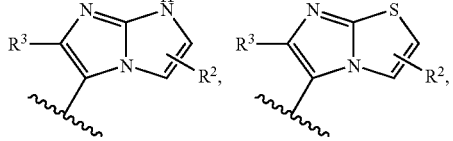

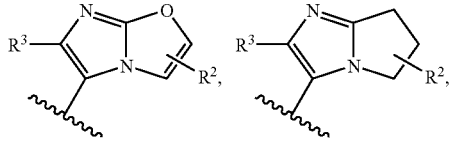

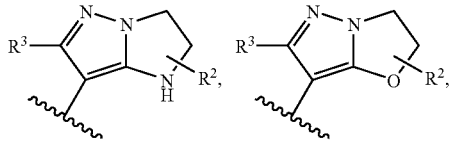

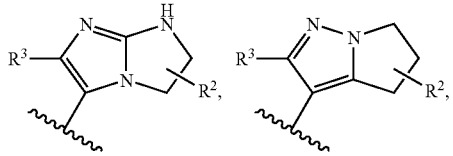

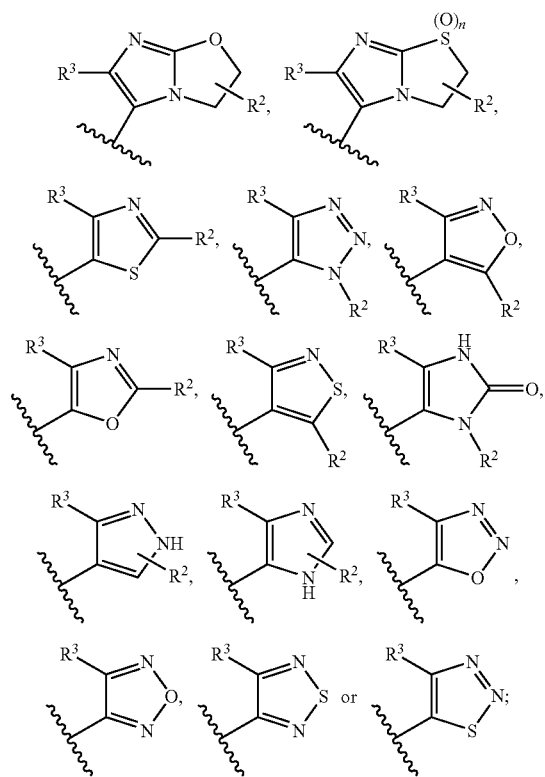

wherein R² can replace hydrogen on either nitrogen or carbon.

In a fourth embodiment the invention provides a compound according to any of the foregoing embodiments wherein

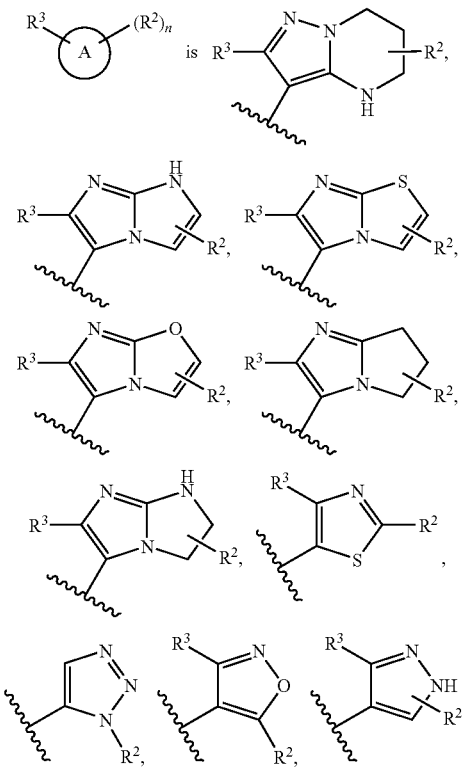

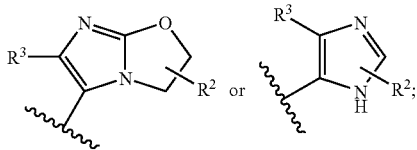

wherein R² can replace hydrogen on either nitrogen or carbon.

In a fifth embodiment the invention provides a compound according to any of the foregoing embodiments wherein R¹ is N(CH₃)₂, optionally substituted (C₁-C₆)alkyl, optionally substituted (C₂-C₆)alkenyl, optionally substituted (C₃-C₆)cycloalkyl, optionally substituted phenyl, optionally substituted piperidinyl, optionally substituted pyrrolidinyl or tetrahydropyranyl.

In a sixth embodiment the invention provides a compound according to any of the foregoing embodiments wherein R³ is phenyl optionally substituted with one or more substituents.

In a seventh embodiment the invention provides a compound according to any of the foregoing embodiments wherein R² for each occurrence is independently H or —(CH₂)ₓ—NRᵃRᵇ or R² is independently optionally substituted (C₁-C₆)alkyl, —(CH₂)ₓ— optionally substituted phenyl, —(CH₂)ₓ— optionally substituted imidazolyl, —(CH₂)ₓ— optionally substituted morpholinyl, —(CH₂)ₓ— optionally substituted piperidinyl, —(CH₂)ₓ— optionally substituted piperazinyl or —(CH₂)ₓ— optionally substituted tetrahydropyranyl.

In a eighth embodiment the invention provides a compound according to any of the foregoing embodiments wherein R¹ is N(CH₃)₂, optionally substituted (C₃-C₄)alkyl, optionally substituted cyclopropyl, optionally substituted cyclobutyl, optionally substituted phenyl or optionally substituted pyrrolidinyl.

In an ninth embodiment the invention provides a compound according to any of the foregoing embodiments wherein R² for each occurrence is independently H, —(CH₂)ₓ—NRᵃRᵇ, optionally substituted (C₁-C₆)alkyl, —(CH₂)ₓ— phenyl, —(CH₂)ₓ— imidazolyl, —(CH₂)ₓ— morpholinyl, optionally substituted —(CH₂)ₓ— piperidinyl and —(CH₂)ₓ— tetrahydropyranyl.

In a tenth embodiment the invention provides a compound according to any of the foregoing embodiments wherein

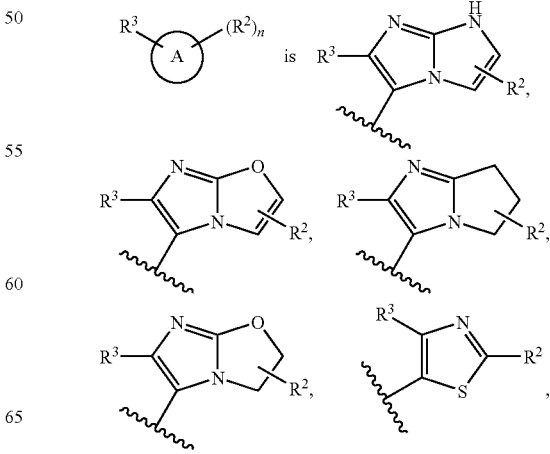

-continued

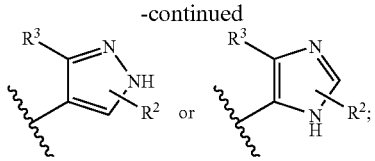

wherein R² can replace hydrogen on either nitrogen or carbon.

In a eleventh embodiment, the invention provides a compound according to any of the foregoing embodiments wherein R² is H, NH₂, optionally substituted (C₁-C₄)alkyl, optionally substituted phenyl or optionally substituted piperidinyl.

In an twelfth embodiment, the invention provides a compound according to any of the foregoing embodiments wherein

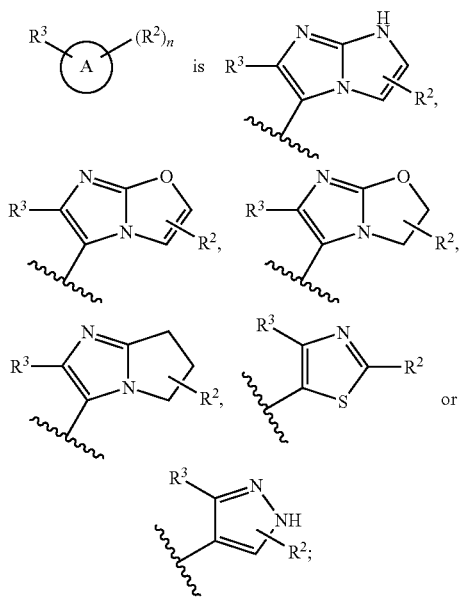

wherein R² can replace hydrogen on either nitrogen or carbon.

In a thirteenth embodiment the invention provides a compound according to any of the foregoing embodiments wherein R³ is phenyl substituted with one, two or three substituents.

In a fourteenth embodiment the invention provides a compound according to any of the foregoing embodiments wherein R³ is substituted phenyl and the substituents are independently halogen or optionally substituted (C₁-C₄) alkyl.

In a fifteenth embodiment the invention provides a compound according to any of the foregoing embodiments wherein R³ is substituted phenyl and the substituents are halogen.

In a sixteenth embodiment the invention provides a compound according to any of the foregoing embodiments wherein R³ is substituted phenyl and the substituents are fluorine.

In a seventeenth embodiment the invention provides a compound according to any of the foregoing embodiments wherein R⁴ is H.

In an eighteenth embodiment the invention provides a compound according to any of the foregoing embodiments wherein the compound is

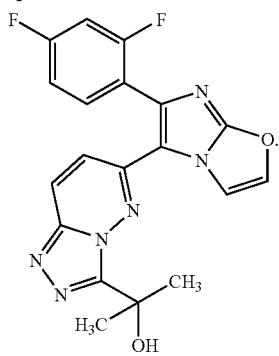

In a nineteenth embodiment the invention provides a compound according to embodiments one through seventeen wherein the compound is

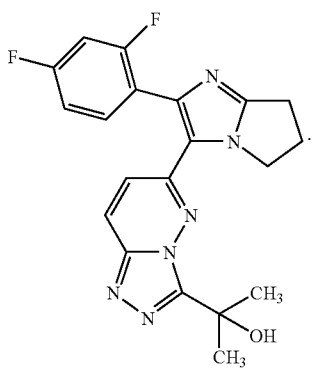

In a twentieth embodiment the invention provides a compound according to according to embodiments one through seventeen wherein R¹ is isopropyl.

In a twenty-first embodiment the invention provides a compound according to embodiments one through seventeen and twenty wherein R² is H.

In a twenty-second embodiment the invention provides a compound according to embodiments one through seventeen and twenty through twenty-one wherein

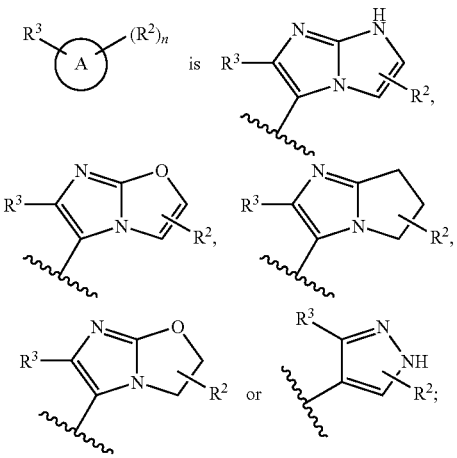

wherein R² can replace hydrogen on either nitrogen or carbon.

In a twenty-third embodiment the invention provides a compound according to embodiments one through seventeen and twenty through twenty-two wherein R³ is phenyl substituted with two fluorine atoms.

In a twenty-fourth embodiment the invention provides a compound according to embodiments one through seventeen and twenty through twenty-three wherein the compound is

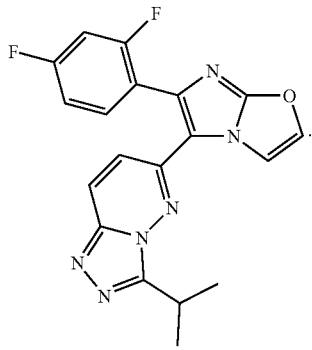

In a twenty-fifth embodiment the invention provides a method of treating a condition in a patient comprising administering a therapeutically effective amount of a compound of any of the foregoing embodiments or a physiologically acceptable salt, pro-drug, isomer or biologically active metabolite thereof to said patient, wherein said condition is selected from the group consisting of rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy, pain, neuropathic pain, ankylosing spondylitis, systemic lupus erythematosus, an ocular condition, a cancer, a solid tumor, sarcoma, fibrosarcoma, osteoma, melanoma, retinoblastoma, a rhabdomyosarcoma, glioblastoma, neuroblastoma, teratocarcinoma, cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, alpha-1 antitrypsin deficiency, amyotrophic lateral sclerosis, anemia, angina pectoris, anterior horn cell degeneration, anti cd3 therapy, antiphospholipid syndrome, anti-receptor hypersensitivity reactions, hypersensitivity reactions, hyperkinetic movement disorders, hypersensitivity pneumonitis, hypertension, hypokinetic movement disorders, aortic and peripheral aneurysms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, atrial fibrillation (sustained or paroxysmal), atrial flutter, atrioventricular block, B cell lymphoma, bone graft rejection, bone marrow transplant (BMT) rejection, small bowel transplant rejection, spinal ataxia, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic salicylate intoxication, colorectal carcinoma, congestive heart failure, conjunctivitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetic ateriosclerotic disease, Diffuses Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, gram negative sepsis, gram positive sepsis, granulomas due to intracellular organisms, hairy cell leukemia, Hallerrorden-Spatz disease, hay fever, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile rheumatoid arthritis, juvenile spinal muscular atrophy, kidney transplant rejection, *legionella*, leishmaniasis, lipedema, liver transplant rejection, lymphederma, malaria, malignant Lymphoma, malignant histiocytosis, malignant melanoma, meningococcemia, metabolic/idiopathic, migraine headache, mitochondrial multi-system disorder, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodyplastic syndrome, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, Kaposi's sarcoma, Hodgkin's disease, lymphoma, myeloma, leukaemia, malignant ascites, hematopoietic cancers Crow-Fukase (POEMS) syndrome (polyneuropathy, organomegaly, endocrinopathy, monoclonal gammopathy, and skin changes syndrome), a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes Simplex, Herpes Zoster, human immunodeficiency virus, parapoxvirus, protozoa or toxoplasmosis, progressive supranucleo palsy, primary pulmonary hypertension, radiation therapy, Raynaud's phenomenon and disease, Refsum's disease, regular narrow QRS tachycardia, renovascular hypertension, restrictive cardiomyopathy, sarcoma, senile chorea, Senile Dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, diabetes, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, disseminated intravascular coagulation, Kawasaki's disease, nephrotic syndrome, chronic fatigue syndrome, Wegener's granulomatosis, Henoch-Schoenlein purpurea, microscopic vasulitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *chlamydia*, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis; *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, age-related macular degeneration, acute idiopathic polyneuritis, acuter or chronic immune disease associated with organ transplantation, acute inflammatory demyelinating polyradiculoneuropathy, acute ischemia, adult Still's disease, allergy, anaphylaxis, anti-phospholipid antibody syndrome, aplastic anemia, atopic eczema, atopic dermatitis, autoimmune dermatitis, autoimmune diabetes, autoimmune disorder associated with *streptococcus* infection, autoimmune enteropathy, autoimmune hepatitis, autoimmune hearing loss, autoimmune lymphoproliferative syndrome (ALPS), autoimmune myocarditis, autoimmune neutropenia, autoimmune premature ovarian failure, autoimmune thrombocytopenia (AITP), autoimmune uveitis, Behcet's disease, blepharitis, bronchiectasis, bullous pemphigoid, catastrophic antiphospholipid syndrome, celiac disease, cervical spondylosis, chronic ischemia, cicatricial pemphigoid, clinical isolated syndrome (CIS) with risk for multiple sclerosis, childhood onset psychiatric disorder, dacrocystitis, dermatomyositis, disc herniation, disc prolapse, drug induced immune hemolytic anemia, endophthalmitis, episcleritis, erythema multiforme, erythema multiforme major, gestational pemphigoid, Guillain-Barre syndrome, heart failure, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell hisiocytosis, livedo reticularis, microscopic polyangiitis, morbus bechterev, motor neuron disorders, mucous membrane pemphigoid, primary progressive multiple sclerosis, secondary progressive multiple sclerosis, relapsing remitting multiple sclerosis, multiple organ failure, myelodysplastic syndrome, nerve root disorder, neuropathy, Non-A Non-B hepatitis, osteolysis, ovarian cancer, pauciarticular JRA, peripheral artery occlusive disease (PAOD), periphral vascular disease (PVD), peripheral artery disease (PAD), phlebitis, polychondritis, polymyalgia rheumatica, poliosis, polyarticular JRA, polyendocrine deficiency syndrome, polymyositis, post-pump syndrome, primary parkinsonism, prostatitis, psoratic arthropathy, pure red cell aplasia, primary adrenal insufficiency, Reiter's disease, recurrent neuromyelitis optica, rheumatic heart disease, SAPHO (synovitis, acne, pustulosis, hyperostosis, and osteitis), scleroderma, secondary amyloidosis, shock lung, sciatica, secondary adrenal insufficiency, septic arthritis, seronegative arthopathy, silicone associated connective tissue disease, Sneddon-Wilkinson Dermatosis, spondylitis ankylosans, Stevens-Johnson Syndrome (SJS), systemic inflammatory response syndrome, temporal arteritis, toxoplasmic retinitis, toxic epidermal necrolysis, TRAPS (Tumor Necrosis factor receptor), type 1 allergic reaction, type II diabetes, urticaria, usual interstitial pneumonia (UIP), vernal conjunctivitis, viral retinitis, Vogt-Koyanagi-Harada syndrome (VKH syndrome) and wet macular degeneration.

In a twenty-sixth embodiment the invention provides a method according to the twenty-fifth embodiment wherein said condition is rheumatoid arthritis, osteoarthritis, psoriatic arthritis, juvenile chronic arthritis, Lyme arthritis, reactive arthritis, pauciarticular juvenile rheumatoid arthritis, polyarticular juvenile rheumatoid arthritis, pain, neuropathic pain or ankylosing spondylitis.

In a twenty-seventh embodiment the invention provides a method according to the twenty-fifth and twenty-sixth embodiments wherein said condition is rheumatoid arthritis.

In a twenty-eighth embodiment the invention provides a pharmaceutical composition comprising the compound of Formula (I),

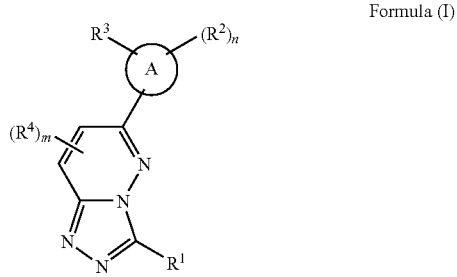

Formula (I)

pharmaceutically acceptable salts thereof, metabolites thereof, isomers thereof, or pro-drugs thereof wherein A is heteroaryl or heterocyclyl;

$R^1$ is —C(O)—($C_1$-$C_6$) optionally substituted alkyl, —C(O)—O—($C_1$-$C_6$) optionally substituted alkyl, —$NR^aR^b$, —($C_1$-$C_6$)alkyl —$NR^a$—$S(O)_2$—($C_1$-$C_6$)alkyl or —($C_1$-$C_6$)alkyl —$NR^a$—C(O)—($C_1$-$C_6$)alkyl; or $R^1$ is optionally substituted ($C_1$-$C_6$)alkyl, optionally substituted ($C_2$-$C_6$)alkenyl, optionally substituted ($C_3$-$C_6$)cycloalkyl, optionally substituted aryl or optionally substituted heterocyclyl;

$R^2$ for each occurrence is independently H, oxo, —$(CR^aR^b)_x$—$NR^a$—C(O)—$NR^a$—($C_3$-$C_6$)cycloalkyl-phenyl or —$(CR^aR^b)_x$—$NR^aR^b$; wherein $R^a$ and $R^b$ are independently H or optionally substituted ($C_1$-$C_6$)alkyl; or $R^2$ for each occurrence is independently optionally substituted ($C_1$-$C_6$)alkyl, —$(CH_2)_x$— optionally substituted aryl, —$(CH_2)_x$—($C_3$-$C_6$) optionally substituted cycloalkyl, —$(CH_2)_x$— optionally substituted heteroaryl, or —$(CH_2)_x$— optionally substituted heterocyclyl;

$R^3$ is aryl optionally substituted with one or more substituents;

$R^4$ for each occurrence is independently H, halo or optionally substituted ($C_1$-$C_4$)alkyl;

m is 1 or 2;

n is 0, 1 or 2; and x for each occurrence is independently 0, 1 or 2;

and a pharmaceutically-acceptable carrier or excipient.

In a twenty-ninth embodiment the invention provides a pharmaceutical composition comprising

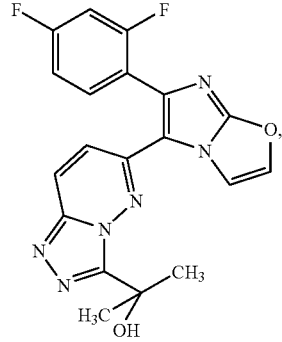

an isomer, pro-drug, metabolite or pharmaceutically acceptable salt thereof and a pharmaceutically-acceptable carrier or excipient.

In a thirtieth embodiment the invention provides a pharmaceutical composition comprising

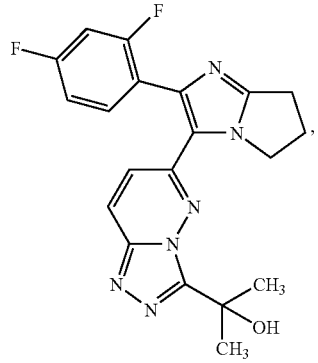

an isomer, pro-drug, metabolite or pharmaceutically acceptable salt thereof and a pharmaceutically-acceptable carrier or excipient.

In a thirty-first embodiment the invention provides a pharmaceutical composition comprising

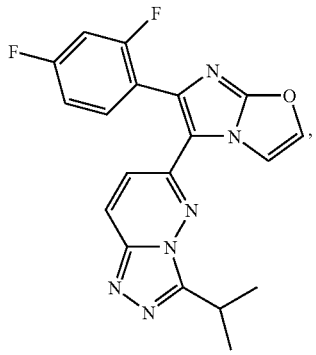

a pro-drug, metabolite or pharmaceutically acceptable salt thereof and a pharmaceutically-acceptable carrier or excipient.

In a thirty-second embodiment the invention provides a pharmaceutical formulation of a compound of Formula (I)

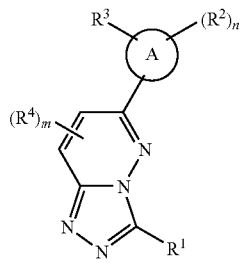

Formula (I)

pharmaceutically acceptable salts thereof, metabolites thereof, isomers thereof, or pro-drugs thereof wherein
A is heteroaryl or heterocyclyl;
$R^1$ is —C(O)—($C_1$-$C_6$) optionally substituted alkyl, —C(O)—O—($C_1$-$C_6$) optionally substituted alkyl, —$NR^aR^b$, —($C_1$-$C_6$)alkyl —$NR^a$—S(O)$_2$—($C_1$-$C_6$)alkyl or —($C_1$-$C_6$)alkyl —$NR^a$—C(O)—($C_1$-$C_6$)alkyl; or
$R^1$ is optionally substituted ($C_1$-$C_6$)alkyl, optionally substituted ($C_2$-$C_6$)alkenyl, optionally substituted ($C_3$-$C_6$)cycloalkyl, optionally substituted aryl or optionally substituted heterocyclyl;
$R^2$ for each occurrence is independently H, oxo, —($CR^aR^b$)$_x$—$NR^a$—C(O)—$NR^a$—($C_3$-$C_6$)cycloalkyl-phenyl or —($CR^aR^b$)$_x$—$NR^aR^b$; wherein
$R^a$ and $R^b$ are independently H or optionally substituted ($C_1$-$C_6$)alkyl; or
$R^2$ for each occurrence is independently optionally substituted ($C_1$-$C_6$)alkyl, —(CH$_2$)$_x$— optionally substituted aryl, —(CH$_2$)$_x$—($C_3$-$C_6$) optionally substituted cycloalkyl, —(CH$_2$)$_x$— optionally substituted heteroaryl, or —(CH$_2$)$_x$— optionally substituted heterocyclyl;
$R^3$ is aryl optionally substituted with one or more substituents;
$R^4$ for each occurrence is independently H, halo or optionally substituted ($C_1$-$C_4$)alkyl;
m is 1 or 2;
n is 0, 1 or 2; and
x for each occurrence is independently 0, 1 or 2;
wherein the pharmaceutical formulation is in an oral form.

In a thirty-third embodiment the invention provides a pharmaceutical formulation according to embodiment thirty-one wherein the pharmaceutical formulation is a tablet.

In a thirty-fourth embodiment the invention provides a pharmaceutical formulation according to embodiments thirty-one or thirty-two wherein the pharmaceutical formulation is a capsule.

In a thirty-fifth embodiment the invention provides a kit comprising a compound according to any one of embodiments one through twenty-three, an isomer, pro-drug, metabolite or pharmaceutically acceptable salt thereof and instructions for the administration of said compound.

In a thirty-sixth embodiment the invention provides a kit comprising a compound of the formula

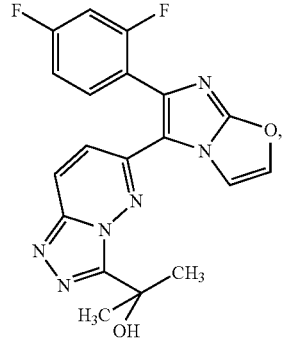

an isomer, pro-drug, metabolite or pharmaceutically acceptable salt thereof and instructions for the administration of said compound.

In a thirty-seventh embodiment the invention provides a kit comprising a compound of the formula

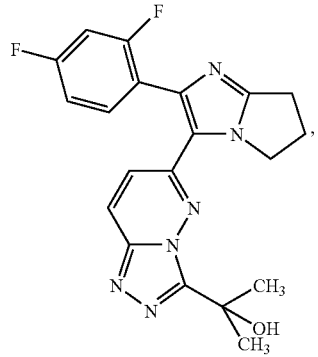

an isomer, pro-drug, metabolite or pharmaceutically acceptable salt thereof and instructions for the administration of said compound.

In a thirty-eighth embodiment the invention provides a kit comprising a compound of the formula

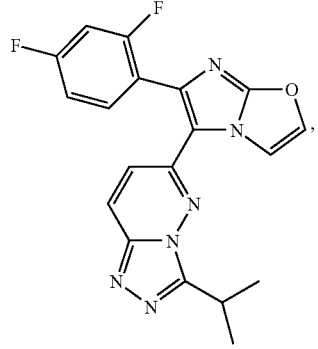

an isomer, pro-drug, metabolite or pharmaceutically acceptable salt thereof and instructions for the administration of said compound.

In a thirty-ninth embodiment the invention provides a method of treating rheumatoid arthritis comprising administering a therapeutically effective amount of a compound of Formula (I) or an isomer, pro-drug, metabolite or pharmaceutically acceptable salt thereof to a patient in need thereof.

In a fortieth embodiment the invention provides a method of treating rheumatoid arthritis comprising administering a therapeutically effective amount of a compound of the formula

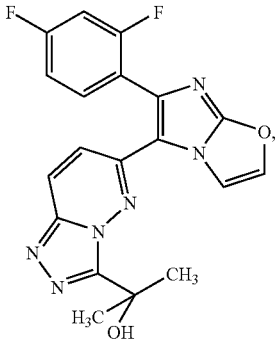

or an isomer, pro-drug, metabolite or pharmaceutically acceptable salt thereof to a patient in need thereof.

In a forty-first embodiment the invention provides a method of treating rheumatoid arthritis comprising administering a therapeutically effective amount of a compound of the formula

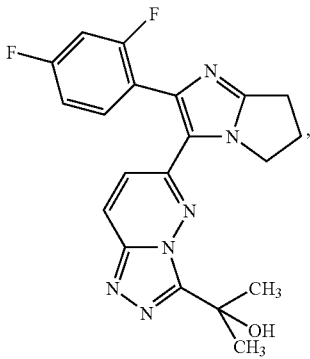

or an isomer, pro-drug, metabolite or pharmaceutically acceptable salt thereof to a patient in need thereof.

In a forty-second embodiment the invention provides a method of treating rheumatoid arthritis comprising administering an effective amount of a compound of the formula

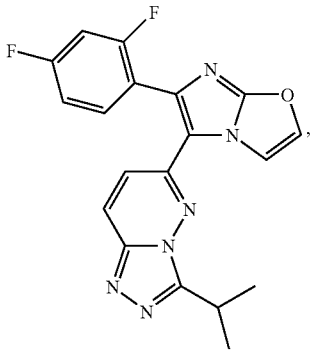

or an isomer, pro-drug, metabolite or pharmaceutically acceptable salt thereof to a patient in need thereof.

In a forty-third embodiment the invention provides a method of treating rheumatoid arthritis according to any of the foregoing embodiments wherein the patient is administered an oral form of the compound or an isomer, pro-drug, metabolite or pharmaceutically acceptable salt thereof.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and Serine/Threonine kinases as a result of their substrate specificity. Serine/Threonine Kinases (S/T kinases) are a large sub-family of protein kinases that specifically transfer a phosphate group to a terminal hydroxyl moiety of specific serine or threonine residues (Hanks et al., (1988) *Science*, 241: 42-52). A number of S/T kinase family members are involved in inflammatory signaling, tumor growth or cellular transformation. For example, the mitogen-activated protein kinases (MAPKs) are S/T kinases that act as intermediates within the signaling cascades of Toll like receptors (TLRs), such as TLR4, growth/survival factors, such as EGF, and death receptors, such as the TNF receptor. Activation of MAPKs, such as extracellular signal-regulated kinases (ERK1-2), p38α, c-Jun N-terminal kinase (JNK) or MAP-KAP-K2 (MK2) have been shown to transduce signaling in cells, such as monocytes/macrophages, resulting in the extracellular production of pro-inflammatory cytokines, such as TNF.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, *Nature Reviews Drug Discovery* 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation. (see G. Panayi, *N Engl J Med* 2001, 344(12), 907; J. Smolen *Nature Reviews Drug Discovery* 2003, 2, 473 and references cited therein). The four known isoforms of p38 MAP kinase (p38 α, β, γ, δ) each showing different expression levels, tissue distributions and regulation, support the concept that they are involved in the etiology of inflammatory, auto-immune and other diseases.

In summary, a number of inhibitors of p38 kinase are under active investigation for the treatment of a variety of disorders (Boehm, Adams *Exp. Opin. Ther. Patents* 2000, 10(1), 25-37). There remains a need for treatment in this field for compounds that are cytokine suppressive, i.e compounds that are capable of inhibiting p38 kinase.

Protein tyrosine kinases (PTKs) are enzymes that catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g. autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Tyrosine kinases can be of the receptor-type (having extracellular, transmembrane and intracellular domains) or the non-receptor type (being wholly intracellular).

Receptor Tyrosine Kinases (RTKs) comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response (e.g., cell division, differentiation, metabolic effects, and changes in the extracellular microenvironment; see Schlessinger and Ullrich, 1992, *Neuron* 9:1-20).

Non-receptor tyrosine kinases represent a collection of cellular enzymes which lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025-2031, which is incorporated herein by reference.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

In a related aspect the invention provides a method for inhibiting p38 in a human subject suffering from a disorder in which p38 activity is detrimental, comprising administering to the human subject a compound of Formula (I) such that p38 activity in the human subject is inhibited and treatment is achieved.

Many autoimmune diseases and disease associated with chronic inflammation, as well as acute responses, have been linked to activation of p38 MAP kinase and overexpression or dysregulation of inflammatory cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

These compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the p38 inhibitors of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™, U.S. Pat. No. 6,090,382), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK or IKK kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, VX-740, Roflumilast, IC-485, CDC-801 and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, or IKK kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (HUMIRA®, U.S. Pat. No. 6,090,382), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, or IKK kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of Formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate, ibuprofen, diclofenac and misoprostol, naproxen, meloxicam, indomethacin, diclofenac, celecoxib, rofecoxib, sulfasalazine, methotrexate, azathioprine, minocyclin, prednisone, enteracept, infliximab, albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, tramcinolone acetonide, beclomethasone dipropionate, ipratropium bromide, azithromycin, pirbuterol acetate, theophylline anhydrous, methylprednisolone sodium succ, clarithromycin, zafirlukast, formoerol fumarate, influenza virus vaccine, methylprednisolone sodium succ, amoxicillin trihydrate, flunisolide/menthol, allergy injection, cromolyn sodium, fexofenadine hydrochloride, levofloxacin, inhaler assist device, guaifenesin, dexamthasone sodium phosphate, moxifloxacin HCl, doxycycline hyclate, fuaifenesin/d-methorphan, p-ephedrine/cod/chlorphenir, gatifloxacin, cetirizine hydrochloride, mometasone furoate, benzonatate, cephalexin, pe/hydrocone/chlorphenir, cetirizine HCl/pseucoephed, phenyphrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, metaproterenol sulfate, mesalamine, azathioprine, mercaptopurine, diphenoxylate/atrop sulf, loperamide hydrochloride, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumag, interferon-gamma, montelukast sodium, formoterol fumarate, triamcinolone acetonide, levofloxacin, guaifenesin, levalbuterol HCl, flunisolide, ceftriaxone sodium, gatifloxacin, amoxicillin/clavulanate, flunisolide/menthol, chlorpheniramine/hydrocodone metaproterenol sulfate, methylprednisolone, mometasone furoate, p-ephedrine/cod/chlorphenir, p-ephedrine/loratadine, terbutaline sulfate, tiotropium bromide, (R,R)-formoterol, TgAAT, Cilomilast, Roflumilast, Interferon-alpha-2α, Interferon-alpha-2β, Interferon-alpha con1, Interferon-alpha-n1, pegylated interferon-alpha-2a, Pegylated interferon-alpha-2β, Ribavirin, Peginterferon alfa-2β, and ribavirin, Ursodeoxycholic Acid, Glycyrrhizic Acid, Thymalfasin, Maxamine, VX-497, any compounds that are used to treat HCV through intervention with the following targets: HCV polymerase, HCV protease, HCV helicase, HCV IRES (internal ribosome entry site), azathioprine, colchicine, albuterol sulfate, gamma interferon, lorazepam, furosemide, lisinopril, cyclophosphamide, actinomycin d, alteplase, levofloxacin, metaproterenol sulfate, morphine sulfate, oxycodone HCl, triamcinolone acetonide, tacrolimus anhydrous, calcium, interferon-alpha, mycophenolate mofetil, Interferon-gamma-1b, clopidogrel bisulfate, atenolol, morphine sulfate, metoprolol succinate, warfarin sodium, isosorbide mononitrate, simvastatin, tenecteplase, torsemide, retavase, losartan potassium, quinapril HCl/mag carb, alteplase, enalaprilat, amiodarone hydrochloride, tirofiban HCl m-hydrate, diltiazem hydrochloride, captopril, irbesartan, propranolol hydrochloride, fosinopril sodium, lidocaine hydrochloride, eptifibatide, cefazolin sodium, atropine sulfate, aminocaproic acid, interferon, sotalol hydrochloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide, calcipotriene, clobetasol propionate, triamcinolone acetonide, halobetasol propionate, tazarotene, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, hydrocortisone, moisturizing formula, folic acid, desonide, coal tar, diflorasone diacetate, etanercept, lactic acid, methoxsalen, HCl/bismuth, subgal/znox/resor, methylprednisolone acetate, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, soap/tribromsalan, thimerosal/boric acid, cyclosporine, alefacept, efalizumab, pimecrolimus, PUVA, UVB, naproxen, leflunomide, hydroxychloroquine sulfate, prednisone, sulindac, betamethasone diprop augmented, triamcinolone acetonide, dimethylsulfoxide, piroxicam, diclofenac sodium, ketoprofen, nabumetone, tolmetin sodium, calcipotriene, cyclosporine, sodium/misoprostol, fluocinonide, glucosamine sulfate, gold sodium thiomalate, hydrocodone bitartrate/apap, risedronate sodium, sulfadiazine, thioguanine, valdecoxib, hydroxychloroquine sulfate, leflunomide, valdecoxib, methylprednisolone, azathioprine, triamcinolone acetonide, propoxyphene napsylate/apap, nabumetone, piroxicam, etodolac, oxaprozin, hydrocodone bitartrate/apap, fentanyl, human recombinant anakinra, tramadol HCl, salsalate, sulindac, yanocobalamin/fa/pyridoxine, acetaminophen, alendronate sodium, prednisolone, morphine sulfate, lidocaine hydrochloride, glucosamine sulf/chondroitin, cyclosporine, amitriptyline HCl, sulfadiazine, oxycodone HCl/acetaminophen, olopatadine HCl, misoprostol, omeprazole, mycophenolate mofetil, ABT-874, anti-IL18 antibody, VX-740, Roflumilast, IC-485, CDC-801, Mesopram, sirolimus, paclitaxel, everolimus, tacrolimus, ABT-578, hydrocodone bitartrate/apap, cyclobenzaprine HCl, oxycodone HCl/acetaminophen, Valdecoxib, codeine phosphate/apap, tramadol HCl/acetaminophen, metaxalone, methocarbamol, lidocaine hydrochloride diclofenac sodium, gabapentin, dexamethasone, carisoprodol, ketorolac tromethamine, diazepam, nabumetone, oxycodone HCl, tizanidine HCl, propoxyphene napsylate/apap, asa/oxycod/oxycodone ter, ibuprofen/hydrocodone bit, etodolac, propoxyphene HCl, amitriptyline HCl, carisoprodol/codeine phos/asa, morphine sulfate, orphenadrine citrate, temazepam, epidermal growth factor, corticosteroids, cyclosporin, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, cyclosporin, FK506, rapamycin, mycophenolate mofetil, leflunomide, NSAIDs, corticosteroids, prednisolone, phosphodiesterase inhibitors, adenosine agonists, antithrombotic agents, complement inhibitors, adrenergic agents, IRAK, NIK, or IKK kinase inhibitors, IL-1β converting enzyme inhibitors, TNFα converting enzyme inhibitors, T-cell signalling inhibitors, metalloproteinase inhibitors, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept infliximab and D2E7 (HUMIRA®, U.S. Pat. No. 6,090,382).

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, roflumilast, Ambrisentan and Darusentan.

Non-limiting examples of therapeutic agents for HCV with which a compound of Formula (I) can be combined include the following: Interferon-alpha-2a, Interferon-alpha-2b, Interferon-alpha con1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, D2E7 (HUMIRA®, U.S. Pat. No. 6,090,382), cyclosporine, alefacept, efalizumab, tacrolimus, pimecrolimus, PUVA, UVB, and sulfasalazine.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab and D2E7 (HUMIRA®, U.S. Pat. No. 6,090,382).

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7, (HUMIRA®, U.S. Pat. No. 6,090,382), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., $-(CH_2)C(O)OH$ or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, ganma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$ alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, $-P(O)(O(C_1-C_6)alkyl)_2$ or glycosyl (the radical resulting from detachment of the hydroxyl of the hemiacetal of a carbohydrate).

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, oxazinyl, hexahydropyrimidinyl, imidazolidinyl, oxazolidinyl, morpholinyl, oxopiperidinyl, oxopyrrolidinyl, piperazinyl, piperidinyl, pyrrolidinyl, quinicludinyl, thiomorpholinyl, tetrahydropyranyl, tetrahydrofuranyl and tropanyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention, the following are heteroaryl rings: azaindolyl, benzo(b)thienyl, benzimidazolyl, benzofuranyl, benzoxazolyl, benzothiazolyl, benzothiadiazolyl, benzoxadiazolyl, dihydropyrazolooxazinyl, dihydropyrazolooxazinyl, dihydropyrroloimidazolyl, dihydroimidazopyrazolyl, dihydropyrazolooxazolyl, dihydroimidazoimidazolyl, dihydropyrrolopyrazolyl, dihydroimidazooxazolyl, furanyl, imidazolyl, imidazolonyl, imidazoimidazolyl, imidazooxazolyl, imidazopyrazinyl, imidazopyrazolyl, imidazopyridinyl, imidazopyrimidinyl, imidazothiazolyl, indolyl, indolinyl, indazolyl, isoindolinyl, isoxazolyl, isothiazolyl, oxadiazolyl, oxazolyl, purinyl, pyranyl, pyrazinyl, pyrazolyl, pyrazolooxazinyl, pyrazolooxazolyl, pyrazolopyrimidinyl, pyridinyl, pyrimidinyl, pyrrolyl, pyrroloimidazolyl, dihydropyrazolooxazolyl, pyrrolopyrimidinyl, pyrazolopyrimidinyl, quinolinyl, quinazolinyl, tetrahydropyrazolopyrimidinyl, tetrahydroimidazopyridinyl, thiazolyl, thiophenyl, tetrahydroindolyl, tetrazolyl, thiadiazolyl, thienyl, thiomorpholinyl and triaozlyl.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "aliphatic" or "an aliphatic group" or notations such as "$(C_0-C_8)$" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a $C_0$ it means that the moiety is not present or in other words, it is a bond. As used herein, "alkyl" means $C_1-C_8$ and includes straight chained or branched hydrocarbons, which are completely saturated. Examples of alkyls are methyl, ethyl, propyl, isopropyl, butyl, pentyl, hexyl and isomers thereof. As used herein, "alkenyl" and "alkynyl" means $C_2-C_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means $C_3$-$C_{12}$ monocyclic or multicyclic (e.g., bicyclic, tricyclic, etc.) hydrocarbons that is completely saturated or has one or more unsaturated bonds but does not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is know to one skilled in the art as being available for substitution can be substituted with one or more and results in a molecule that is a kinase inhibitor. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and OCF$_3$), alkoxyalkoxy, alkoxyalkyl, alkoxycarbonyl, alkoxycarbonylheterocycloalkoxy, alkoxycarbonylpiperidinyl-, alkyl groups (which itself can also be substituted, such as —($C_1$-$C_6$)-alkyl-OR, —$C_1$-$C_6$-alkyl-N(R)$_2$, and —CF$_3$), alkylamino, alkylcarbonyl, alkylester, alkylnitrile, alkylsulfonyl, amino, aminoalkoxy, alkyl-O—C(O)—, alkyl-heterocyclyl, alkyl-cycloalkyl, alkynyl, amido groups, amino, aminoalkyl, aminocarbonyl, carbonitrile, carbonylalkoxy, carboxamido, CF$_3$, CN, —C(O)OH, —C(O)H, —C(O)—C(CH$_3$)$_3$, CF$_3$, COH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., (which can be substituted), halogen or halo group (F, Cl, Br, I), hydroxy, nitro, oxo, OCF$_3$, S(O)$_2$CH$_3$, S(O)$_2$CF$_3$, sulfonyl, N-alkylamino, N,N-dialkylamino (in which the alkyl groups can also be substituted), —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, OCF$_3$, oxo, phenyl, —SO$_2$CH$_3$, —SO$_2$CR$_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocycolthio, cycloalkylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, —N(R)—C(O)R, —N(R)—C(O)OR, OR—C(O)-heterocyclyl-OR, R$_c$ and —CH$_2$OR$_c$;

wherein R$_3$ is ($C_1$-$C_4$)alkyl, ($C_3$-$C_6$)cycloalkyl or phenyl;
  wherein p is 0, 1 or 2;
  where R$_c$ for each occurrence is independently hydrogen, optionally substituted alkyl, optionally substituted aryl, —($C_1$-$C_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$—OH;
  wherein t is an integer from about 1 to about 6;
  $Z^{105}$ for each occurrence is independently a covalent bond, alkyl, alkenyl or alkynyl; and
  $Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;
  E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together form a five- or six-membered heterocyclic ring.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

Enzyme Assays

The in vitro potency of compounds of Formula (I) in inhibiting one or more of the protein kinases discussed herein or described in the art may be determined by the procedures detailed below.

The potency of compounds of Formula (I) can be determined by the amount of inhibition of the phosphorylation of an exogenous substrate (e.g., a synthetic peptide (Z. Songyang et al., Nature. 373:536-539) by a test compound relative to control.

p38 Kinase Assay

Materials: Active p38α enzyme can be purchased from Millipore. Anti-phospho-MBP specific antibody can be purchased from Millipore and Europium (Eu)-cryptate labeled from Cis-Bio International. SAXL (streptavidin linked XL) can be obtained from Prozyme. Biotin-MBP-peptide (Biot-Ahx-VHFFKNIVTPRTPPPSQGKGAEGQR-OH) can be made by New England Peptide. An HTRF reader RUBYstar can be acquired from BMG Labtech.

The kinase assay is performed using the homogenous time-resolved fluorescence (HTRF) method (Mabile, 1991; Mathis, 1993). In a 40 µL reaction volume, the assay mixture contains 4.1 nM p38α, 0.5 µM biotin-MBP-peptide, 1 mM ATP and compound (to a final 5% DMSO concentration) in a buffer containing 20 mM MOPS pH 7.2, 10 mM $MgCl_2$, 5 mM EGTA, 5 mM β-phosphoglycerol, 1 mM $Na_3VO_4$, 0.01% Triton-X-100, and 1 mM DTT. The reaction is carried out at ambient temperature in 96 half-well black plates (Corning). At a designated time point, usually 60 min, 10 µL of 0.5 M EDTA is added to quench the reaction. The products are detected by addition of the revelation reagents, 11 ng anti-phospho-MBP-Eu antibody and 0.34 µg SAXL, respectively. The plates are incubated in the dark at 4° C. overnight, and read in the HTRF reader RUBYstar. The ratio between the signal at 665 nm and 620 nm at various inhibitor concentrations is used to calculate the amount of activity. Activity counts are converted to percent activity, and percent activity is measured from 0.0032 to 50 µM. $IC_{50}$'s were determined by fitting the percent activity data to the equation percent activity=100%/(1+([inhibitor]/IC50)) using non-linear least means-squares curve fitting.

References
(1) M. Mabile, G. Mathis, E. J. P., Jolu, D. Pouyat, C. Dumont, Patent WO 92:13264, 1991
(2) G. Mathis, Clin. Chem. 39 (1993) 1953-1959

Cellular Assays

LPS-induced TNF Production and p-HSP27 Accumulation in the THP-1 Cells:

Materials:

THP-1 cells, ATCC, Catalog #TIB-202

Media reagents were purchased from Invitrogen, RPMI, Catalog #11875; L-Glutamine, Catalog #25030; Penicillin-Streptomycin, Catalog #15140, Beta-Mercaptoethanol Catalog #21985, Sodium Pyruvate Catalog #11360, Sodium Bicarbonate Catalog #25080, and Fetal Bovine Sera, Catalog #26140

Assay Plates, Corning, Catalog #3599

Filtration Plates, Millipore, Catalog #MABVN1250

Dimethyl sulphoxide (DMSO), Sigma, Catalog #D2650

Lipopolysaccharides from *Escherichia coli* 0127:B8 (LPS), Sigma, Catalog #L4516

Cell Wash Buffer, Upstate, Catalog #43-010

Cell Lysis Buffer, Bio-Rad Catalog #171-304011

Phospho-HSP27 Beadmate Kit, Upstate, Catalog #46-607

Streptavidin-Phycoerythrin, Upstate, Catalog #45-001

Tumor Necrosis Factor Alpha (TNF) assay kits, Meso Scale Discovery (MSD), Catalog #K111BHA-4

Recombinant human TNF, R&D Systems, Catalog #210-TA

Thiazolyl Blue Tetrazolium Bromide (MTT), Sigma, Catalog #M2128

Sodium Dodecyl Sulfate (SDS), Mallinckrodt Baker, Inc., Catalog #4095

Dulbecco's Phosphate-Buffered Saline (D-PBS), Invitrogen, Catalog #14190

Methods:

THP-1 cells were cultured according to ATCC guidelines. Cells were incubated in low serum RPMI media (0.5% fetal bovine serum) for about 18 hours prior to assay set-up. Cells were then seeded at a density of $2\times10^5$ cells/well in either flat-bottomed 96-well Assay Plates or Filtration Plates, for assessment of either Tumor Necrosis Factor Alpha (TNF) release or phosphorylated Heat Shock Protein-27 (p-HSP27) accumulation, respectively. Compound stocks and dilutions were made in 100% DMSO before further dilution into media and application to cells. The final assay volume was 200 µL/well, and the final concentration of DMSO was 0.5%. Six-point dilution (1:5) curves were run for test compounds. Positive and negative control wells in which DMSO was applied without compound, either with or without addition of LPS, were also included in each experiment. Compounds and cells were pre-incubated in a $CO_2$ (5%) and temperature (37° C.) controlled incubator for 1 hour prior to addition of the Lipopolysaccharide (LPS) agonist. LPS was applied to all assay wells, except to negative control wells, to give a final assay concentration of 1 µg/mL LPS. LPS induced p-HSP27 protein accumulation was measured after 1 hour, and appreciable TNF cytokine release was measured after 3 hours.

For the p-HSP27 assay, after incubation with LPS (1 hour), plates were vacuum filtered on a plate manifold apparatus to remove media and compounds. Cells were washed twice with Cell Wash Buffer using vacuum filtration, shaken for 20 minutes with 100 µl/well cold Cell Lysis Buffer, and then stored frozen (−20° C.) until analysis. p-HSP27 protein was assayed using the Upstate Beadmate Kit, following the directions of the manufacturer. Plates were read and analyzed on the Bio-Plex instrument Serial Number LX100000346001 with Bio-Plex Manager 4.1.1 Software. Potency of compound to inhibit p-HSP27 in vitro was determined by using the percent reduction of measured fluorescence in wells with compound compared to control wells without compound. Results were represented as $IC_{50}$ values.

For the TNF and cell integrity assays, after incubation with LPS (3 hours), assay plates were spun at 183 g (1000 rpm in Beckman/Coulter Allegra 6KR centrifuge) for 10 minutes. Cell-free supernatant (100 μL/well) was collected and TNF levels were determined utilizing Meso Scale Discovery TNF kits and a standard curve made with recombinant human TNF protein. Potency of compound to inhibit measured TNF levels in vitro was determined, and the results were represented as $IC_{50}$ values. For assessment of cell integrity after treatment with test compound, the remaining cells (100 μL/well) were returned to incubator (5% $CO_2$, 37° C.) overnight. Then, 50 μl/well of 2.5 mg/mL MTT/D-PBS was added to cells for 3 hours (5% $CO_2$, 37° C.), followed by 50 μL/well of 20% SDS for 3 hours (5% $CO_2$, 37° C.). The $OD_{570}$ was measured on a Molecular Devices SpectraMax 190 spectrophotometer.

LPS-induced TNF Production in Human Whole Blood:
Materials:
Blood Collection Tubes, Sodium Heparin Vacutainer, Becton Dickenson, Catalog #366480
Assay Plates, Corning, Catalog #3599
Dilution Plates, Corning, Catalog #3365
Dimethyl sulphoxide (DMSO), Sigma, Catalog #D2650
HEPES Buffer Solution (1M), Invitrogen, Catalog #15630
Lipopolysaccharides from *Escherichia coli* 0127:B8 (LPS), Sigma, Catalog #L4516
Human TNF Cytokine Assay Kit, Meso Scale Discovery (MSD), Catalog #K111BHB
Recombinant Human Tumor Necrosis Factor Alpha (rhTNF), R & D Systems, Catalog #210-TA
Methods:

Blood was drawn into Blood Collection Tubes from healthy donors. Compounds were prepared in DMSO and serial diluted (1:3) with DMSO in dilution plate(s) to give 8 dilution points for each compound tested. Further dilution (1:100) of compound was made into RPMI Media, 20 mM HEPES. Into wells of 96-well Assay Plate(s), 100 μL/well of diluted compound or control (1% DMSO in RPMI Media, 20 mM HEPES) and 80 μL of blood were applied and pre-incubated for 30 minutes in an incubator set at 37° C. Tumor Necrosis Factor Alpha (TNF) was then stimulated with the addition of (20 μL/well) Lipopolysaccharides from *Escherichia coli* 0127:B8 (LPS) for 3.5 hours at 37° C. The final concentration of LPS in the assay was 50 ng/mL. Plates were spun at 183 g (1000 rpm in Beckman/Coulter Allegra 6KR centrifuge) for 10 minutes. Cell-free plasma (75 μL/well) was collected and TNF levels were determined utilizing Meso Scale Discovery TNF kits and a standard curve made with recombinant human TNF protein. Potency of a compound to inhibit TNF in vitro was determined by using the percent reduction of measured TNF in wells with compound compared to control wells without compound. Results were represented as $IC_{50}$ values.

Reference:
Current Protocols in Immunology (2005) 7.18B-7.18B12.
LPS-induced TNF Production in vivo
Materials:
Lipopolysaccharide (LPS) from *Escherichia coli*, serotype 0111:B4 (Sigma, cat #L-4130, lot #095K4056)
Phosphate Buffered Saline pH 7.2 (Gibco)
PEG 200 (Sigma, cat #P3015)
Methylcellulose (Sigma, cat #M7027)
0.02% Tween 80 (Sigma Aldrich, Cat # P-4780)
0.5% HPMC (Sigma Aldrich, Cat# H3785-100G)
milliQ $H_2O$ (Abbott Bioresearch Center)
Male or female Lewis rats, 150-250 g (Charles River Laboratories)
Rat Tumor Necrosis Factor α (TNFα) ELISA kit (R&D Systems cat #RTA00)
Methods:

The test compound is prepared into a vehicle containing 5% PEG 200, in 0.5% Methylcellulose or a vehicle containing 0.02% Tween 80, 0.5% HPMC in milliQ $H_2O$ at the desired concentrations for dosing (0.1, 0.3, 1, 3, 10, 30, 100 mg/kg). Lewis rats are pre-dosed with the compound(s) orally (p.o.) at 0.002 mL/gram body weight one-two hours prior to the LPS challenge. Negative control includes rats treated with vehicle alone. LPS is dissolved in phosphate buffered saline, sonicated and the rats are injected with 1 mg/kg intravenously (i.v.) at 0.001 mL/gram body weight. One hour after the LPS challenge the rats are bled by cardiac puncture and either serum or heparinized plasma is analyzed for TNFα by ELISA. The compound concentration is also determined in the serum or plasma.

The average concentration of TNFα in the vehicle treated group is taken as a maximal (100 percent) response. The mean TNFα levels in the compound treated groups are expressed as a percent of the maximal response. The percent of maximal TNFα responses at various doses or serum concentrations of the compound(s) are further analyzed using a four parameter curve fit of logarithmically transformed data (Graphpad Prism 4 software) to generate $ED_{50}$ and $EC_{50}$ as well as $ED_{80}$ and $EC_{80}$.

Relevant Reference(s):
Azab A, et al. (1998) *Life Sci.* 63: 323-327.
Martinez E F, et. al (2004) *Biochem. Pharma.* 68:1321-1329.

The teachings of all references, including journal articles, patents and published patent applications, are incorporated herein by reference in their entirety.

Compounds of the invention may be prepared using the synthetic transformations illustrated in Schemes I-XXII. Starting materials are commercially available or may be prepared by the procedures described herein, by literature procedures, or by procedures that would be well known to one skilled in the art of organic chemistry. Methods for preparing imidazooxazole (X=O) or imidazothiazole (X=S) compounds of the invention are illustrated in Scheme I. When not commercially available, bromoketones 2 may be prepared from ketones 1 by methods known to one skilled in the art (see, for example, Larock, R. C. "Comprehensive Organic Transformations: A Guide to Functional Group Preparations, $2^{nd}$ edition", 1999, Wiley-VCH or General Procedures A.1 and A.2). Substituted imidazooxazole (X=O) or imidazothiazole (X=S) 4 may be prepared from bromoketones 2 and aminooxazoles (X=O) or aminothiazoles (X=S) 3 by methods known in the literature (see, for example, WO2004110990A2) or by General Procedure B or B.1 below (Scheme I, step b). In Scheme I, step c, a suitably substituted imidazooxazole (X=O) or imidazothiazole (X=S) 4 is halogenated (X'=halo) using methods known to one skilled in the art (see, for example, Larock, R. C. above or General Procedure C or C.1 below). The resulting compounds 5 may be further reacted in a number of ways. For example, Negishi reaction (step d) with another heteroaryl halide (such as compounds 11, Scheme II) may directly give triazolopyridazines 6 (see, for example, General Procedure I or I.1). Alternatively, Negishi reaction (step e) with 3-chloro-6-iodopyridazine (*Tetrahedron* 1999, 55(52), 15067-15070) gives chloropyridazines 7. These compounds may be reacted with hydrazine or hydrazine hydrate to give hydrazinylpyridazines 8 (Scheme I, step f) using methods such as those described in General Procedure D. These hydrazinylpyridazines 8 may then be converted to triazolopyridazines 6 by methods such as those described in General Procedures E, E.1, G, AG, AN or AQ (step g). Further functionalization of triazolopyridazines 6 can be performed, if desired, using reactions known to one skilled in the art (see, for example, Larock, R. C. above or the General Procedures below). For example, formation of amides, ureas, or sulfonamides can be achieved by reaction of compounds 6 containing a primary or secondary amine (see, for example, General Procedures T, T.1, U, and U.1). Examples of additional transformations that can be achieved by reaction of compounds 6, but which are in no way limiting, are the formation of ketones from esters (see General Procedure AF), alcohols from ketones (see General Procedure AD), alkylfluorides from alcohols (see General Procedure AJ), alkylation of alcohols and amines with alkyl halides and alkyl sulfonates (see General Procedures AA, X, X.1, and AE). Also, deprotection of compounds 6 to yield an unprotected compound can be performed using conditions such as those described in Greene, T. W. and Wuts, P. G. M. "Protective Groups in Organic Synthesis, 3$^{rd}$ Edition", 1999, Wiley-Interscience. For example, a protecting group such as a t-butoxycarbonyl group can be removed from a protected amine to yield the unprotected amine (see, for example, General Procedure Q or Q.1) and the deprotected compounds 6 may then be reacted further as described above.

Scheme I:

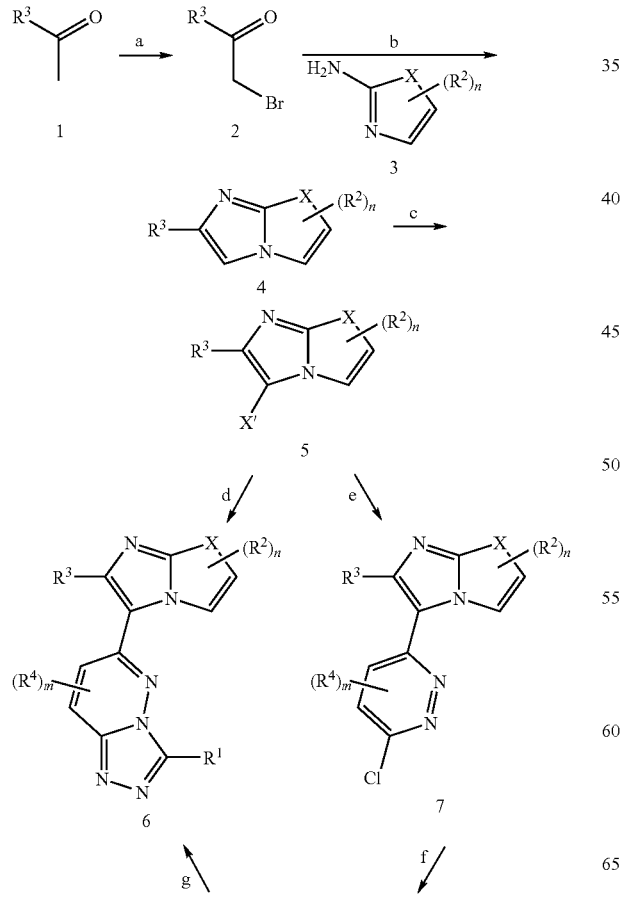

-continued

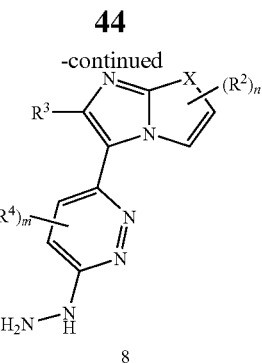

As shown in Scheme II, step a, chlorohydrazinylpyridazines 9 may be converted to chlorotriazolopyridazines 10 by methods known to one skilled in the art (such as those described in General Procedures E, E.1, G, AG, AN or AQ). Further reaction of chlorotriazolopyridazines 10, such as the conditions described in General Procedure H, gives iodotriazolopyridazines 11 (step b). Compounds 10 and 11 are themselves useful intermediates as described in Schemes I and III.

Scheme II:

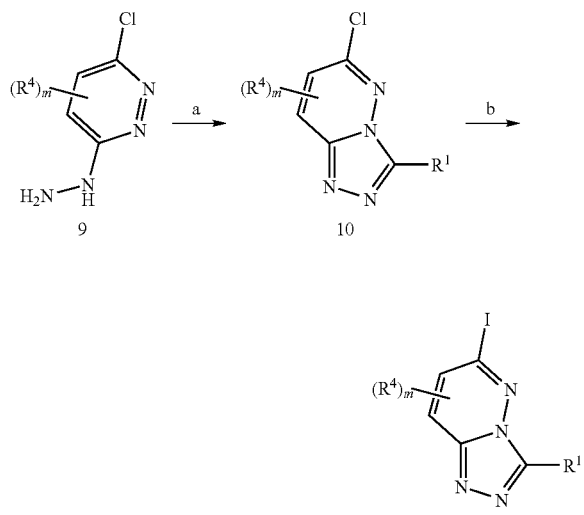

Methods for preparing pyrazole compounds of the invention are illustrated in Scheme III. When not commercially available, terminal alkynes 14 may be prepared by methods known to one skilled in the art (see, for example, Larock, R. C. above). For example, Sonogashira reaction (step a) of aryl halides 12 with ethynyltrimethylsilane gives alkynyl silanes 13 (using conditions such as those described in General Procedure J). General Procedure F describes one method for preparing terminal alkynes 14 from alkynyl silanes 13 (step b). Regardless of source, terminal alkynes 14 may undergo Sonogashira reaction (step c) with halotriazolopyridazines 15 (such as chlorotriazolopyridazines 10 or iodotriazolopyridazines 11 described in Scheme II) to give alkynes 16 (see, for example, General Procedure J). The hydration of alkynes 16 (step d) gives ketones 17 using conditions such as those described in General Procedure K or K.1. As shown in step e, ketones 17 are converted to pyrazoles 18 (see, for example, General Procedure L or L.1). Further functionalization of pyrazoles 18 can be performed, if desired, as described for compounds 6 above or in the General Procedures below.

Scheme III:

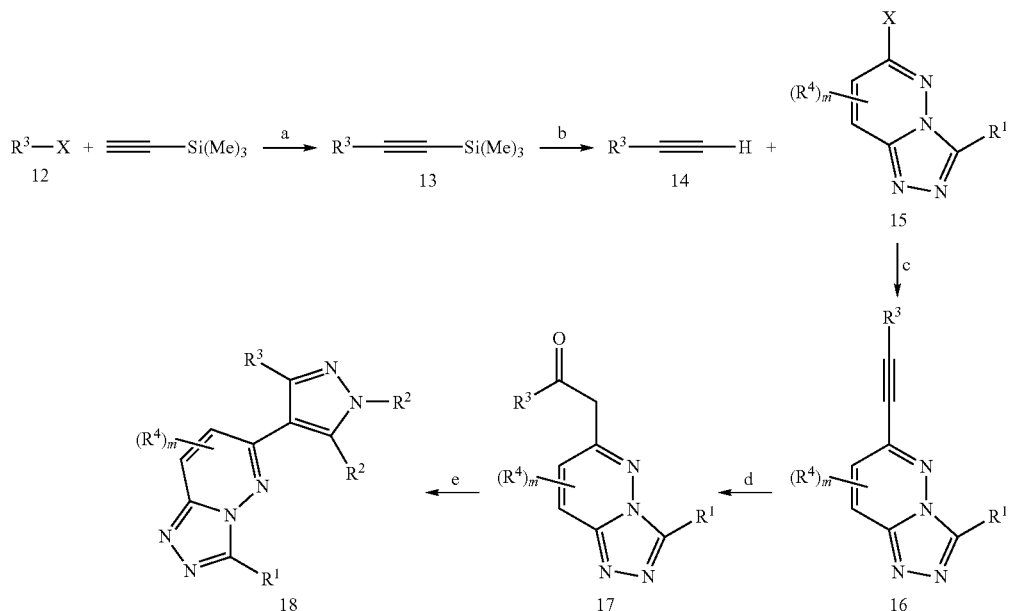

Methods for preparing thiazole compounds of the invention are illustrated in Scheme IV. As shown in step a, ketones 17 may be may be brominated by methods known to one skilled in the art (see, for example, Larock, R. C., as above or General Procedures A.1 and A.2). These bromoketones 19 are reacted with thioamides, thioureas, or thiocarboxamides (step b) to give thiazoles 20 (see, for example, General Procedures O, O.1, P and P.1). Further functionalization of thiazoles 20 can be performed, if desired, as described for compounds 6 above or in the General Procedures below.

Scheme IV:

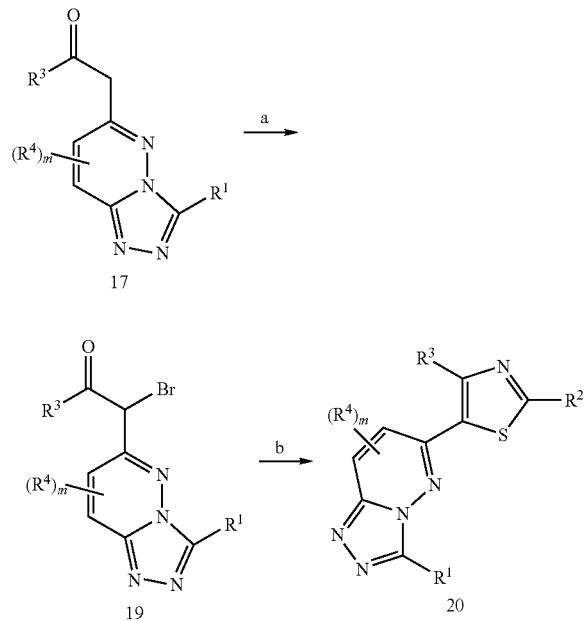

Methods for preparing imidazole compounds of the invention are illustrated in Scheme V. As shown in step a, ketones 17 may be may be converted to diketones 21 by methods known to one skilled in the art (see, for example, WO 2006/026306) or as described in General Procedure M. These diketones 21 are further reacted with an aldehyde in the presence of ammonium acetate with or without an additional amine (step b) to give imidazoles 22 (see, for example, General Procedure N). Further functionalization of imidazoles 22 can be performed, if desired, as described for compounds 6 above or in the General Procedures below.

Scheme V:

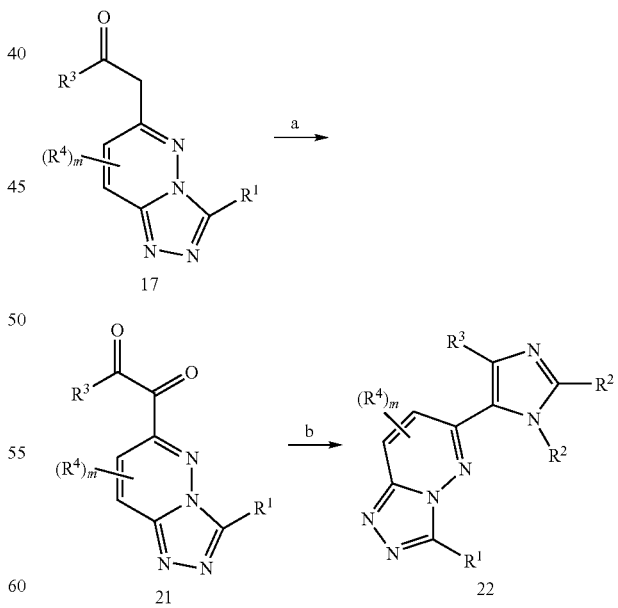

Methods for preparing dihydropyrroloimidazole or tetrahydroimidazopyridine compounds of the invention are illustrated in Scheme VI. Dihydropyrroloimidazoles or tetrahydroimidazopyridines 24 may be prepared from bromoketones 2 and 2-iminopyrrolidines or 2-iminopiperidines 23 by methods known in the literature (see, for example, *J. Med. Chem.*, 2002, 45, 999-1001) or by General Procedure R below (step a). In step b, suitably substituted dihydropyrroloimidazoles or tetrahydroimidazopyridines 24 are halogenated using methods known to one skilled in the art (see, for example, Larock, R. C. above or General Procedure C or C.1 below). The resulting compounds 25 may be further reacted in a number of ways. For example, Negishi reaction (step c) with another heteroaryl halide (such as compounds 11, Scheme II) may directly give triazolopyridazines 26 (see, for example, General Procedure I or I.1). Alternatively, Negishi reaction (step d) with 3-chloro-6-iodopyridazine (*Tetrahedron* 1999, 55(52), 15067-15070) gives chloropyridazines 27. These compounds may be reacted with hydrazine or hydrazine hydrate to give hydrazinylpyridazines 28 (step e) using methods such as those described in General Procedure D. These hydrazinylpyridazines 28 may then be converted to triazolopyridazines 26 by methods such as those described in General Procedures E, E.1, G, AG, AN or AQ. Further functionalization of dihydropyrroloimidazoles or tetrahydroimidazopyridines 28 can be performed, if desired, as described for compounds 6 above or in the General Procedures below.

Scheme VI:

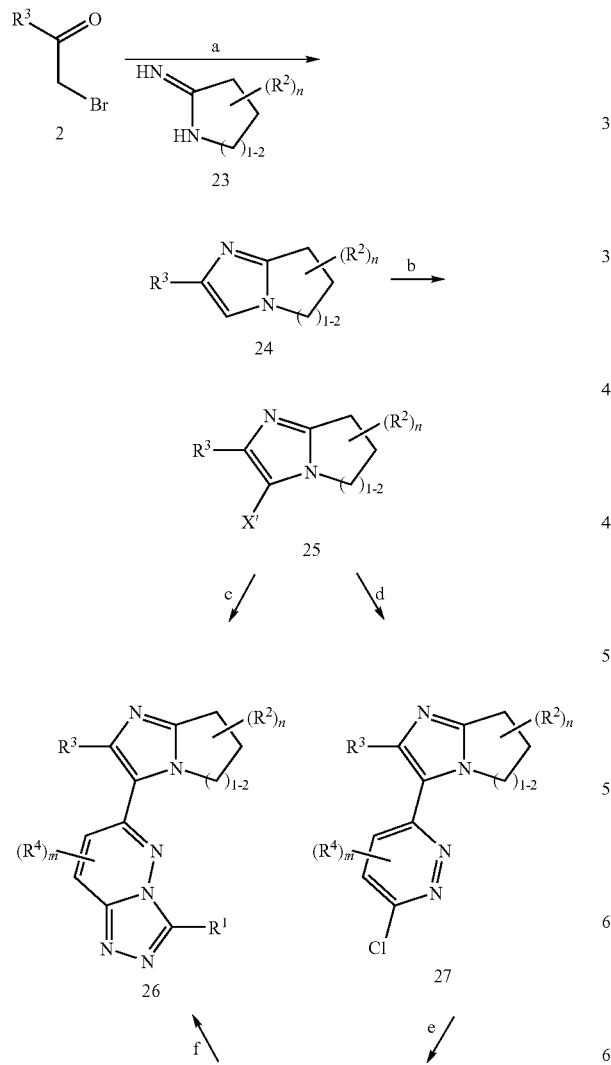

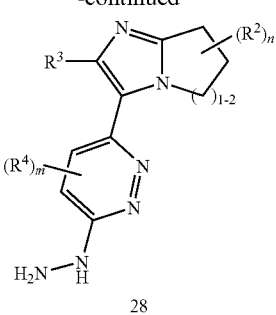

Methods for preparing oxazole compounds of the invention are illustrated in Scheme VII. Halotriazolopyridazines 15 may undergo Stille coupling with tetravinylstannane to give alkenes 29 by methods known to one skilled in the art or as described in Preparation #1. Alkenes 29 may be oxidatively cleaved to aldehydes 30 by methods known to one skilled in the art or as described in Preparation #2. Aldehydes 30 are reacted with TOSMIC reagents 31 to give oxazoles 32 using conditions such as those described in General Procedure S. If not commercially available, the TOSMIC reagents 31 may be prepared as described in the literature (*J. Med. Chem.* 2002, 45, 1697-1711) or as described in Preparation #3. Further functionalization of oxazoles 32 can be performed, if desired, as described for compounds 6 above or in the General Procedures below.

Scheme VII:

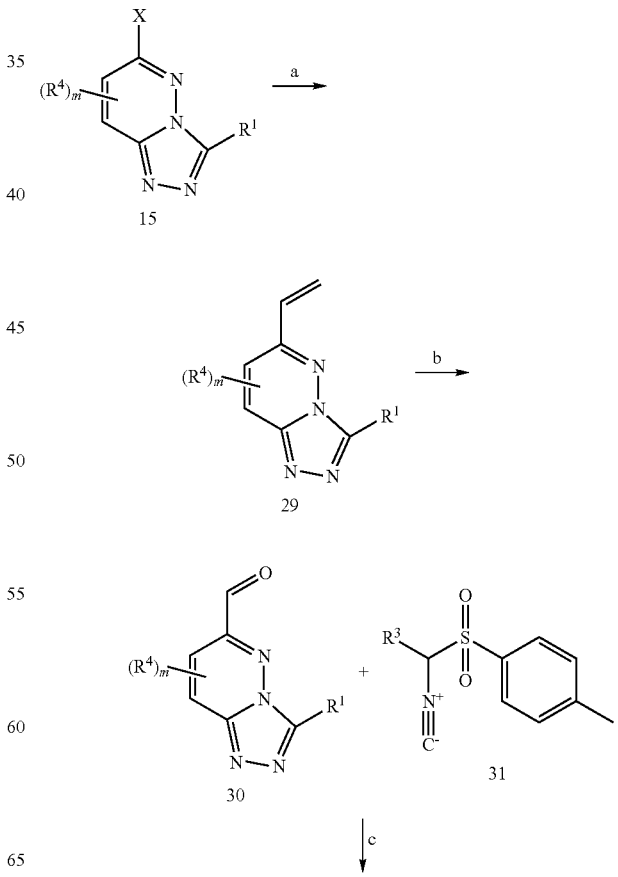

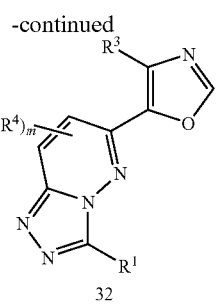

32

Alternatively, methods for preparing imidazole compounds 34 of the invention with substitution on the nitrogen are illustrated in Scheme VIII. As shown in step a, aldehydes 30 are reacted with amines to give imines 33 using conditions such as those described in General Procedure AP. These imines 33 can be further reacted with TOSMIC reagents 31 to give imidazoles 34 using conditions such as those described in General Procedure AB. Further functionalization of imidazoles 34 can be performed, if desired, as described for compounds 6 above or in the General Procedures below.

Scheme VIII:

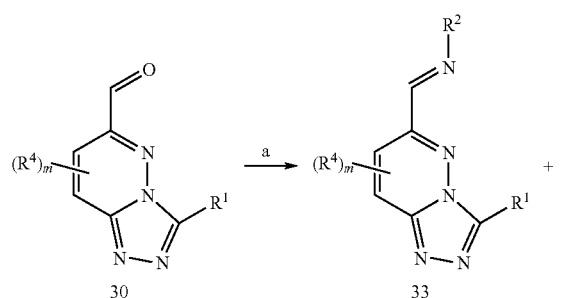

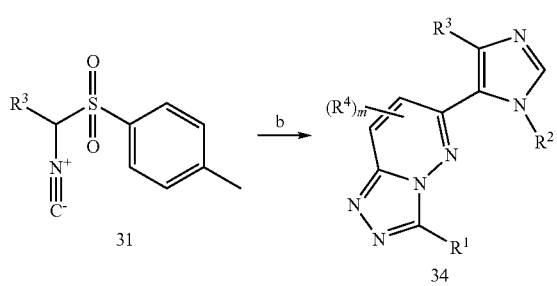

Methods for preparing imidazoimidazole compounds 36 of the invention are illustrated in Scheme IX. Imidazooxazoles 35 may undergo a reaction with primary amines using General Procedure AC in a manner similar to furan ring systems (see, for example *J. Med. Chem.* 2006, 49, 4248 or *Bioorg. Med. Chem.* 2005, 13, 1497) to replace the oxygen with a substituted nitrogen. Further functionalization of imidazoimidazoles 36 can be performed, if desired, as described for compounds 6 above or in the General Procedures below.

Scheme IX:

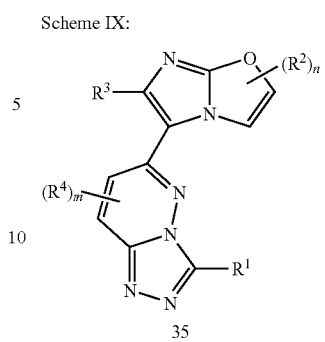

Methods for preparing substituted 3-amino-[1,2,4]triazolo[4,3-b]pyridazine compounds 39 and 41 of the invention are illustrated in Scheme X. The 3-amino-[1,2,4]triazolo[4,3-b]pyridazines may be substituted at the 6-position with X=halogen, aryl or heteroaryl. Hydrazinylpyridazines 37 may be reacted with 1-(chloro(dialkylamino)methylene)dialkylaminium hexafluorophosphate(V) salts 38 using methods known to one skilled in the art or as described in General Procedure AG to give 3-amino-[1,2,4]triazolo[4,3-b]pyridazines 39 with two substituents, $R^6$ and $R^7$, on the nitrogen. Alternatively, hydrazinylpyridazines 37 may be reacted with isothiocyanates 40 using methods known to one skilled in the art or as described in General Procedure AQ to give 3-amino-[1,2,4]triazolo[4,3-b]pyridazines 41 with only one substituent, $R^6$, on the nitrogen. Further functionalization of 3-amino-[1,2,4]triazolo[4,3-b]pyridazine compounds 39 and 41 can be performed, if desired, as described for compounds 6 above or in the General Procedures below.

Scheme X:

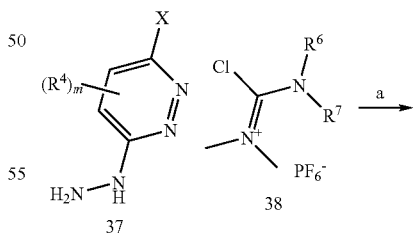

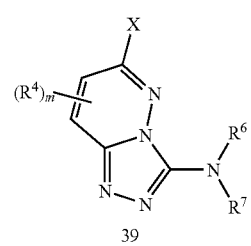

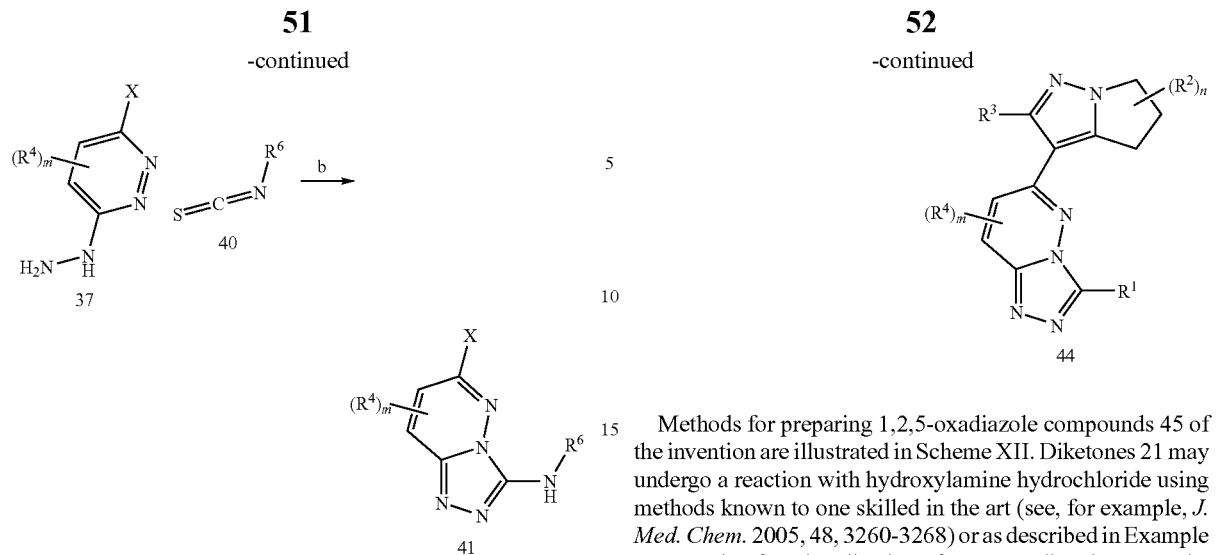

Methods for preparing 5,6-dihydro-4H-pyrrolo[1,2-b]pyrazole compounds 44 of the invention are illustrated in Scheme XI. Ketones 17 may be reacted with 1-aminopyrrolidin-2-ones 42 using methods known to one skilled in the art (see, for example, WO 2005/092894 and WO 2004/048383) or as described in Example #13 to give the intermediate 43. The intermediate 43 is subsequently cyclized using methods known to one skilled in the art (see, for example, WO 2005/092894 and WO 2004/048383) or as described in Example #13 to form the 5,6-dihydro-4H-pyrrolo[1,2-b]pyrazole compounds 44. Further functionalization of 5,6-dihydro-4H-pyrrolo[1,2-b]pyrazoles 44 can be performed, if desired, as described for compounds 6 above or in the General Procedures below.

Scheme XI:

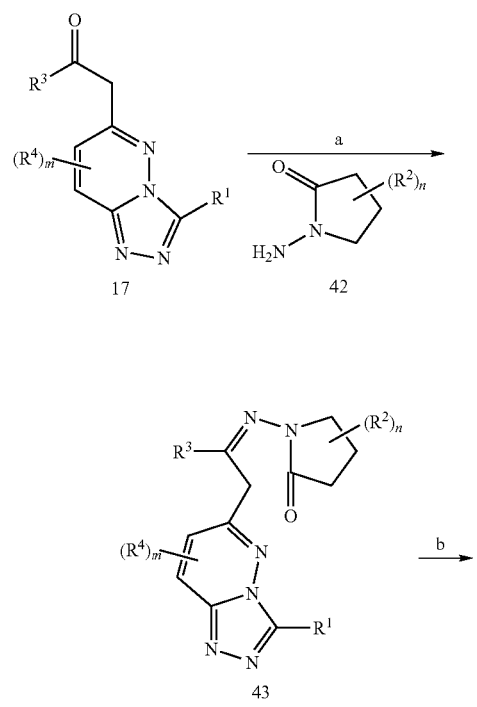

Methods for preparing 1,2,5-oxadiazole compounds 45 of the invention are illustrated in Scheme XII. Diketones 21 may undergo a reaction with hydroxylamine hydrochloride using methods known to one skilled in the art (see, for example, *J. Med. Chem.* 2005, 48, 3260-3268) or as described in Example #14. Further functionalization of 1,2,5-oxadiazoles 45 can be performed, if desired, as described for compounds 6 above or in the General Procedures below.

Scheme XII:

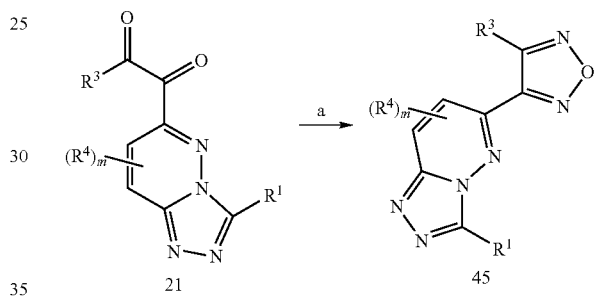

Methods for preparing imidazopyrazine (X=N, Y=CR²) or imidazopyrimidine (X=CR², Y=N) compounds 49 of the invention are illustrated in Scheme XIII. In step a, suitably substituted α-bromoketones 2 are reacted with optionally substituted 2-amino heterocycles 46. These types of cyclization reactions are well established in the literature (see, for example, Spitzer, et al., *J Med Chem* 1988, 31, 1590-1595). This reaction is typically conducted in an organic solvent (such as EtOH or DMF) at temperatures at or below reflux (such as about 80° C.). Products 47 are typically isolated from the reaction mixture as solids by concentrating the mixture and then are used crude after extractive work up with a suitable organic solvent (such as DCM or EtOAc) or are purified either by crystallizing or triturating in an organic solvent (such as DCM, EtOH or EtOAc) or by flash silica gel chromatography. Compounds 47 can be used as is or first undergo functional group manipulation using methods known to one skilled in the art (see, for example, Larock, R. C. as above). For example, if R¹=CO₂Me, a one- or two-step decarboxylation (using, for example, 1M HCl or LiOH.H₂O followed by 1M HCl) may be done to get R¹=H. In step b, a suitably substituted imidazopyrazines (X=N, Y=CR²) or imidazolpyrimidines (X=CR², Y=N) 47 are halogenated using methods known to one skilled in the art (see, for example, Larock, R. C. above or General Procedure C below). The resulting compounds 48 may be further reacted in a number of ways. For example, Negishi reaction (step c) with another heteroaryl halide (such as compounds 11, Scheme II) may directly give triazolopyridazines 49 (see, for example, General Procedure I or I.1). Alternatively, Negishi reaction (step d) with 3-chloro-6-iodopyridazine (*Tetrahedron* 1999, 55(52), 15067-15070) gives chloropyridazines 50. These compounds may be reacted with hydrazine or hydrazine hydrate to give hydrazinylpyridazines 51 (step e) using methods such as those described in General Procedure D. These hydrazinylpyridazines 51 may then be converted to triazolopyridazines 49 by methods such as those described in General Procedures E, E.1, G, AG, AN or AQ. Further functionalization of imidazopyrazine (X=N, Y=CR²) or imidazopyrimidine (X=CR², Y=N) compounds 49 can be performed, if desired, as described for compounds 6 above or in the General Procedures below.

Scheme XIII:

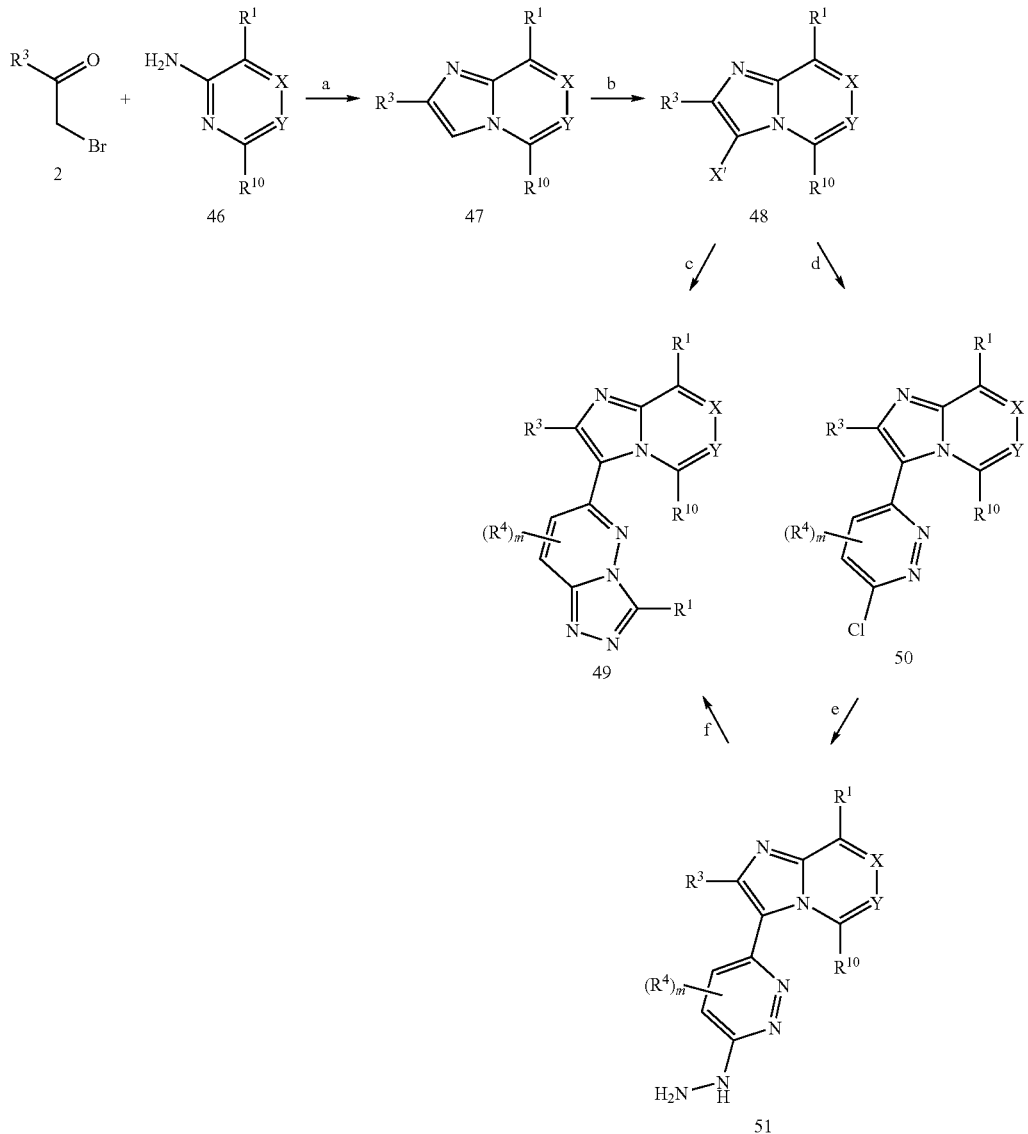

Methods for preparing 1,2,3-thiadiazole compounds 54 of the invention are illustrated in Scheme XIV. Ketones 17 may undergo a reaction with hydrazinecarboxylates 52 using methods known to one skilled in the art (see, for example, *Bioorg. Med. Chem. Lett.* 1996, 6, 87) or as described in Example #18. The intermediates 53 are subsequently cyclized using methods known to one skilled in the art or as described in Example #18 or based on literature methods (for example, *Bioorg. Med. Chem. Lett.* 1996, 6, 87) to form the 1,2,3-thiadiazole compounds 54. Further functionalization of 1,2,3-thiadiazole compounds 54 can be performed, if desired, as described for compounds 6 above or in the General Procedures below.

Scheme XIV:

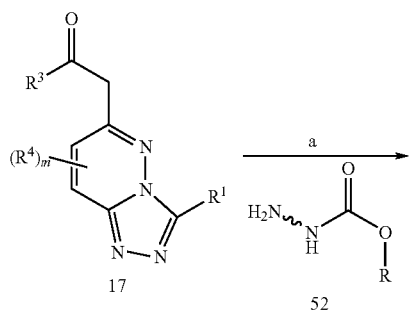

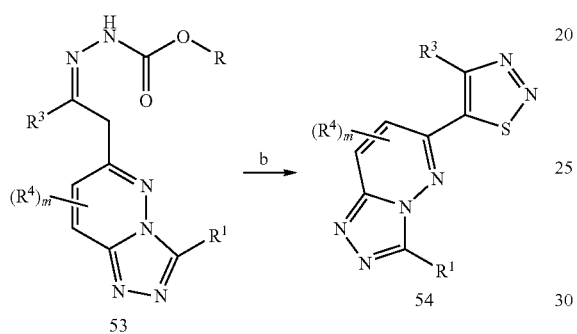

Methods for preparing 1H-imidazol-2(3H)-one compounds 57 of the invention are illustrated in Scheme XV. Ketones 17 may undergo a reaction with sodium nitrite using methods known to one skilled in the art or as described in Example #20, step A to give the intermediates 55. The intermediates 55 can then be reduced using methods known to one skilled in the art (see, for example, Larock, R. C., as above) or as described in Example #20, step B to give an α-aminoketone 56. The α-aminoketone 56 is then reacted with a cyanate using conditions described in the literature (see, for example, US 2005/075384) or as described in Example #20, step C to give the 1H-imidazol-2(3H)-one compounds 57. Further functionalization of 1H-imidazol-2(3H)-one compounds 57 can be performed, if desired, as described for compounds 6 above or in the General Procedures below.

Methods for preparing pyrazolo[1,5-a]pyrimidine compounds 59 or 2,3-dihydro-1H-imidazo[1,2-b]pyrazole compounds 60 of the invention are illustrated in Scheme XVI. As shown in step a, ketones 17 may be may be converted to appropriately substituted 3-aminopyrazoles 58 by methods known to one skilled in the art (see, for example, *J. Heterocyclic Chem.* 1980, 17, 73) or as described in either Example #23. As shown in step b, the appropriately substituted 3-aminopyrazoles 58 (R=H) can then be converted to pyrazolo[1,5-a]pyrimidines using methods known to one skilled in the art (see, for example *Bioorg. Med. Chem. Lett.* 2007, 17, 1641) or as described in Example #24. Alternatively, as shown in step c, with appropriately substituted 3 aminopyrazoles (for example, R=—CH$_2$CH$_2$OH), a cyclization reaction can be performed using methods known to one skilled in the art (see, for example *Bioorg. Med. Chem. Lett.* 2004, 12, 1347) or as described in Example #25. Further functionalization of pyrazolo[1,5-a]pyrimidine compounds 59 or 2,3-dihydro-1H-imidazo[1,2-b]pyrazole compounds 60 can be performed, if desired, as described for compounds 6 above or in the General Procedures below.

Scheme XV:

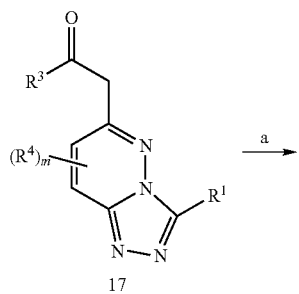

Scheme XVI:

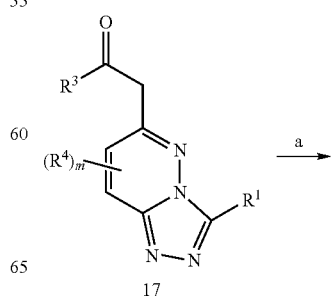

Scheme XVII:

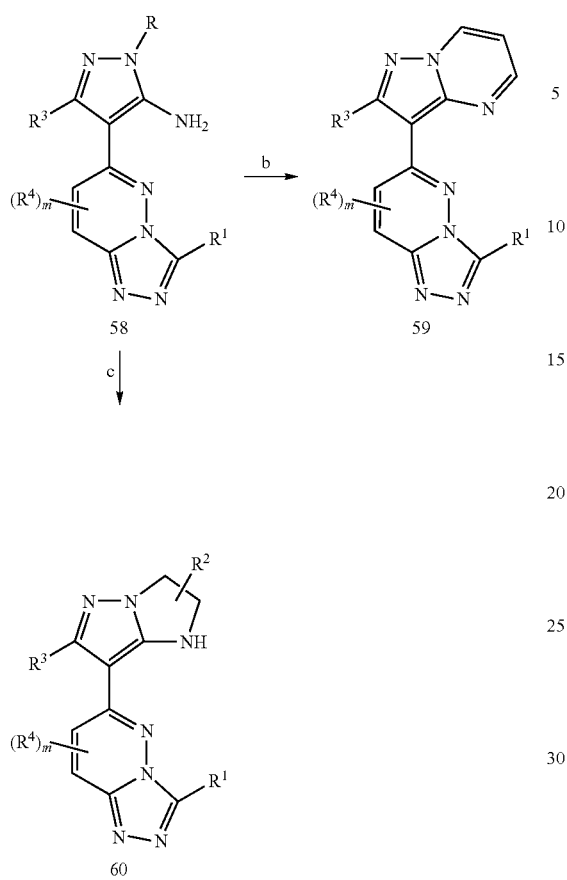

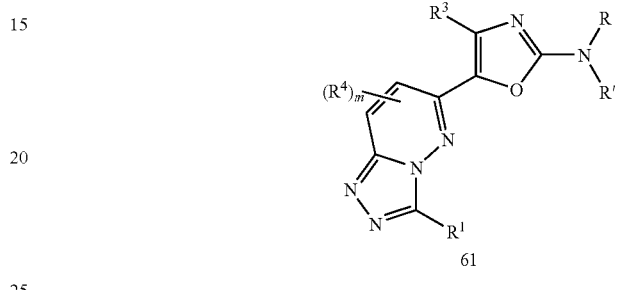

Methods for preparing 2-aminooxazole compounds 61 of the invention are illustrated in Scheme XVII. Appropriate α-haloketones 19 may be converted to 2-aminooxazoles 61 using methods known to one skilled in the art (see, for example *Bioorg Med. Chem. Lett.* 2005, 15, 2865) or as described in Example #28. Further functionalization of 2-aminooxazole compounds 61 can be performed, if desired, as described for compounds 6 above or in the General Procedures below.

Methods for preparing 5-alkylisoxazole compounds 65 of the invention are illustrated in Scheme XVIII. As shown in step a, appropriately substituted alkynones 62 can be converted to a alkynoximes 63 using methods known to one skilled in the art (see, for example *J. Org. Chem.* 2007, 72, 9643) or as described in Example #31, step A. As shown in step b, the alkynoximes 63 can be converted to a 5-substituted isoxazoles 64 using methods known to one skilled in the art (see, for example *J. Org. Chem.* 2007, 72, 9643) or as described in Example #31, step B. The resulting compounds 64 may be further reacted in a number of ways. For example, Negishi reaction (step c) with another heteroaryl halide (such as compounds 11, Scheme II) may directly give triazolopyridazines 65 (see, for example, General Procedure I or I.1). Alternatively, Negishi reaction (step d) with 3-chloro-6-iodopyridazine (*Tetrahedron* 1999, 55(52), 15067-15070) gives chloropyridazines 66. These compounds may be reacted with hydrazine or hydrazine hydrate to give hydrazinylpyridazines 67 (step e) using methods such as those described in General Procedure D. These hydrazinylpyridazines 67 may then be converted to triazolopyridazines 65 by methods such as those described in General Procedures E, E.1, G, AG, AN or AQ. Further functionalization of 5-alkylisoxazole compounds 65 can be performed, if desired, as described for compounds 6 above or in the General Procedures below.

Scheme XVIII:

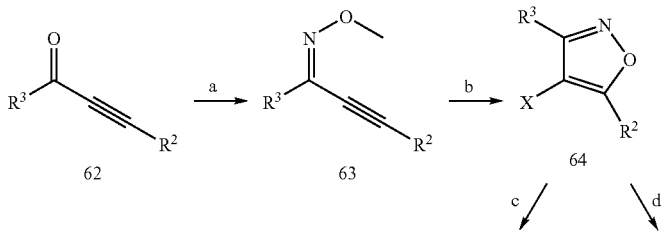

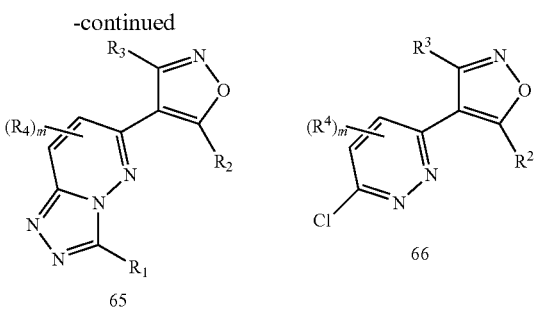

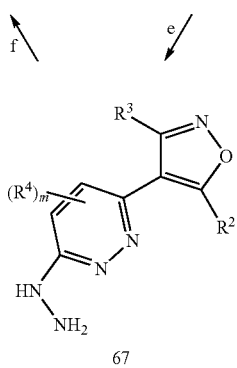

Methods for preparing 5-aminoisoxazole compounds 71 of the invention are illustrated in Scheme XIX. Halotriazolopyridazines 15 may undergo nucleophilic aromatic substitution with malononitriles by methods known to one skilled in the art or as described in Example #32, step A to give intermediates 68. Intermediates 68 may then be decarboxylated using methods known to one skilled in the art (see, for example, Larock, R. C., as above) or as described in Example #32, step B to give nitrites 69. The nitrites 69 can then be reacted with hydroxyimidoyl chlorides 70 to give a 5-aminoisoxazole 71 using methods known to one skilled in the art (see, for example *Org. Lett.* 2006, 8, 3679) or as described in Example #32, step D. If the hydroxyimidoyl chlorides 70 are not commercially available, they can be prepared by one skilled in the art (see, for example *Tetrahedron* 2007, 63, 12388 or *Bioorg. Med. Chem. Lett.* 2007, 17, 3736) or as described in Example #32, steps C and D. Further functionalization of the 5-aminoisoxazole compounds 71 can be performed, if desired, as described for compounds 6 above or in the General Procedures below.

Scheme XIX:

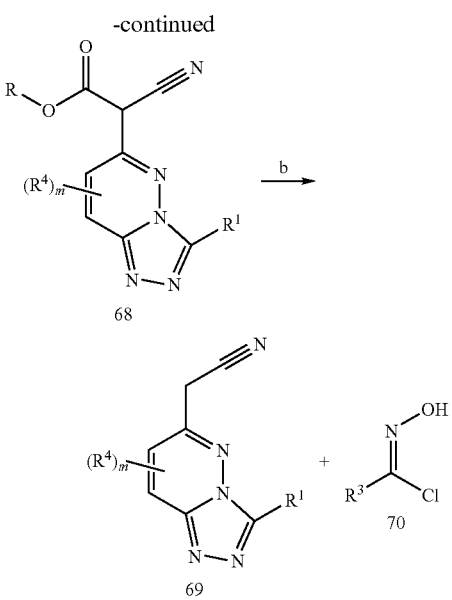

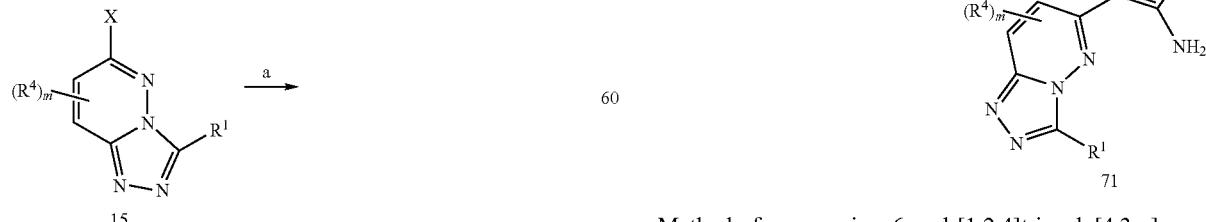

Methods for preparing 6-aryl-[1,2,4]triazolo[4,3-a]pyrazine compounds 75 are illustrated in Scheme XX. Appropriately substituted dihalopyrazines 72 can be reacted with hydrazine or hydrazine hydrate to give hydrazinylpyrazines 73 (step a) using methods such as those described in Example #33, step A. These hydrazinylpyrazines 73 may then be converted to 6-aryl-[1,2,4]triazolo[4,3-a]pyrazines 74 by methods such as those described in General Procedures E, E.1, G, AG, AN or AQ. The resulting compounds 74 may then further reacted in a Negishi reaction (step c) with another heteroaryl halide (such as compounds 5, 25, 48 or 64) to give the 6-aryl-[1,2,4]triazolo[4,3-a]pyrazine compounds 75 using methods such as those described in General Procedure I or I.1. Further functionalization of 6-aryl-[1,2,4]triazolo[4,3-a]pyrazine compounds 75 can be performed, if desired, as described for compounds 6 above or in the General Procedures below.

Scheme XX:

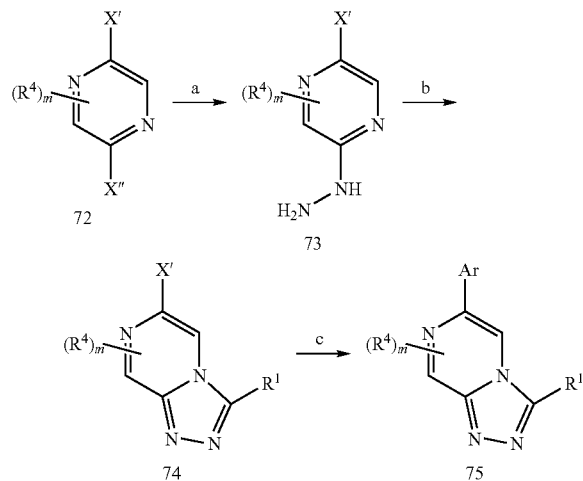

Methods for preparing 6-aryl-[1,2,4]triazolo[3,4-b][1,3,4]thiadiazole compounds 78 are illustrated in Scheme XXI. Heteroarylcarboxylic acids 76 can be reacted with 4-amino-4H-1,2,4-triazole-3-thiols using methods known to one skilled in the art (see, for example *Eur. J. Med. Chem.* 2007, 42, 823) or as described in Example #38 to give 6-aryl-[1,2,4]triazolo[3,4-b][1,3,4]thiadiazoles 78. Further functionalization of 6-aryl-[1,2,4]triazolo[3,4 b][1,3,4]thiadiazole compounds 78 can be performed, if desired, as described for compounds 6 above or in the General Procedures below.

Scheme XXI:

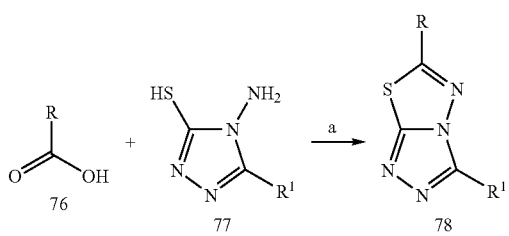

Methods for preparing [1,2,4]triazolo[4,3-a]pyrimidine compounds 81 are illustrated in Scheme XXII. Appropriately substituted pyrimidines 79 can be reacted with hydrazine or hydrazine hydrate to give hydrazinylpyrimidines 80 (step a) using methods such as those described in Example #39, step C. These hydrazinylpyrimidines 80 may then be converted to [1,2,4]triazolo[4,3-a]pyrazines 81 by methods such as those described in General Procedures E, E.1, G, AG, AN or AQ. Further functionalization [1,2,4]triazolo[4,3-a]pyrimidine compounds 81 can be performed, if desired, as described for compounds 6 above or in the General Procedures below.

Scheme XXII:

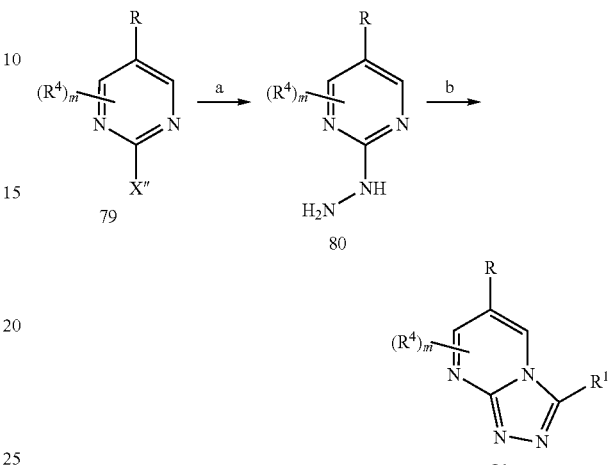

Abbreviations
ACN Acetonitrile
APCI Atmospheric pressure chemical ionization
b.p. Boiling point
Boc tert-Butoxycarbonyl
BOP-Cl Bis(2-oxo-3-oxazolidinyl)phosphinic chloride
t-BuOH tert-Butyl alcohol
d day(s)
DAST Diethylaminosulfur trifluoride
DCC Dicyclohexylcarbodiimide
DCE Dichloroethane
DCM Dichloromethane (methylene chloride)
DIAD Diisopropyl azodicarboxylate
DIBAL-H Diisobutylaluminum hydride
DIPEA N,N-Diisopropylethylamine
DMA N,N-Dimethylacetamide
DMAP 4-(Dimethylamino)pyridine
DME 1,2-Dimethoxyethane
DMF N,N-Dimethylformamide
DMSO Dimethyl sulfoxide
EDCI N-(3-Dimthylaminopropyl)-N'-Ethylcarbodiimide Hydrochloride
EGTA Ethylene glycol-bis(β-aminoethyl ether)-N,N,N',N'-tetraacetic acid
ELSD Evaporative light scattering detection
equiv Equivalent (molar equivalent)
EtOAc Ethyl acetate
EtOH Ethyl alcohol
Et$_2$O Diethyl ether
FIA Flow injection analysis
h hour(s)
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HOAc Acetic acid
HOBT 1-Hydroxybenzotriazole
HPLC High-pressure liquid chromatography.
IPA Isopropyl alcohol
i-PrMgBr Isopropyl magnesium bromide i-PrMgCl Isopropyl magnesium chloride
LC/MS Liquid chromatography/mass spectrometry
M Molar
min Minutes
m.p. Melting point
MS Mass Spectrometer
MTBE tert-Butyl methyl ether
MeOH Methyl alcohol
MOPS Morpholinopropanesulfonic acid
N Normal
NBS N-Bromosuccinimide
NCS N-Chlorosuccinimide
$NH_4OAc$ Ammonium acetate
NIS N-Iodosuccinimide
NMM N-Methylmorpholine
NMR Nuclear magnetic resonance
n-PrOH n-Propyl alcohol
$Pd(PPh_3)_4$ Tetrakis(triphenylphosphine)palladium(0)
$PhI(OAc)_2$ Iodobenzene diacetate [(diacetoxyiodo)benzene]
$PPh_3$ Triphenylphosphine
RP-HPLC Reverse-phase high-pressure liquid chromatography
$R_f$ Retention factor
$R_t$ Retention time
TBDMS tert-Butyldimethylsilyl
TBAF Tetrabutylammonium fluoride
TBDMSOTf tert-Butyldimethylsilyl trifluoromethanesulfonate
TEA Triethylamine
TFA Trifluoroacetic acid
THF Tetrahydrofuran
TOSMIC Toluenesulfonylmethyl isocyanide
TMS Trimethylsilyl
TMSCl Trimethylsilyl chloride
TLC Thin layer chromatography
UV Ultraviolet light
wt % Weight percent

GENERAL PROCEDURES AND EXAMPLES

The general synthetic schemes that were utilized to construct the majority of compounds disclosed in this application are described below in Schemes 1-45. These schemes are provided for illustrative purposes only and are not to be construed as limiting the scope of the invention.

Scheme 1. Halogenation of a ketone with bromine (General Procedure A.1)

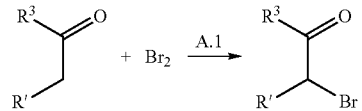

Scheme 2. Halogenation of a ketone with pyridinium tribromide (General Procedure A.2)

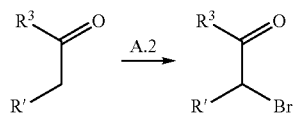

Scheme 3. Cyclization to form an imidazo [1,2-b]oxazole (General Procedure B or B.1)

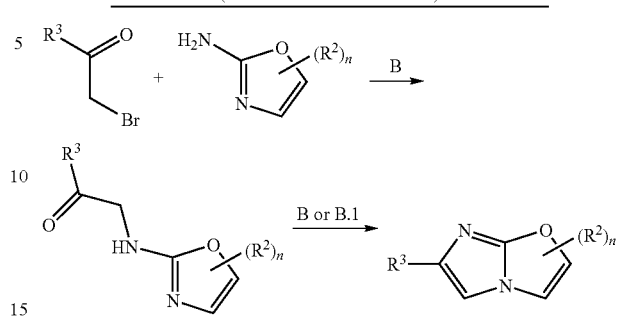

Scheme 4. Halogenation of a heterocycle with NIS or NBS (General Procedure C or C.1)

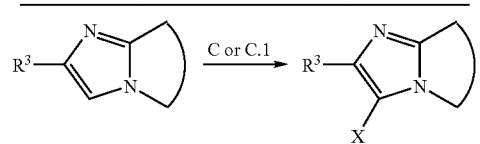

Scheme 5. Displacement of an aryl or heteroaryl halide with an amine or hydrazine (General Procedure D)

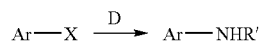

Scheme 6. Hydrazone formation followed by cyclization with iodobenzene diacetate (General Procedure E or E.1)

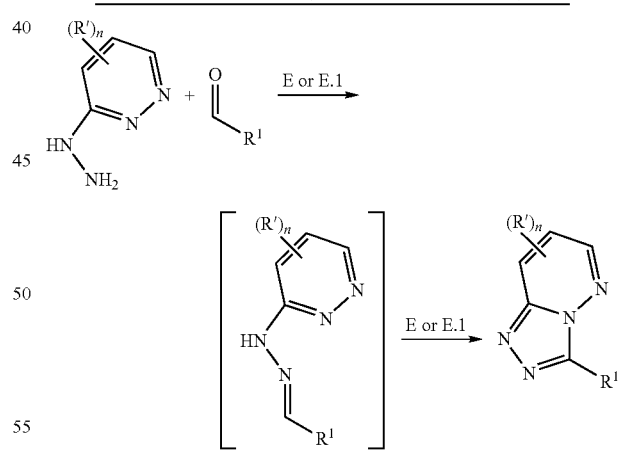

Scheme 7. Formation of a terminal alkyne from an alkynyl silane (General Procedure F)

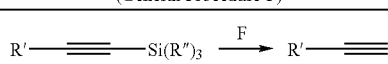

Scheme 8. Cyclization of a hydrazinylpyridazine with an acid chloride
(General Procedure G)

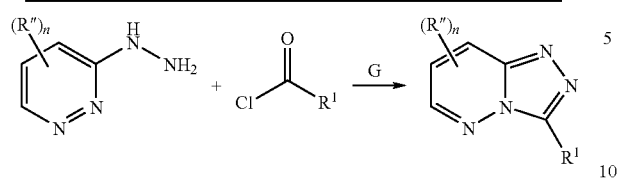

Scheme 9. Formation of a heteroaryl iodide from a heteroaryl chloride
(General Procedure H)

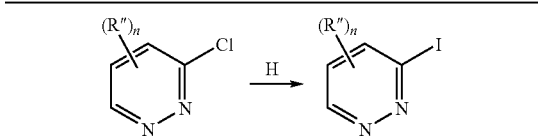

Scheme 10. Negishi coupling of a heteroaryl halide and
a heteroaryl halide (General Procedure I or I.1)

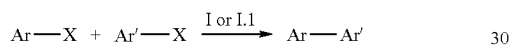

Scheme 11. Sonagashira reaction involving an aryl halide and
a terminal alkyne (General Procedure J)

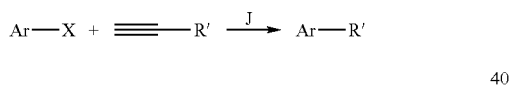

Scheme 12. Hydration of an alkyne to a ketone with an acid
(General Procedure K or K.1)

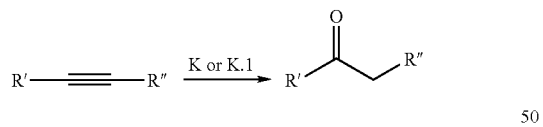

Scheme 13. Formation of a pyrazole (General Procedure L or L.1)

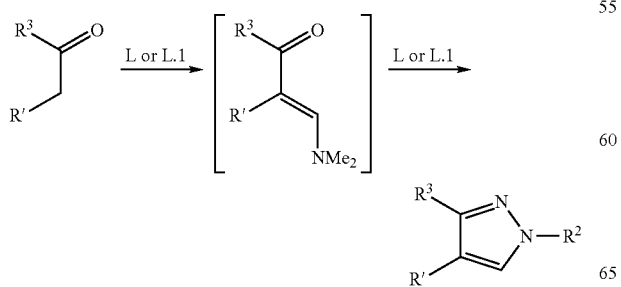

Scheme 14. Formation of a diketone from a ketone
(General Procedure M)

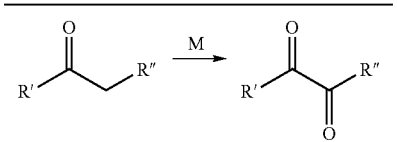

Scheme 15. Formation of an imidazole
(General Procedure N)

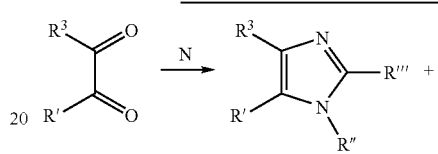

Scheme 16. Preparation of a thiazole from a bromoketone
(General Procedure O or O.1)

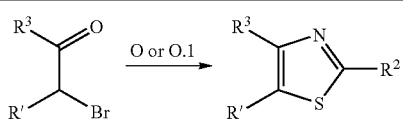

Scheme 17. Formation of a 2-aminothiazole
(General Procedure P or P.1)

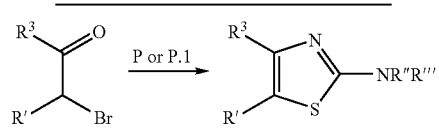

Scheme 18. Acidic cleavage of a Boc-protected amine
(General Procedure Q or Q.1)

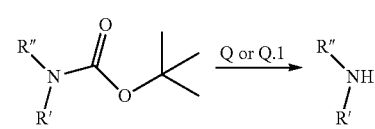

Scheme 19. Formation of a dihydropyrrolo[1,2-a]imidazole or tetrahydroimidazo[1,2-a]pyridine
(General Procedure R)

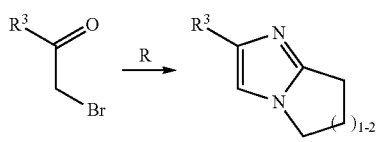

Scheme 20. Cyclization of an aldehyde with a TOSMIC reagent to give an oxazole
(General Procedure S)

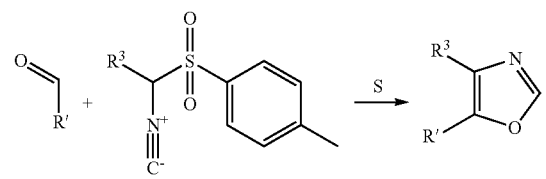

Scheme 21a. Acylation of a amine
(General Procedure T)

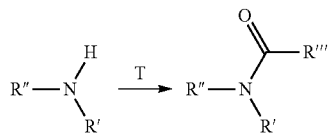

Scheme 21b. Acylation of an amine or hydrazine
(General Procedure T.1)

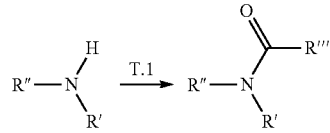

Scheme 22. Formation of a sulfonamide from an amine
(General Procedure U or U.1)

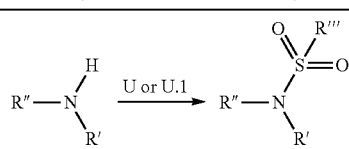

Scheme 23. Hydrolysis of an ester
(General Procedure V or V.1)

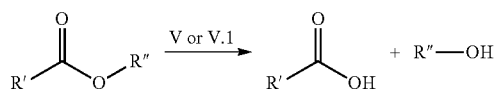

Scheme 24. Formation of a mesylate or tosylate
(General Procedure W)

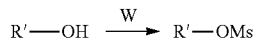

Scheme 25a. Displacement of a mesylate
(General Procedure X)

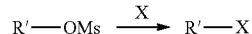

Scheme 25b. Displacement of a mesylate or tosylate
(General Procedure X.1)

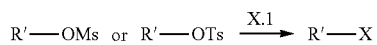

Scheme 26. Reductive amination
(General Procedure Y)

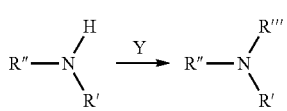

Scheme 27. Mitsunobu reaction of a pyrazole
(General Procedure Z)

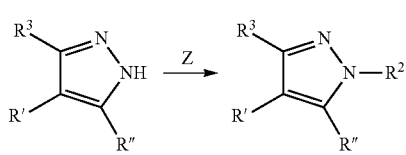

Scheme 28. Alkylation of an amine
(General Procedure AA)

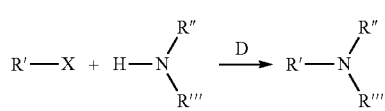

Scheme 29. Cyclization of an imine with a TOSMIC reagent
(General Procedure AB)

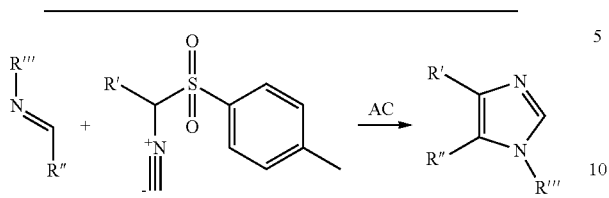

Scheme 30. Formation of an imidazo[1,2-a]imidazole
(General Procedure AC)

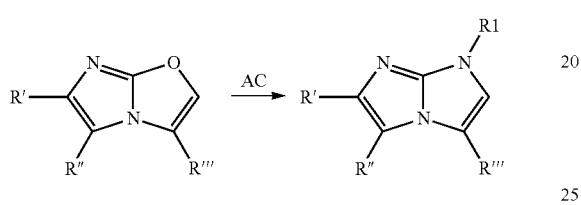

Scheme 31. Formation of a tertiary alcohol from a
ketone using a methyl Grignard
(General Procedure AD)

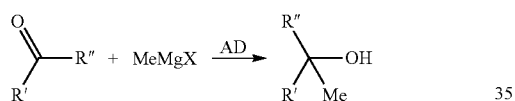

Scheme 32. Alkylation of an alcohol
(General Procedure AE)

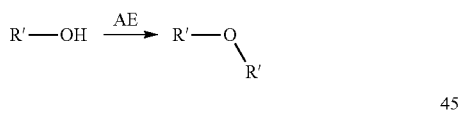

Scheme 33. Formation of a ketone from an ester
using a methyl Grignard
(General Procedure AF)

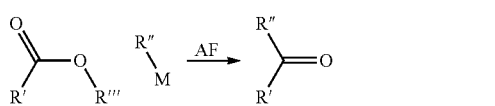

Scheme 34. Formation of a 3-aminotriazolopyridazine
(General Procedure AG)

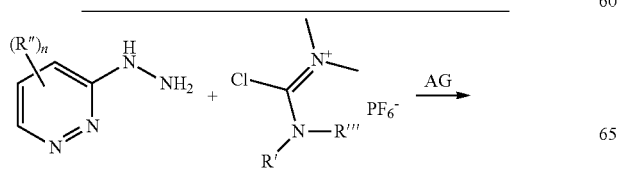

-continued

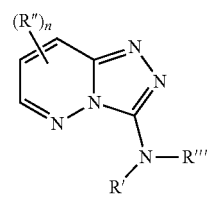

Scheme 35. Dess-Martin periodinane oxidation of an
alcohol to an aldehyde
(General Procedure AI.1)

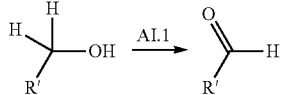

Scheme 36. Swern oxidation of an alcohol to an
aldehyde
(General Procedure AI.2)

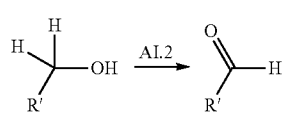

Scheme 37. Reaction of alcohol with DAST
(General Procedure AJ)

Scheme 38. Monosilylation of a diol
(General Procedure AK)

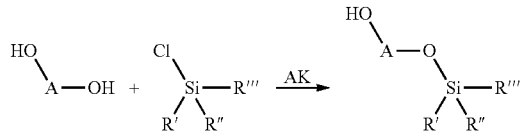

Scheme 39. Reduction of an ester to an alcohol
(General Procedure AL)

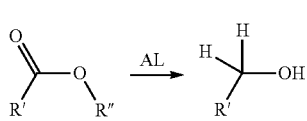

Scheme 40. Deprotection of a silyl protected alcohol
(General Procedure AM)

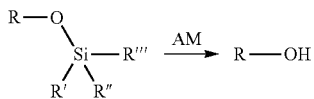

Scheme 41. Cyclization of a pyridazinylhydrazide
(General Procedure AN)

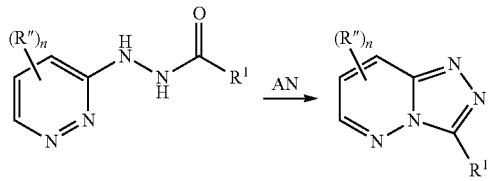

Scheme 42. Preparation of a thiourea
(General Procedure AO)

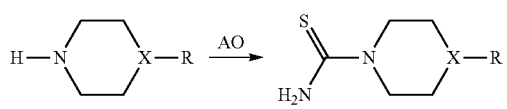

Scheme 43. Formation of an imine
(General Procedure AP)

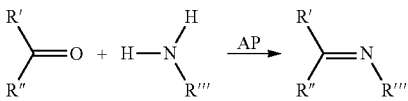

Scheme 44. Cyclization of a hydrazinylpyridazine
with a thioisocyanate
(General Procedure AQ)

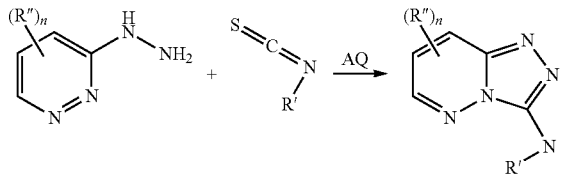

Scheme 45. Amide or hydrazide formation
(General Procedure AR)

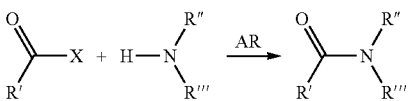

LIST OF GENERAL PROCEDURES

| | |
|---|---|
| General Procedure A.1 | Halogenation of a ketone with bromine |
| General Procedure A.2 | Halogenation of a ketone with pyridinium tribromide |
| General Procedure B or B.1 | Cyclization to form an imidazo[1,2-b]oxazole |
| General Procedure C or C.1 | Halogenation of a heterocycle with NIS or NBS |
| General Procedure D | Displacement of an aryl or heteroaryl halide with an amine or hydrazine |
| General Procedure E or E.1 | Hydrazone formation followed by cyclization with iodobenzene diacetate |
| General Procedure F | Formation of a terminal alkyne from an alkynyl silane |
| General Procedure G | Cyclization of a hydrazinylpyridazine with an acid chloride |
| General Procedure H | Formation of a heteroaryl iodide from a heteroaryl chloride |
| General Procedure I or I.1 | Negishi coupling of a heteroaryl halide and a heteroaryl halide |
| General Procedure J | Sonagashira reaction involving an aryl halide and a terminal alkyne |
| General Procedure K or K.1 | Hydration of an alkyne to a ketone with an acid |
| General Procedure L or L.1 | Formation of a pyrazole |
| General Procedure M | Formation of a diketone from a ketone |
| General Procedure N | Formation of an imidazole |
| General Procedure O or O.1 | Preparation of a thiazole from a bromoketone |
| General Procedure P or P.1 | Formation of a 2-aminothiazole |
| General Procedure Q or Q.1 | Acidic cleavage of a Boc-protected amine |
| General Procedure R | Formation of a dihydropyrrolo[1,2-a]imidazole or tetrahydroimidazo[1,2-a]pyridine |
| General procedure S | Cyclization of an aldehyde with a TOSMIC reagent to give an oxazole |
| General procedure T | Acylation of an amine |
| General Procedure T.1 | Acylation of an amine or hydrazine |
| General procedure U or U.1 | Formation of a sulfonamide from an amine |
| General procedure V or V.1 | Hydrolysis of an ester |
| General procedure W | Formation of a mesylate or tosylate |
| General procedure X | Displacement of a mesylate |
| General procedure X.1 | Displacement of a mesylate or tosylate |
| General procedure Y | Reductive amination |
| General procedure Z | Mitsunobu reaction of a pyrazole |
| General procedure AA | Alkylation of an amine |

| | -continued |
|---|---|
| General procedure AB | Cyclization of an imine with a TOSMIC reagent |
| General procedure AC | Formation of an imidazo[1,2-a]imidazole |
| General procedure AD | Formation of a tertiary alcohol from a ketone using a methyl Grignard |
| General procedure AE | Alkylation of an alcohol |
| General procedure AF | Formation of a ketone from an ester using a methyl Grignard |
| General procedure AG | Formation of a 3-aminotriazolopyridazine |
| General procedure AI.1 | Dess-Martin periodinane oxidation of an alcohol to an aldehyde |
| General procedure AI.2 | Swern oxidation of an alcohol to an aldehyde |
| General procedure AJ | Reaction of an alcohol with DAST |
| General procedure AK | Monosilylation of a diol |
| General procedure AL | Reduction of an ester to an alcohol |
| General procedure AM | Deprotection of a silyl protected alcohol |
| General procedure AN | Cyclization of a pyridazinylhydrazide |
| General procedure AO | Preparation of a thiourea |
| General procedure AP | Formation of an imine |
| General procedure AQ | Cyclization of a hydrazinylpyridazine with a thioisocyanate |
| General procedure AR | Amide or hydrazide formation |

The following examples are ordered according to the final general procedure used in their preparation. The synthetic routes to any novel intermediates are detailed by sequentially listing the general procedure (letter codes) in parentheses after their name. A worked example of this protocol is given below using Example #E.1.1 as a non-limiting illustration. Example #E.1.1 is 5-(3-tert-butyl-[1,2,4]triazolo[4,3-b]pyridazin-6-yl)-6-(2,5-difluorophenyl)imidazo[2,1-b]oxazole, which was prepared from 6-(2,5-difluorophenyl)-5-(6-hydrazinylpyridazin-3-yl)imidazo[2,1-b]oxazole using General Procedure E as represented in the following synthetic scheme:

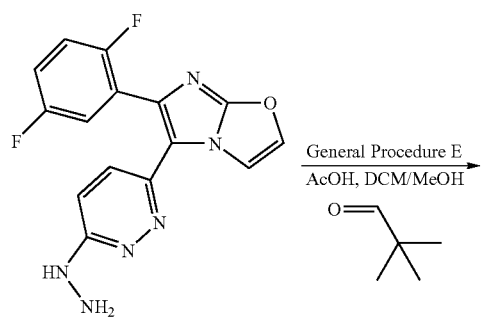

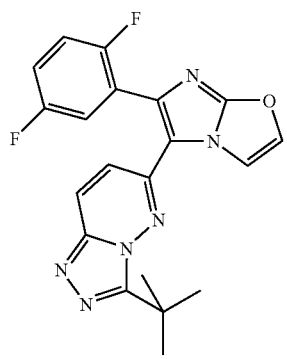
Example #E.1.1

The precursor to Example #E.1.1, 6-(2,5-difluorophenyl)-5-(6-hydrazinylpyridazin-3-yl)imidazo[2,1-b]oxazole, was prepared by the noted reaction sequence: using General Procedure A.1 from 1-(2,5-difluorophenyl)ethanone [Matrix], General Procedure B from oxazole-2-amine [GL Synthesis], General Procedure C with NIS, General Procedure I from 1-chloro-4-iodopyridazine (prepared using General Procedure H from 3,6-dichloropyridazine), and General Procedure D with hydrazine hydrate), which translates to the following synthetic scheme:

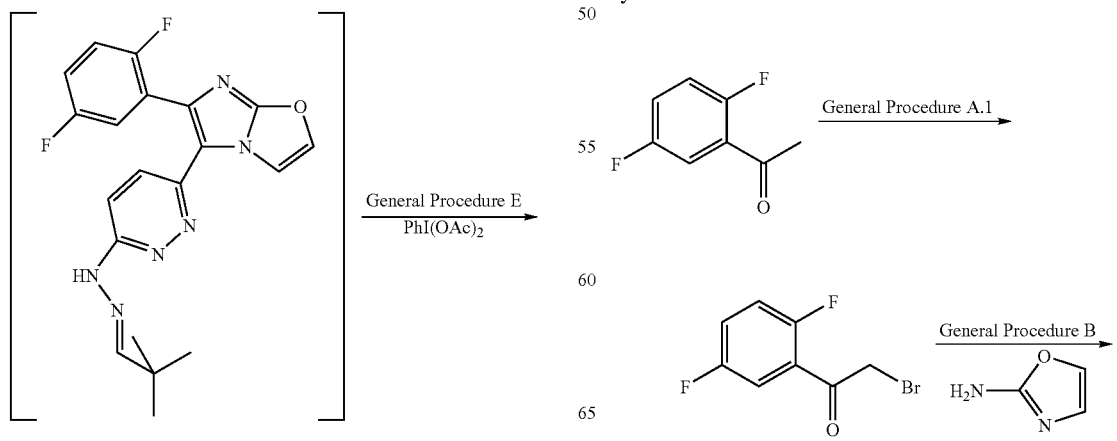

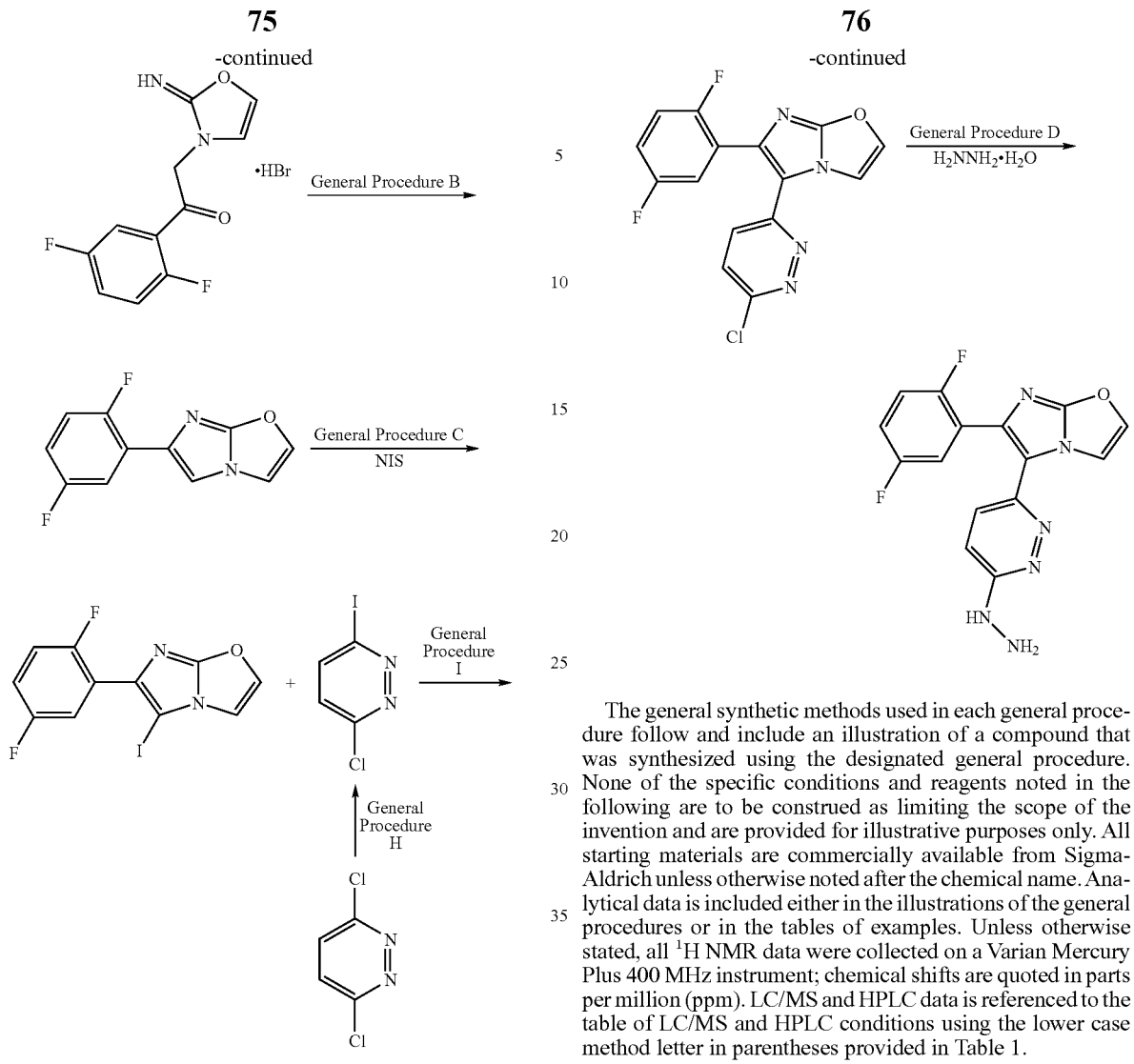

The general synthetic methods used in each general procedure follow and include an illustration of a compound that was synthesized using the designated general procedure. None of the specific conditions and reagents noted in the following are to be construed as limiting the scope of the invention and are provided for illustrative purposes only. All starting materials are commercially available from Sigma-Aldrich unless otherwise noted after the chemical name. Analytical data is included either in the illustrations of the general procedures or in the tables of examples. Unless otherwise stated, all $^1$H NMR data were collected on a Varian Mercury Plus 400 MHz instrument; chemical shifts are quoted in parts per million (ppm). LC/MS and HPLC data is referenced to the table of LC/MS and HPLC conditions using the lower case method letter in parentheses provided in Table 1.

TABLE 1

LC/MS and HPLC methods

| Method | Conditions |
|---|---|
| a | LC/MS: The column used for the chromatography was a 50 × 4.6 mm Zorbax XDB C18 column (5 μm particles). The gradient was 5-95% B in 3.7 min with a hold at 95% B for 1 min (1.3 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization |
| b | LC/MS: The column used for the chromatography was a 4.6 × 30 mm Vydac Genesis C8 column (4 μm particles). The gradient was 5-60% B in 1.5 min then 60-95% B to 2.5 min with a hold at 95% B for 1.2 min (1.3 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization. |
| c | LC/MS: The column used for the chromatography was a 4.6 × 30 mm Vydac Genesis C8 column (4 μm particles). The gradient was 30-95% B in 2 min then hold at 95% B to 5.7 min (1.0 mL/min flow rate). Mobile phase A was 10 mM ammonium acetate and mobile phase B was HPLC grade acetonitrile. Detection methods are diode array (DAD) and evaporative light scattering (ELSD) detection as well as positive/negative electrospray ionization. |
| d | HPLC: The column used for the chromatography was a 21.2 × 250 mm Hypersil C18 HS column (8 μm particles). The gradient was 15-100% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |

TABLE 1-continued

LC/MS and HPLC methods

| Method | Conditions |
|---|---|
| e | HPLC: The column used for the chromatography was a 21.2 × 250 mm Hypersil C18 HS column (8 μm particles). The gradient was 0-80% B over 50 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| f | HPLC: The column used for the chromatography was a 21.2 × 250 mm Hypersil C18 HS column (8 μm particles). The gradient was 5-95% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| g | LC/MS: The column used for the chromatography is a 4.6 × 50 mm MAC-MOD Halo C18 column (2.7 μm particles). The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| h | LC/MS: The column used for the chromatography is a 4.6 × 50 mm MAC-MOD Halo C8 column (2.7 μm particles). The gradient was 5-60% B in 0.75 min then 60-95% B to 1.15 min with a hold at 95% B for 0.75 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| i | LC/MS: The column used for the chromatography is a 4.6 × 50 mm MAC-MOD Halo C8 column (2.7 μm particles). The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| j | LC/MS: The column used for the chromatography is a 4.6 × 50 mm MAC-MOD Halo C8 column (2.7 μm particles). The gradient was 30-60% B in 1.50 min then 60-95% B to 2.5 min with a hold at 95% B for 1.2 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| k | LC/MS: The column used for the chromatography is a 4.6 × 50 mm MAC-MOD Halo C8 column (2.7 μm particles). The gradient was 30-60% B in 0.75 min then 60-95% B to 1.15 min with a hold at 95% B for 0.75 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| l | HPLC: The column used for the chromatography was a 21.2 × 250 mm Hypersil C18 HS column (8 μm particles). The gradient was 5-100% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| m | HPLC: The column used for the chromatography was a 21.2 × 250 mm Hypersil C18 HS column (8 μm particles). The gradient was 20-100% B over 14 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| n | HPLC: The column used for the chromatography was a 21.2 × 250 mm Hypersil C18 HS column (8 μm particles). The gradient was 20-100% B over 20 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| o | LC/MS: The column used for the chromatography is a 4.6 × 30 mm Vydac Genesis C8 column (4 μm particles). The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade acetonitrile. Detection methods are diode array (DAD) as well as positive/negative electrospray ionization and $MS^2$ data dependent scanning on the positive ion scan (45 eV collision energy). |
| p | HPLC: The column used for the chromatography was a 21.2 × 250 mm Hypersil C18 HS column (8 μm particles). The gradient was 10-100% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |

Preparation #1: 3-Isopropyl-6-vinyl-[1,2,4]triazolo[4,3-b]pyridazine

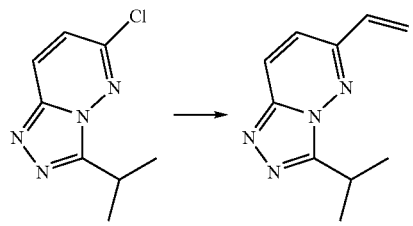

The 6-chloro-3-isopropyl-[1,2,4]triazolo[4,3-b]pyridazine (8.60 g, 43.7 mmol, Preparation #G.1), tetravinylstannane (11.91 g, 52.50 mmol), $PdCl_2(PPh_3)_2$ (3.07 g, 4.37 mmol) and lithium chloride (3.71 g, 87.0 mmol) were added to DMF (65 mL) and then the mixture was heated to about 85° C. for about 1 h. The reaction was cooled to ambient temperature and then concentrated under reduced pressure. Water and EtOAc were added to the residue and then the mixture was filtered through Celite®. The filtrate was transferred to a separatory funnel and the layers were separated then the aqueous layer was extracted with EtOAc. The combined organic solutions were dried over $MgSO_4$ and filtered prior to concentrating under reduced pressure to provide an oil which was purified by flash chromatography on silica gel with EtOAc as an eluent. The material was purified further by flash chromatography on silica gel with DCM/MeOH (95:5) as an eluent to give the title compound (3.28 g, 39.8%) as a light yellow oil which crystallized on standing: $^1H$ NMR (DMSO-$d_6$) δ 1.39 (d, 6H), 3.53 (m, 1H), 5.84 (d, 1H), 6.44 (d, 1H), 6.82 (dd, 1H), 7.69 (d, 1H), 8.28 (d, 1H); LC/MS (Table 1, Method a) $R_t$=2.06 min; MS m/z: 189.2 $(M+H)^+$.

Preparation #2: 3-Isopropyl-[1,2,4]triazolo[4,3-b]pyridazine-6-carbaldehyde

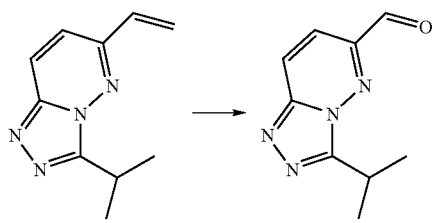

The 3-isopropyl-6-vinyl-[1,2,4]triazolo[4,3-b]pyridazine (3.28 g, 17.4 mmol, Preparation #1) in 1,4-dioxane (75 mL) and water (15 mL) was treated with osmium tetroxide (3.5 mL, 0.28 mmol, 2.5 wt % in 2-methyl 1-propanol) and then sodium periodate (7.45 g, 34.9 mmol) was added. The mixture was stirred at ambient temperature for about 1 h and then diluted with 1,4-dioxane (50 mL) and filtered through Celite®. The filter cake was washed with 1,4-dioxane then EtOAc. The filtrate was concentrated under reduced pressure and then the residue was purified by flash chromatography on silica gel with DCM/MeOH (9:1) as an eluent to give the title compound (2.30 g, 69.4%) as a beige solid: $^1H$ NMR $(CDCl_3)$ δ 1.61 (d, 6H), 3.76 (m, 1H), 7.65 (d, 1H), 8.21 (m, 1H), 10.06 (d, 1H).

Preparation #3: 2,4-Difluoro-1-(isocyano(tosyl)methyl)benzene

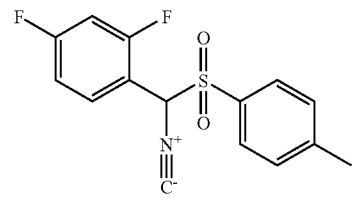

Step A: 4-Methylbenzenesulfinic Acid

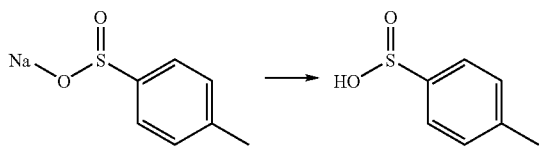

To a round bottom flask was added sodium 4-methylbenzenesulfinate (25 g, 140 mmol), MTBE (40 mL) and water (80 mL). To the reaction mixture was added concentrated HCl (12.7 mL, 154 mmol) dropwise via addition funnel over about 15 min. The resulting layers were separated and the aqueous layer extracted with MTBE (2×50 mL). The organic layers were combined and dried with $MgSO_4$, filtered and concentrated in vacuo. The resulting solid was triturated with heptane, filtered, and dried under vacuum to provide the title compound (21.5 g, 98%). LC/MS (Table 1, Method a) $R_t$=1.12 min; MS m/z: 155.1 $(M-H)^-$.

Step B: N-((2,4-Difluorophenyl)(tosyl)methyl)formamide

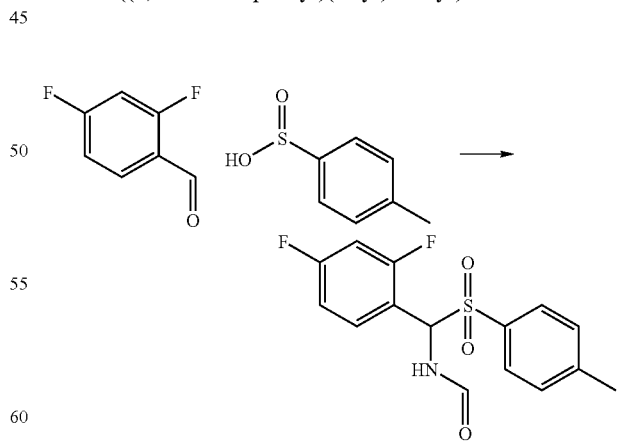

To a round bottom flask was added 4-methylbenzenesulfinic acid (5.00 g, 32.0 mmol), (1S)-(+)-10-camphorsulfonic acid (0.074 g, 0.320 mmol), 2,4-difluorobenzaldehyde (3.85 mL, 35.2 mmol) and formamide (6.38 mL, 160 mmol). The reaction mixture was stirred at about 65° C. for about 16

Step C:
2,4-Difluoro-1-(isocyano(tosyl)methyl)benzene

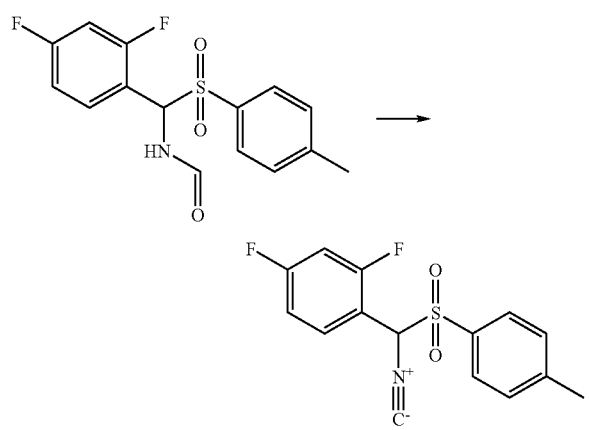

To a solution of N-((2,4-difluorophenyl)(tosyl)methyl)formamide (7.31 g, 22.5 mmol) in DME (100 mL) at about –10° C. was added phosphorus oxychloride (Fluka, 6.28 mL, 67.4 mmol) followed by dropwise addition of TEA (15.7 mL, 112 mmol) in DME (10 mL). The reaction mixture was stirred at about –5° C. for about 3 h. The reaction mixture was poured into ice-cold water (250 mL) and extracted with EtOAc (3×50 mL). The organic layer was dried with MgSO$_4$, filtered and concentrated in vacuo. The crude material was purified by silica gel chromatography using heptane/EtOAc (gradient; 1:0 to 1:1) to give the title compound (1.38 g, 20.0%), as a yellow solid. LC/MS (Table 1, Method a) R$_t$=2.96 min; MS m/z: 306.1 (M–H)⁻.

Preparation #4:
2,5-Difluoro-1-(isocyano(tosyl)methyl)benzene

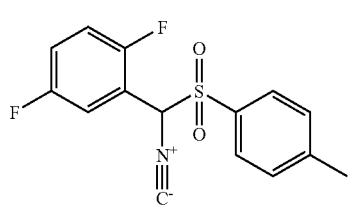

Step A:
N-((2,5-Difluorophenyl)(tosyl)methyl)formamide

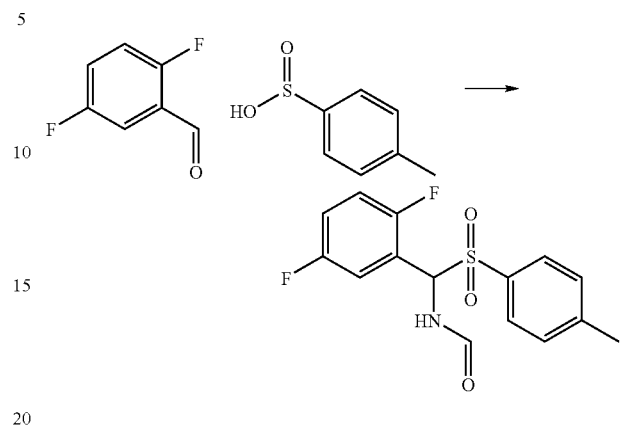

To a round bottom flask was added 4-methylbenzenesulfinic acid (5.00 g, 32.0 mmol, Preparation #3, Step A), (1S)-(+)-10-camphorsulfonic acid (0.074 g, 0.32 mmol), 2,5-difluorobenzaldehyde (3.83 mL, 35.2 mmol) and formamide (6.38 mL, 160 mmol). The reaction mixture was stirred at about 65° C. for about 16 h. The reaction mixture had solidified overnight. The solid was broken up and suspended in MeOH. The chunks of solid were ground to a powder with a spatula and the solid was filtered and washed with MeOH. The filter cake was dried under vacuum at about 60° C. to give the title compound (5.92 g, 56.8%) as a white powder. LC/MS (Table 1, Method a) R$_t$=2.37 min; MS m/z: 343.1 (M+NH$_3$)⁺.

Step B:
2,5-Difluoro-1-(isocyano(tosyl)methyl)benzene

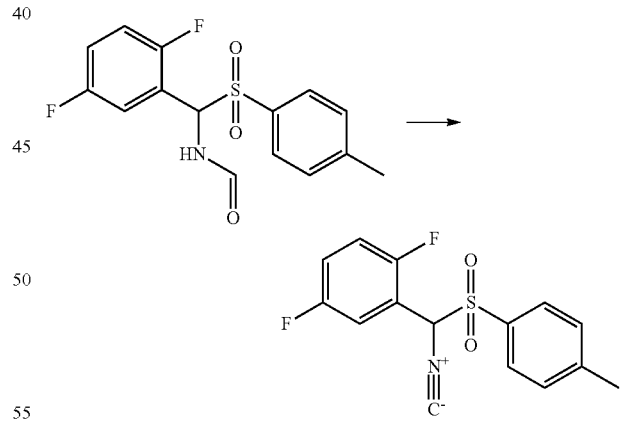

To a solution of N-((2,5-difluorophenyl)(tosyl)methyl)formamide (5.92 g, 18.2 mmol) in DME (100 mL) at about –10° C. was added phosphorus oxychloride (Fluka, 5.09 mL, 54.6 mmol) followed by dropwise addition of TEA (12.7 mL, 91.0 mmol) in DME (10 mL). The reaction mixture was stirred at about –5° C. for about 3 h. The reaction mixture was poured into ice-cold water (250 mL) and extracted with EtOAc (3×50 mL). The organic layer was dried with MgSO$_4$, filtered and concentrated in vacuo. The crude material was purified by silica gel chromatography using heptane/EtOAc (gradient;

1:0 to 1:1) to give the title compound (1.90 g, 34.0%) as a yellow solid. LC/MS (Table 1, Method a) R$_t$=2.94 min; MS m/z: 306.1 (M−H)⁻.

Preparation #5: 5-Methyloxazol-2-amine

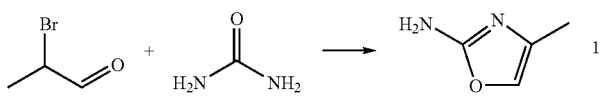

The 2-bromopropanal (62.8 g, 458 mmol, prepared according to *J. Med. Chem.* 2005, 48, 7215) and urea (30.3 g, 504 mmol) were heated at about 100° C. for about 16 h, then cooled and extracted with DCM (3×50 mL). The aqueous solution was basified with 50% aqueous NaOH then extracted with DCM (3×50 mL). The combined extracts from the basic solution were dried over MgSO$_4$, filtered and concentrated under reduced pressure to give the title compound (2.17 g, 4.8%) as an oil, which crystallized on standing. Further extraction gave a second crop (2.47 g, 5.5%) of title compound. Total yield was 4.64 g (10%): ¹H NMR (CDCl$_3$) δ 6.30 (s, 1H), 4.70 (bs, 2H), 2.20 (3H, s).

Preparation #6: 6-(2,4-Difluorophenyl)-5-iodo-2,3-dihydroimidazo[2,1-b]oxazole

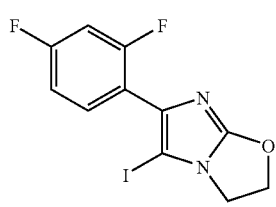

Step A: 6-(2,4-Difluorophenyl)-2,3-dihydroimidazo[2,1-b]oxazole

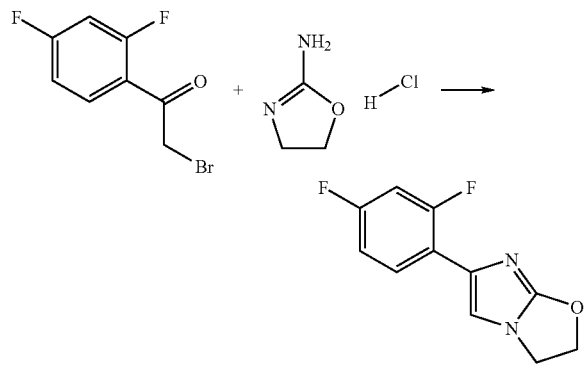

The oxazolidin-2-imine hydrochloride (TCI, 5.00 g, 40.8 mmol) and 2-bromo-1-(2,4-difluorophenyl)ethanone (7.99 g, 34.0 mmol, Example #8, Step A) were dissolved in DMF (34.7 mL) then Na$_2$CO$_3$ (9.01 g, 85.0 mmol) was added. The mixture was stirred for about 15 min and then it was heated to about 80° C. for about 5 h. The mixture was cooled then filtered and the filtrate was concentrated under reduced pressure. The material was purified by flash chromatography on silica gel using DCM/EtOAc (gradient 1:0 to 0:1) to give the title compound (2.02 g, 26%): LC/MS (Table 1, Method g) R$_t$=1.94 min; MS m/z: 223.1 (M+H)⁺.

Step B: 6-(2,4-Difluorophenyl)-5-iodo-2,3-dihydroimidazo[2,1-b]oxazole

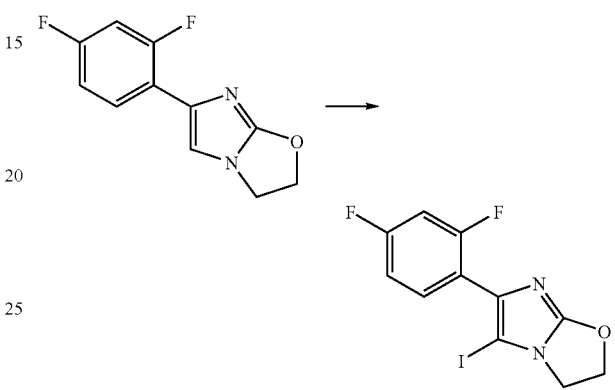

The 6-(2,4-difluorophenyl)-2,3-dihydroimidazo[2,1-b]oxazole (0.500 g, 2.25 mmol) was dissolved in DMF (6 mL) then NIS (0.533 g, 2.25 mmol) was added in one portion. The mixture was stirred at ambient temperature for about 15 min. The solvent was removed under reduced pressure then the residue was dissolved in DCM (6 mL) and purified by flash chromatography on silica gel using DCM/EtOAc (1:1) as an eluent. The desired fractions were combined and concentrated under reduced pressure to give a brown solid that was then triturated with water (10 mL). The solid was collected by filtration then dried under vacuum at about 70° C. for about 12 h to give the title compound (0.635 g, 81%): LC/MS (Table 1, Method h) R$_t$=1.39 min; MS m/z: 349 (M+H)⁺.

General Procedure A.1: Halogenation of a Ketone with Bromine

To a flask containing a ketone (preferably 1 equiv) in a suitable organic solvent (such as DCM, ACN, or HOAc, preferably DCM) is added bromine (0.9-1.5 equiv, preferably 0.99 equiv) neat or as a solution in the aforementioned organic solvent (preferably as a solution in organic solvent) over a period of about 5 min to 2 h (preferably about 1 h) at about 040° C. (preferably about 23° C.). Once the bromine is completely added, the reaction mixture is stirred for about 15 min-4 h (preferably about 1 h) at about 0-40° C. (preferably about 23° C.). Cold water is added and the mixture is stirred for about 5-30 min (preferably about 15 min) at about 23° C. The layers are separated and the organic solution is optionally washed with water and/or brine and is dried over Na$_2$SO$_4$ or MgSO$_4$, then decanted or filtered, and the solvent is removed under reduced pressure to give the target compound. The crude product can be used without additional purification.

Optionally, the crude material can be purified by crystallization or trituration from an appropriate solvent or solvents to give the target compound.

Illustration of General Procedure A.1

Preparation #A.1:
2-Bromo-1-(2,4,5-trifluorophenyl)ethanone

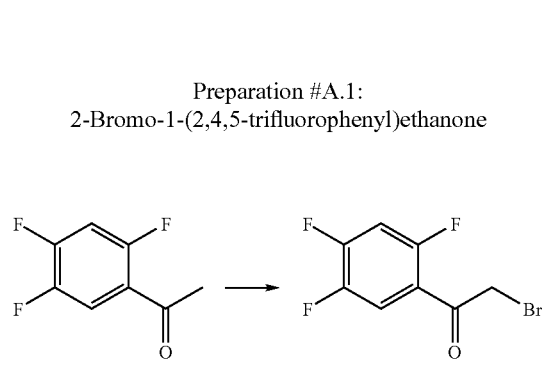

A 1 L 3-neck round bottom flask was charged with 1-(2,4,5-trifluorophenyl)ethanone (49.7 g, 285 mmol) and DCM (350 mL). The flask was equipped with a 250 mL dropping funnel that contained a solution of bromine (14.6 mL, 283 mmol) in DCM (125 mL). This solution was added to the reaction flask over about 1 h at about 23° C. Once addition of the solution was complete, the reaction mixture was stirred for about 1 h at about 23° C. Ice water was added to the reaction flask and the layers were stirred for about 15 min. The layers were separated and the organic solution was then washed with water and brine, dried over MgSO$_4$, filtered, and the solvent was removed under reduced pressure to give the title compound as a pale yellow solid (70.3 g, 97%): LC/MS (Table 1, Method b) R$_t$=2.20 min; MS m/z 251.0 (M+H)$^+$.

General Procedure A.2: Halogenation of a Ketone with Pyridinium Tribromide

Pyridinium tribromide (1-1.5 equiv, preferably 1.15 equiv) is added to a solution of a ketone (preferably 1 equiv) in an organic solvent (such as 1,4-dioxane or THF, preferably THF) and the resulting reaction mixture is stirred at ambient temperature for about 3-6 h (preferably about 3-4 h). The crude mixture is diluted with an organic solvent (for example, DCM) and washed with water. The layers are separated and the organic solution is optionally washed with water and/or brine and is dried over Na$_2$SO$_4$ or MgSO$_4$, then decanted or filtered, and the solvent is removed under reduced pressure to give the target compound. The crude product is used without additional purification. Optionally, the crude material can be purified by crystallization or trituration from an appropriate solvent or solvents to give the target compound.

Illustration of General Procedure A.2

Preparation #A.2: 2-Bromo-1-(2,4-difluorophenyl)-2-(3-isopropyl-[1,2,4]triazolo[4,3-b]pyridazin-6-yl)ethanone

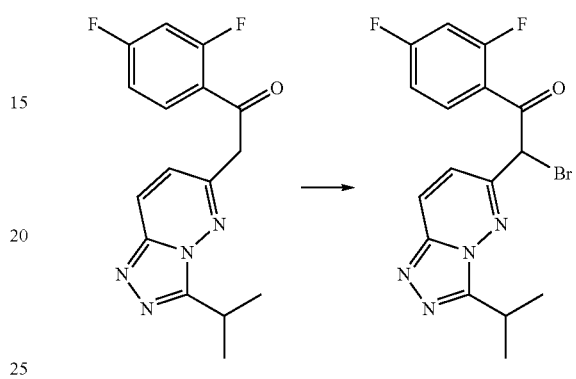

Pyridinium tribromide (0.567 g, 1.77 mmol) was added to a solution of 1-(2,4-difluorophenyl)-2-(3-isopropyl-[1,2,4]triazolo[4,3-b]pyridazin-6-yl)ethanone (0.488 g, 1.54 mmol; Preparation #K.1) in THF (6 mL) and the resulting reaction mixture was stirred at ambient temperature for about 4 h. The crude mixture was diluted with DCM (20 mL) and washed with water. The organic layer was dried over MgSO$_4$, filtered, and concentrated under reduced pressure to give the crude title compound (0.61 g, 100%): LC/MS (Table 1, Method a) R$_t$=3.28 min; MS m/z: 396.9 (M+H)$^+$.

General Procedure B: Cyclization to Form an Imidazo[1,2-b]oxazole

To a flask containing a bromoketone (1-2 equiv, preferably 1.5 equiv) in an organic solvent or solvents (such as THF, ACN, DCM, 1,4-dioxane, or THF/ACN, preferably THF/ACN) is added an oxazole-2-amine (preferably 1 equiv). The mixture is stirred at about 0-70° C. (preferably about 23° C.) for about 2-30 h (preferably about 20 h). The reaction mixture is cooled to about −78-0° C. (preferably about −10° C.) for about 5-30 min (preferably about 15 min) and the solid is collected by vacuum filtration, washed with additional organic solvent (such as THF, ACN, DCM, or 1,4-dioxane, preferably ACN), and dried under vacuum. To this intermediate (preferably 1 equiv) is added an organic solvent (for example, toluene). A solution of TiCl$_4$ (1-5 equiv, preferably 2.5 equiv, in an organic solvent (for example, toluene) is added over about 15 min-1 h (preferably about 30 min) at about −10-23° C. (preferably about 0° C.). The resulting mixture is stirred at about −10-23° C. (preferably about 0° C.) for about 30 min-1 h (preferably about 30 min), followed by heating to about 70-110° C. (preferably about 100° C.) for about 30 min-5 h (preferably about 3 h). The mixture is cooled and the organic solvent is optionally decanted off. Ice water is added to the reaction flask with stirring. The resulting thick suspension is stirred at ambient temperature for about 1-12 h (preferably about 1 h) followed by the addition of a base (for example, Na$_2$CO$_3$) and an organic solvent (such as EtOAc or DCM). The resulting mixture is stirred at ambient temperature for about 30 min-2 h (preferably about 1 h). The layers Illustration of General Procedure B Preparation #B.1:
6-(2,4,5-Trifluorophenyl)imidazo[2,1-b]oxazole

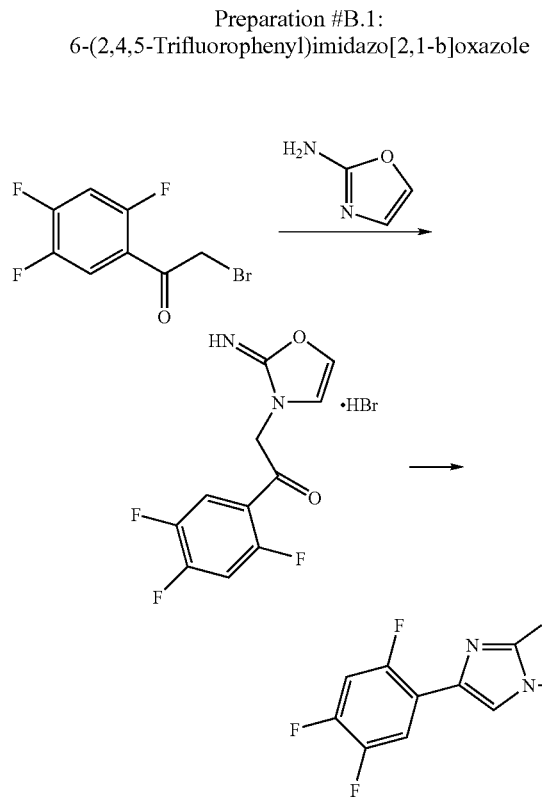

A round bottom flask was charged with 2-bromo-1-(2,4,5-trifluorophenyl)ethanone (50.0 g, 198 mmol), oxazole-2-amine (GL Synthesis, 11.1 g, 132 mmol), THF (200 mL), and ACN (330 mL). The resulting mixture was stirred at about 23° C. for about 20 h. The suspension was cooled to about −10° C. for about 15 min and the solid was collected by vacuum filtration, washed with additional ACN (150 mL), and dried under vacuum to give 2-(2-iminooxazol-3(2H)-yl)-1-(2,4,5-trifluorophenyl)ethanone hydrobromide (35.1 g, 79%) as a white solid. A portion of this material (20.0 g, 59.3 mmol) was suspended in toluene (140 mL) and the suspension was cooled to about 0° C. To the flask was added a 1.0 M solution of TiCl$_4$ in toluene (154 mL) over about 30 min. The mixture was stirred at about 0° C. for about 30 min and was then heated to about 100° C. for about 3 h. The mixture was cooled to ambient temperature, the toluene was decanted off, and ice was added with stirring to the remaining residue. The mixture was adjusted to about pH 8 with the addition of solid Na$_2$CO$_3$, followed by the addition of EtOAc. The mixture was stirred for about 1 h and then passed through a pad of Celite®. The layers were separated and the organic solution was dried over MgSO$_4$, filtered, and concentrated to dryness under reduced pressure to give the title compound as a white solid (11.7 g, 83%): LC/MS (Table 1, Method b) R$_f$=2.11 min; MS m/z 239.1 (M+H)$^+$.

General Procedure B.1: Cyclization to Form an Imidazo[1,2-b]oxazole

A flask containing polyphosphoric acid (1.54 g/mol, preferably 2 g/mol) is heated to about 50-100° C. (preferably about 80-90° C.). The 3-(2-aryl-2-oxoethyl)oxazol-2(3H)-iminium (preferably 1 equiv) is added in portions over about 1-4 h (preferably about 2 h). The reaction mixture is heated at about 50-100° C. (preferably about 80-90° C.) for about 12-48 h (preferably about 20-24 h). The reaction mixture is cooled to about 0° C. and slowly quenched with water and a base (such as 10-50% NaOH or 10-50% KOH, preferably 30% NaOH) to about pH 5-6. The resulting solid is collected by filtration and rinsed with water followed by drying in vacuo to give the target compound. Optionally, the product can be purified by crystallization or trituration from an appropriate solvent or solvents, or by chromatography to give the target compound.

Illustration of General Procedure B.1

Preparation #B.1.1:
6-(2,4-Difluorophenyl)imidazo[2,1-b]oxazole

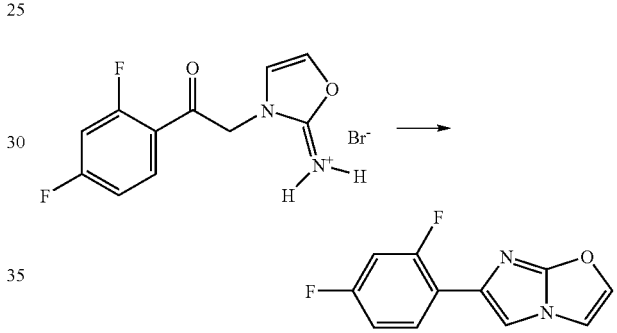

Polyphosphoric acid (124.4 g) was charged to a flask and heated to about 80° C. 1-(2,4-Difluorophenyl)-2-(2-iminooxazol-3(2H)-yl)ethanone hydrobromide salt (19.8 g, 62.0 mmol, Preparation #B.1 intermediate) was transferred to the flask in approximately 3 g portions over about 2 h. The thick solution was mixed and heated at about 80-90° C. for about 22 h. The reaction mixture was slowly transferred to a flask containing water (150 mL) and 30% aqueous NaOH (150 mL) that had been cooled to about 5-10° C. The pH of the resulting slurry was adjusted to about 5.4 by addition of 30% aqueous NaOH and the product was isolated by filtration. The wet cake was rinsed with warm water (3×150 mL) and dried under vacuum to give the title compound (9.5 g, 69%): MS m/z 221.1 (M+H)$^+$ FIA (APCI)

General Procedure C: Halogenation of a Heterocycle with NIS or NBS

A solution of a heterocycle (for example, 6-(aryl)imidazo[2,1-b]oxazole or 2-(aryl)-6,7-dihydro-5H-pyrrolo[1,2-a]imidazole; preferably 1 equiv), a halogenating agent such as NBS or NIS (0.95-1.2 equiv, preferably 1.1 equiv) and a suitable solvent (such as DMF) is stirred at ambient temperature. After about 0.5-8 h, preferably about 0.5-3 h, the reaction is poured into water. If present, the resulting precipitate is filtered, washing with additional water, and dried in a vacuum oven at about 55-65° C. to give the target compound. The entire aqueous solution, for cases where no precipitate forms, or the filtrate, if desired, is extracted with an organic solvent (such as DCM or EtOAc, preferably DCM). The combined organic layers may be washed with saturated aqueous NaHCO$_3$, 5% aqueous NaS$_2$O$_3$, and/or brine. The solid obtained from filtration may also be dissolved in an organic solvent (such as DCM or EtOAc, preferably DCM) and washed as above. The organic layer from any of these options is dried over Na$_2$SO$_4$ or MgSO$_4$, then decanted or filtered, and concentrated under reduced pressure to give the target compound. The crude product can be used without additional purification or can be purified by crystallization or trituration from an appropriate solvent or solvents, and/or by chromatography to give the target compound.

Illustration of General Procedure C

Preparation #C.1:
6-(2,4-Difluorophenyl)-5-iodoimidazo[2,1-b]oxazole

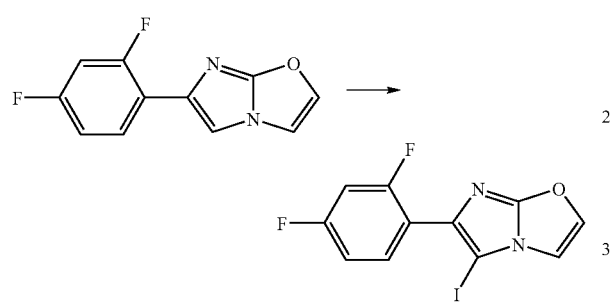

A solution of 6-(2,4-difluorophenyl)imidazo[2,1-b]oxazole (30.0 g, 136 mmol; Example #8, step B), NIS (31.6 g, 140 mmol), and DMF (350 mL) was stirred at ambient temperature. After about 1 h, the reaction was poured into water (2 L) and the resulting precipitate was filtered and washed with additional water. The brown solid was dissolved in DCM and washed with saturated aqueous NaHCO$_3$. The organic layer was dried over MgSO$_4$, filtered, and concentrated under reduced pressure to dryness. The solid was dissolved in DCM, filtered through Florosil® and then concentrated under reduced pressure to a volume of about 0.5 L. The organic layer was washed with 5% aqueous NaS$_2$O$_3$, dried over MgSO$_4$, filtered, and concentrated under reduced pressure to dryness to give the title compound as a yellow solid (34.5 g, 73%): LC/MS (Table 1, Method a) R$_f$=2.67 min; MS m/z: 346.9 (M+H)$^+$.

General Procedure C.1: Halogenation of a Heterocycle with NIS or NBS

A solution of a heterocycle (for example, 6-(aryl)imidazo[2,1-b]oxazole or 2-(aryl)-6,7-dihydro-5H-pyrrolo[1,2-a]imidazole; preferably 1 equiv), a halogenating agent such as NBS or NIS (0.95-1.2 equiv, preferably 1.0-1.1 equiv) and a suitable solvent (such as DMF) is stirred at ambient temperature. After about 0.5-48 h (preferably about 0.5-3 h) the mixture is poured into water. If present, the resulting precipitate is filtered, washed with additional water, and dried in a vacuum oven at about 55-65° C. to give the target compound. Otherwise the entire mixture, or the filtrate, if desired, is extracted with an organic solvent (such as Et$_2$O, DCM or EtOAc, preferably Et$_2$O or DCM). The combined organic layers may be washed with water, saturated aqueous NaHCO$_3$, 5% aqueous NaS$_2$O$_3$, and/or brine. The solid obtained from filtration may also be dissolved in an organic solvent (such as Et$_2$O, DCM or EtOAc, preferably Et$_2$O or DCM) and washed as above. The organic layer from any of these options is dried over a drying agent, such as Na$_2$SO$_4$ or MgSO$_4$, then decanted or filtered, and concentrated under reduced pressure. The resulting solid can be used without further purification or optionally be purified by crystallization or trituration from an appropriate solvent or solvents, and/or by chromatography to give the target compound.

Illustration of General Procedure C.1

Preparation #C.1.1: 2-(2,4-Difluorophenyl)-3-iodo-5,6,7,8-tetrahydroimidazo[1,2-a]pyridine

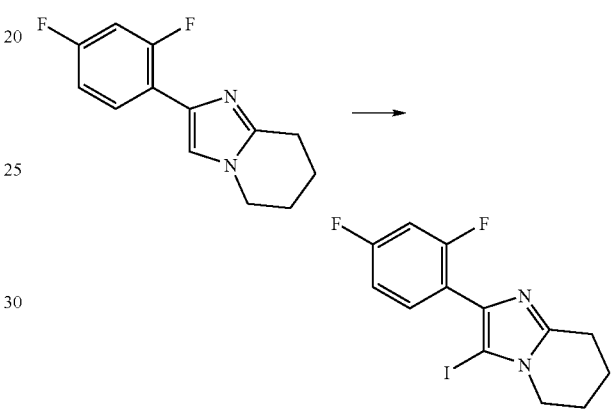

A solution of 2-(2,4-difluorophenyl)-5,6,7,8-tetrahydroimidazo[1,2-a]pyridine (3.25 g, 13.9 mmol, prepared using General Procedure R from Example #8, Step A with 2-iminopiperidine hydrochloride), NIS (3.12 g, 13.9 mmol), and DMF (35 mL) was stirred at ambient temperature. After stirring overnight, the reaction mixture was partitioned between Et$_2$O (400 mL) and water (200 mL). The organic phase was separated and dried over Na$_2$SO$_4$, filtered, and concentrated in vacuo. The crude material was purified by silica gel chromatography using heptane/EtOAc (gradient from 100:0 to 0:100) to give the title compound (3.44 g, 69%). LC/MS (Table 1, Method a) R$_f$=3.32 min; MS m/z: 361.0 (M+H)$^+$.

General Procedure D: Displacement of an Aryl or Heteroaryl Halide with an Amine or Hydrazine To a flask containing an aryl or heteroaryl halide (preferably 1 equiv) is added an organic solvent (such as 1,4-dioxane, butanol, ethanol, or propanol, preferably butanol). Water is optionally added to the reaction flask as a co-solvent. To the mixture is added an amine, hydrazine, or hydrazine hydrate (1-15 equiv, preferably 12 equiv) and the reaction mixture is heated at about 50-100° C. (preferably about 100° C.) for about 1-48 h (preferably about 20 h). Water and an organic solvent (such as EtOAc or DCM) are added to the reaction mixture and the layers are separated. The organic solution is washed with water and brine, dried over Na$_2$SO$_4$ or MgSO$_4$, decanted or filtered, and concentrated to dryness under reduced pressure to give the title compound. Optionally, the crude reaction mixture is directly concentrated under reduced pressure to give the title compound.

Illustration of General Procedure D

Preparation #D.1: 5-(6-Hydrazinylpyridazin-3-yl)-6-(2,4,5-trifluorophenyl)imidazo[2,1-b]oxazole

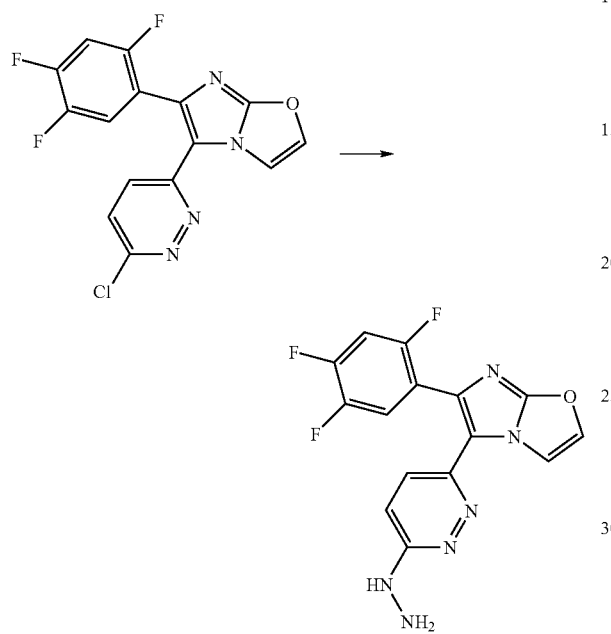

A flask was charged with 5-(6-chloropyridazin-3-yl)-6-(2,4,5-trifluorophenyl)imidazo[2,1-b]oxazole (0.25 g, 0.71 mmol; prepared using General Procedure H from 3,6-dichloropyridazine followed by General Procedure I from 5-iodo-6-(2,4,5-trifluorophenyl)imidazo[2,1-b]oxazole [Example #7, step C]) and n-butanol (2.0 mL) to give a tan suspension. Water (1.0 mL) was added, followed by hydrazine hydrate (0.42 mL, 8.6 mmol). The resulting mixture was heated at about 100° C. for about 20 h. To the cooled reaction mixture were added EtOAc and water and the layers were separated. The aqueous solution was extracted with EtOAc (2×50 mL) and the combined organic extracts were dried over MgSO$_4$, filtered, and the solvents were removed under reduced pressure to give the title compound (0.19 g, 77%): LC/MS (Table 1, Method b) R$_t$=1.58 min; MS m/z 347.1 (M+H)$^+$.

General Procedure E: Hydrazone Formation Followed by Cyclization with Iodobenzene Diacetate A mixture of a substituted pyridazin-2-yl-hydrazine (preferably 1 equiv), an aldehyde (1-5 equiv, preferably 1 equiv), and a suitable organic solvent (such as MeOH and/or DCM) with or without about 1-5 drops (preferably 3 drops) of a suitable acid (such as HOAc, HCl, or H$_2$SO$_4$, preferably HOAc) is stirred at about 0-60° C. (preferably about 10-60° C.) for about 0.5-24 h (preferably about 0.5-12 h). After this time, the reaction is optionally concentrated under reduced pressure then dissolved in a suitable organic solvent (such as DCM or MeOH) and iodobenzene diacetate (1-3 equiv, preferably 1 equiv) is added. The reaction is allowed to stir at ambient temperature for about 0.5-8 h (preferably about 1 h). If the product precipitates during the reaction or upon cooling, it is directly filtered and dried under vacuum to yield the target compound. Alternatively, the mixture may be concentrated under reduced pressure and purified by chromatography, trituration with an appropriate solvent, or crystallization from one or more solvents to yield the target compound.

Illustration of General Procedure E

Example #E.1.1

5-(3-tert-Butyl-[1,2,4]triazolo[4,3-b]pyridazin-6-yl)-6-(2,5-difluorophenyl)imidazo[2,1-b]oxazole

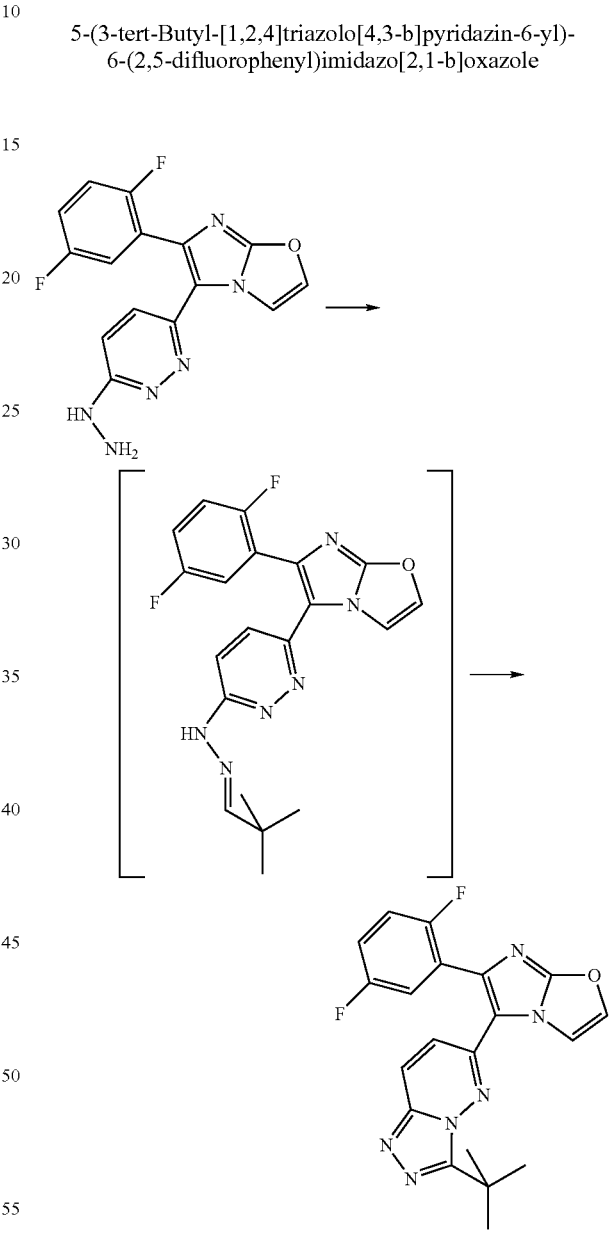

A mixture of 6-(2,5-difluorophenyl)-5-(6-hydrazinylpyridazin-3-yl)imidazo[2,1-b]oxazole (0.30 g, 0.84 mmol; prepared using General Procedure A.1 from 1-(2,5-difluorophenyl)ethanone [Matrix], General Procedure B from oxazole-2-amine [GL Synthesis], General Procedure C with NIS, General Procedure I from 1-chloro-4-iodopyridazine (prepared using General Procedure H from 3,6-dichloropyridazine), and General Procedure D with hydrazine hydrate), trimethylacetaldehyde (0.076 g, 0.88 mmol), and glacial acetic acid (1 drop) was dissolved in DCM (6 mL) and MeOH (1 mL) and stirred at ambient temperature for about 1 h. Iodobenzene diacetate (0.28 g, 0.88 mmol) was added and was stirred for about 1 h at ambient temperature. The reaction was diluted with DCM (75 mL) and washed with saturated $Na_2CO_3$ solution (150 mL) and water (100 mL). The organic layer was dried over $MgSO_4$, filtered, and concentrated under reduced pressure. The crude material was purified by silica gel chromatography using DCM/MeOH (gradient, 97:3 to 90:10). After concentration of the clean fractions, the resulting cream solid was solubilized in hot MeOH, sonicated while cooling, and concentrated under reduced pressure. The resulting solid was dried in a vacuum oven at about 70° C. overnight to provide the title compound as a cream solid (0.22 g, 66%): LC/MS (Table 1, Method a) $R_t$=2.37 min; MS m/z: 395.2 $(M+H)^+$.

General Procedure E.1: Hydrazone Formation Followed by Cyclization with Iodobenzene Diacetate A mixture of a substituted pyridazin-2-yl-hydrazine (preferably 1 equiv), an aldehyde (1-5 equiv, preferably 1.2 equiv), and a suitable organic solvent (such as MeOH and/or DCM) with or without about 1-5 drops (preferably 3 drops) of a suitable acid (such as HOAc, HCl, or $H_2SO_4$, preferably HOAc) is stirred at about 0-75° C. (preferably about 10-70° C.) for about 10 min-48 h (preferably about 1 h). The reaction is optionally concentrated under reduced pressure then dissolved in a suitable organic solvent (such as DCM or MeOH) and iodobenzene diacetate (1-3 equiv, preferably 1.0-1.3 equiv) is added. Optionally, the hydrazone intermediate can be collected by vacuum filtration and a suitable organic solvent (such as DCM or MeOH) is added, followed by the addition of iodobenzene diacetate (1-3 equiv, preferably 1.0-

TABLE E.1

Examples prepared from 6-(2,5-difluorophenyl)-5-(6-hydrazinylpyridazin-3-yl)imidazo[2,1-b]oxazole (prepared using General Procedure A.1 from 1-(2,5-difluorophenyl)ethanone [Matrix], General Procedure B from oxazole-2-amine [GL Synthesis], General Procedure C with NIS, General Procedure I from 1-chloro-4-iodopyridazine (prepared using General Procedure H from 3,6-dichloropyridazine), and General Procedure D with hydrazine hydrate) using General Procedure E

| Aldehyde | Product | Example # | $R_t$ min (method) | m/z ESI+ $(M + H)^+$ |
|---|---|---|---|---|
| 1-Methylcyclobutanecarbaldehyde (prepared according to U.S. Pat. No. 4754059, Example 8) | 6-(2,5-Difluorophenyl)-5-(3-(1-methylcyclobutyl)-[1,2,4]triazolo[4,3-b]pyridazin-6-yl)imidazo[2,1-b]oxazole | E.1.2 | 2.43 (a) | 407.2 |

TABLE E.2

Examples prepared from 5-(6-hydrazinylpyridazin-3-yl)-6-(2,4,5-trifluorophenyl)imidazo[2,1-b]oxazole (Preparation #D.1) using General Procedure E

| Aldehyde | Product | Example # | $R_t$ min (method) | m/z ESI+ $(M + H)^+$ |
|---|---|---|---|---|
| Trimethylacetaldehyde | 5-(3-tert-Butyl-[1,2,4]triazolo[4,3-b]pyridazin-6-yl)-6-(2,4,5-trifluorophenyl)imidazo[2,1-b]oxazole | E.2.1 | 2.46 (a) | 413.2 |
| 1-Methylcyclobutanecarbaldehyde (prepared according to U.S. Pat. No. 4754059, Example 8) | 5-(3-(1-Methylcyclobutyl)-[1,2,4]triazolo[4,3-b]pyridazin-6-yl)-6-(2,4,5-trifluorophenyl)imidazo[2,1-b]oxazole | E.2.2 | 2.55 (a) | 425.2 |

TABLE E.3

Examples prepared from 6-(2,4-difluorophenyl)-5-(6-hydrazinylpyridazin-3-yl)imidazo[2,1-b]oxazole (Example #40, Step B) using General Procedure E

| Aldehyde | Product | Example # | $R_t$ min (method) | m/z ESI+ $(M + H)^+$ |
|---|---|---|---|---|
| Trimethylacetaldehyde | 5-(3-tert-Butyl-[1,2,4]triazolo[4,3-b]pyridazin-6-yl)-6-(2,4-difluorophenyl)imidazo[2,1-b]oxazole | E.3.1 | 2.15 (a) | 395.2 |

1.3 equiv). The reaction is stirred at ambient temperature for about 5 min-24 h (preferably about 0.5-1 h). If the product precipitates during the reaction or upon cooling, it can be collected by vacuum filtration to give the target compound. Alternatively, the reaction mixture may be optionally diluted with an organic solvent (such as DCM or EtOAc). The organic layer is washed with an aqueous base such as saturated aqueous NaHCO$_3$. The layers are separated and the organic solution is optionally washed with water and brine. The organic layer is dried over a suitable drying agent (such as Na$_2$SO$_4$ or MgSO$_4$), filtered, and concentrated to dryness under reduced pressure. The crude product can be purified by chromatography, trituration with an appropriate solvent, and/or crystallization from one or more solvents to yield the target compound.

Illustration of General Procedure E.1

Preparation #E.1.1.1: 3-(1-(tert-Butyldimethylsilyloxy)-2-methylpropan-2-yl)-6-(2-(2,4-difluorophenyl)-6,7-dihydro-5H-pyrrolo[1,2-a]imidazol-3-yl)-[1,2,4]triazolo[4,3-b]pyridazine

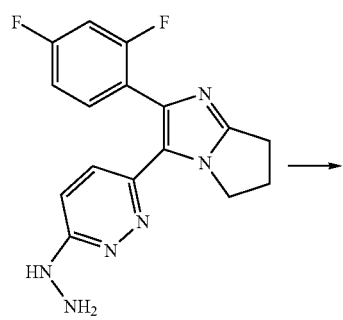

→

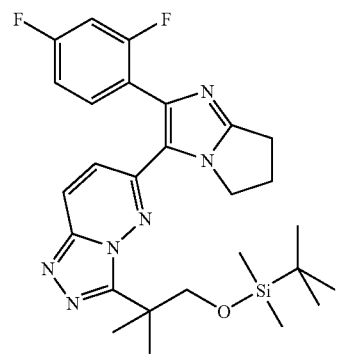

2-(2,4-Difluorophenyl)-3-(6-hydrazinylpyridazin-3-yl)-6,7-dihydro-5H-pyrrolo[1,2-a]imidazole (6.00 g, 18.3 mmol, Example #35, Step E) was suspended in DCM (125 μL) then 3-(tert-butyldimethylsilyloxy)-2,2-dimethylpropanal (4.15 g, 19.2 mmol, *J. Org. Chem.*, 2002, 67, 2474-2480) was added. The mixture was stirred at ambient temperature for about 2 h. Iodobenzene diacetate (6.00 g, 18.6 mmol) was added then the mixture was stirred for about 30 min. Saturated aqueous NaHCO$_3$ (150 mL) was added then the layers were separated. The organic layer was dried over MgSO$_4$, filtered and concentrated in vacuo. The material was purified by flash chromatography on silica gel with EtOAc as an eluent to give the title compound (8.67 g, 90%): LC/MS (Table 1, Method g) R$_t$=2.77 min; MS m/z: 525.3.2 (M+H)$^+$.

TABLE E.1.1

Preparations prepared from 2-(2,4-difluorophenyl)-3-(6-hydrazinylpyridazin-3-yl)-6,7-dihydro-5H-pyrrolo[1,2-a]imidazole (Example #35, Step E) using General Procedure E.1

| Aldehyde | Product | Example # | R$_t$ min (method) | m/z ESI+ (M + H)$^+$ |
|---|---|---|---|---|
| 1-(tert-Butyldimethylsilyloxy)cyclopropanecarbaldehyde [prepared according to *Bioorg. Med. Chem. Lett.*, 17(22), 6290-6294, 2007] | 3-(1-(tert-Butyldimethylsilyloxy)cyclopropyl)-6-(2-(2,4-difluorophenyl)-6,7-dihydro-5H-pyrrolo[1,2-a]imidazol-3-yl)-[1,2,4]triazolo[4,3-b]pyridazine | E.1.1.2 | 1.57 (k) | 509.4 |
| 1-((tert-Butyldimethylsilyloxy)methyl)cyclobutanecarbaldehyde [Preparation #AK.1.1] | 3-(1-((tert-Butyldimethylsilyloxy)methyl)cyclobutyl)-6-(2-(2,4-difluorophenyl)-6,7-dihydro-5H-pyrrolo[1,2-a]imidazol-3-yl)-[1,2,4]triazolo[4,3-b]pyridazine | E.1.1.3 | 2.83 (h) | 537.2 |

TABLE E.1.2

Examples prepared from 6-(2,4-difluorophenyl)-5-(6-hydrazinylpyridazin-3-yl)imidazo[2,1-b]oxazole (Example #40, Step B) using General Procedure E.1

| Aldehyde | Product | Example # | $R_t$ min (method) | m/z ESI+ (M + H)+ |
|---|---|---|---|---|
| Cyclopropanecarbaldehyde | 5-(3-Cyclopropyl-[1,2,4]triazolo[4,3-b]pyridazin-6-yl)-6-(2,4-difluorophenyl)imidazo[2,1-b]oxazole | E.1.2.1 | 1.97 (b) | 379.2 |
| Methacrolein | 6-(2,4-Difluorophenyl)-5-(3-(prop-1-en-2-yl)-[1,2,4]triazolo[4,3-b]pyridazin-6-yl)imidazo[2,1-b]oxazole | E.1.2.2 | 2.52 (g) | 379.2 |
| Tetrahydro-2H-pyran-4-carbaldehyde (CHN Technologies) | 6-(2,4-Difluorophenyl)-5-(3-(tetrahydro-2H-pyran-4-yl)-[1,2,4]triazolo[4,3-b]pyridazin-6-yl)imidazo[2,1-b]oxazole | E.1.2.3 | 2.10 (g) | 423.2 |
| Tetrahydro-2H-pyran-3-carbaldehyde | 6-(2,4-Difluorophenyl)-5-(3-(tetrahydro-2H-pyran-3-yl)-[1,2,4]triazolo[4,3-b]pyridazin-6-yl)imidazo[2,1-b]oxazole | E.1.2.4 | 1.86 (g) | 422.9 |
| 2-(2-Methoxyethoxy)acetaldehyde [prepared according to *Zhongguo Yiyao Gongye Zazhi* 2002, 33(6), 269-270] | 6-(2,4-Difluorophenyl)-5-(3-((2-methoxyethoxy)methyl)-[1,2,4]triazolo[4,3-b]pyridazin-6-yl)imidazo[2,1-b]oxazole | E.1.2.5 | 1.81 (g) | 427.1 |
| 1-(Hydroxymethyl)cyclopropanecarbaldehyde [prepared using AI.1 from cyclopropane-1,1-diyldimethanol] | (1-(6-(6-(2,4-Difluorophenyl)imidazo[2,1-b]oxazol-5-yl)-[1,2,4]triazolo[4,3-b]pyridazin-3-yl)cyclopropyl)methanol | E.1.2.6 | 1.67 (g) | 409.3 |
| 1-(Methoxymethyl)cyclopropanecarbaldehyde [prepared using AE from cyclopropane-1,1-diyldimethanol, AI.1] | 6-(2,4-Difluorophenyl)-5-(3-(1-(methoxymethyl)cyclopropyl)-[1,2,4]triazolo[4,3-b]pyridazin-6-yl)imidazo[2,1-b]oxazole | E.1.2.7 | 1.89 (g) | 423.1 |
| 2-Methoxyacetaldehyde (Scandanavian Formulas) | 6-(2,4-Difluorophenyl)-5-(3-(methoxymethyl)-[1,2,4]triazolo[4,3-b]pyridazin-6-yl)imidazo[2,1-b]oxazole | E.1.2.8 | 1.85 (g) | 383.1 |
| 1-Formylcyclopropanecarbonitrile [prepared according to US 2007/0135461, Example 739, Steps 1 and 2] | 1-(6-(6-(2,4-Difluorophenyl)imidazo[2,1-b]oxazol-5-yl)-[1,2,4]triazolo[4,3-b]pyridazin-3-yl)cyclopropanecarbonitrile | E.1.2.9 | 1.93 (g) | 404.8 |
| 3-Methyloxetane-3-carbaldehyde [prepared according to WO1994/05281, example 17 step 1] | 6-(2,4-Difluorophenyl)-5-(3-(3-methyloxetan-3-yl)-[1,2,4]triazolo[4,3-b]pyridazin-6-yl)imidazo[2,1-b]oxazole | E.1.2.10 | 1.85 (g) | 409.1 |
| 4-Methyltetrahydro-2H-pyran-4-carbaldehyde [prepared according to WO2006/001752, Method S steps 1 through 3] | 6-(2,4-Difluorophenyl)-5-(3-(4-methyltetrahydro-2H-pyran-4-yl)-[1,2,4]triazolo[4,3-b]pyridazin-6-yl)imidazo[2,1-b]oxazole | E.1.2.11 | 1.91 (g) | 437.2 |
| 3-Methoxy-3-methylbutanal [prepared using AI.1 from 3-methoxy-3-methylbutan-1-ol] | 6-(2,4-Difluorophenyl)-5-(3-(2-methoxy-2-methylpropyl)-[1,2,4]triazolo[4,3-b]pyridazin-6-yl)imidazo[2,1-b]oxazole | E.1.2.12 | 1.98 (g) | 425.2 |
| 2,2-Dimethyl-3-oxopropanenitrile [prepared using AL from ethyl 2-cyano-2-methylpropanoate (TCI) using, AI.1] | 2-(6-(6-(2,4-Difluorophenyl)imidazo[2,1-b]oxazol-5-yl)-[1,2,4]triazolo[4,3-b]pyridazin-3-yl)-2-methylpropanenitrile | E.1.2.13 | 2.04 (g) | 406.2 |

TABLE E.1.3

Examples prepared from 2-(2,4-difluorophenyl)-3-(6-hydrazinylpyridazin-3-yl)-6,7-dihydro-5H-pyrrolo[1,2-a]imidazole (Example #35, Step E) using General Procedure E.1

| Aldehyde | Product | Example # | $R_t$ min (method) | m/z ESI+ $(M + H)^+$ |
|---|---|---|---|---|
| 3-Hydroxy-3-methylbutanal [Example #40, step C] | 1-(6-(2-(2,4-Difluorophenyl)-6,7-dihydro-5H-pyrrolo[1,2-a]imidazol-3-yl)-[1,2,4]triazolo[4,3-b]pyridazin-3-yl)-2-methylpropan-2-ol | E.1.3.1 | 1.63 (g) | 411.2 |
| 1-Formylcyclopropanecarbonitrile [prepared according to US 2007/0135461, Example 739, Steps 1 and 2] | 1-(6-(2-(2,4-Difluorophenyl)-6,7-dihydro-5H-pyrrolo[1,2-a]imidazol-3-yl)-[1,2,4]triazolo[4,3-b]pyridazin-3-yl)cyclopropanecarbonitrile | E.1.3.2 | 1.85 (g) | 403.9 |
| 3-Methoxy-3-methylbutanal [prepared using AI.1 from 3-methoxy-3-methylbutan-1-ol] | 6-(2-(2,4-Difluorophenyl)-6,7-dihydro-5H-pyrrolo[1,2-a]imidazol-3-yl)-3-(2-methoxy-2-methylpropyl)-[1,2,4]triazolo[4,3-b]pyridazine | E.1.3.3 | 1.75 (g) | 425.2 |
| 3-Methyloxetane-3-carbaldehyde [prepared using AI.1 from 3-methyloxetan-3-yl)methanol] | 6-(2-(2,4-Difluorophenyl)-6,7-dihydro-5H-pyrrolo[1,2-a]imidazol-3-yl)-3-(3-methyloxetan-3-yl)-[1,2,4]triazolo[4,3-b]pyridazine | E.1.3.4 | 1.71 (g) | 409.2 |
| 2,6-Difluorobenzaldehyde | 3-(2,6-Difluorophenyl)-6-(2-(2,4-difluorophenyl)-6,7-dihydro-5H-pyrrolo[1,2-a]imidazol-3-yl)-[1,2,4]triazolo[4,3-b]pyridazine | E.1.3.5 | 1.94 (a) | 451.2 |

TABLE E.1.4

Preparations prepared from 6-(2,4-difluorophenyl)-5-(6-hydrazinylpyridazin-3-yl)imidazo[2,1-b]oxazole (Example #40, Step B) using General Procedure E.1

| Aldehyde | Product | Example # | $R_t$ min (method) | m/z ESI+ $(M + H)^+$ |
|---|---|---|---|---|
| 1-((tert-Butyldimethylsilyloxy)methyl)cyclobutanecarbaldehyde [prepared according to DE 19735574 A1, Example #8c] | 5-(3-(1-((tert-Butyldimethylsilyloxy)methyl)cyclobutyl)-[1,2,4]triazolo[4,3-b]pyridazin-6-yl)-6-(2,4-difluorophenyl)imidazo[2,1-b]oxazole | E.1.4.1 | 3.01 (h) | 537.2 |

General Procedure F: Formation of a Terminal Alkyne from an Alkynyl Silane

A mixture of an alkynyl silane (preferably 1 equiv), an organic solvent (such as MeOH, or EtOH; preferably MeOH), and a base (such as $K_2CO_3$, 0.1-2.0 equiv, preferably 0.1 equiv) is stirred at ambient temperature for about 1-36 h (preferably about 3-16 h). The reaction is quenched with water and then extracted with an organic solvent (such as EtOAc, $Et_2O$, DCM or pentane; preferably $Et_2O$ or pentane). The combined organic layers may be optionally washed with brine, dried over $Na_2SO_4$ or $MgSO_4$, and then decanted or Illustration of General Procedure F Preparation #F.1: 1-Ethynyl-2,4,5-trifluorobenzene

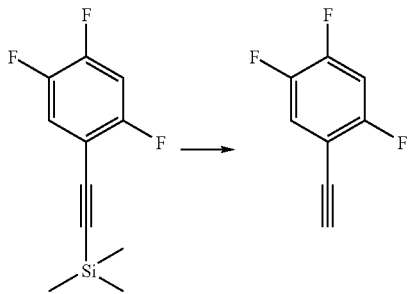

A mixture of trimethyl((2,4,5-trifluorophenyl)ethynyl)silane (10 g, 46 mmol, prepared using General Procedure J from 1-bromo-2,4,5-trifluorobenzene and ethynyltrimethylsilane), $K_2CO_3$ (0.64 g, 4.6 mmol) and MeOH (25 mL) was stirred at ambient temperature for about 3.5 h. The reaction was quenched with water and extracted with $Et_2O$. The organic layer was concentrated under reduced pressure. The crude material was purified by silica gel chromatography using pentane as eluent to give the title compound as oil (1.5 g, 21% yield): LC/MS (Table 1, Method a) $R_t$=3.58 min; $^1$H NMR ($CDCl_3$) $\delta$3.38 (s, 1 H), 7.00-7.06 (m, 1 H), 7.35-7.40 (m, 1 H). Additional product (5.6 g, ~40% purity, ~33%) was recovered from rotary evaporator condenser.

General Procedure G: Cyclization of a Hydrazinylpyridazine with an Acid Chloride To a mixture of a substituted hydrazinylpyridazine (preferably 1 equiv) and an organic solvent (such as 1,4-dioxane) is added an acid chloride (1-10 equiv, preferably 1-3 equiv) and then the reaction is heated at reflux for about 1-18 h (preferably about 4-8 h). Alternatively, a substituted hydrazinylpyridazine is heated in an acid chloride (5-20 equiv, preferably 10-15 equiv) at about 60-110° C. (preferably about 80-100° C.). The reaction is cooled to ambient temperature and poured into water. The pH is adjusted to about pH 8-14 (preferably about pH 9-12) with the slow addition of a base such as $Na_2CO_3$ or NaOH and is then extracted with an organic solvent such as EtOAc or DCM. The combined organic layers may be optionally washed with brine, dried over $Na_2SO_4$ or $MgSO_4$, and then decanted or filtered prior to concentrating under reduced pressure. The crude product is used as is or is purified by crystallization or trituration from an appropriate solvent or solvents, or by chromatography to give the target compound.

Illustration of General Procedure G

Preparation #G.1: 6-Chloro-3-isopropyl-[1,2,4]triazolo[4,3-b]pyridazine

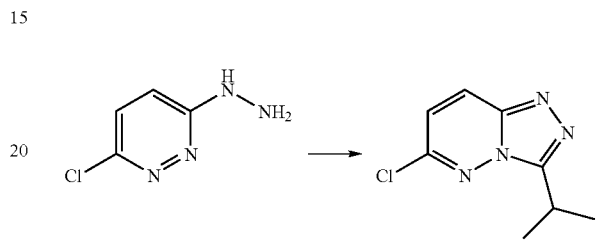

A mixture of 3-chloro-6-hydrazinylpyridazine (200 g, 1.38 mol) and isobutyryl chloride (175 mL, 1.66 mol) in 1,4-dioxane (2 L) was heated at about 90° C. overnight. The suspension was cooled to about 5° C. in an ice bath and then water (2 L) was added followed by slow addition of $Na_2CO_3$ (275 g, 2.59 mol). The resulting solution was extracted with DCM (3×1 L). The combined organic extracts were dried over $MgSO_4$, concentrated under reduced pressure, and dried under vacuum overnight to give the title compound (255 g, 94%): LC/MS (Table 1, Method a) $R_t$=2.04 min; MS m/z: 197.1 $(M+H)^+$.

General Procedure H: Formation of a Heteroaryl Iodide from a Heteroaryl Chloride A mixture of a heteroaryl chloride (preferably 1 equiv), sodium iodide (1-10 equivalents, preferably 1-2 equiv), and hydriodic acid (preferably 57% in water, stabilized; 1-10 equiv, preferably 5-10 equiv) is heated at reflux for about 3 h to 25 d (preferably about 3 h-4 days). If the reaction is progressing slowly, additional hydriodic acid and/or sodium iodide may be added to the reaction. Alternatively, the reaction is filtered and the solid is subjected to additional hydriodic acid and/or sodium iodide. The reaction is then cooled to ambient temperature and the pH is adjusted to about pH 8-14 (preferably about pH 9-12) with the slow addition of a base such as aqueous NaOH, while cooling either by adding ice to the reaction flask or externally in an ice bath. The basic mixture is extracted with an organic solvent such as EtOAc or DCM. The combined organic layers may be optionally washed with brine, dried over $Na_2SO_4$ or $MgSO_4$, and then decanted or filtered prior to concentrating under reduced pressure. If analysis of the crude material indicates the reaction is incomplete, the crude product may be subjected to additional hydriodic acid and/or sodium iodide as above. The crude product may be used as is or is purified by crystallization or trituration from an appropriate solvent or solvents, or by chromatography to give the target compound.

Illustration of General Procedure H

Preparation #H.1: 6-Iodo-3-isopropyl-[1,2,4]triazolo[4,3-b]pyridazine

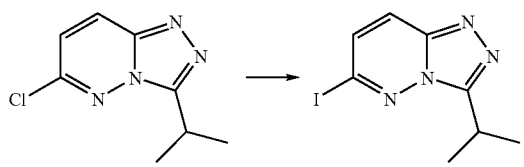

Two reactions were set up side by side as follows. Each 250 mL round bottom flask was charged with 6-chloro-3-isopropyl-[1,2,4]triazolo[4,3-b]pyridazine (7.5 g, 38.1 mmol, Preparation #G.1), sodium iodide (8.58 g, 57.2 mmol) and hydriodic acid (57 wt % in water, stabilized with <1.5% hypophosphorous acid; 52.1 mL, 381 mmol). The mixture was heated in an oil bath to about 90° C. with stirring for about 4 days. The combined reactions were filtered then the filtrate was basified with 25 wt % aqueous NaOH. The solids from the filtration were then added to the filtrate (still basic) and extracted with DCM (750 mL). The organic phase was dried over MgSO$_4$, filtered, and concentrated under reduced pressure. The crude product was crystallized from DMF (90 mL, about 90° C.) to give the title compound (17.3 g, 78%): LC/MS (Table 1, Method a) R$_t$=1.67 min; MS m/z: 289.0 (M+H)$^+$.

General Procedure I: Negishi Coupling of a Heteroaryl Halide and a Heteroaryl Halide To an appropriately dried flask containing a heteroaryl halide (preferably 1 equiv) in a suitable solvent (such as THF) at a suitable temperature (about −50° C. to ambient temperature, preferably at about −50-0° C.) is added a suitable Grignard reagent dropwise (1-3 equiv, preferably 1.2 equiv, such as i-PrMgCl or i-PrMgBr, preferably i-PrMgCl). The reaction mixture is stirred at about −50-0° C. for about 15 min to 1 h (preferably about 15 min). To a separate flask containing either anhydrous solid zinc chloride (1-2 equiv, preferably 1.3 equiv) or a commercially available zinc chloride solution (1-2 equiv, preferably 1.3 equiv) in a suitable solvent (such as THF) is optionally added a suitable Grignard reagent dropwise (0-1 equiv, preferably 0-0.2 equiv, such as i-PrMgCl or i-PrMgBr, preferably i-PrMgCl). This solution is then added dropwise to the heteroaryl Grignard solution at about −50° C. to ambient temperature (preferably at about −50-0° C.). The reaction mixture is stirred at about −50° C. to ambient temperature (preferably at about −50-0° C.) for about 30 min to 1 h (preferably about 30 min). To a separate flask containing a heteroaryl halide (0.9 to 1.5 equiv, preferably 0.9 equiv) is added suitable solvent (such as DMF), with heating until all solids are dissolved, and then a suitable catalyst (such as Pd(PPh$_3$)$_4$; 0.01-0.1 equiv, preferably 0.04 equiv) is added. This mixture is then added to the zincate suspension in one portion. The reaction mixture is then heated at about 50-100° C. (preferably about 50-80° C.) for about 3 min to 18 h (preferably about 3 min-2 h). After cooling to about ambient temperature, the solvents are removed under reduced pressure. To the residue is added an organic solvent (for example, EtOAc or DCM) and an acidic solution (preferably 1N HCl). The layers are separated and the organic layer is washed with additional acidic solution (preferably 1N HCl). The organic layer is then washed with a higher concentration of acidic solution (such as 5N HCl or 6N HCl) about 1-4 times (preferably 3 times) and then discarded. The combined higher concentration acidic washes are then neutralized with an appropriate base (such as solid Na$_2$CO$_3$). The aqueous layer is then back extracted about 1-4 times (preferably 3 times) with an appropriate organic solvent (for example, EtOAc or DCM). The combined organic layers may be optionally washed with water or brine, dried over Na$_2$SO$_4$ or MgSO$_4$, then decanted or filtered, prior to concentrating under reduced pressure. The crude product is purified by crystallization or trituration from an appropriate solvent or solvents, or by chromatography to give the target compound. Optionally, the reaction mixture may be concentrated to dryness and dissolved in an appropriate organic solvent (for example, DCM or EtOAc). The organic solution is washed with water, dried over Na$_2$SO$_4$ or MgSO$_4$, then decanted or filtered, concentrated under reduced pressure, and is purified by crystallization or trituration from an appropriate solvent or solvents, or by chromatography to give the target compound.

Illustration of General Procedure I

Example #I.1.1

6-(2,4-Difluorophenyl)-5-(3-isopropyl-[1,2,4]triazolo[4,3-b]pyridazin-6-yl)imidazo[2,1-b]oxazole

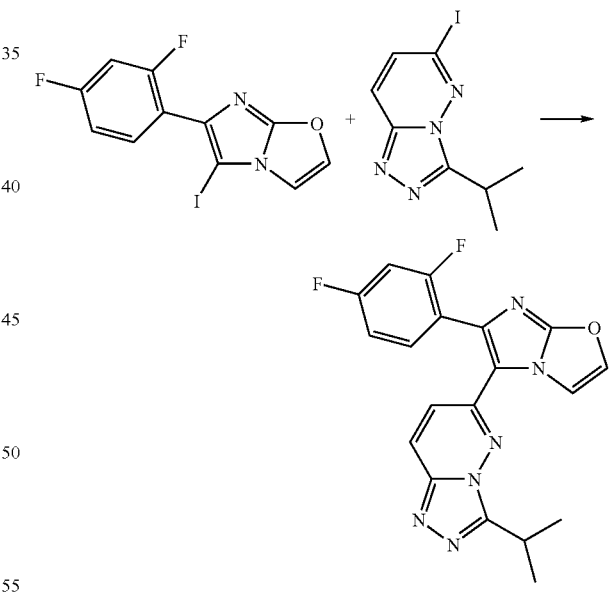

In a dry three-neck flask, 6-(2,4-difluorophenyl)-5-iodoimidazo[2,1-b]oxazole (15.0 g, 43.3 mmol, Preparation #C.1) was dissolved in THF (113 mL) under an atmosphere of nitrogen. The reaction mixture was cooled to about −50° C. and then i-PrMgCl (2.0 M in THF, 15.3 mL, 30.5 mmol) was added dropwise. The reaction mixture was stirred at about −50° C. for about 15 min. In a separate dry flask, zinc chloride (7.98 g, 58.5 mmol) was dissolved in THF (88 mL). The zinc chloride solution was added dropwise to the heteroaryl Grignard and formed a light yellow suspension. The reaction mixture was stirred while warming to about 0° C. over about 30 min. In a separate flask, a mixture of 6-iodo-3-isopropyl-[1,2,4]triazolo[4,3-b]pyridazine (11.9 g, 41.2 mmol; Preparation #H.1) and DMF (120 mL) was heated at about 80° C. until all of the solids were in solution then Pd(Ph$_3$P)$_4$ (Strem, 2.00 g, 1.73 mmol) was added. This solution was poured into the reaction flask and the mixture was immediately heated to about 80° C. in an oil bath. After heating at about 80° C. for about 30 min, the mixture was cooled to ambient temperature. The reaction was concentrated in vacuo and the residue was partitioned between in DCM (200 mL) and 1N HCl (50 mL). The layers were separated, the aqueous layer was discarded, and the organic layer was washed with additional 1N HCl (total of 400 mL). An orange solid was filtered from the organic layer and discarded (inorganic materials). The organic layer was extracted with 5N HCl (160 mL) and then discarded. The acidic aqueous layer was basified with solid Na$_2$CO$_3$ (about 40 g) and extracted with DCM. The emulsion that formed during extraction was filtered through Florisil® and washed with DCM (1 L) to give a yellow solution that was concentrated under reduced pressure, dissolved in DCM (200 mL), and washed with water (500 mL). The organic layer was then dried over MgSO$_4$, filtered, and concentrated under reduced pressure under reduced pressure to give a yellow solid that was triturated with ACN and filtered to give the title compound as white solid (3.89 g). The mother liquor was concentrated and further purified by flash silica gel chromatography using DCM/MeOH (gradient, 1:0 to 19:1). The product-containing fractions were combined and concentrated under reduced pressure to give additional title compound as white solid (0.80 g). The Florisil® from the emulsion filtration was eluted with DCM/MeOH 9:1 (1 L) and then MeOH (1 L). These filtrates were combined and concentrated under reduced pressure. The residue was then dissolved in DCM (300 mL), and the organic solution washed with water (500 mL), dried over MgSO$_4$, filtered, and concentrated under reduced pressure to give a reddish-brown solid that was triturated with ACN and filtered to give a slightly pink solid. This solid was then triturated with MeOH and washed with ACN to give additional title compound as a cream colored solid (3.84 g). The mother liquor was concentrated and the resulting solid was triturated with ACN then filtered to give additional title compound as a light yellow solid (1.17 g). The final mother liquor was concentrated and then further purified by flash silica gel chromatography using DCM/MeOH (gradient, 1:0 to 19:1). The product-containing fractions were combined and concentrated under reduced pressure to give additional title compound as light yellow product (1.3 g). In total the reaction yielded 11 g (66%) of the title compound: LC/MS (Table 1, Method a) R$_t$=2.36 min; MS m/z: 381.2 (M+H)$^+$.

TABLE I.1

Examples prepared from 6-(2,4-difluorophenyl)-5-iodoimidazo[2,1-b]oxazole (Preparation #C.1) using General Procedure I

| Triazolopyridazine | Product | Example # | R$_t$ min (method) | m/z ESI+ (M + H)$^+$ |
|---|---|---|---|---|
| 6-Iodo-3-(1-methylcyclobutyl)-[1,2,4]triazolo[4,3-b]pyridazine [prepared using H from 3,6-dichloropyridazine, D with hydrazine, E from 1-methylcyclobutanecarbaldehyde (U.S. Pat. No. 4754059 Example 8)] | 6-(2,4-Difluorophenyl)-5-(3-(1-methylcyclobutyl)-[1,2,4]triazolo[4,3-b]pyridazin-6-yl)imidazo[2,1-b]oxazole | I.1.2 | 2.09 (a) | 407.2 |

TABLE I.2

Examples prepared from 6-(2,5-difluorophenyl)-5-iodoimidazo[2,1-b]oxazole (prepared using General Procedure A.1 from 1-(2,5-difluorophenyl)ethanone [Matrix], General Procedure B from oxazole-2-amine [GL Synthesis], General Procedure C with NIS) using General Procedure I

| Heteroaryl Halide | Product | Example # | R$_t$ min (method) | m/z ESI+ (M + H)$^+$ |
|---|---|---|---|---|
| 6-Iodo-3-isopropyl-[1,2,4]triazolo[4,3-b]pyridazine (Preparation #H.1) | 6-(2,5-Difluorophenyl)-5-(3-isopropyl-[1,2,4]triazolo[4,3-b]pyridazin-6-yl)imidazo[2,1-b]oxazole | I.2.1 | 2.24 (a) | 381.2 |

General Procedure I.1: Negishi Coupling of a Heteroaryl Halide and a Heteroaryl Halide To an appropriately dried flask containing a heteroaryl halide (preferably 1 equiv) in a suitable solvent (such as THF) at a suitable temperature (about −60° C.-ambient temperature, preferably at about −60-0° C.) is added a suitable Grignard reagent dropwise (1-3 equiv, preferably 1.2 equiv, such as i-PrMgCl or i-PrMgBr, preferably i-PrMgCl). The reaction mixture is stirred at about −60-0° C. for about 15 min-1 h (preferably about 15 min). To a separate flask containing either anhydrous solid zinc chloride (1-2 equiv, preferably 1.3 equiv) or a commercially available zinc chloride solution (1-2 equiv, preferably 1.3 equiv) in a suitable solvent (such as THF) is optionally added a suitable Grignard reagent dropwise (0-1 equiv, preferably 0-0.2 equiv, such as i-PrMgCl or i-PrMgBr, preferably i-PrMgCl). This solution is then added dropwise to the heteroaryl Grignard solution at about −60° C.-ambient temperature (preferably at about −60-0° C.). The reaction mixture is stirred at about −60° C.-ambient temperature (preferably at about −60-0° C.) for about 30 min-2 h (preferably about 30 min). To a separate flask containing a heteroaryl halide (0.9-1.5 equiv, preferably 0.9 equiv) is added a suitable solvent (such as DMF or DMA) which is optionally heated until all the solids are dissolved. Then a suitable catalyst (such as Pd(PPh$_3$)$_4$; 0.01-0.1 equiv, preferably 0.04 equiv) is added. This mixture is then added to the reaction flask in one portion. The reaction mixture is then stirred at about 20-100° C. (preferably about 50-80° C.) for about 3 min to 18 h (preferably about 3 min-3 h). After cooling to about ambient temperature, the mixture is optionally filtered to remove the solid salts. The solvents are removed under reduced pressure. The crude material is optionally triturated with an appropriate solvent (such as, heptane, ether, propanol, preferably n-propanol). To the residue is added an organic solvent (for example, EtOAc or DCM) and an acidic solution (1-6N HCl, preferably 1N HCl). The layers are separated and the organic layer is optionally extracted with additional acidic solution (1-6N HCl, preferably 1N HCl). The organic layer is then optionally washed with a higher concentration of acidic solution (such as 5-6N HCl) about 1-4 times (preferably 3 times). The acidic aqueous layers are combined, optionally washed with an organic solvent (such as EtOAc or DCM) and then neutralized with an appropriate base (such as solid Na$_2$CO$_3$ or saturated aqueous Na$_2$CO$_3$, saturated aqueous NaHCO$_3$ or 10-50% aqueous NaOH) and the solid may optionally be collected by filtrations. Alternatively, the aqueous layer is then back extracted about 1-4 times (preferably 3 times) with an appropriate organic solvent (for example, EtOAc or DCM). The combined organic layers or the organic layer from the initial acid wash may be optionally washed with water or brine, dried over Na$_2$SO$_4$ or MgSO$_4$, then decanted or filtered, prior to concentrating under reduced pressure. The crude product is purified by crystallization or trituration from an appropriate solvent or solvents, or by chromatography to give the target compound. Alternatively, the reaction mixture may be concentrated to dryness and dissolved in an appropriate organic solvent (for example, DCM or EtOAc). The organic solution is washed with water, dried over Na$_2$SO$_4$ or MgSO$_4$, then decanted or filtered, concentrated under reduced pressure, and is purified by crystallization or trituration from an appropriate solvent or solvents, or by chromatography to give the target compound.

Illustration of General Procedure I.1

Example #I.1.1.1

6-(2-(2,4-Difluorophenyl)-5,6,7,8-tetrahydroimidazo[1,2-a]pyridin-3-yl)-3-isopropyl-[1,2,4]triazolo[4,3-b]pyridazine

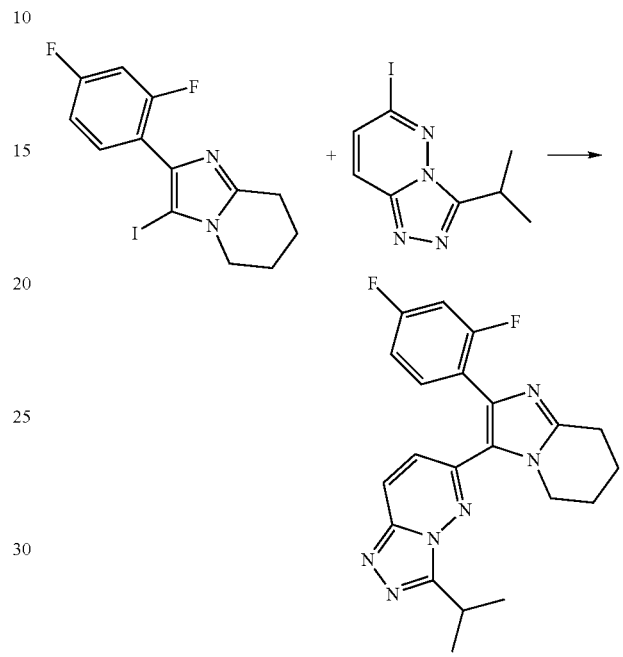

A dried round bottom flask was charged with 2-(2,4-difluorophenyl)-3-iodo-5,6,7,8-tetrahydroimidazo[1,2-a]pyridine (1.50 g, 4.17 mmol, Example #C.1.1) and THF (20 mL) under an atmosphere of nitrogen to give a brown suspension. The reaction mixture was cooled to about 30° C. and then i-PrMgCl (2.0 M in THF, 2.5 mL, 5.0 mmol) was added dropwise. The reaction mixture was stirred at about −25° C. for about 15 min. In a separate dry flask, zinc chloride (0.70 g, 5.1 mmol) was dissolved in THF (20 mL). The zinc chloride solution was added dropwise to the heteroaryl Grignard solution and formed a brown suspension. The reaction mixture was stirred for about 30 min. In a separate flask, a mixture 6-iodo-3-isopropyl-[1,2,4]triazolo[4,3-b]pyridazine (1.14 g, 3.96 mmol; Preparation #H.1) and DMF (20 mL) was heated until all of the solids were in solution and then cooled down to about 30° C. To the DMF solution, Pd(Ph$_3$P)$_4$ (Strem, 0.19 g, 0.164 mmol) was added. This solution was poured into the zincate suspension and the mixture was immediately heated to about 80° C. in an oil bath. After heating at about 80° C. for about 3 h, the mixture was cooled to ambient temperature. The reaction was concentrated in vacuo and the residue was partitioned between in DCM (50 mL) and 1N HCl (100 mL). The layers were separated and the aqueous layer was washed with additional DCM (50 mL) and basified with solid Na$_2$CO$_3$. Upon basification, a yellow precipitate formed that was collected by vacuum filtration. The crude material was purified by silica gel chromatography using DCM/MeOH/NH$_4$OH 990/9/1 to give a glass-like solid that was triturated and washed with Et$_2$O to give the title compound (0.111 g, 7%): LC/MS (Table 1, Method a) R$_f$=2.75 min; MS m/z: 395.5 (M+H)$^+$.

TABLE I.1.1

Examples prepared from 2-(2,4-difluorophenyl)-3-iodo-5,6,7,8-tetrahydroimidazo[1,2-a]pyridine (Example #C.1.1) using General Procedure I.1

| Heteroaryl Halide | Product | Example # | $R_t$ min (method) | m/z ESI+ (M + H)+ |
|---|---|---|---|---|
| 3-Cyclopropyl-6-iodo-[1,2,4]triazolo[4,3-b]pyridazine [prepared using D from Preparation #9, Step A with hydrazine, E.1 with cyclopropanecarbaldehyde] | 3-Cyclopropyl-6-(2-(2,4-difluorophenyl)-5,6,7,8-tetrahydroimidazo[1,2-a]pyridin-3-yl)-[1,2,4]triazolo[4,3-b]pyridazine | I.1.1.2 | 2.07 (a) | 393.2 |
| Ethyl 6-iodo-[1,2,4]triazolo[4,3-b]pyridazine-3-carboxylate [Example #37, Step C] | Ethyl 6-(2-(2,4-difluorophenyl)-5,6,7,8-tetrahydroimidazo[1,2-a]pyridin-3-yl)-[1,2,4]triazolo[4,3-b]pyridazine-3-carboxylate | I.1.1.3 | 2.23 (a) | 425.1 |
| Ethyl 6-iodo-[1,2,4]triazolo[4,3-b]pyridazine-3-carboxylate [Example #37, Step C] | Isopropyl 6-(2-(2,4-difluorophenyl)-5,6,7,8-tetrahydroimidazo[1,2-a]pyridin-3-yl)-[1,2,4]triazolo[4,3-b]pyridazine-3-carboxylate | I.1.1.4 | 2.29 (a) | 439.2 |

25

TABLE I.1.2

Examples prepared from 6-(2,4-difluorophenyl)-5-iodoimidazo[2,1-b]oxazole (Preparation #C.1) using General Procedure I.1

| Heteroaryl Halide | Product | Example # | $R_t$ min (method) | m/z ESI+ (M + H)+ |
|---|---|---|---|---|
| 3-Cyclobutyl-6-iodo-[1,2,4]triazolo[4,3-b]pyridazine [prepared using G from 3-chloro-6-hydrazinylpyridazine and cyclobutanecarbonyl chloride, H] | 5-(3-Cyclobutyl-[1,2,4]triazolo[4,3-b]pyridazin-6-yl)-6-(2,4-difluorophenyl)imidazo[2,1-b]oxazole | I.1.2.1 | 2.47 (a) | 393.2 |
| 6-Iodo-3-(trifluoromethyl)-[1,2,4]triazolo[4,3-b]pyridazine [prepared using D from Example #9, Step A with hydrazine, E.1 from 2,2,2-trifluoroacetaldehyde hydrate (Alfa Aesar)] | 6-(2,4-Difluorophenyl)-5-(3-(trifluoromethyl)-[1,2,4]triazolo[4,3-b]pyridazin-6-yl)imidazo[2,1-b]oxazole | I.1.2.2 | 2.27 (g) | 407.1 |
| 6-Iodo-N,N-dimethyl-[1,2,4]triazolo[4,3-b]pyridazin-3-amine (Preparation #AG.1) | 6-(6-(2,4-Difluorophenyl)imidazo[2,1-b]oxazol-5-yl)-N,N-dimethyl-[1,2,4]triazolo[4,3-b]pyridazin-3-amine | I.1.2.3 | 1.86 (g) | 381.9 |

TABLE I.1.3

Examples prepared from 6-(2,4-difluorophenyl)-5-iodo-2-methylimidazo[2,1-b]oxazole (prepared using General Procedure B from 2-bromo-1-(2,4-difluorophenyl)ethanone with 5-methyloxazol-2-amine [Preparation #5], General Procedure A with NIS) using General Procedure I.1

| Heteroaryl Halide | Product | Example # | $R_t$ min (method) | m/z ESI+ (M + H)+ |
|---|---|---|---|---|
| 6-Iodo-3-isopropyl-[1,2,4]triazolo[4,3-b]pyridazine [Preparation #H.1] | 6-(2,4-Difluorophenyl)-5-(3-isopropyl-[1,2,4]triazolo[4,3-b]pyridazin-6-yl)-2-methylimidazo[2,1-b]oxazole | I.1.3.1 | 2.14 (g) | 394.9 |

TABLE I.1.4

Examples prepared from 2-(2,4-difluorophenyl)-3-iodo-6,7-dihydro-5H-pyrrolo[1,2-a]imidazole (Example #6, Step B) using General Procedure I.1

| Heteroaryl Halide | Product | Example # | $R_t$ min (method) | m/z ESI+ $(M + H)^+$ |
|---|---|---|---|---|
| 3-tert-Butyl-6-iodo-[1,2,4]triazolo[4,3-b]pyridazine [prepared using G from 3-chloro-6-hydrazinylpyridazine and pivaloyl chloride, H] | 3-tert-Butyl-6-(2-(2,4-difluorophenyl)-6,7-dihydro-5H-pyrrolo[1,2-a]imidazol-3-yl)-[1,2,4]triazolo[4,3-b]pyridazine | I.1.4.1 | 2.91 (a) | 395.2 |
| 6-Iodo-3-(1-methylcyclobutyl)-[1,2,4]triazolo[4,3-b]pyridazine [prepared using E.1 from 3-chloro-6-hydrazinylpyridazine and 1-methylcyclobutanecarbaldehyde (U.S. Pat. No. 4754059 Example 8), H] | 6-(2-(2,4-Difluorophenyl)-6,7-dihydro-5H-pyrrolo[1,2-a]imidazol-3-yl)-3-(1-methylcyclobutyl)-[1,2,4]triazolo[4,3-b]pyridazine | I.1.4.2 | 3.00 (a) | 407.2 |
| 6-Iodo-3-(tetrahydro-2H-pyran-4-yl)-[1,2,4]triazolo[4,3-b]pyridazine [prepared using D from Preparation #9, Step A with hydrazine, E from tetrahydro-2H-pyran-4-carbaldehyde (Pharmacore)] | 6-(2-(2,4-Difluorophenyl)-6,7-dihydro-5H-pyrrolo[1,2-a]imidazol-3-yl)-3-(tetrahydro-2H-pyran-4-yl)-[1,2,4]triazolo[4,3-b]pyridazine | I.1.4.3 | 1.81 (a) | 423.2 |
| 6-Iodo-3-(cyclobutyl)-[1,2,4]triazolo[4,3-b]pyridazine [prepared using G from 3-chloro-6-hydrazinylpyridazine with cyclobutanecarbonyl chloride, H] | 3-Cyclobutyl-6-(2-(2,4-difluorophenyl)-6,7-dihydro-5H-pyrrolo[1,2-a]imidazol-3-yl)-[1,2,4]triazolo[4,3-b]pyridazine | I.1.4.4 | 1.89 (a) | 393.2 |
| Ethyl 6-iodo-[1,2,4]triazolo[4,3-b]pyridazine-3-carboxylate (Example #37, Step C) | Ethyl 6-(2-(2,4-difluorophenyl)-6,7-dihydro-5H-pyrrolo[1,2-a]imidazol-3-yl)-[1,2,4]triazolo[4,3-b]pyridazine-3-carboxylate | I.1.4.5 | 1.88 (g) | 410.9 |

TABLE I.1.5

Examples prepared from 6-(2,4-difluorophenyl)-5-iodo-2,3-dihydroimidazo[2,1-b]oxazole (Preparation #6) using General Procedure I.1

| Heteroaryl Halide | Product | Example # | $R_t$ min (method) | m/z ESI+ $(M + H)^+$ |
|---|---|---|---|---|
| 6-Iodo-3-isopropyl-[1,2,4]triazolo[4,3-b]pyridazine [Preparation #H.1] | 6-(2,4-Difluorophenyl)-5-(3-isopropyl-[1,2,4]triazolo[4,3-b]pyridazin-6-yl)-2,3-dihydroimidazo[2,1-b]oxazole | I.1.5.1 | 1.93 (g) | 383.2 |

General Procedure J: Sonagashira Reaction Involving an Aryl Halide and a Terminal Alkyne A solution of aryl halide (preferably 1 equiv) in an organic solvent (preferably DMF) is evacuated and purged with nitrogen optionally 1-5 times (preferably 3-5 times). To the reaction mixture is added a terminal alkyne (1-3 equiv, preferably 1-1.5 equiv), CuI (0.01-0.2 equiv, preferably 0.05 equiv), TEA (1-5 equiv, preferably 2-3 equiv) and a catalyst with or without an additional ligand (for example, bis(triphenylphosphine)palladium(II) chloride [0.01-0.5 equiv, preferably 0.05-0.1 equiv] or palladium(II) acetate [0.01-0.5 equiv, preferably 0.01-0.1 equiv] with triphenylphosphine [0.04-1.0 equiv, preferably 0.04-0.4 equiv]). The reaction mixture is evacuated and purged with nitrogen optionally 1-5 times (preferably 3-5 times). The reaction mixture is heated to about 40-90° C. (preferably about 60° C.) for about 1-14 h (preferably about 3-6 h). The reaction mixture is optionally concentrated under reduced pressure, diluted with or partitioned between water and an organic solvent (for example, EtOAc or DCM), and filtered to remove insoluble material. The solid is then washed with additional solvent. The layers are separated and the aqueous layer is optionally extracted with a suitable organic solvent (for example, EtOAc or DCM). The combined organic layers may be optionally washed with brine, dried over $Na_2SO_4$ or $MgSO_4$, then decanted or filtered prior to concentrating under reduced pressure. The material is optionally purified by crystallization and/or trituration from an appropriate solvent or solvents, and/or by chromatography to give the target compound.

Illustration of General Procedure J

Preparation #J.1: 6-((2,4-Difluorophenyl)ethynyl)-3-isopropyl-[1,2,4]triazolo[4,3-b]pyridazine

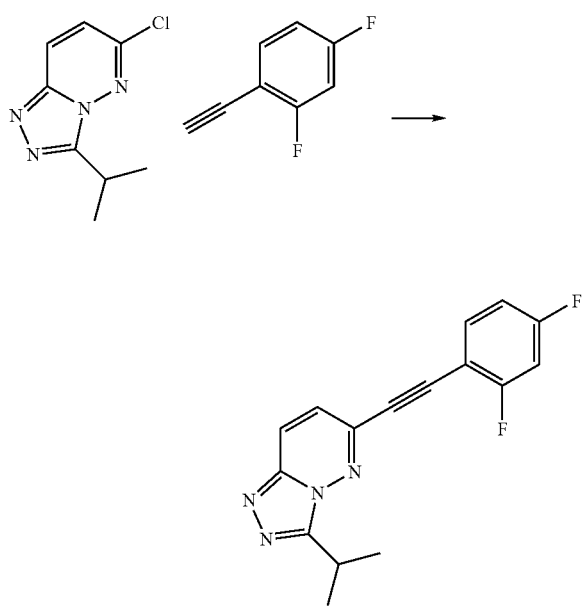

A solution of 6-chloro-3-isopropyl-[1,2,4]triazolo[4,3-b]pyridazine (20.0 g, 102 mmol, Preparation #G.1) in DMF (300 mL) was evacuated and purged with nitrogen 3 times. To the reaction mixture was added 1-ethynyl-2,4-difluorobenzene (21.1 g, 153 mmol), CuI (0.969 g, 5.09 mmol), TEA (42.5 mL, 305 mmol) and bis(triphenylphosphine)palladium (II) chloride (3.57 g, 5.09 mmol). The reaction mixture was evacuated and purged with nitrogen 3 times. The reaction mixture was heated to about 60° C. for about 6 h, cooled to ambient temperature, and diluted with EtOAc (500 mL). The organic solution was washed with water (3×500 mL), brine (500 mL), dried over MgSO$_4$, filtered, and concentrated in vacuo. The crude material was dissolved in a minimal amount of hot DCM and allowed to cool to ambient temperature. The solid 1,2-bis(2,4-difluorophenyl)ethyne (6.7 g, 26.3%) was filtered off and the filtrate was purified by silica gel chromatography using heptane/EtOAc (gradient, 1:1 to 0:1) to give product. The product was then precipitated by dissolving in EtOAc (500 mL) and adding heptane (100 mL portions) while concentrating in vacuo. The solid was collected by vacuum filtration and dried under vacuum to give the title compound (19.5 g, 64%) as an off white solid. LC/MS (Table 1, Method a) R$_t$=2.72 min; MS m/z: 299.1 (M+H)$^+$.

General Procedure K: Hydration of an Alkyne to a Ketone with an Acid

To a round bottom flask is added an alkyne (preferably 1 equiv) and an acid (such as H$_2$SO$_4$, formic acid or trifluoromethanesulfonic acid, preferably H$_2$SO$_4$; 3-100 equiv, preferably 3-25 equiv). The reaction mixture is heated to about 50-120° C. (preferably about 90-120° C.) for about 15-60 min (preferably about 15-30 min). The reaction mixture is diluted with ice water and partitioned with an organic solvent (such as DCM). The aqueous layer is neutralized with base (such as 50% aqueous NaOH) to a pH of about 4-7 (preferably about pH 7). The mixture is optionally filtered to remove insoluble material while washing the solid with additional solvent. The layers are separated and the aqueous layer is optionally extracted with additional organic solvent. The combined organic layers may be optionally washed with brine, dried over Na$_2$SO$_4$ or MgSO$_4$, then decanted or filtered prior to concentrating under reduced pressure. The material is optionally purified by crystallization and/or trituration from an appropriate solvent or solvents, and/or by chromatography to give the target compound.

Illustration of General Procedure K

Preparation #K.1: 1-(2,4-Difluorophenyl)-2-(3-isopropyl-[1,2,4]triazolo[4,3-b]pyridazin-6-yl)ethanone

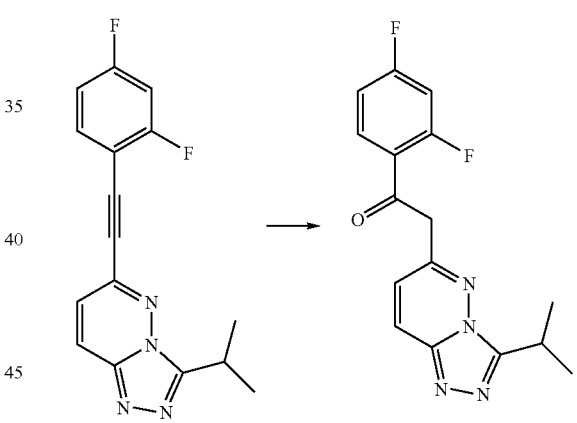

To a round bottom flask was added 6-((2,4-difluorophenyl)ethynyl)-3-isopropyl-[1,2,4]triazolo[4,3-b]pyridazine (19.5 g, 65.4 mmol, Preparation #J.1) and concentrated H$_2$SO$_4$ (145 mL, 1630 mmol). The reaction mixture was heated to about 90° C. for about 15 min. The reaction mixture was diluted with ice water (1000 mL) and partitioned with DCM (500

TABLE J.1

Preparations prepared from 1-ethynyl-2,4-difluorobenzene using General Procedure J

| Heteroaryl Halide | Product | Example # | R$_t$ min (method) | m/z ESI+ (M + H)$^+$ |
|---|---|---|---|---|
| 3-tert-Butyl-6-chloro-[1,2,4]triazolo[4,3-b]pyridazine (prepared using G from 3-chloro-6-hydrazinylpyridazine and pivaloyl chloride) | 3-tert-Butyl-6-((2,4-difluorophenyl)ethynyl)-[1,2,4]triazolo[4,3-b]pyridazine | J.1.1 | 2.67 (a) | 313.1 | mL). The aqueous layer was neutralized with 50% aqueous NaOH (about 350 mL) to about pH 7. The organic layer was isolated and the aqueous layer was extracted with DCM (3×500 mL). The combined organic extracts were dried over MgSO$_4$, filtered, and concentrated in vacuo to give 19.5 g of crude material. The crude material was purified by silica gel chromatography using EtOAc/acetone (gradient, 1:0 to 0:1) to give title compound (17.1 g, 83%) as a brown solid. LC/MS (Table 1, Method a) R$_f$=2.41 min; MS m/z: 317.2 (M+H)$^+$.

General Procedure K.1: Hydration of an Alkyne to a Ketone with an Acid

To a round bottom flask is added an alkyne (preferably 1 equiv) and an acid (such as H$_2$SO$_4$, formic acid or trifluoromethanesulfonic acid, preferably H$_2$SO$_4$; 3-100 equiv, preferably 3-25 equiv). The reaction mixture is heated to about 50-120° C. (preferably about 90-120° C.) for about 10 min-8 h (preferably about 10 min-1 h). To the reaction mixture is added ice and optionally water and then the mixture is partitioned with an organic solvent (such as DCM). The aqueous layer is neutralized with base (such as solid KOH, solid Na$_2$CO$_3$, 50% aqueous NaOH or saturated aqueous NaHCO$_3$) to a pH of about 4-7 (preferably about pH 7). The mixture is optionally filtered to remove insoluble material while washing the solid with additional solvent. In either case, the layers are separated and the aqueous layer is optionally extracted with additional organic solvent (such as DCM). The combined organic layers may be optionally washed with brine, dried over Na$_2$SO$_4$ or MgSO$_4$, then decanted or filtered prior to concentrating under reduced pressure. The material is optionally purified by crystallization and/or trituration from an appropriate solvent or solvents, and/or by chromatography to give the target compound.

Illustration of General Procedure K.1

Preparation #K.1.1: 2-(3-tert-Butyl-[1,2,4]triazolo[4,3-b]pyridazin-6-yl)-1-(2,4-difluorophenyl)ethanone

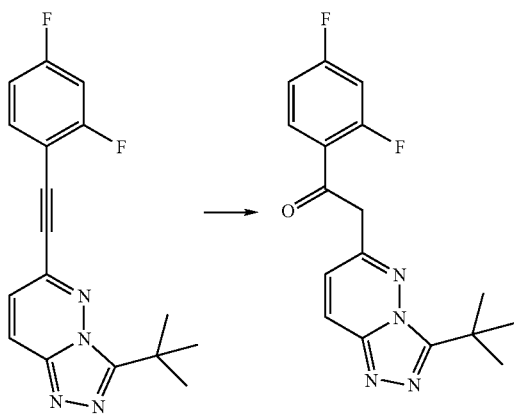

To a round bottom flask was added 3-tert-butyl-6-((2,4-difluorophenyl)ethynyl)-[1,2,4]triazolo[4,3-b]pyridazine (4.20 g, 13.5 mmol, Example #9, Step D) and concentrated H$_2$SO$_4$ (50 mL, 560 mmol). The reaction mixture was heated to about 90° C. for about 2 h. The reaction mixture was quenched with ice (500 g) and extracted with DCM (500 mL). The aqueous layer was neutralized to pH of about 7.0 with solid NaOH and additional ice (1000 g) was added to maintain a temperature of about 0-10° C. The aqueous layer was extracted with DCM (3×200 mL). The combined organic extracts were dried over Na$_2$SO$_4$, filtered and concentrated in vacuo. The crude material was purified by silica gel chromatography using MeOH/DCM (10:90) to give the title compound (4.4 g, 99%) as a solid. LC/MS (Table 1, Method a) R$_f$=3.20 min; MS m/z: 331.1 (M+H)$^+$.

General Procedure L: Formation of a Pyrazole

A mixture of a ketone (preferably 1 equiv), an organic solvent (such as toluene, benzene or xylenes, preferably toluene) and N,N-dimethylformamide dimethyl acetal (1-10 equiv, preferably 1.8 equiv) is heated at about 80-110° C. (preferably about 100° C.) for about 0.5-2 h (preferably about 0.5-1 h). The reaction is cooled to ambient temperature and then concentrated under reduced pressure. The residue is dissolved in an organic solvent (such as 1,4-dioxane or DME, preferably 1,4-dioxane) and a hydrazine (1-10 equiv, preferably 1.8 equiv) is added and the mixture is heated at about 80-110° C. (preferably about 100° C.) for about 0.5-2 h (preferably about 0.5-1 h) to give the pyrazole. Alternatively a mixture of a ketone (preferably 1 equiv), an organic solvent (such as EtOH, MeOH, n-PrOH or IPA, preferably EtOH) and a hydrazine (1-10 equiv, preferably 1.8 equiv) is added along with a few drops of an organic acid (preferably acetic acid) and the mixture is heated at about 60-95° C. (preferably about 75° C.) for about 0.5-2 h (preferably about 0.5-1 h). The reaction is cooled to ambient temperature then N,N-dimethylformamide dimethyl acetal (2-10 equiv, preferably 3.5 equiv) is added and the mixture is heated at about 60-95° C. (preferably about 75° C.) for about 0.5-2 h (preferably about 0.5-1 h). Water is added and the mixture is heated at about 60-95° C. (preferably about 75° C.) for about 0.5-2 h (preferably about 1 h) to give the pyrazole. In either case, the reaction mixture is cooled to ambient temperature then concentrated under reduced pressure. The crude product is purified by crystallization or trituration from an appropriate solvent or solvents, or by chromatography to give the target compound.

Illustration of General Procedure L

Example #L.1.1

6-(3-(2,4-Difluorophenyl)-1H-pyrazol-4-yl)-3-isopropyl-[1,2,4]-triazolo[4,3-b]pyridazine

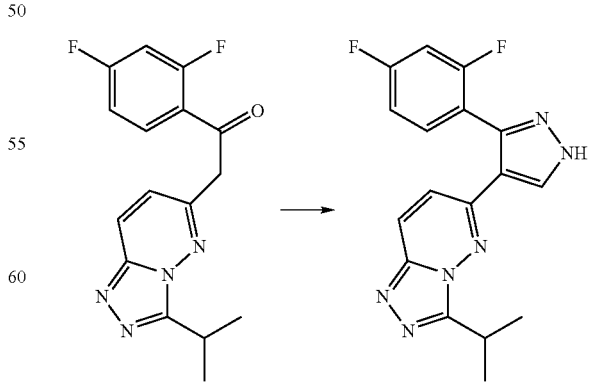

The 1-(2,4-difluorophenyl)-2-(3-isopropyl-[1,2,4]triazolo[4,3-b]pyridazin-6-yl)ethanone (0.20 g, 0.63 mmol, Preparation #K.1), N,N-dimethylformamide dimethyl acetal (0.14 g, 1.14 mmol) and toluene (2 mL) were heated in an about 110° C. oil bath. After about 30 min, the mixture was cooled and the solvent was concentrated under reduced pressure. The residue was dissolved in 1,4-dioxane (2 mL) and hydrazine (0.0360 mL, 1.14 mmol) was added. The mixture was heated to about 95° C. in an oil bath for about 30 min, cooled to ambient temperature, and then concentrated under reduced pressure. The material was purified by RP-HPLC (Table 1, Method d). Concentration of the desired fractions under reduced pressure resulted in precipitation of a tan solid that was collected by filtration and then dried to give the title compound (0.054 g, 25%): LC/MS (Table 1, Method a) $R_f$=1.69 min; MS m/z: 341.2 (M+H)$^+$.

General Procedure L.1: Formation of a Pyrazole

A mixture of a ketone (preferably 1 equiv), an organic solvent (such as toluene, benzene or xylenes, preferably toluene) and N,N-dimethylformamide dimethyl acetal (1-10 equiv, preferably 1.8 equiv) is heated at about 80-110° C. (preferably about 85-100° C.) for about 5 min-2 h (preferably about 5 min-1 h). The reaction is cooled to ambient temperature and then concentrated under reduced pressure. The residue is dissolved in an organic solvent (such as 1,4-dioxane or DME, preferably 1,4-dioxane) and a hydrazine or hydrazine hydrochloride (1-10 equiv, preferably 1.8 equiv) is added and the mixture is heated at about 80-110° C. (preferably about 100° C.) for about 0.5-2 h (preferably about 0.5-1 h) to give

TABLE L.1

Examples prepared from 1-(2,4-difluorophenyl)-2-(3-isopropyl-[1,2,4]triazolo[4,3-b]pyridazin-6-yl)ethanone (Preparation #K.1) using General Procedure L

| Hydrazine | Product | Example # | $R_t$ min (method) | m/z ESI+ (M + H)$^+$ |
|---|---|---|---|---|
| Methylhydrazine | 6-(3-(2,4-Difluorophenyl)-1-methyl-1H-pyrazol-4-yl)-3-isopropyl-[1,2,4]triazolo[4,3-b]pyridazine | L.1.2 | 2.14 (a) | 355.2 |
| 2-Hydroxyethylhydrazine | 2-(3-(2,4-Difluorophenyl)-4-(3-isopropyl-[1,2,4]triazolo[4,3-b]pyridazin-6-yl)-1H-pyrazol-1-yl)ethanol | L.1.3 | 1.72 (a) | 385.2 |
| 2-Hydroxyethylhydrazine | 2-(5-(2,4-Difluorophenyl)-4-(3-isopropyl-[1,2,4]triazolo[4,3-b]pyridazin-6-yl)-1H-pyrazol-1-yl)ethanol | L.1.4 | 1.70 (a) | 385.2 |

TABLE L.2

Examples prepared from hydrazine using General Procedure L

| Ketone | Product | Example # | $R_t$ min (method) | m/z ESI+ (M + H)$^+$ |
|---|---|---|---|---|
| 2-(3-Isopropyl-[1,2,4]triazolo[4,3-b]pyridazin-6-yl)-1-(3-(trifluoromethyl)phenyl)ethanone (prepared using J from 1-ethynyl-3-(trifluoromethyl)benzene and Preparation #G.1, K with H$_2$SO$_4$) | 3-Isopropyl-6-(3-(3-(trifluoromethyl)phenyl)-1H-pyrazol-4-yl)-[1,2,4]triazolo[4,3-b]pyridazine | L.2.1 | 2.16 (a) | 373.2 |
| 1-(2,4-Difluorophenyl)-2-(3-(1-methylcyclobutyl)-[1,2,4]triazolo[4,3-b]pyridazin-6-yl)ethanone (prepared using H from 3,6-dichloropyridazine, J from ethynyl-2,4-difluorobenzene, D from hydrazine, E from 1-methylcyclobutanecarbaldehyde [U.S. Pat. No. 4754059 Example 8], K with H$_2$SO$_4$) | 6-(3-(2,4-Difluorophenyl)-1H-pyrazol-4-yl)-3-(1-methylcyclobutyl)-[1,2,4]triazolol[4,3-b]pyridazine | L.2.2 | 1.87 (a) | 367.2 |
| 1-(2,5-Difluorophenyl)-2-(3-isopropyl-[1,2,4]triazolo[4,3-b]pyridazin-6-yl)ethanone (prepared using J from 2-bromo-1,4-difluorobenzene and ethynyltrimethylsilane, F with K$_2$CO$_3$, J from Preparation #G.1, K with H$_2$SO$_4$) | 6-(3-(2,5-Difluorophenyl)-1H-pyrazol-4-yl)-3-isopropyl-[1,2,4]triazolo[4,3-b]pyridazine | L.2.3 | 1.92 (a) | 341.2 |
| 2-(3-Isopropyl-[1,2,4]triazolo[4,3-b]pyridazin-6-yl)-1-(2,4,5-trifluorophenyl)ethanone (prepared using J from Preparation #F.1 and Preparation #G.1, K with H$_2$SO$_4$) | 3-Isopropyl-6-(3-(2,4,5-trifluorophenyl)-1H-pyrazol-4-yl)-[1,2,4]triazolo[4,3-b]pyridazine | L.2.4 | 2.73 (a) | 359.15 | the pyrazole. Alternatively a mixture of a ketone (preferably 1 equiv), an organic solvent (such as EtOH, MeOH, n-PrOH or IPA, preferably EtOH) and a hydrazine or hydrazine hydrochloride (1-10 equiv, preferably 1.8 equiv) optionally along with a few drops of an organic acid (preferably HOAc) is heated at about 60-95° C. (preferably about 75-85° C.) for about 5 min-2 h (preferably about 5 min-1 h). The reaction is cooled to ambient temperature then N,N-dimethylformamide dimethyl acetal (2-20 equiv, preferably 3-17 equiv) is added and the mixture is heated at about 60-95° C. (preferably about 75° C.) for about 0.5-2 h (preferably about 0.5-1 h). Water is added and the mixture is heated at about 60-95° C. (preferably about 75° C.) for about 5 min-2 h (preferably about 20 min-1 h) to give the pyrazole. In either case, the reaction mixture is cooled to ambient temperature then optionally concentrated under reduced pressure. The crude product is purified by crystallization or trituration from an appropriate solvent or solvents, or by chromatography to give the target compound.

Illustration of General Procedure L.1
Example #L.1.1.1

6-(1-(2,6-Dichlorophenyl)-3-(2,4-difluorophenyl)-1H-pyrazol-4-yl)-3-isopropyl-[1,2,4]triazolo[4,3-b]pyridazine

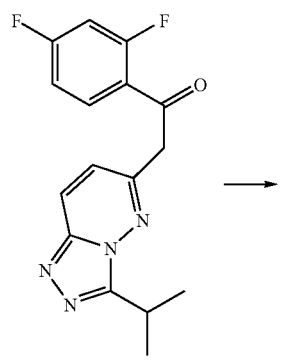

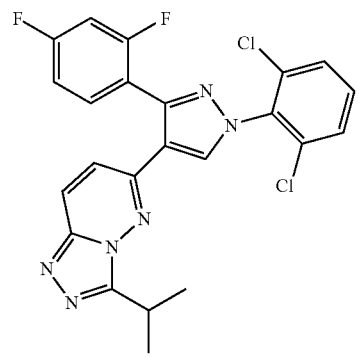

The 1-(2,4-difluorophenyl)-2-(3-isopropyl-[1,2,4]triazolo[4,3-b]pyridazin-6-yl)ethanone (0.200 g, 0.632 mmol, Preparation #K.1) in EtOH (2 mL) was treated with (2,6-dichlorophenyl)hydrazine hydrochloride (0.148 g, 0.696 mmol) then the mixture was heated at about 85° C. for about 10 min. The mixture was cooled then N,N-dimethylformamide dimethyl acetal (1.50 mL, 11.2 mmol) was added and the mixture was heated to about 85° C. for about 1 h. The mixture was cooled then water (2 mL) was added and the mixture was heated to about 60° C. for about 20 min. The mixture was then allowed to cool to ambient temperature then purified by RP-HPLC (Table 1, Method f) to give the title compound (0.107 g, 35%): LC/MS (Table 1, Method g) $R_f$=2.93 min; MS m/z: 485.2 (M+H)$^+$.

TABLE L.1.1

Examples prepared from 1-(2,4-difluorophenyl)-2-(3-isopropyl-[1,2,4]triazolo[4,3-b]pyridazin-6-yl)ethanone (Preparation #K.1) using General Procedure L.1

| Hydrazine | Product | Example # | $R_t$ min (method) | m/z ESI+ (M + H)$^+$ |
|---|---|---|---|---|
| 4-Hydrazinylpyridine hydrochloride [U.S. Pat. No. 4939159, Example 6, step 1] | 6-(3-(2,4-Difluorophenyl)-1-(pyridin-4-yl)-1H-pyrazol-4-yl)-3-isopropyl-[1,2,4]triazolo[4,3-b]pyridazine | L.1.1.2 | 2.39 (a) | 418.3 |

TABLE L.1.2

Examples prepared from hydrazine using General Procedure L.1

| Ketone | Product | Example # | $R_t$ min (method) | m/z ESI+ (M + H)$^+$ |
|---|---|---|---|---|
| 2-(3-Cyclobutyl-[1,2,4]triazolo[4,3-b]pyridazin-6-yl)-1-(2,4-difluorophenyl)ethanone [prepared using G from 3-chloro-6-hydrazinylpyridazine with cyclobutanecarbonyl chloride, J with ethynyl-2,4-difluorobenzene, K.1 with H$_2$SO$_4$] | 3-Cyclobutyl-6-(3-(2,4-difluorophenyl)-1H-pyrazol-4-yl)-[1,2,4]triazolo[4,3-b]pyridazine | L.1.2.1 | 2.17 (a) | 353.2 |

TABLE L.1.2-continued

Examples prepared from hydrazine using General Procedure L.1

| Ketone | Product | Example # | R, min (method) | m/z ESI+ (M + H)+ |
|---|---|---|---|---|
| 2-(3-Cyclopropyl-[1,2,4]triazolo[4,3-b]pyridazin-6-yl)-1-(2,4-difluorophenyl)ethanone [prepared using G from 3-chloro-6-hydrazinylpyridazine with cyclopropanecarbonyl chloride, J with ethynyl-2,4-difluorobenzene, K.1 with H$_2$SO$_4$] | 3-Cyclopropyl-6-(3-(2,4-difluorophenyl)-1H-pyrazol-4-yl)-[1,2,4]triazolo[4,3-b]pyridazine | L.1.2.2 | 2.02 (a) | 339.2 |
| 1-(2,4-Difluorophenyl)-2-(3-(1-methylcyclopropyl)-[1,2,4]triazolo[4,3-b]pyridazin-6-yl)ethanone [prepared using G from 3-chloro-6-hydrazinylpyridazine with 1-methylcyclopropanecarbonyl chloride (Eur. Pat. Appl., 295839, 21 Dec. 1988), J with ethynyl-2,4-difluorobenzene, K.1 with H$_2$SO$_4$] | 6-(3-(2,4-Difluorophenyl)-1H-pyrazol-4-yl)-3-(1-methylcyclopropyl)-[1,2,4]triazolo[4,3-b]pyridazine | L.1.2.3 | 2.10 (a) | 353.2 |

General Procedure M: Formation of a Diketone from a Ketone

To a flask is added an appropriately substituted ketone (preferably 1 equiv), DMSO, and a brominating agent (such as NBS, pyridinium tribromide or bromine; preferably NBS; preferably 1 equiv). The reaction mixture is stirred at about 20-80° C. (preferably ambient temperature) for about 1-7 d (preferably about 3 d). The reaction mixture is partitioned between an organic solvent (such as EtOAc or DCM, preferably EtOAc) and water. The layers are separated, the aqueous layer is optionally extracted with additional organic solvent, and the organic layer(s) may be optionally washed with brine, dried over Na$_2$SO$_4$ or MgSO$_4$ and then decanted or filtered prior to concentrating under reduced pressure. The crude product is purified by crystallization or trituration from an appropriate solvent or solvents, or by chromatography to give the target compound.

Illustration of General Procedure M

Preparation #M.1: 1-(2,4-Difluorophenyl)-2-(3-isopropyl-[1,2,4]triazolo[4,3-b]pyridazin-6-yl)ethane-1,2-dione

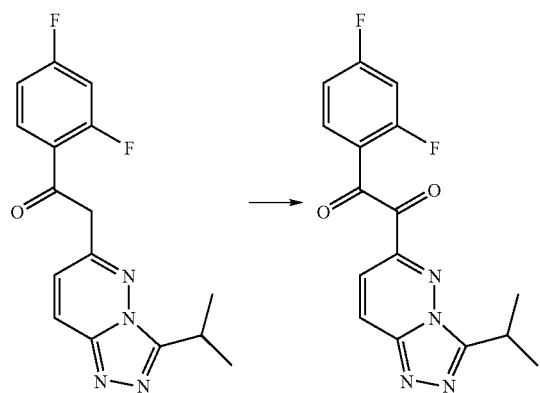

To a round bottom flask was added 1-(2,4-difluorophenyl)-2-(3-isopropyl-[1,2,4]triazolo[4,3-b]pyridazin-6-yl)ethanone (1.50 g, 4.74 mmol, Preparation #K.1) followed by DMSO (15 mL) and NBS (0.844 g, 4.74 mmol). The reaction mixture was stirred at about ambient temperature for about 3 d. The reaction mixture was partitioned between EtOAc and water. The layers were separated, and the organic layer was washed with brine, dried over MgSO$_4$, filtered, and concentrated in vacuo. The crude material was purified by silica gel chromatography using heptane/EtOAc (gradient, 1:0 to 0:1) to give the title compound (1.14 g, 73%): LC/MS (Table 1, Method a) R$_t$=2.4 min; MS m/z: 331.1 (M+H)$^+$.

General Procedure N: Formation of an Imidazole

A flask is charged with diketone (preferably 1 equiv) and aldehyde or aldehyde equivalent such as hexamethylenetetramine (1-5 equiv, preferably 2 equiv). The mixture is treated with NH$_4$OAc (2-15 equiv, preferably 15 equiv) and optionally treated with another amine (such as methyl amine in THF; 2-15 equiv, preferably 15 equiv) in an acid (such as HOAc or H$_2$SO$_4$; preferably HOAc). The reaction mixture is stirred at about 22-90° C. (preferably about 80° C.) for about 0.5-24 h (preferably about 2 h). The mixture is adjusted to about pH 8-14 (preferably to about pH 10). The reaction mixture is partitioned between an organic solvent (such as EtOAc or DCM, preferably EtOAc) and water. The layers are separated and the combined organic layers may be optionally washed with brine, dried over Na$_2$SO$_4$ or MgSO$_4$, then decanted or filtered, prior to concentrating under reduced pressure. The crude product is purified by crystallization or trituration from an appropriate solvent or solvents, or by chromatography to give the target compound.

Illustration of General Procedure N

Example #N.1.1 tert-Butyl 4-(4-(2,4-difluorophenyl)-5-(3-isopropyl-[1,2,4]triazolo[4,3-b]pyridazin-6-yl)-1H-imidazol-2-yl)piperidine-1-carboxylate

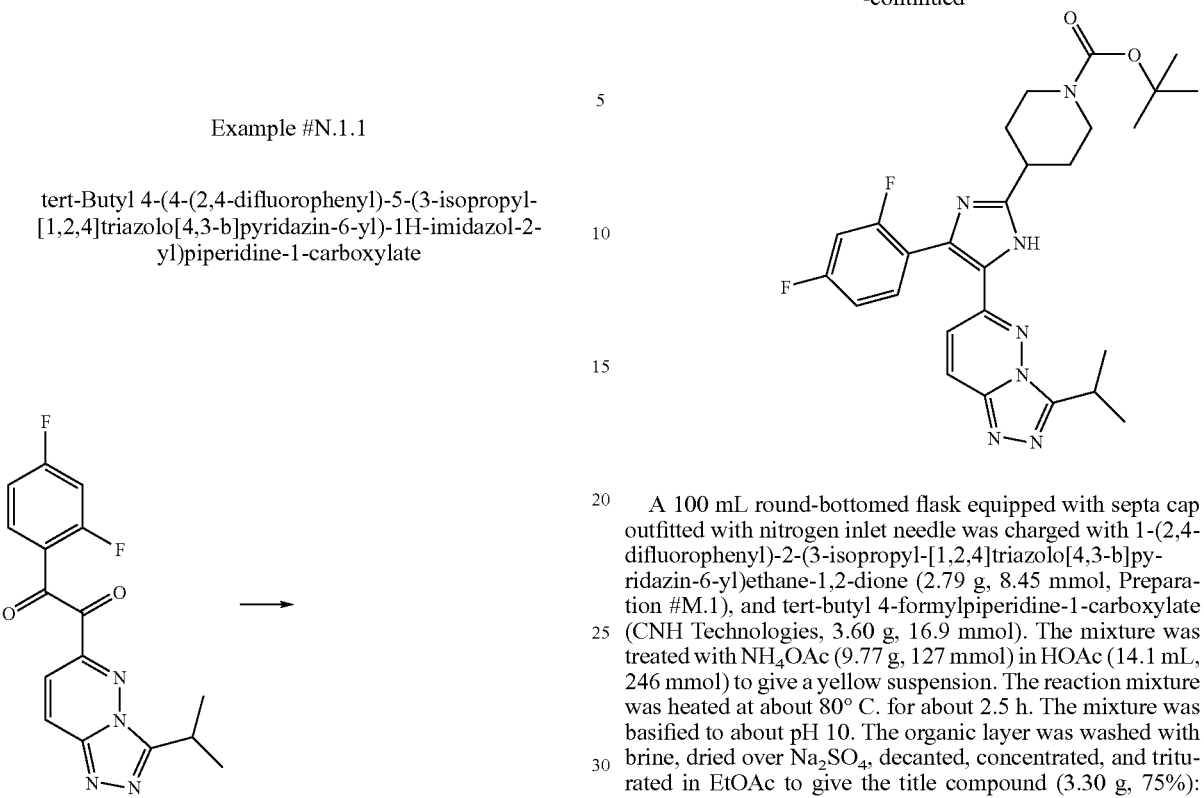

A 100 mL round-bottomed flask equipped with septa cap outfitted with nitrogen inlet needle was charged with 1-(2,4-difluorophenyl)-2-(3-isopropyl-[1,2,4]triazolo[4,3-b]pyridazin-6-yl)ethane-1,2-dione (2.79 g, 8.45 mmol, Preparation #M.1), and tert-butyl 4-formylpiperidine-1-carboxylate (CNH Technologies, 3.60 g, 16.9 mmol). The mixture was treated with $NH_4OAc$ (9.77 g, 127 mmol) in HOAc (14.1 mL, 246 mmol) to give a yellow suspension. The reaction mixture was heated at about 80° C. for about 2.5 h. The mixture was basified to about pH 10. The organic layer was washed with brine, dried over $Na_2SO_4$, decanted, concentrated, and triturated in EtOAc to give the title compound (3.30 g, 75%): LC/MS (Table 1, Method b) $R_t$=2.6 min; MS m/z: 524.3 $(M+H)^+$.

TABLE N.1

Examples prepared from 1-(2,4-difluorophenyl)-2-(3-isopropyl-[1,2,4]triazolo[4,3-b]pyridazin-6-yl)ethane-1,2-dione (Preparation #M.1) and ammonium acetate using General Procedure N

| Aldehyde or aldehyde equiv | Product | Example # | $R_t$ min (method) | m/z ESI+ $(M + H)^+$ |
|---|---|---|---|---|
| Trimethylacetaldehyde | 6-(2-tert-Butyl-5-(2,4-difluorophenyl)-1H-imidazol-4-yl)-3-isopropyl-[1,2,4]triazolo[4,3-b]pyridazine | N.1.2 | 2.5 (b) | 397.2 |
| Hexamethyleneteramine | 6-(5-(2,4-Difluorophenyl)-1H-imidazol-4-yl)-3-isopropyl-[1,2,4]triazolo[4,3-b]pyridazine | N.1.3 | 1.8 (b) | 341.1 |
| 1-Methylpiperidine-4-carbaldehyde [ChemBridge Corporation] | 6-(4-(2,4-Difluorophenyl)-2-(1-methylpiperidin-4-yl)-1H-imidazol-5-yl)-3-isopropyl-[1,2,4]triazolo[4,3-b]pyridazine | N.1.4 | 1.6 (b) | 439.2 |
| 2,6-Difluorobenzaldehyde | 6-(5-(2,4-Difluorophenyl)-2-(2,6-difluorophenyl)-1H-imidazol-4-yl)-3-isopropyl-[1,2,4]triazolo[4,3-b]pyridazine | N.1.5 | 2.15 (a) | 453.2 |
| 2,6-Dichlorobenzaldehyde | 6-(2-(2,6-Dichlorophenyl)-5-(2,4-difluorophenyl)-1H-imidazol-4-yl)-3-isopropyl-[1,2,4]triazolo[4,3-b]pyridazine | N.1.6 | 2.23 (a) | 485.1 |

TABLE N.2

Examples prepared from 1-(2,4-difluorophenyl)-2-(3-isopropyl-[1,2,4]triazolo[4,3-b]pyridazin-6-yl)ethane-1,2-dione (Preparation #M.1), ammonium acetate, and 2.0 M methyl amine in THF using General Procedure N

| Aldehyde | Product | Example # | $R_t$ min (method) | m/z ESI+ $(M + H)^+$ |
|---|---|---|---|---|
| tert-Butyl 4-formylpiperidine-1- | tert-Butyl 4-(5-(2,4-difluorophenyl)-4-(3-isopropyl- | N.2.1 | 2.7 (b) | 538.3 |

TABLE N.2-continued

Examples prepared from 1-(2,4-difluorophenyl)-2-(3-isopropyl-[1,2,4]triazolo[4,3-b]pyridazin-6-yl)ethane-1,2-dione (Preparation #M.1), ammonium acetate, and 2.0 M methyl amine in THF using General Procedure N

| Aldehyde | Product | Example # | R<sub>t</sub> min (method) | m/z ESI+ (M + H)+ |
|---|---|---|---|---|
| carboxylate [CNH Technologies] | [1,2,4]triazolo[4,3-b]pyridazin-6-yl)-1-methyl-1H-imidazol-2-yl)piperidine-1-carboxylate | | | |

General Procedure O: Preparation of a Thiazole from a Bromoketone

A mixture of a substituted aryl or heteroaryl bromoketone (preferably 1 equiv), an organic solvent (such as MeOH, THF, or DMF; preferably DMF), and a substituted thioamide (1-10 equiv, preferably 1-2 equiv) is stirred at ambient temperature for about 2-36 h (preferably about 14-24 h). The reaction is quenched with a base (such as saturated aqueous Na$_2$CO$_3$ or saturated aqueous NaHCO$_3$) and then extracted with organic solvent (such as EtOAc, Et$_2$O, or DCM; preferably Et$_2$O). The combined organic layers may be optionally washed with brine, dried over Na$_2$SO$_4$ or MgSO$_4$, and then decanted or filtered prior to concentrating under reduced pressure. The crude product is purified by crystallization or trituration from an appropriate solvent or solvents, or by chromatography to give the target compound.

Illustration of General Procedure O

Example #O.1.1 tert-Butyl 4-(5-(3-isopropyl-[1,2,4]triazolo[4,3-b]pyridazin-6-yl)-4-(2,4,5-trifluorophenyl)thiazol-2-yl)piperidine-1-carboxylate

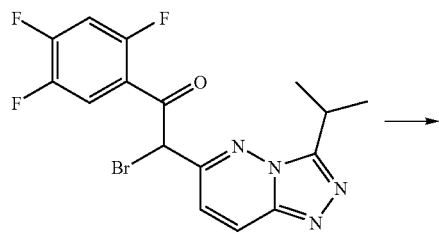

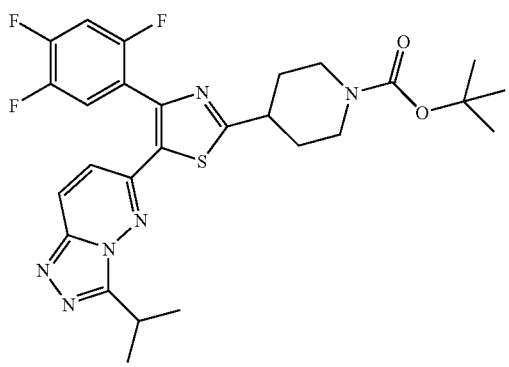

A mixture of 2-bromo-2-(3-isopropyl-[1,2,4]triazolo[4,3-b]pyridazin-6-yl)-1-(2,4,5-trifluorophenyl)ethanone (0.90 g, 2.2 mmol; prepared using General Procedure J from Preparation #F.1 and Preparation #G.1, General Procedure K with H$_2$SO$_4$, and General Procedure A.2), tert-butyl 4-(aminocarbothioyl)tetrahydropyridine-1-(2H)-carboxylate (Maybridge, 0.8 g, 3.3 mmol) and DMF (20 mL) was stirred at ambient temperature for about 24 h. The reaction was quenched with saturated aqueous NaHCO$_3$ and extracted with Et$_2$O (300 mL). The organic layer was dried over Na$_2$SO$_4$, decanted, and concentrated. The crude material was loaded onto a silica gel column and eluted with a gradient of 0-10% MeOH in DCM to give the title compound (0.41 g, 34%): LC/MS (Table 1, Method a) R$_t$=4.18 min; MS m/z: 559.3 (M+H)+.

TABLE O.2

Examples prepared from 2-bromo-1-(2,4-difluorophenyl)-2-(3-isopropyl-[1,2,4]triazolo[4,3-b]pyridazin-6-yl)ethanone (Preparation #A.2) using General Procedure O

| Thioamide | Product | Example # | R<sub>t</sub> min (method) | m/z ESI+ (M + H)+ |
|---|---|---|---|---|
| Thiopropionamide (TCI) | 4-(2,4-Difluorophenyl)-2-ethyl-5-(3-isopropyl-[1,2,4]triazolo[4,3-b]pyridazin-6-yl)thiazole | O.2.2 | 2.42 (a) | 386.2 |

General Procedure O.1: Preparation of a Thiazole from a Bromoketone

A mixture of a substituted aryl or heteroaryl bromoketone (preferably 1 equiv), an organic solvent (such as MeOH, THF, or DMF; preferably DMF), and a substituted thioamide (1-10 equiv, preferably 1-2 equiv) is stirred at ambient temperature for about 2-72 h (preferably about 14-24 h). The reaction is quenched with a base (such as saturated aqueous $Na_2CO_3$ or saturated aqueous $NaHCO_3$) and then extracted with an organic solvent (such as EtOAc, $Et_2O$, or DCM; preferably $Et_2O$). The combined organic layers may be optionally washed with brine, dried over $Na_2SO_4$ or $MgSO_4$, and then decanted or filtered prior to concentrating under reduced pressure. The crude product is purified by crystallization or trituration from an appropriate solvent or solvents, or by chromatography to give the target compound.

Illustration of General Procedure O.1

Preparation #0.1.1.1: tert-Butyl 4-(5-(3-tert-butyl-[1,2,4]triazolo[4,3-b]pyridazin-6-yl)-4-(2,4-difluorophenyl)thiazol-2-yl)piperidine-1-carboxylate

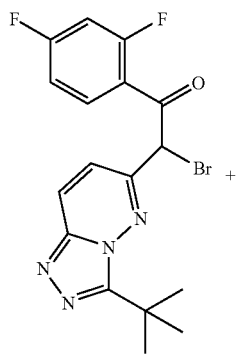

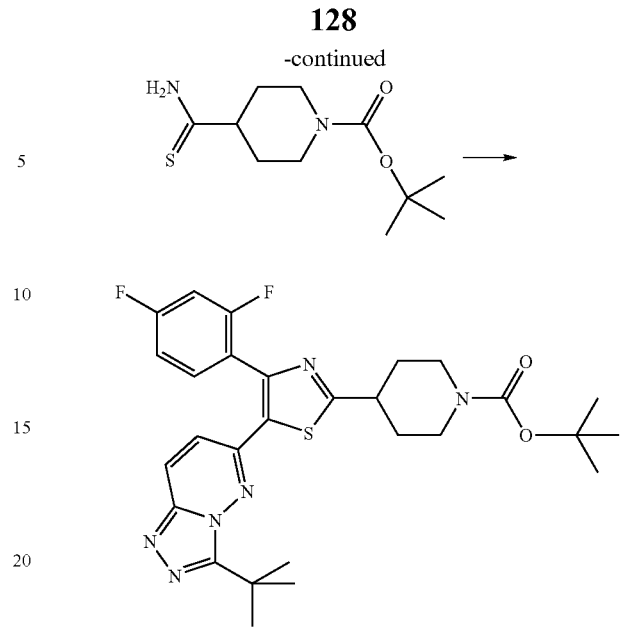

A mixture of 2-bromo-2-(3-tert-butyl-[1,2,4]triazolo[4,3-b]pyridazin-6-yl)-1-(2,4-difluorophenyl)ethanone (3.78 g, 9.24 mmol; prepared using General Procedure A.2 from Preparation #K.1.1), tert-butyl 4-(aminocarbothioyl)tetrahydropyridine-1-(2H)-carboxylate (3.08 g, 12.6 mmol, Maybridge) and DMF (60 mL) was stirred at ambient temperature for about 2 d. The reaction was diluted with saturated aqueous $Na_2CO_3$ and extracted with $Et_2O$ (2×200 mL). The organic layers were combined, dried over $Na_2SO_4$ and concentrated. The crude material was loaded onto a silica gel column and eluted with a gradient of 30-100% EtOAc in heptane to give the title compound (3.5 g, 68%): LC/MS (Table 1, Method a) $R_t$=2.64 min; MS m/z: 555.4 $(M+H)^+$.

TABLE O.1.2

Examples prepared from 2-bromo-1-(2,4-difluorophenyl)-2-(3-isopropyl-[1,2,4]triazolo[4,3-b]pyridazin-6-yl)ethanone (Preparation #A.2) using General Procedure O.1

| Thioamide | Product | Example # | $R_t$ min (method) | m/z ESI+ $(M + H)^+$ |
|---|---|---|---|---|
| tert-Butyl 4-carbamothioylpiperazine-1-carboxylate | tert-Butyl 4-(4-(2,4-difluorophenyl)-5-(3-isopropyl-[1,2,4]triazolo[4,3-b]pyridazin-6-yl)thiazol-2-yl)piperazine-1-carboxylate | O.1.2.1 | 4.05 (a) | 542.4 |
| tert-Butyl 4-carbamothioylpiperidine-1-carboxylate (Maybrige) | tert-Butyl 4-(4-(2,4-difluorophenyl)-5-(3-isopropyl-[1,2,4]triazolo[4,3-b]pyridazin-6-yl)thiazol-2-yl)piperidine-1-carboxylate | O.1.2.2 | 4.12 (a) | 542.7 |

General Procedure P: Formation of a 2-aminothiazole

A solution of 2-bromo-1-(aryl)ethanone (preferably 1 equiv) and a thiocarboxamide or thiourea (0.9-1.2 equiv, preferably 0.9 equiv) is heated to about 55-80° C. (preferably about 75° C.) in an organic solvent (such as acetone, THF, EtOH, preferably EtOH) for about 3-24 h. After cooling to ambient temperature, the crude mixture is partitioned between an organic solvent (for example, DCM) and water. The organic layer may be optionally washed with brine, dried over $Na_2SO_4$ or $MgSO_4$, and then decanted or filtered prior to concentrating under reduced pressure. The crude product is purified by crystallization or trituration from an appropriate solvent or solvents, or by chromatography to give the target compound.

Illustration of General Procedure P

Example #P.1.1

4-(2,4-Difluorophenyl)-5-(3-isopropyl-[1,2,4]triazolo[4,3-b]pyridazin-6-yl)-2-(piperidin-1-yl)thiazole

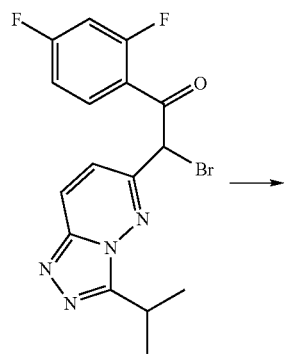

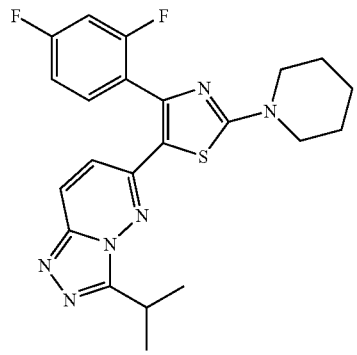

A mixture of 2-bromo-1-(2,4-difluorophenyl)-2-(3-isopropyl-[1,2,4]triazolo[4,3-b]pyridazin-6-yl)ethanone (0.250 g, 0.632 mmol; Preparation #A.2) and piperidine-1-carbothioamide (Oakwood Products Inc., 0.082 g, 0.57 mmol) in EtOH (3 mL) was heated to reflux for about 3 h. After cooling to ambient temperature, the crude mixture was partitioned between DCM and water. The organics were dried over MgSO$_4$, filtered, concentrated under reduced pressure, and purified by silica gel chromatography using heptane/EtOAc (linear gradient, 50:50 to 0:100) to give the title compound (0.098 g, 35%): LC/MS (Table 1, Method a) R$_t$=4.18 min; MS m/z: 441.8 (M+H)$^+$.

TABLE P.1

Examples prepared from 2-bromo-1-(2,4-difluorophenyl)-2-(3-isopropyl-[1,2,4]triazolo[4,3-b]pyridazin-6-yl)ethanone (Preparation #A.2) using General Procedure P

| Thiocarboxamide or Thiourea | Product | Example # | R$_t$ min (method) | m/z ESI+ (M + H)$^+$ |
|---|---|---|---|---|
| Thiourea | 5-(2,4-Difluorophenyl)-4-(3-isopropyl-[1,2,4]triazolo[4,3-b]pyridazin-6-yl)thiazol-2-amine | P.1.2 | 2.76 (a) | 273.2 |
| 1-tert-Butylthiourea [VWR] | N-tert-Butyl-4-(2,4-difluorophenyl)-5-(3-isopropyl-[1,2,4]triazolo[4,3-b]pyridazin-6-yl)thiazol-2-amine | P.1.3 | 3.93 (a) | 429.2 |
| 4-Methylpiperazine-1-carbothioamide [Chembridge Corp.] | 4-(2,4-Difluorophenyl)-5-(3-isopropyl-[1,2,4]triazolo[4,3-b]pyridazin-6-yl)-2-(4-methylpiperazin-1-yl)thiazole | P.1.4 | 2.50 (a) | 456.2 |

General Procedure P.1: Formation of a 2-aminothiazole

A solution of 2-aryl-2-bromo-1-(aryl)ethanone (preferably 1 equiv) and a thiocarboxamide or thiourea (0.9-3 equiv, preferably 0.9 equiv) is heated to about 30-100° C. (preferably about 40-50° C.) in an organic solvent (such as acetone, THF, EtOH, preferably EtOH) for about 1-24 h. After cooling to ambient temperature, the solvent is optionally removed under reduced pressure. The crude mixture is dissolved in an organic solvent (for example, DCM or EtOAc, preferably DCM) and washed with water. The organic layer may be optionally washed with brine, dried over Na$_2$SO$_4$ or MgSO$_4$, and then decanted or filtered prior to concentrating under reduced pressure. The crude product is purified by crystallization or trituration from an appropriate solvent or solvents, or by chromatography to give the target compound.

Illustration of General Procedure P.1

Example #P.1.1.1

4-(2,4-Difluorophenyl)-5-(3-isopropyl-[1,2,4]triazolo[4,3-b]pyridazin-6-yl)-2-(4-isopropylpiperazin-1-yl)thiazole

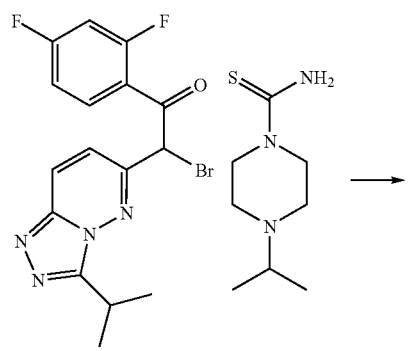

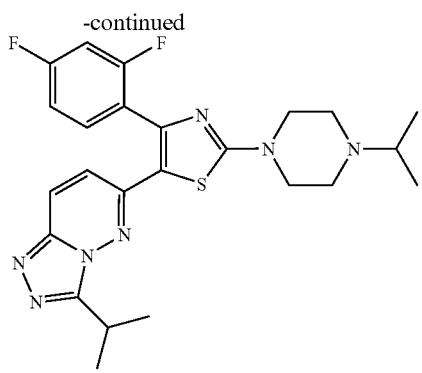

To a solution of 2-bromo-1-(2,4-difluorophenyl)-2-(3-isopropyl-[1,2,4]triazolo[4,3-b]pyridazin-6-yl)ethanone (0.49 g, 1.24 mmol, Preparation #A.2) in EtOH (10 µL) was added 4-isopropylpiperazine-1-carbothioamide (0.21 g, 1.12 mmol, Preparation #AO.1.1). The reaction mixture was stirred at about 40° C. for about 2.5 h. The reaction mixture was cooled to ambient temperature and the solvent was removed under reduced pressure. DCM (35 mL) and water (20 mL) were added. The layers were partitioned and the organic layer was washed with additional water (200 mL). The organic layer was dried over MgSO$_4$, filtered, and the solvent was removed under reduced pressure. The crude residue was purified by silica gel column chromatography DCM/MeOH (gradient from 100:0 to 90:10) to afford the title compound (0.34 g, 56%) as a yellow solid: LC/MS (Table 1, Method a) R$_t$=2.06 min; MS m/z: 484.2 (M+H)$^+$.

TABLE P.1.1

Examples prepared from 2-bromo-1-(2,4-difluorophenyl)-2-(3-isopropyl-[1,2,4]triazolo[4,3-b]pyridazin-6-yl)ethanone (Preparation #A.2) using General Procedure P.1

| Thiocarboxamide or Thiourea | Product | Example # | R$_t$ min (method) | m/z ESI+ (M + H)$^+$ |
|---|---|---|---|---|
| 4-Acetylpiperazine-1-carbothioamide [Preparation #AO.1.2] | 1-(4-(4-(2,4-Difluorophenyl)-5-(3-isopropyl-[1,2,4]triazolo[4,3-b]pyridazin-6-yl)thiazol-2-yl)piperazin-1-yl)ethanone | P.1.1.2 | 2.30 (a) | 484.2 |
| 4-tert-Butylpiperazine-1-carbothioamide [Preparation #AO.1.3] | 2-(4-tert-Butylpiperazin-1-yl)-4-(2,4-difluorophenyl)-5-(3-isopropyl-[1,2,4]triazolo[4,3-b]pyridazin-6-yl)thiazole | P.1.1.3 | 2.02 (a) | 498.2 |
| 4-Cyclopropylpiperazine-1-carbothioamide [Preparation #AO.1.4] | 2-(4-Cyclopropylpiperazin-1-yl)-4-(2,4-difluorophenyl)-5-(3-isopropyl-[1,2,4]triazolo[4,3-b]pyridazin-6-yl)thiazole | P.1.1.4 | 3.08 (a) | 482.3 |
| Morpholine-4-carbothioamide [Maybridge Int.] | 4-(4-(2,4-Difluorophenyl)-5-(3-isopropyl-[1,2,4]triazolo[4,3-b]pyridazin-6-yl)thiazol-2-yl)morpholine | P.1.1.5 | 3.40 (a) | 443.2 |

General Procedure Q: Acidic Cleavage of a Boc-protected Amine

To a solution of a Boc-protected amine (preferably 1 equiv) in an organic solvent (for example, THF, 1,4-dioxane, DME, DCM or acetone, preferably 1,4-dioxane or DCM) is added an acid (such as HCl or TFA; 1-10 equiv). The mixture is stirred at about 0-80° C. After about 1-24 h (preferably about 1-3 h), the reaction is concentrated under reduced pressure then the residue is partitioned between a basic aqueous solution (such as Na$_2$CO$_3$, NaHCO$_3$ or NaOH, preferably NaOH) and an organic solvent (such as EtOAc). The organic extract is dried over Na$_2$SO$_4$ or MgSO$_4$ and then filtered prior to concentrating under reduced pressure. The crude product is purified by crystallization or trituration from an appropriate solvent or solvents, or by chromatography to give the target compound.

Illustration of General Procedure Q

Example #Q.1.1

4-(2,4-Difluorophenyl)-5-(3-isopropyl-[1,2,4]triazolo[4,3-b]pyridazin-6-yl)-2-(piperidin-4-yl)thiazole

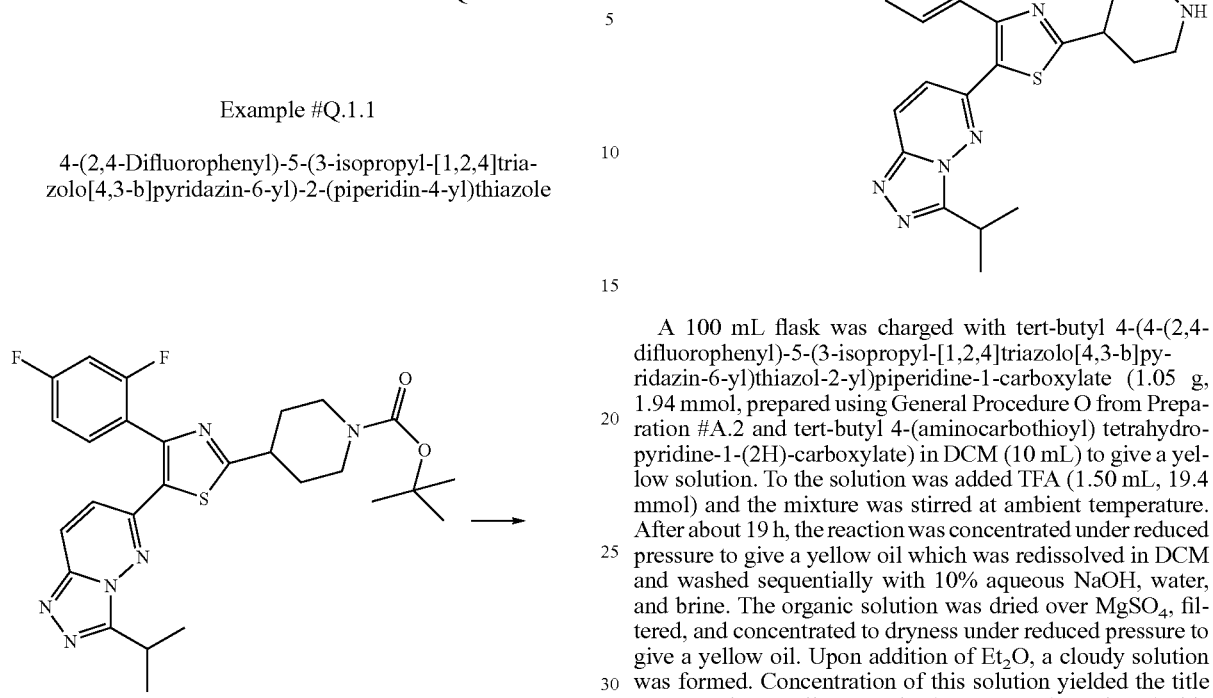

A 100 mL flask was charged with tert-butyl 4-(4-(2,4-difluorophenyl)-5-(3-isopropyl-[1,2,4]triazolo[4,3-b]pyridazin-6-yl)thiazol-2-yl)piperidine-1-carboxylate (1.05 g, 1.94 mmol, prepared using General Procedure O from Preparation #A.2 and tert-butyl 4-(aminocarbothioyl) tetrahydropyridine-1-(2H)-carboxylate) in DCM (10 mL) to give a yellow solution. To the solution was added TFA (1.50 mL, 19.4 mmol) and the mixture was stirred at ambient temperature. After about 19 h, the reaction was concentrated under reduced pressure to give a yellow oil which was redissolved in DCM and washed sequentially with 10% aqueous NaOH, water, and brine. The organic solution was dried over $MgSO_4$, filtered, and concentrated to dryness under reduced pressure to give a yellow oil. Upon addition of $Et_2O$, a cloudy solution was formed. Concentration of this solution yielded the title compound as a yellow powder (0.65 g, 76%): LC/MS (Table 1, Method a) $R_t$=1.54 min; MS m/z: 441.2 (M+H)$^+$.

TABLE Q.1

Examples prepared with TFA using General Procedure Q

| Boc-protected amine | Product | Example # | $R_t$ min (method) | m/z ESI+ (M + H)$^+$ |
|---|---|---|---|---|
| tert-Butyl 4-(4-(2,4-difluorophenyl)-5-(3-isopropyl-[1,2,4]triazolo[4,3-b]pyridazin-6-yl)-1H-imidazol-2-yl)piperidine-1-carboxylate (Example #N.1.1) | 6-(3-(2,4-Difluorophenyl)-2-(piperidin-4-yl)-1H-imidazol-4-yl)-3-isopropyl-[1,2,4]triazolo[4,3-b]pyridazine | Q.1.2 | 1.5 (b) | 424.2 |
| tert-Butyl 4-(5-(3-isopropyl-[1,2,4]triazolo[4,3-b]pyridazin-6-yl)-4-(2,4,5-trifluorophenyl)thiazol-2-yl)piperidine-1-carboxylate (Example #O.1.1) | 5-(3-Isopropyl-[1,2,4]triazolo[4,3-b]pyridazin-6-yl)-2-(piperidin-4-yl)-4-(2,4,5-trifluorophenyl)thiazole | Q.1.3 | 1.86 (a) | 459.2 |

TABLE Q.2

Examples prepared with HCl using General Procedure Q

| Boc-protected amine | Product | Example # | $R_t$ min (method) | m/z ESI+ (M + H)$^+$ |
|---|---|---|---|---|
| tert-Butyl 4-(3-(2,4-difluorophenyl)-4-(3-isopropyl-[1,2,4]triazolo[4,3-b]pyridazin-6-yl)-1H-pyrazol-1-yl)piperidine-1-carboxylate (prepared using Z from Example #L.1.1 and tert-butyl 4-hydroxypiperidine-1-carboxylate) | 6-(3-(2,4-Difluorophenyl)-1-(piperidin-4-yl)-1H-pyrazol-4-yl)-3-isopropyl-[1,2,4]triazolo[4,3-b]pyridazine | Q.2.1 | 1.50 (a) | 424.2 |

TABLE Q.2-continued

Examples prepared with HCl using General Procedure Q

| Boc-protected amine | Product | Example # | $R_t$ min (method) | m/z ESI+ $(M + H)^+$ |
|---|---|---|---|---|
| tert-Butyl 4-(5-(2,4-difluorophenyl)-4-(3-isopropyl-[1,2,4]triazolo[4,3-b]pyridazin-6-yl)-1H-pyrazol-1-yl)piperidine-1-carboxylate (prepared using Z from Example #L.1.1 and tert-butyl 4-hydroxypiperidine-1-carboxylate) | 6-(5-(2,4-Difluorophenyl)-1-(piperidin-4-yl)-1H-pyrazol-4-yl)-3-isopropyl-[1,2,4]triazolo[4,3-b]pyridazine | Q.2.2 | 1.50 (a) | 424.2 |

General Procedure Q.1: Acidic Cleavage of a Boc-protected Amine

To a solution of a Boc-protected amine (preferably 1 equiv) in an organic solvent (for example, THF, 1,4-dioxane, DME, DCM, MeOH or acetone, preferably 1,4-dioxane or DCM) is added an acid (such as HCl or TFA; 1-20 equiv). The mixture is stirred at about 0-100° C. After about 15 min-24 h (preferably about 20 min-3 h), the reaction is optionally concentrated under reduced pressure and is partitioned between a basic aqueous solution (such as $Na_2CO_3$, $NaHCO_3$ or NaOH, preferably NaOH) and an organic solvent (such as EtOAc or DCM). The organic extract is dried over $Na_2SO_4$ or $MgSO_4$ and then filtered prior to concentrating under reduced pressure. The crude product is purified by crystallization or trituration from an appropriate solvent or solvents, or by chromatography to give the target compound.

Illustration of General Procedure Q.1

Example #Q.1.1.1

6-(3-(2,4-Difluorophenyl)-1-(pyrrolidin-3-yl)-1H-pyrazol-4-yl)-3-isopropyl-[1,2,4]triazolo[4,3-b]pyridazine

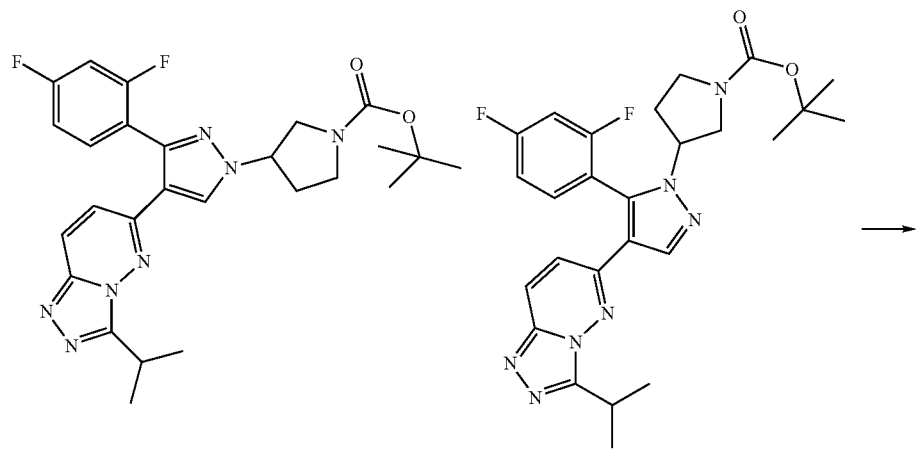

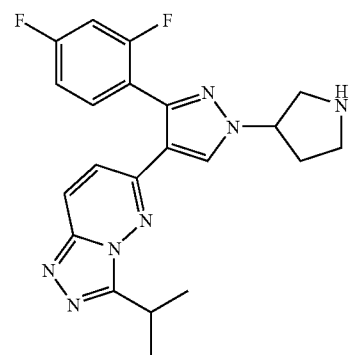

To a round bottom flask was added tert-butyl 3-(3-(2,4-difluorophenyl)-4-(3-isopropyl-[1,2,4]triazolo[4,3-b]pyridazin-6-yl)-1H-pyrazol-1-yl)pyrrolidine-1-carboxylate and tert-butyl 3-(5-(2,4-difluorophenyl)-4-(3-isopropyl-[1,2,4]triazolo[4,3-b]pyridazin-6-yl)-1H-pyrazol-1-yl)pyrrolidine-1-carboxylate (0.446 g, 0.875 mmol, Preparation #X.1.1.1) as a mixture of regioisomers followed by 1,4-dioxane (10 mL) and concentrated hydrochloric acid (3.50 mL, 17.5 mmol). The reaction mixture was heated to about 85° C. for about 20 min. The reaction mixture was partitioned between saturated aqueous NaHCO$_3$ and DCM (50 mL). The organic layer was isolated and the aqueous layer extracted with DCM (2×50 mL). The combined organic layers were dried with MgSO$_4$, filtered and concentrated in vacuo. The reaction mixture was purified by flash chromatography (40 g RediSep® silica gel; DCM/MeOH with 5% 2.0 M ammonia in EtOH gradient from 1:0 to 80:20) to give the title compound (0.265 g, 74%): LC/MS (Table 1, Method g) R$_t$=1.75 min; MS m/z: 410.3 (M+H)$^+$.

TABLE Q.1.1

Examples prepared with HCl using General Procedure Q.1

| Boc-protected amine | Product | Example # | R$_t$ min (method) | m/z ESI+ (M + H)$^+$ |
|---|---|---|---|---|
| tert-Butyl 4-(6-(2-(2,4-difluorophenyl)-6,7-dihydro-5H-pyrrolo[1,2-a]imidazol-3-yl)-[1,2,4]triazolo[4,3-b]pyridazin-3-yl)piperidine-1-carboxylate [prepared using D from Example #9, Step A with hydrazine, E.1 with tert-butyl 2-(4-formylpiperidin-1-yl)acetate (Tyger), I.1 with Example #6, step B] | 6-(2-(2,4-Difluorophenyl)-6,7-dihydro-5H-pyrrolo[1,2-a]imidazol-3-yl)-3-(piperidin-4-yl)-[1,2,4]triazolo[4,3-b]pyridazine | Q.1.1.2 | 1.37 (g) | 422.3 |

TABLE Q.1.2

Examples prepared with TFA using General Procedure Q.1

| Boc-protected amine | Product | Example # | R$_t$ min (method) | m/z ESI+ (M + H)$^+$ |
|---|---|---|---|---|
| tert-Butyl 2-(6-(6-(2,4-difluorophenyl)imidazo[2,1-b]oxazol-5-yl)-[1,2,4]triazolo[4,3-b]pyridazin-3-yl)propan-2-ylcarbamate [prepared using I.1 from Preparation #C.1 with Example #9, Step A, D with hydrazine, E.1 with tert-butyl 2-methyl-1-oxopropan-2-ylcarbamate (prepared using AI.1 with tert-butyl 1-hydroxy-2-methylpropan-2-ylcarbamate)] | 2-(6-(6-(2,4-Difluorophenyl)imidazo[2,1-b]oxazol-5-yl)-[1,2,4]triazolo[4,3-b]pyridazin-3-yl)propan-2-amine | Q.1.2.1 | 1.48 (g) | 396 |
| tert-Butyl 2-(4-(4-(2,4-difluorophenyl)-5-(3-isopropyl-[1,2,4]triazolo[4,3-b]pyridazin-6-yl)thiazol-2-yl)piperazin-1-yl)-2-oxoethyl(methyl)carbamate [prepared using AR from (Example #5) with 2-(tert-butoxycarbonyl(methyl)amino)acetic acid (Acros)] | 1-(4-(4-(2,4-Difluorophenyl)-5-(3-isopropyl-[1,2,4]triazolo[4,3-b]pyridazin-6-yl)thiazol-2-yl)piperazin-1-yl)-2-(methylamino)ethanone | Q.1.2.2 | 1.97 (a) | 513.3 |

General Procedure R: Formation of a Dihydropyrrolo[1,2-a]imidazole or Tetrahydroimidazo[1,2-a]pyridine A mixture of the 2-bromo-1-(aryl)ethanone (preferably 1 equiv), a 2-iminopyrrolidine or a 2-iminopiperidine (1-5 equiv, preferably 3 equiv), and a base such as Na$_2$CO$_3$ (2-10 equiv, preferably 6 equiv) is heated to about 60-120° C. (preferably about 80° C.) for about 0.5-3 d (preferably 0.5-1 d) in an organic solvent (such as 1,4-dioxane or DMF, preferably DMF). The reaction mixture is cooled to ambient temperature, poured into water, and extracted with an organic solvent (such as EtOAc or DCM, preferably EtOAc). The organic extracts are dried over MgSO$_4$ or Na$_2$SO$_4$, filtered or decanted, and concentrated under reduced pressure. The crude product is used as is or is purified by crystallization or trituration from an appropriate solvent or solvents, or by chromatography to give the target compound.

Illustration of General Procedure R

Preparation #R.1: 2-(2,4-Difluorophenyl)-6,7-dihydro-5H-pyrrolo[1,2-a]imidazole

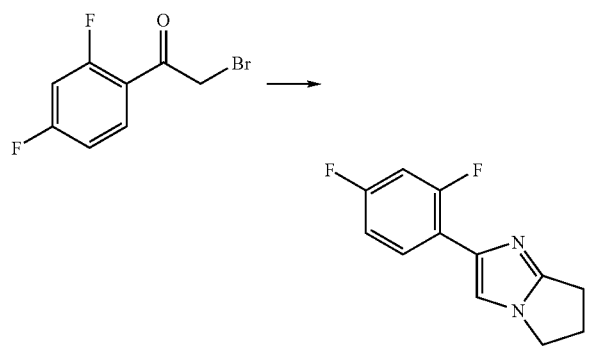

A mixture of 2-bromo-1-(2,4-difluorophenyl)ethanone (7.05 g, 30.0 mmol, prepared using General Procedure A.1 from 1-(2,4-difluorophenyl)ethanone), 2-iminopyrrolidine hydrochloride (10.9 g, 90 mmol, prepared following the procedure in *J. Med. Chem.*, 2002, 45, 999-1001) and Na$_2$CO$_3$ (21.1 g, 199 mmol) in DMF (30 mL) was stirred overnight at about 80° C. The reaction mixture was cooled to ambient temperature, poured into water, and extracted with EtOAc. The organics were dried over MgSO$_4$, filtered and concentrated under reduced pressure to give the crude title compound (6.61 g, 100%): LC/MS (Table 1, Method a) R$_t$=2.72 min; MS m/z: 221.0 (M+H)$^+$.

General Procedure S: Cyclization of an Aldehyde with a TOSMIC Reagent to Give an Oxazole To a solution of aldehyde (1-2 equiv, preferably 1.2 equiv) in an organic solvent (such as 1,4-dioxane or THF, preferably 1,4-dioxane) is added a TOSMIC reagent (preferably 1 equiv), a base (such as potassium carbonate; 1-5 equiv, preferably 2.4 equiv) and protic organic solvent (for example MeOH or EtOH, preferably MeOH). The reaction mixture is heated to about 50-80° C. (preferably about 80° C.) for about 1-12 h (preferably about 1-3 h). The reaction mixture is optionally concentrated under reduced pressure, diluted with or partitioned between water and an organic solvent (for example, EtOAc or DCM), filtered to remove insoluble material, and washed with additional solvent. The layers are separated and the aqueous layer is optionally extracted with additional organic solvent. The combined organic layers may be optionally washed with brine, dried over Na$_2$SO$_4$ or MgSO$_4$, then decanted or filtered prior to concentrating under reduced pressure. The material is optionally purified by crystallization and/or trituration from an appropriate solvent or solvents, and/or by chromatography to give the target compound.

Illustration of General Procedure S

Example #S.1.1

4-(2,5-Difluorophenyl)-5-(3-isopropyl-[1,2,4]triazolo[4,3-b]pyridazin-6-yl)oxazole

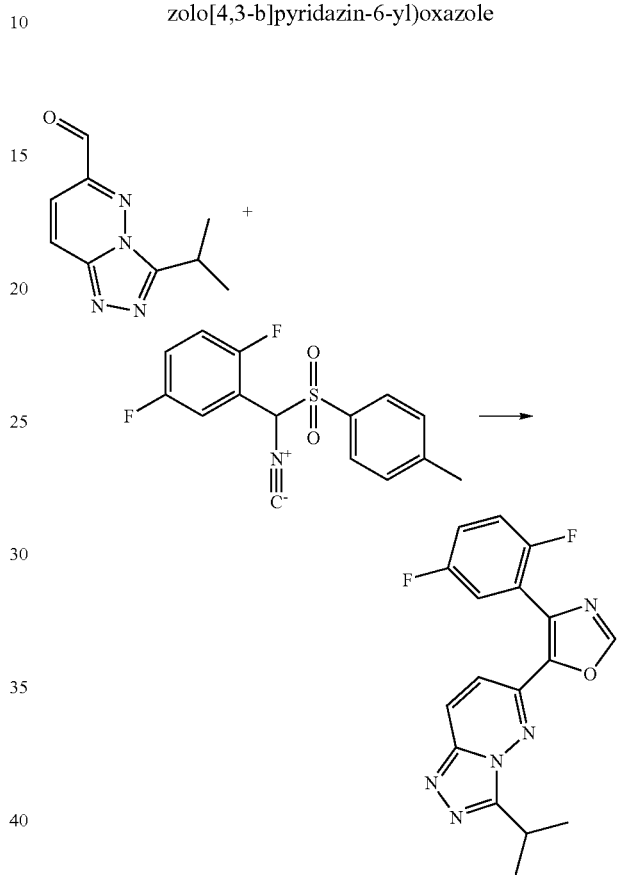

To a solution of 3-isopropyl-[1,2,4]triazolo[4,3-b]pyridazine-6-carbaldehyde (0.150 g, 0.789 mmol, Preparation #2) in 1,4-dioxane (3 mL) was added 1,4-difluoro-2-(isocyano(tosyl)methyl)benzene (0.202 g, 0.657 mmol, Preparation #4), K$_2$CO$_3$ (0.218 g, 1.58 mmol) and MeOH (3.00 mL). The reaction mixture was heated to about 80° C. for about 3 h. The reaction mixture was diluted with water (50 mL) and extracted with DCM (50 mL). The organic layer was dried with MgSO$_4$, filtered and concentrated in vacuo. The crude material was purified by silica gel chromatography using heptane/EtOAc (gradient; 1:1 to 0:1) to give the title compound (0.161 g, 71% yield). LC/MS (Table 1, Method a) R$_t$=2.20 min; MS m/z: 342.1 (M+H)$^+$.

TABLE S.1

Examples prepared from 3-isopropyl-[1,2,4]triazolo[4,3-b]pyridazine-6-carbaldehyde (Preparation #2) using General Procedure S

| Tosmic Reagent | Product | Example # | R$_t$ min (method) | m/z ESI+ (M + H)$^+$ |
|---|---|---|---|---|
| 1-Fluoro-4-(isocyano(tosyl)methyl)benzene | 4-(4-Fluorophenyl)-5-(3-isopropyl-[1,2,4]triazolo[4,3-b]pyridazin-6-yl)oxazole | S.1.2 | 2.27 (a) | 324.2 |

TABLE S.1-continued

Examples prepared from 3-isopropyl-[1,2,4]triazolo[4,3-b]pyridazine-6-carbaldehyde (Preparation #2) using General Procedure S

| Tosmic Reagent | Product | Example # | $R_t$ min (method) | m/z ESI+ (M + H)+ |
|---|---|---|---|---|
| 2,4-Difluoro-1-(isocyano(tosyl)methyl)-benzene (Preparation #3) | 4-(2,4-Difluorophenyl)-5-(3-isopropyl-[1,2,4]triazolo[4,3-b]pyridazin-6-yl)oxazole | S.1.3 | 2.20 (a) | 342.4 |

General Procedure T: Acylation of an Amine

A flask is charged with an amine (preferably 1 equiv) and a suitable organic base, such as TEA or DIPEA, (1-3 equiv, preferably 1.2 equiv) in an organic solvent (such as THF or DCM, preferably THF). The mixture is maintained at about 0-22° C. (preferably about 0° C.) for about 5-60 min, preferably about 10 min. An acyl chloride (1-1.5 equiv, preferably 1.1 equiv) is added. The resulting mixture is allowed to stir at about 0-22° C. (preferably about 22° C.) for about 0.5-24 h, preferably about 16 h. Additional acyl chloride (0.2-1.0 equiv, preferably 0.2 equiv) is optionally added, as needed to consume the starting amine as monitored by TLC, LC/MS, or HPLC, and the mixture is optionally stirred for about another 0.5-24 h. The reaction is concentrated under reduced pressure. The crude product is purified by crystallization or trituration from an appropriate solvent or solvents, or by chromatography to give the target compound.

Illustration of General Procedure T

Example #T.1.1

1-(4-(5-(2,4-Difluorophenyl)-4-(3-isopropyl-[1,2,4]triazolo[4,3-b]pyridazin-6-yl)-1H-imidazol-2-yl)piperidin-1-yl)ethanone

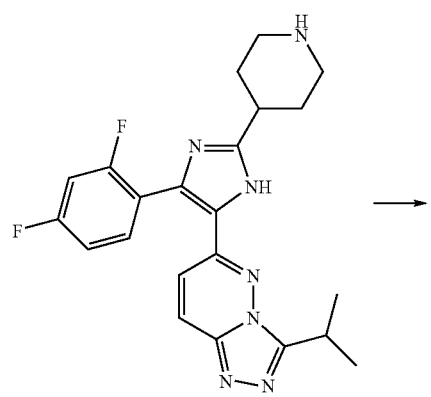

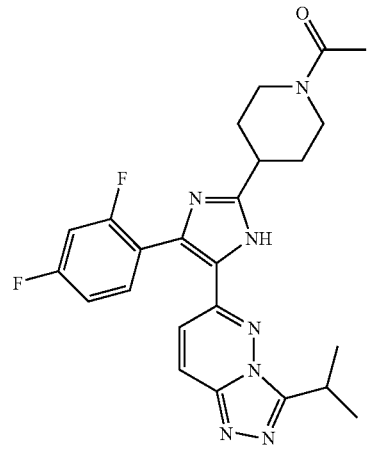

In a 100 mL round-bottomed flask equipped with rubber septum and nitrogen inlet needle was charged with 6-(3-(2,4-difluorophenyl)-2-(piperidin-4-yl)-1H-imidazol-4-yl)-3-isopropyl-[1,2,4]triazolo[4,3-b]pyridazine (0.200 g, 0.472 mmol, Example #Q.1.2) and TEA (0.072 mL, 0.52 mmol) in THF (5.0 mL) to give a white suspension. The reaction mixture was cooled at about 0° C. for about 10 min. Acetyl chloride (0.035 mL, 0.50 mmol) was added dropwise via syringe to give a yellow suspension. The resulting suspension was allowed to stir at about ambient temperature for about 24 h. Additional acetyl chloride (0.010 mL, 0.142 mmol) was added dropwise via syringe. After about 2 h, the mixture was concentrated in vacuo, purified via silica gel chromatography using DCM/MeOH (gradient, 1:0 to 95:5) and recrystallized from ACN to provide the title compound (0.095 g, 42%): LC/MS (Table 1, Method b) $R_t$=1.8 min; MS m/z: 466.2 (M+H)+.

TABLE T.2

Examples prepared from 6-(3-(2,4-difluorophenyl)-1-(piperidin-4-yl)-1H-pyrazol-4-yl)-3-isopropyl-[1,2,4]triazolo[4,3-b]pyridazine (Example #Q.2.1) using General Procedure T

| Acylating Agent | Product | Example # | $R_t$ min (method) | m/z ESI+ (M + H)+ |
|---|---|---|---|---|
| Acetic anhydride | 1-(4-(3-(2,4-Difluorophenyl)-4-(3-isopropyl-[1,2,4]triazolo[4,3- | T.2.1 | 2.15 (a) | 466.2 |

TABLE T.2-continued

Examples prepared from 6-(3-(2,4-difluorophenyl)-1-(piperidin-4-yl)-1H-pyrazol-4-yl)-3-isopropyl-[1,2,4]triazolo[4,3-b]pyridazine (Example #Q.2.1) using General Procedure T

| Acylating Agent | Product | Example # | $R_t$ min (method) | m/z ESI+ (M + H)+ |
|---|---|---|---|---|
| Methoxyacetyl chloride | b]pyridazin-6-yl)-1H-pyrazol-1-yl)piperidin-1-yl)ethanone 1-(4-(3-(2,4-Difluorophenyl)-4-(3-isopropyl-[1,2,4]triazolo[4,3-b]pyridazin-6-yl)-1H-pyrazol-1-yl)piperidin-1-yl)-2-methoxyethanone | T.2.2 | 2.18 (a) | 496.2 |

General Procedure T.1: Acylation of an Amine or Hydrazine

A flask is charged with an amine or hydrazine (preferably 1 equiv) and a suitable organic base, such as TEA, pyridine or DIPEA, (1-20 equiv, preferably 1.2 equiv) in an organic solvent (such as THF or DCM, preferably THF). The mixture is optionally maintained at about 0-30° C. (preferably about 0° C.) for about 5 min-24 h (preferably about 10 min). An acyl chloride (1-5 equiv, preferably 1.1-1.5 equiv) is added. The resulting mixture is allowed to stir at about 0-30° C. (preferably about 22° C.) for about 10 min-24 h (preferably about 16 h). Additional acyl chloride (0.2-1.0 equiv, preferably 0.2 equiv) is optionally added, as needed to consume the starting amine as monitored by TLC, LC/MS, or HPLC, and the mixture is optionally stirred for about another 10 min-24 h. The reaction is optionally concentrated under reduced pressure. The crude reaction mixture or the residue obtained from concentrating under reduced pressure is optionally partitioned between a basic aqueous solution (such as $Na_2CO_3$, $NaHCO_3$ or NaOH, preferably NaOH) and an organic solvent (such as EtOAc, $Et_2O$ or DCM). The organic extract is optionally dried over $Na_2SO_4$ or $MgSO_4$ and then filtered prior to concentrating under reduced pressure. The crude product is purified by crystallization or trituration from an appropriate solvent or solvents, or by chromatography to give the target compound. Illustration of General Procedure T.1

Example #T.1.1.1

1-(3-(3-(2,4-Difluorophenyl)-4-(3-isopropyl-[1,2,4]triazolo[4,3-b]pyridazin-6-yl)-1H-pyrazol-1-yl)pyrrolidin-1-yl)ethanone

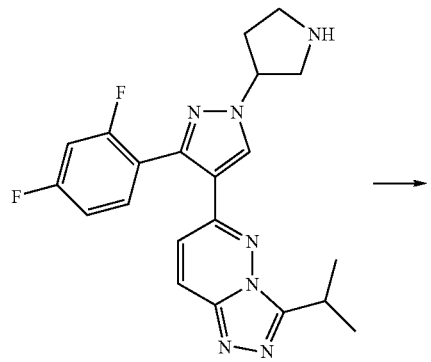

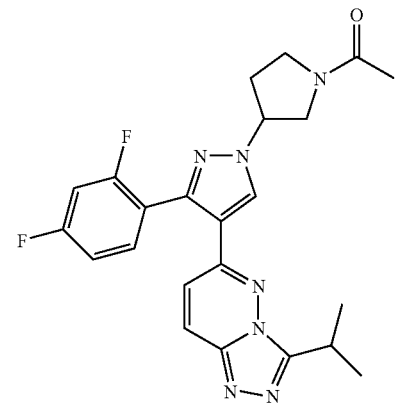

To a round bottom flask was added 6-(3-(2,4-difluorophenyl)-1-(pyrrolidin-3-yl)-1H-pyrazol-4-yl)-3-isopropyl-[1,2,4]triazolo[4,3-b]pyridazine (0.150 g, 0.366 mmol, Example #Q.1.1.1), DCM (10 mL), DIPEA (0.077 mL, 0.440 mmol) and acetyl chloride (0.029 mL, 0.403 mmol). The reaction mixture was stirred at ambient temperature for about 10 min. The reaction mixture was diluted with DCM (50 mL) and washed with saturated aqueous $NaHCO_3$ (50 mL), dried with $MgSO_4$, filtered and concentrated in vacuo. The crude material was purified by flash chromatography (40 g RediSep® silica gel; DCM/MeOH gradient from 1:0 to 9:1) to give the title compound (0.140 g, 84%): LC/MS (Table 1, Method g) $R_t$=2.07 min; MS m/z: 452.4 (M+H)+.

TABLE T.1.1

Examples prepared from acetyl chloride using General Procedure T.1

| Amine | Product | Example # | $R_t$ min (method) | m/z ESI+ (M + H)+ |
|---|---|---|---|---|
| 6-(2-(2,4-Difluorophenyl)-6,7-dihydro-5H-pyrrolo[1,2- | 1-(4-(6-(2-(2,4-Difluorophenyl)-6,7- | T.1.1.2 | 1.69 (g) | 464.3 |

TABLE T.1.1-continued

Examples prepared from acetyl chloride using General Procedure T.1

| Amine | Product | Example # | $R_t$ min (method) | m/z ESI+ $(M + H)^+$ |
|---|---|---|---|---|
| a]imidazol-3-yl)-3-(piperidin-4-yl)-[1,2,4]triazolo[4,3-b]pyridazine [Example #Q.1.1.2] | dihydro-5H-pyrrolo[1,2-a]imidazol-3-yl)-[1,2,4]triazolo[4,3-b]pyridazin-3-yl)piperidin-1-yl)ethanone | | | |
| 6-(1-(Azetidin-3-yl)-3-(2,4-difluorophenyl)-1H-pyrazol-4-yl)-3-isopropyl-[1,2,4]triazolo[4,3-b]pyridazine [prepared using X.1 from tert-butyl 3-(methylsulfonyloxy)azetidine-1-carboxylate and Example #L.1.1, Q.1 with HCl] | 1-(3-(3-(2,4-Difluorophenyl)-4-(3-isopropyl-[1,2,4]triazolo[4,3-b]pyridazin-6-yl)-1H-pyrazol-1-yl)azetidin-1-yl)ethanone | T.1.1.3 | 1.94 (a) | 438.3 |
| 4-(2,4-Difluorophenyl)-5-(3-isopropyl-[1,2,4]triazolo[4,3-b]pyridazin-6-yl)-2-(piperidin-4-yl)thiazole [Example #Q.1.1] | 1-(4-(4-(2,4-Difluorophenyl)-5-(3-isopropyl-[1,2,4]triazolo[4,3-b]pyridazin-6-yl)thiazol-2-yl)piperidin-1-yl)ethanone | T.1.1.4 | 2.94 (a) | 494.1 |
| 2-(6-(6-(2,4-Difluorophenyl)imidazo[2,1-b]oxazol-5-yl)-[1,2,4]triazolo[4,3-b]pyridazin-3-yl)propan-2-amine [Example #Q.1.2.1] | N-(2-(6-(6-(2,4-Difluorophenyl)imidazo[2,1-b]oxazol-5-yl)-[1,2,4]triazolo[4,3-b]pyridazin-3-yl)propan-2-yl)acetamide | T.1.1.5 | 1.72 (g) | 438.1 |

TABLE T.1.2

Examples prepared from 4-(2,4-difluorophenyl)-5-(3-isopropyl-[1,2,4]triazolo[4,3-b]pyridazin-6-yl)-2-(piperidin-4-yl)thiazole (Example #Q.1.1) using General Procedure T.1

| Acid chloride | Product | Example # | $R_t$ min (method) | m/z ESI+ $(M + H)^+$ |
|---|---|---|---|---|
| 3-Methylbutanoyl chloride | 1-(4-(4-(2,4-Difluorophenyl)-5-(3-isopropyl-[1,2,4]triazolo[4,3-b]pyridazin-6-yl)thiazol-2-yl)piperidin-1-yl)-3-methylbutan-1-one | T.1.2.1 | 2.75 (a) | 525.3 |
| Dimethylcarbamic chloride [Lancaster] | 4-(4-(2,4-Difluorophenyl)-5-(3-isopropyl-[1,2,4]triazolo[4,3-b]pyridazin-6-yl)thiazol-2-yl)-N,N-dimethylpiperidine-1-carboxamide | T.1.2.2 | 2.49 (a) | 512.3 |

TABLE T.1.3

Examples prepared from 4-(2,4-difluorophenyl)-5-(3-isopropyl-[1,2,4]triazolo[4,3-b]pyridazin-6-yl)-2-(piperazin-1-yl)thiazole (Example #5) using General Procedure T.1

| Acylating Agent | Product | Example # | $R_t$ min (method) | m/z ESI+ $(M + H)^+$ |
|---|---|---|---|---|
| Dimethylamino acetyl chloride | 1-(4-(4-(2,4-Difluorophenyl)-5-(3-isopropyl-[1,2,4]triazolo[4,3-b]pyridazin-6-yl)thiazol-2-yl)piperazin-1-yl)-2-(dimethylamino)ethanone | T.1.3.1 | 2.27 (a) | 527.7 |
| 2-Chloro-2-oxoethyl acetate | 2-(4-(4-(2,4-Difluorophenyl)-5-(3-isopropyl-[1,2,4]triazolo[4,3-b]pyridazin-6-yl)thiazol-2-yl)piperazin-1-yl)-2-oxoethyl acetate | T.1.3.2 | 2.87 (a) | 542.5 |

General Procedure U: Formation of a Sulfonamide from an Amine

A mixture of an amine (preferably 1 equiv), an organic solvent (such as DCM, THF, or DMF; preferably DCM), and a base (such as TEA, pyridine, preferably TEA, 2-10 equiv, preferably 4 equiv) is stirred at about 0-60° C. (preferably about 0-4° C.). Then a sulfonylating agent (such as an alkyl-sulfonyl chloride; 1-1.5 equiv, preferably 1 equiv) is added. The reaction temperature is maintained at about 0-60° C. (preferably about 0-4° C.) for about 1-6 h (preferably about 1-2 h). The reaction is quenched with a base (such as saturated aqueous $Na_2CO_3$ or saturated aqueous $NaHCO_3$) and then extracted with organic solvent (such as EtOAc, $Et_2O$, or DCM; preferably DCM). The combined organic layers may be optionally washed with brine, dried over $Na_2SO_4$ or $MgSO_4$, and then decanted or filtered prior to concentrating under reduced pressure. The crude product is purified by crystallization or trituration from an appropriate solvent or solvents, or by chromatography to give the target compound.

Illustration of General Procedure U
Example #U.1.1
4-(2,4-Difluorophenyl)-5-(3-isopropyl-[1,2,4]triazolo[4,3-b]pyridazin-6-yl)-2-(1-(methylsulfonyl)piperidin-4-yl)thiazole A mixture of 4-(2,4-difluorophenyl)-5-(3-isopropyl-[1,2,4]triazolo[4,3-b]pyridazin-6-yl)-2-(piperidin-4-yl)thiazole (0.25 g, 0.57 mmol, Example #Q.1.1), TEA (0.32 mL, 2.3 mmol) and DCM (5 mL) was cooled to about 0-4° C. Methanesulfonyl chloride (0.044 mL, 0.57 mmol) was added. The reaction mixture was stirred at about 04° C. for about 1 h. The reaction was quenched with saturated aqueous $Na_2CO_3$ solution. The aqueous layer was extracted with DCM (200 mL). The organic layer was dried over $Na_2SO_4$, decanted, and concentrated. The crude product was purified by RP-HPLC (Table 1, Method e) to give the title compound (0.14 g, 48%): LC/MS (Table 1, Method a) $R_t$=2.49 min; MS m/z: 519.2 $(M+H)^+$.

TABLE U.1

Examples prepared with methanesulfonyl chloride using General Procedure U

| Amine | Product | Example # | $R_t$ min (method) | m/z ESI+ $(M + H)^+$ |
|---|---|---|---|---|
| 6-(3-(2,4-Difluorophenyl)-1-(piperidin-4-yl)-1H-pyrazol-4-yl)-3-isopropyl-[1,2,4]triazolo[4,3-b]pyridazine (Example #Q.1.2) | 6-(3-(2,4-Difluorophenyl)-1-(1-(methylsulfonyl)piperidin-4-yl)-1H-pyrazol-4-yl)-3-isopropyl-[1,2,4]triazolo[4,3-b]pyridazine | U.1.2 | 2.38 (a) | 502.2 |

General Procedure U.1: Formation of a Sulfonamide from an Amine

A mixture of an amine (preferably 1 equiv), an organic solvent (such as DCM, THF, or DMF; preferably DCM), and a base (such as TEA, DIPEA, pyridine, preferably TEA or DIPEA, 1.5-20 equiv, preferably 1.5-4 equiv) is stirred at about 0-60° C. (preferably about 0-20° C.). Then a sulfonylating agent (such as a sulfonyl chloride; 1-5 equiv, preferably 1 equiv) is added. The reaction temperature is maintained at about 0-60° C. (preferably about 04° C.) for about 10 min-6 h (preferably about 10 min-2 h). The reaction mixture is purified directly or optionally quenched with a base (such as saturated aqueous $Na_2CO_3$ or saturated aqueous $NaHCO_3$) and then extracted with organic solvent (such as EtOAc, $Et_2O$, or DCM; preferably DCM). The combined organic layers may be optionally washed with brine, dried over $Na_2SO_4$ or $MgSO_4$, and then decanted or filtered prior to concentrating under reduced pressure. The crude product is purified by crystallization or trituration from an appropriate solvent or solvents, or by chromatography to give the target compound.

Illustration of General Procedure U.1
Example #U.1.1.1

6-(3-(2,4-Difluorophenyl)-1-(1-(methylsulfonyl)pyrrolidin-3-yl)-1H-pyrazol-4-yl)-3-isopropyl-[1,2,4]triazolo[4,3-b]pyridazine

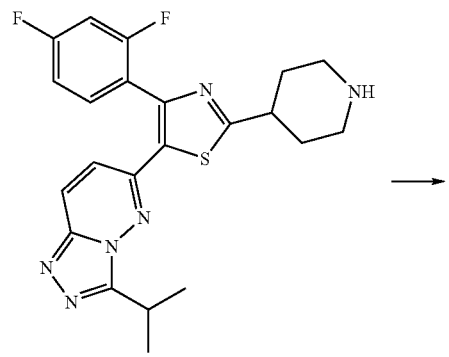

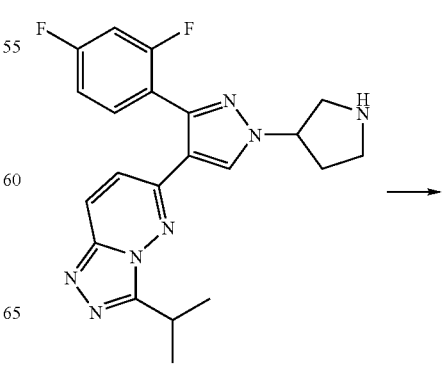

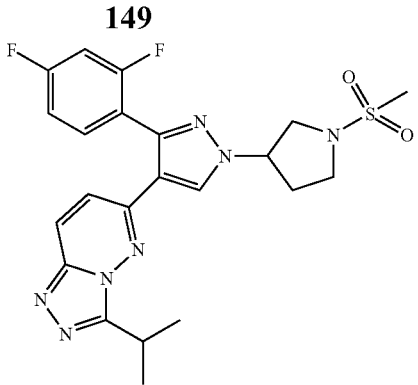

To a round bottom flask was added 6-(3-(2,4-difluorophenyl)-1-(pyrrolidin-3-yl)-1H-pyrazol-4-yl)-3-isopropyl-[1,2,4]triazolo[4,3-b]pyridazine (0.105 g, 0.256 mmol, Example #Q.1.1.1), DCM (5 mL) and DIPEA (0.054 mL, 0.31 mmol). Then methanesulfonyl chloride (0.020 mL, 0.26 mmol) was added. The reaction mixture was stirred at ambient temperature for about 10 min. The reaction mixture was purified directly by flash chromatography (40 g RediSep® silica gel; DCM/MeOH gradient from 1:0 to 9:1) to give the title compound (0.120 g, 96%): LC/MS (Table 1, Method g) $R_t$=2.28 min; MS m/z: 488.3 (M+H)$^+$.

TABLE U.1.1

Examples prepared with methanesulfonyl chloride using General Procedure U.1

| Amine | Product | Example # | $R_t$ min (method) | m/z ESI+ (M + H)$^+$ |
|---|---|---|---|---|
| 4-(2,4-Difluorophenyl)-5-(3-isopropyl-[1,2,4]triazolo[4,3-b]pyridazin-6-yl)-2-(piperazin-1-yl)thiazole [Example #5] | 4-(2,4-Difluorophenyl)-5-(3-isopropyl-[1,2,4]triazolo[4,3-b]pyridazin-6-yl)-2-(4-(methylsulfonyl)piperazin-1-yl)thiazole | U.1.1.2 | 3.12 (a) | 520.5 |
| 2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-amine [prepared using E.1 from Example #35, Step E with tert-butyl 2-methyl-1-oxopropan-2-ylcarbamate (prepared using AI.1 from tert-butyl 1-hydroxy-2-methylpropan-2-ylcarbamate), Q.1 with HCl] | N-(2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-yl)methanesulfonamide | U.1.1.3 | 1.60 (g) | 438.2 |
| 2-(6-(6-(2,4-Difluorophenyl)imidazo[2,1-b]oxazol-5-yl)-[1,2,4]triazolo[4,3-b]pyridazin-3-yl)propan-2-amine (Example #Q.1.2.1) | N-(2-(6-(6-(2,4-Difluorophenyl)imidazo-[2,1-b]oxazol-5-yl)-[1,2,4]triazolo[4,3-b]pyridazin-3-yl)propan-2-yl)methanesulfonamide | U.1.1.4 | 1.80 (g) | 474.1 |

General Procedure V: Hydrolysis of an Ester

A flask is charged with an ester (preferably 1 equiv) in suitable solvent (such as THF or THF/MeOH, preferably THF). A suitable base (such as aqueous NaOH, KOH, or LiOH, preferably 2.5M aqueous NaOH; 1-10 equivalents, preferably 1 equiv) is added. The reaction mixture is stirred at about 22-40° C. (preferably ambient temperature) for about 0.5-24 h (preferably about 0.5 h). Additional base is optionally added as needed to consume the starting ester as monitored by TLC, LC/MS, or HPLC. The reaction mixture is optionally stirred at about 22-40° C. (preferably ambient temperature) for about an additional 1-16 h (preferably about 1 h). The solution is treated with acid (such as 1N HCl or HOAc; preferably 1N HCl) to acidic pH (preferably about pH 5). The reaction mixture is partitioned between an organic solvent (such as DCM or EtOAc, preferably DCM) and water. The layers are separated and the combined organic layers may be optionally washed with brine, dried over $Na_2SO_4$ or $MgSO_4$, then decanted or filtered prior to concentrating under reduced pressure. The crude product is purified by crystallization or trituration from an appropriate solvent or solvents, or by chromatography to give the target compound.

Illustration of General Procedure U.1

Example #U.1.1.1

6-(3-(2,4-Difluorophenyl)-1-(1-(methylsulfonyl)pyrrolidin-3-yl)-1H-pyrazol-4-yl)-3-isopropyl-[1,2,4]triazolo[4,3-b]pyridazine

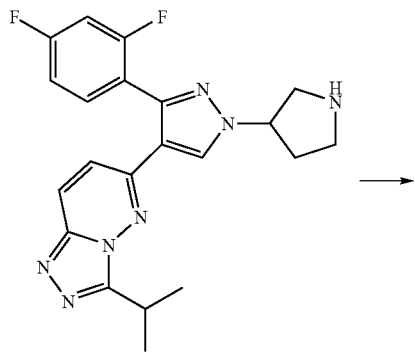

⟶

Example #V.1.1

1-(4-(5-(2,4-Difluorophenyl)-4-(3-isopropyl-[1,2,4]triazolo[4,3-b]pyridazin-6-yl)-1H-imidazol-2-yl)piperidin-1-yl)-2-hydroxyethanone

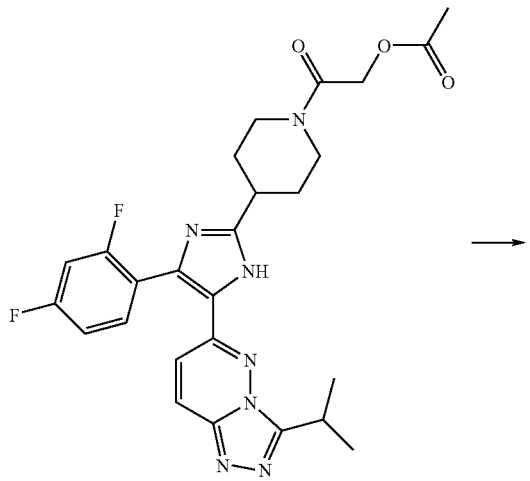

⟶

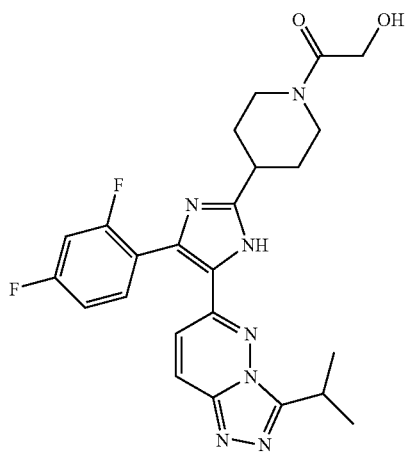

A 100 mL round-bottomed flask equipped with rubber septum and nitrogen inlet needle was charged with 2-(4-(5-(2,4-difluorophenyl)-4-(3-isopropyl-[1,2,4]triazolo[4,3-b]pyridazin-6-yl)-1H-imidazol-2-yl)piperidin-1-yl)-2-oxoethyl acetate (0.145 g, 0.277 mmol, prepared using General Procedure T from 6-(3-(2,4-difluorophenyl)-2-(piperidin-4-yl)-1H-imidazol-4-yl)-3-isopropyl-[1,2,4]triazolo[4,3-b]pyridazine (Example #Q.1.2) and acetoxyacetyl chloride) in THF (5.0 mL). A 2.5M aqueous NaOH solution (0.274 mL, 0.685 mmol) was added dropwise via syringe to give a yellow solution. The reaction mixture was stirred at about ambient temperature for about 20 min. Additional 2.5M aqueous NaOH (0.274 mL, 0.685 mmol) was added dropwise via syringe. The reaction mixture was stirred at about ambient temperature for about 1 h. The solution was acidified with 1N HCl to about pH 5. The reaction mixture was partitioned between DCM and water. The layers were separated and the organic layer was washed with brine, dried over MgSO$_4$, filtered and concentrated in vacuo. The crude material was purified by silica gel chromatography using DCM/MeOH (gradient, 1:0 to 9:1) to provide the title compound (0.107 g, 80%): LC/MS (Table 1, Method b) R$_t$=1.7 min; MS m/z: 482.2 (M+H)$^+$.

TABLE V.1

Examples prepared with NaOH using General Procedure V

| Ester | Product | Example # | R$_t$ min (method) | m/z ESI+ (M + H)$^+$ |
|---|---|---|---|---|
| 2-(4-(4-(2,4-Difluorophenyl)-5-(3-isopropyl-[1,2,4]triazolo[4,3-b]pyridazin-6-yl)thiazol-2-yl)piperidin-1-yl)-2-oxoethyl acetate (prepared using T from Example #Q.1.1 and 2-chloro-2-oxoethyl acetate) | 1-(4-(4-(2,4-Difluorophenyl)-5-(3-isopropyl-[1,2,4]triazolo[4,3-b]pyridazin-6-yl)thiazol-2-yl)piperidin-1-yl)-2-hydroxyethanone | V.1.2 | 2.14 (a) | 499.2 |

General Procedure V.1: Hydrolysis of an Ester

A flask is charged with an ester (preferably 1 equiv) in suitable solvent (such as THF, 1,4-dioxane or THF/MeOH, preferably THF). A suitable base (such as aqueous NaOH, KOH, or LiOH, preferably 1.0-2.5M aqueous NaOH; 1-10 equivalents, preferably 1 equiv) is added. The reaction mixture is stirred at about 0-80° C. (preferably about 10-40° C.) for about 0.5-24 h (preferably about 0.5 h). Additional base is optionally added as needed to consume the starting ester as monitored by TLC, LC/MS, or HPLC. The reaction mixture is optionally stirred at about 0-80° C. (preferably about 10-40° C.) for about 0.5-24 h (preferably about 0.5 h). The solution is optionally treated with acid (such as 1N HCl or HOAc; preferably 1N HCl) to acidic pH (preferably about pH 5). The reaction mixture is partitioned between an organic solvent (such as DCM or EtOAc, preferably DCM) and water. The layers are separated and the aqueous layer is optionally washed with additional organic solvent (such as DCM or EtOAC). The combined organic layers may be optionally washed with brine, dried over $Na_2SO_4$ or $MgSO_4$, then decanted or filtered prior to concentrating under reduced pressure. The crude product is purified by crystallization or trituration from an appropriate solvent or solvents, or by chromatography to give the target compound.

Illustration of General Procedure V.1

Example #V.1.1.1

2-Hydroxy-1-(4-(5-(3-isopropyl-[1,2,4]triazolo[4,3-b]pyridazin-6-yl)-4-(2,4,5-trifluorophenyl)thiazol-2-yl)piperidin-1-yl)ethanone

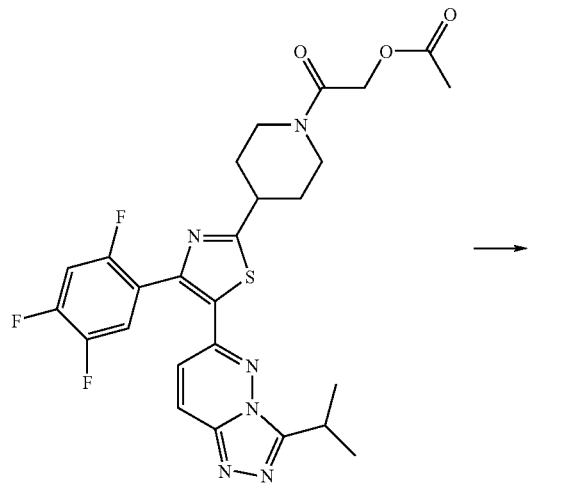

→

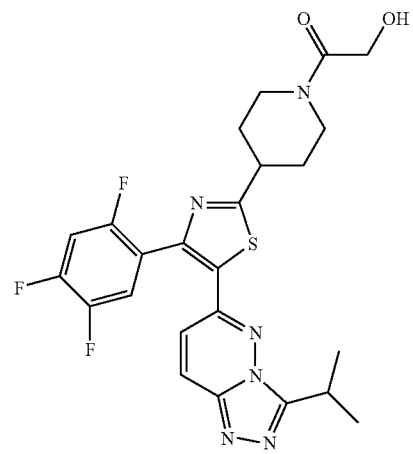

A round-bottomed flask equipped with rubber septum and nitrogen inlet needle was charged with 2-(4-(5-(3-isopropyl-[1,2,4]triazolo[4,3-b]pyridazin-6-yl)-4-(2,4,5-trifluorophenyl)thiazol-2-yl)piperidin-1-yl)-2-oxoethyl acetate (0.22 g, 0.39 mmol, prepared using General Procedure Q.1 from Preparation #O.1.1.1 with TFA, General Procedure T.1 with acetoxyacetyl chloride) in THF (5.0 mL). A 1.0 M aqueous NaOH solution (2 mL, 2 mmol) was added. The reaction mixture was stirred at about 40° C. for about 1 h. The reaction was diluted with water and then extracted with EtOAc (2×100 mL). The combined organic layers were washed with water, dried over $Na_2SO_4$, filtered and concentrated in vacuo. The crude product was purified by RP-HPLC (Table 1, Method f) to give the title compound (0.145 g, 71%): LC/MS (Table 1, Method a) $R_t$=2.89 min; MS m/z: 518.1 (M+H)$^+$.

TABLE V.1.1

Examples prepared with NaOH using General Procedure V.1

| Ester | Product | Example # | $R_t$ min (method) | m/z ESI+ (M + H)$^+$ |
|---|---|---|---|---|
| 2-(4-(3-(2,4-Difluorophenyl)-4-(3-isopropyl-[1,2,4]triazolo[4,3-b]pyridazin-6-yl)-1H-pyrazol-1-yl)piperidin-1-yl)-2-oxoethyl acetate [prepared using T.1 from Example #Q.2.1 and 2-chloro-2-oxoethyl acetate] | 1-(4-(3-(2,4-Difluorophenyl)-4-(3-isopropyl-[1,2,4]triazolo[4,3-b]pyridazin-6-yl)-1H-pyrazol-1-yl)piperidin-1-yl)-2-hydroxyethanone | V.1.1.2 | 2.06 (a) | 482.3 |

TABLE V.1.1-continued

Examples prepared with NaOH using General Procedure V.1

| Ester | Product | Example # | $R_t$ min (method) | m/z ESI+ (M + H)+ |
|---|---|---|---|---|
| 2-(4-(4-(2,4-Difluorophenyl)-5-(3-isopropyl-[1,2,4]triazolo[4,3-b]pyridazin-6-yl)thiazol-2-yl)piperazin-1-yl)-2-oxoethyl acetate [prepared using T.1 from Example #5 and 2-chloro-2-oxoethyl acetate] | 1-(4-(4-(2,4-Difluorophenyl)-5-(3-isopropyl-[1,2,4]triazolo[4,3-b]pyridazin-6-yl)thiazol-2-yl)piperazin-1-yl)-2-hydroxyethanone | V.1.1.3 | 2.63 (a) | 500.5 |
| 2-(4-(5-(3-Isopropyl-[1,2,4]triazolo[4,3-b]pyridazin-6-yl)-4-(2,4,5-trifluorophenyl)thiazol-2-yl)piperidin-1-yl)-2-oxoethyl acetate [prepared using T.1 from Example #Q.1.3 with 2-chloro-2-oxoethyl acetate] | 2-Hydroxy-1-(4-(5-(3-isopropyl-[1,2,4]triazolo[4,3-b]pyridazin-6-yl)-4-(2,4,5-trifluorophenyl)thiazol-2-yl)piperidin-1-yl)ethanone | V.1.1.4 | 2.89 (a) | 518.1 |

General Procedure W: Formation of a Mesylate or Tosylate

To a solution of an alcohol (preferably 1 equiv) in an organic solvent (for example, THF, 1,4-dioxane, DCM, toluene, Et$_2$O or DME, preferably DCM) at about 0-30° C. (preferably about 0° C.) is added a mesylating agent (for example, methanesulfonyl chloride, methanesulfonic anhydride or methanesulfonyl fluoride, preferably methanesulfonyl chloride) (1-3 equiv, preferably 1.2 equiv) or a tosylating agent (for example, p-toluenesulfonyl chloride) (1-3 equiv, preferably 1.2 equiv), and an organic base (such as pyridine, TEA, DMAP or DIPEA, preferably pyridine). After about 1-18 h (preferably about 12 h), the reaction is concentrated under reduced pressure. The residue is partitioned between water and an organic solvent (such as EtOAc). The organic extract is dried over Na$_2$SO$_4$ or MgSO$_4$ and then filtered prior to concentrating under reduced pressure. The crude product is purified by crystallization or trituration from an appropriate solvent or solvents, or by chromatography to give the target compound.

Illustration of General Procedure W

Preparation #W.1: 2-(3-(2,4-Difluorophenyl)-4-(3-isopropyl-[1,2,4]triazolo[4,3-b]pyridazin-6-yl)-1H-pyrazol-1-yl)ethyl methanesulfonate

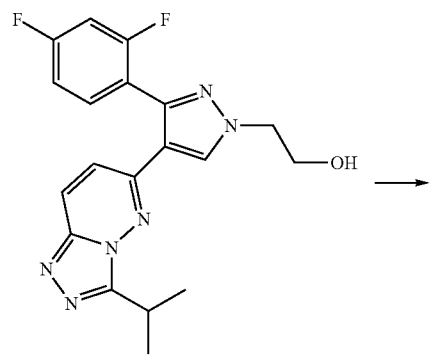

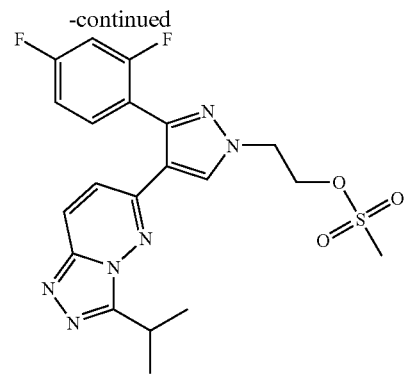

The 2-(3-(2,4-difluorophenyl)-4-(3-isopropyl-[1,2,4]triazolo[4,3-b]pyridazin-6-yl)-1H-pyrazol-1-yl)ethanol (0.60 g, 1.6 mmol; Example #L.1.3) was suspended in DCM (6 mL) and then the pyridine (0.25 mL, 3.1 mmol) was added and the mixture was cooled to about 0° C. The methanesulfonyl chloride (0.15 mL, 1.9 mmol) was added and then the mixture was stirred in the ice bath for about 30 min. A few crystals of DMAP were added and then the mixture was stirred at ambient temperature overnight. The solution was cooled in an ice bath and then ice water was added to the mixture. The mixture was transferred to a separatory funnel and the layers were separated and the aqueous layer was extracted with DCM. The organic extracts were combined and dried over MgSO$_4$ and then filtered prior to concentrating under reduced pressure to give the target compound (1.0 g, >100%) which contained pyridine: LC/MS (Table 1, Method a) R$_t$=2.32 min; MS m/z: 463.2 (M+H)+.

General Procedure X: Displacement of a Mesylate

To a solution of a mesylate (preferably 1 equiv) in an organic solvent (for example, THF, 1,4-dioxane, DCM, toluene, Et$_2$O, acetone, MeOH, EtOH, DMF or DME, preferably MeOH or DMF) is added a suitable nucleophile (for example primary or secondary amines, cyanide salts, heterocyclic amines or their alkali salts) (1-10 equiv, preferably 8 equiv). After about 1-18 h (preferably about 2 h) at about 0-100° C. (preferably about 70° C.) the reaction is concentrated under reduced pressure. The residue is partitioned between water and an organic solvent (such as EtOAc). The organic extract is dried over Na$_2$SO$_4$ or MgSO$_4$, and then filtered prior to concentrating under reduced pressure. The crude product is purified by crystallization or trituration from an appropriate solvent or solvents, or by chromatography to give the target compound.

Illustration of General Procedure X

Example #X.1.1

4-(2-(3-(2,4-Difluorophenyl)-4-(3-isopropyl-[1,2,4]triazolo[4,3-b]pyridazin-6-yl)-1H-pyrazol-1-yl)ethyl)morpholine

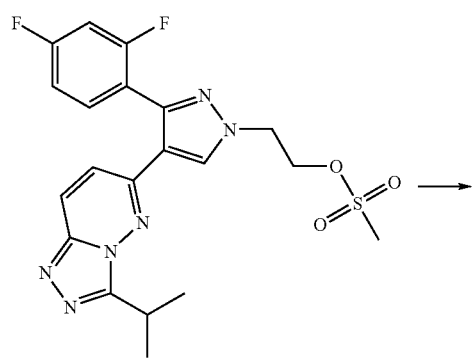

-continued

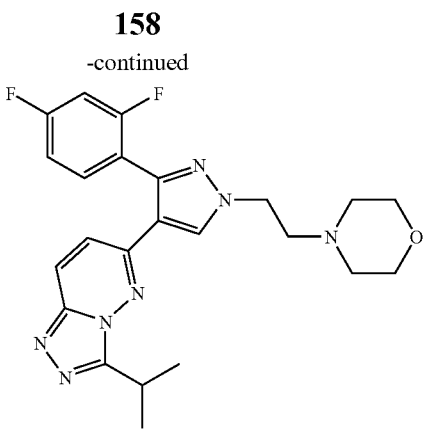

The 2-(3-(2,4-difluorophenyl)-4-(3-isopropyl-[1,2,4]triazolo[4,3-b]pyridazin-6-yl)-1H-pyrazol-1-yl)ethyl methanesulfonate (0.24 g, 0.52 mmol; Preparation #W.1) was dissolved in MeOH (4 mL) then morpholine (0.36 g, 4.2 mmol) was added. The mixture was heated at about 70° C. in an oil bath for about 2 h then cooled and concentrated under reduced pressure. The crude material was purified by RP-HPLC (Table 1, Method d). The appropriate fractions were concentrated under reduced pressure then basified with 2 N NaOH. Extraction of the solution with EtOAc followed by drying of the organic extract over MgSO$_4$ and then filtration prior to concentrating under reduced pressure gave the title compound (0.10 g, 43%): LC/MS (Table 1, Method a) R$_t$=2.09 min; MS m/z: 454.2 (M+H)$^+$.

TABLE X.1

Examples prepared from 2-(3-(2,4-difluorophenyl)-4-(3-isopropyl-[1,2,4]triazolo[4,3-b]pyridazin-6-yl)-1H-pyrazol-1-yl)ethyl methanesulfonate (Preparation #W.1) using General Procedure X

| Nucleophile | Product | Example # | R$_t$ min (method) | m/z ESI+ (M + H)$^+$ |
|---|---|---|---|---|
| Dimethylamine | 2-(3-(2,4-Difluorophenyl)-4-(3-isopropyl-[1,2,4]triazolo[4,3-b]pyridazin-6-yl)-1H-pyrazol-1-yl)-N,N-dimethylethanamine | X.1.2 | 1.84 (a) | 412.2 |
| Imidazole, sodium derivative | 6-(1-(2-(1H-imidazol-1-yl)ethyl)-3-(2,4-difluorophenyl)-1H-pyrazol-4-yl)-3-isopropyl-[1,2,4]triazolo[4,3-b]pyridazine | X.1.3 | 1.83 (a) | 435.2 |

General Procedure X.1: Displacement of a Mesylate or Tosylate

To a reaction flask is added a nucleophile (for example primary or secondary amines, cyanide salts, heterocyclic amines or their alkali salts, heterocycles, and azides) (preferably 1 equiv), an organic solvent (for example, THF, 1,4-dioxane, DCM, toluene, Et$_2$O, acetone, MeOH, EtOH, DMF or DME, preferably MeOH or DMF) and a base (for example NaH, K$_2$CO$_3$, Cs$_2$CO$_3$, NaHCO$_3$, Na$_2$CO$_3$, NaOH, KOH, TEA, DIPEA or pyridine, preferably NaH or K$_2$CO$_3$). Alternatively, the nucleophile may be added to the base. The reaction mixture is stirred about 15 min-24 h (preferably about 30 min-2 h) and then a mesylate or tosylate is added (1-5 equiv, preferably 1-2 equiv). The reaction is stirred at ambient temperature for about 5 min-2 h (preferably 30 min) and then is heated at about 0-100° C. (preferably about 20-80° C.) for about 15 min-18 h (preferably about 30 min-2 h). The reaction is optionally concentrated under reduced pressure. The resi due or reaction mixture is partitioned between water and an organic solvent (such as DCM or EtOAc). The organic layer is separated and the aqueous layer is optionally washed with additional organic solvent (DCM or EtOAc). The combined organic layers are dried with a drying agent (such as Na₂SO₄ or MgSO₄) and then filtered prior to concentrating under reduced pressure. The crude product is purified by crystallization or trituration from an appropriate solvent or solvents, or by chromatography to give the target compound.

Illustration of General Procedure X.1

Preparation #X.1.1.1: tert-Butyl 3-(3-(2,4-difluorophenyl)-4-(3-isopropyl-[1,2,4]triazolo[4,3-b]pyridazin-6-yl)-1H-pyrazol-1-yl)pyrrolidine-1-carboxylate

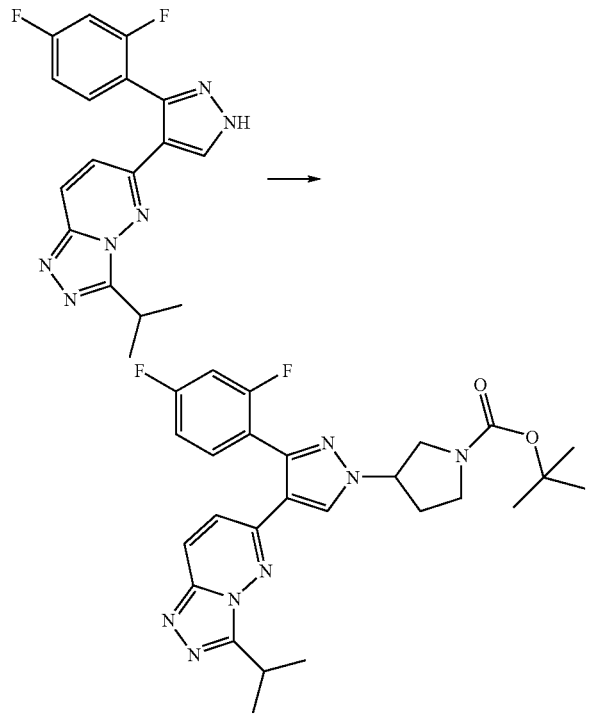

To a round bottom flask was added NaH (0.065 g, 1.6 mmol), DMF (4 mL) and 6-(3-(2,4-difluorophenyl)-1H-pyrazol-4-yl)-3-isopropyl-[1,2,4]triazolo[4,3-b]pyridazine (0.500 g, 1.47 mmol, Example #L.1.1). The reaction mixture was stirred for about 30 min at ambient temperature. tert-Butyl 3-(tosyloxy)pyrrolidine-1-carboxylate (0.652 g, 1.91 mmol, prepared according to US 2002/0151712, Example #34c) was added and the reaction mixture was stirred for about 30 min at ambient temperature. The reaction mixture was heated to about 75° C. for about 1 h. The reaction mixture was diluted with DCM (50 mL), washed with water (50 mL), dried with MgSO₄, filtered and concentrated in vacuo. The reaction mixture was purified by flash chromatography (40 g RediSep® silica gel; DCM/MeOH gradient from 1:0 to 90:10) to give the title compound (0.446 g, 60%) as a mixture of regioisomers: LC/MS (Table 1, Method g) $R_f$=3.66 min; MS m/z: 510.4 (M+H)⁺.

General Procedure Y: Reductive Amination

To a solution of the amine substrate (preferably 1 equiv) in an organic solvent (for example DCM, EtOAc, DMF or DCE, preferably DCE) is added an aldehyde or ketone (1-10 equiv, preferably 1-2 equiv) and sodium triacetoxyborohydride (1-10 equiv, preferably 1-2 equiv). The resulting mixture is allowed to stir at ambient temperature for about 0.5-20 h (preferably about 0.5-3 h). Acetic acid (catalytic-10 equiv, preferably 1 drop-4 equiv) is added to progress the reaction when necessary. Upon completion, the reaction solution is treated with an aqueous solution of an appropriate base (NaOH, NaHCO₃, or Na₂CO₃ preferably NaHCO₃) and DCM. The organic extract is dried over Na₂SO₄ or MgSO₄ and then filtered prior to concentrating under reduced pressure. The crude product is purified by crystallization or trituration from an appropriate solvent or solvents, or by chromatography to give the target compound.

Illustration of General Procedure Y

Example #Y.1

6-(3-(2,4-Difluorophenyl)-1-(1-methylpiperidin-4-yl)-1H-pyrazol-4-yl)-3-isopropyl-[1,2,4]triazolo[4,3-b]pyridazine

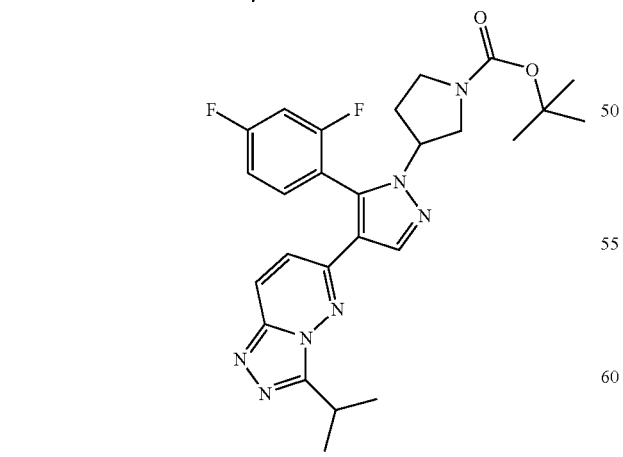

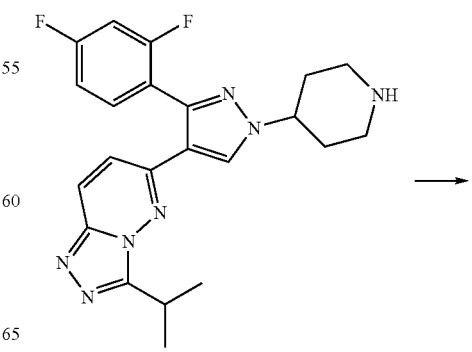

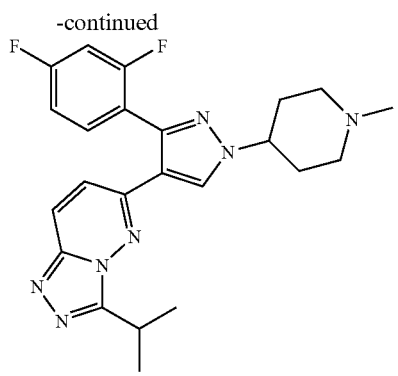

The 6-(3-(2,4-difluorophenyl)-1-(piperidin-4-yl)-1H-pyrazol-4-yl)-3-isopropyl-[1,2,4]triazolo[4,3-b]pyridazine (0.10 g, 0.24 mmol; Example #Q.2.1) was suspended in DCE (5 mL) and then formaldehyde (30% solution in water, 0.12 g, 1.18 mmol) and sodium triacetoxyborohydride (0.10 g, 0.47 mmol) were added. After about 1 h, the mixture was concentrated under reduced pressure, dissolved in DMF/HOAc, and purified by RP-HPLC (Table 1, Method d). The appropriate fractions were combined and concentrated under reduced pressure and then the mixture was basified with 2 N NaOH and extracted with EtOAc. The organic solution was dried over MgSO$_4$, filtered, and concentrated under reduced pressure. Evaporation several times with Et$_2$O/heptane gave a white solid which was collected by filtration and dried under vacuum to give the title compound (0.042 g, 41%): LC/MS (Table 1, Method a) R$_t$=1.83 min; MS m/z: 438.2 (M+H)$^+$.

TABLE Y.1

Examples prepared from 6-(3-(2,4-difluorophenyl)-1-(piperidin-4-yl)-1H-pyrazol-4-yl)-3-isopropyl-[1,2,4]triazolo[4,3-b]pyridazine (Example #Q.2.1) using General Procedure Y

| Aldehyde or Ketone | Product | Example # | R$_t$ min (method) | m/z ESI+ (M + H)$^+$ |
|---|---|---|---|---|
| Trimethylacetaldehyde | 6-(3-(2,4-Difluorophenyl)-1-(1-neopentylpiperidin-4-yl)-1H-pyrazol-4-yl)-3-isopropyl-[1,2,4]triazolo[4,3-b]pyridazine | Y.1.2 | 2.16 (a) | 494.3 |
| Isobutyraldehyde | 6-(3-(2,4-Difluorophenyl)-1-(1-isobutylpiperidin-4-yl)-1H-pyrazol-4-yl)-3-isopropyl-[1,2,4]triazolo[4,3-b]pyridazine | Y.1.3 | 2.00 (a) | 480.3 |
| Acetone | 6-(3-(2,4-Difluorophenyl)-1-(1-isopropylpiperidin-4-yl)-1H-pyrazol-4-yl)-3-isopropyl-[1,2,4]triazolo[4,3-b]pyridazine hydrochloride | Y.1.4 | 1.87 (a) | 466.3 |

TABLE Y.2

Examples prepared from 4-(2,4-difluorophenyl)-5-(3-isopropyl-[1,2,4]triazolo[4,3-b]pyridazin-6-yl)-2-(piperidin-4-yl)thiazole (Example #Q.1.1) using General Procedure Y

| Aldehyde or Ketone | Product | Example # | R$_t$ min (method) | m/z ESI+ (M + H)$^+$ |
|---|---|---|---|---|
| Formaldehyde | 4-(2,4-Difluorophenyl)-5-(3-isopropyl-[1,2,4]triazolo[4,3-b]pyridazin-6-yl)-2-(1-methylpiperidin-4-yl)thiazole | Y.2.1 | 2.31 (a) | 455.9 |
| Acetone | 4-(2,4-Difluorophenyl)-5-(3-isopropyl-[1,2,4]triazolo[4,3-b]pyridazin-6-yl)-2-(1-isopropylpiperidin-4-yl)thiazole | Y.2.2 | 2.47(a) | 483.4 |
| Cyclopropanecarbaldehyde | 2-(1-(Cyclopropylmethyl)piperidin-4-yl)-4-(2,4-difluorophenyl)-5-(3-isopropyl-[1,2,4]triazolo[4,3-b]pyridazin-6-yl)thiazole | Y.2.3 | 2.43(a) | 495.3 |
| Cyclobutanone | 2-(1-Cyclobutylpiperidin-4-yl)-4-(2,4-difluorophenyl)-5-(3-isopropyl-[1,2,4]triazolo[4,3-b]pyridazin-6-yl)thiazole | Y.2.4 | 2.36(a) | 495.6 |
| Pivalaldehyde | 4-(2,4-Difluorophenyl)-5-(3-isopropyl-[1,2,4]triazolo[4,3-b]pyridazin-6-yl)-2-(1-neopentylpiperidin-4-yl)thiazole | Y.2.5 | 2.72(a) | 511.7 |
| Acetaldehyde | 4-(2,4-Difluorophenyl)-2-(1-ethylpiperidin-4-yl)-5-(3-isopropyl-[1,2,4]triazolo[4,3-b]pyridazin-6-yl)thiazole | Y.2.6 | 2.24(a) | 469.4 |

TABLE Y.3

Examples prepared from 5-(3-tert-butyl-[1,2,4]triazolo[4,3-b]pyridazin-6-yl)-4-(2,4-difluorophenyl)-2-(piperidin-4-yl)thiazole (prepared using A.2 from 2-(3-tert-butyl-[1,2,4]triazolo[4,3-b]pyridazin-6-yl)-1-(2,4-difluorophenyl)ethanone (Example #9, Step E, intermediate), O.1 with tert-butyl 4-carbamothioylpiperidine-1-carboxylate [Maybridge], Q.1 with TFA) using General Procedure Y

| Aldehyde or Ketone | Product | Example # | $R_t$ min (method) | m/z ESI+ $(M + H)^+$ |
|---|---|---|---|---|
| Formaldehyde | 5-(3-tert-Butyl-[1,2,4]triazolo[4,3-b]pyridazin-6-yl)-4-(2,4-difluorophenyl)-2-(1-methylpiperidin-4-yl)thiazole | Y.3.1 | 1.65 (a) | 469.2 |

General Procedure Z: Mitsunobu Reaction of a Pyrazole

To a solution of a pyrazole (preferably 1 equiv) in an organic solvent (for example, THF, 1,4-dioxane or DME, preferably THF) is added an alcohol (1-3 equiv, preferably 1.3 equiv), Ph$_3$P (1-3 equiv, preferably 1.5 equiv) and then a dialkyl azodicarboxylate (preferably diethyl azodicarboxylate) (1-3 equiv, preferably 1.5 equiv) at ambient temperature. The reaction mixture is stirred about 1-3 h (preferably about 1 h), the reaction is concentrated under reduced pressure. The crude product is purified by crystallization or trituration from an appropriate solvent or solvents, or by chromatography to give the target compound.

Illustration of General Procedure Z

Example #Z.1.1

6-(3-(2,4-Difluorophenyl)-1-(tetrahydro-2H-pyran-4-yl)-1H-pyrazol-4-yl)-3-isopropyl-[1,2,4]triazolo[4,3-b]pyridazine

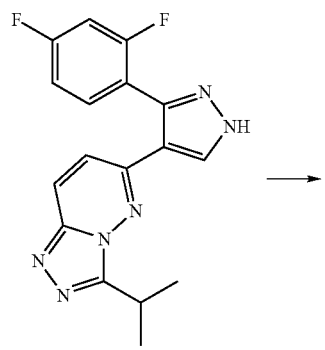

→

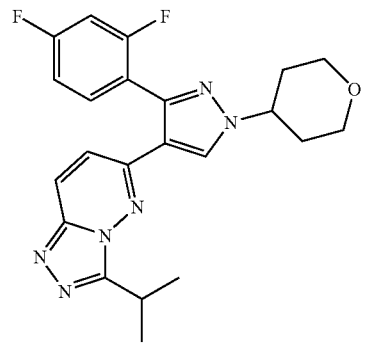

The 6-(3-(2,4-difluorophenyl)-1H-pyrazol-4-yl)-3-isopropyl-[1,2,4]triazolo[4,3-b]pyridazine (0.30 g, 0.88 mmol) in THF (4 mL) was treated with tetrahydro-2H-pyran-4-ol (0.12 g, 1.1 mmol; Example #L.1.1) and Ph$_3$P (0.35 g, 1.3 mmol). Diethyl azodicarboxylate (40 wt % in toluene, 0.52 mL, 1.32 mmol; TCI) was then added and the mixture stirred at ambient temperature for about 1 h. The reaction was concentrated under reduced pressure and then purified by silica gel chromatography using EtOAc/MeOH (stepwise gradient, 95:5 then 9:1) to isolate lower $R_f$ major product with impurities. The material was purified further by RP-HPLC (Table 1, Method d). Concentration of the desired fractions under reduced pressure resulted in a solid that was collected by filtration and then dried to give the title compound (0.063 g, 17%) as a white solid: LC/MS (Table 1, Method a) $R_t$=2.40 min; MS m/z: 425.2 (M+H)$^+$.

TABLE Z.1

Examples prepared from 6-(3-(2,4-difluorophenyl)-1H-pyrazol-4-yl)-3-isopropyl-[1,2,4]triazolo[4,3-b]pyridazine (Example #L.1.1) using General Procedure Z

| Alcohol | Product | Example # | $R_t$ min (method) | m/z ESI+ $(M + H)^+$ |
|---|---|---|---|---|
| 1-tert-Butylpiperidin-4-ol (*J. Org. Chem.* 2006, 71, 8602-8609) | 6-(1-(1-tert-Butylpiperidin-4-yl)-3-(2,4-difluorophenyl)-1H-pyrazol-4-yl)-3-isopropyl-[1,2,4]triazolo[4,3-b]pyridazine | Z.1.2 | 1.94 (a) | 480.3 |

General Procedure AA: Alkylation of an Amine

To a solution of an amine (preferably 1 equiv) in an organic solvent (for example, THF, 1,4-dioxane, DCM, toluene, Et$_2$O, acetone, MeOH, EtOH, DMF or DME, preferably DMF) is added a suitable alkylating agent (for example primary or secondary alkyl halides, mesylates or tosylates) (1-4 equiv, preferably 1.5 equiv) and a base (for example K$_2$CO$_3$, Cs$_2$CO$_3$, NaHCO$_3$, Na$_2$CO$_3$, NaOH, KOH, TEA, DIPEA or pyridine, preferably K$_2$CO$_3$). Optionally, additional alkylating agent is added as needed to consume the starting amine as monitored by LC/MS, HPLC or TLC. After about 1-18 h (preferably about 2 h) at about 0-100° C. (preferably about 65-70° C.), the reaction is concentrated under reduced pressure. The residue is partitioned between water and an organic solvent (such as EtOAc). The organic extract is dried over Na$_2$SO$_4$ or MgSO$_4$ and then filtered prior to concentrating under reduced pressure. The crude product is purified by crystallization or trituration from an appropriate solvent or solvents, aqueous work up, and/or by chromatography to give the target compound.

Illustration of General Procedure AA

Example #AA.1.1

6-(3-(2,4-Difluorophenyl)-1-(1-(2-methoxyethyl) piperidin-4-yl)-1H-pyrazol-4-yl)-3-isopropyl-[1,2,4] triazolo[4,3-b]pyridazine

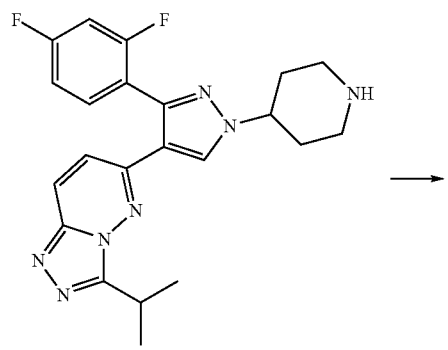

→

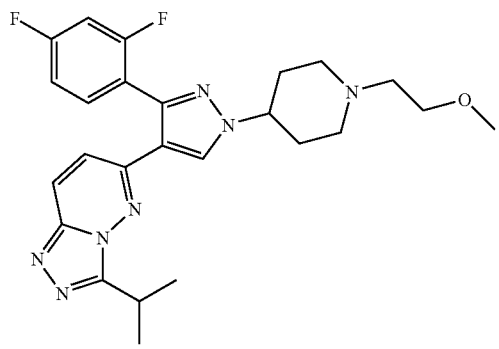

The 6-(3-(2,4-difluorophenyl)-1-(piperidin-4-yl)-1H-pyrazol-4-yl)-3-isopropyl-[1,2,4]triazolo[4,3-b]pyridazine (0.15 g, 0.35 mmol; Example #Q.1.2) was dissolved in DMF (4 mL) and then the K$_2$CO$_3$ (0.10 g, 0.71 mmol) and 1-bromo-2-methoxyethane (0.075 g, 0.53 mmol) were added. The mixture was heated at about 65° C. in an oil bath for about 1 h then another portion of 1-bromo-2-methoxyethane (0.075 g, 0.53 mmol) was added. After about 1 h, a third portion of 1-bromo-2-methoxyethane (0.075 g, 0.53 mmol) was added. The mixture was heated for about 1 h longer then cooled and concentrated under reduced pressure. The material was purified by RP-HPLC (Table 1, Method d). The appropriate fractions were concentrated and then basified with 2N NaOH and then extracted with EtOAc. Drying over MgSO$_4$ and evaporating gave an oil which was purified further by flash chromatography on silica with DCM/MeOH (9:1) as an eluent. Concentration of the appropriate fractions followed by trituration with Et$_2$O/heptane resulted in a solid which was collected by filtration to provide the title compound (0.086 g, 50%): LC/MS (Table 1, Method a) R$_t$=1.90 min; MS m/z: 482.2 (M+H)$^+$.

TABLE AA.1

Examples prepared from 4-(2,4-difluorophenyl)-5-(3-isopropyl-[1,2,4]triazolo[4,3-b]pyridazin-6-yl)-2-(piperidin-4-yl)thiazole (Example #Q.1.1) using General Procedure AA

| Alkylating Agent | Product | Example # | R$_t$ min (method) | m/z ESI+ (M + H)$^+$ |
|---|---|---|---|---|
| (Bromomethyl)cyclobutane | 2-(1-(Cyclobutylmethyl)piperidin-4-yl)-4-(2,4-difluorophenyl)-5-(3-isopropyl-[1,2,4]triazolo[4,3-b]pyridazin-6-yl)thiazole | AA.1.2 | 1.67 (a) | 509.3 |

General Procedure AB: Cyclization of an Imine with a TOSMIC Reagent

A mixture of an imine (preferably 1 equiv), a base (1-3 equiv, preferably 1 equiv) (such as $K_2CO_3$ or tert-butylamine, preferably $K_2CO_3$) and a TOSMIC reagent (0.5-10 equiv, preferably 1 equiv) is heated at about 40-100° C. (preferably about 60° C.) for about 1-48 h (preferably 17 h) in an organic solvent (such as DMF, DCM, 1,4-dioxane or methanol, preferably DMF). The reaction mixture is optionally concentrated in vacuo and partitioned between an organic solvent (such as DCM, $Et_2O$ or EtOAc) and an aqueous base (such as saturated aqueous $NaHCO_3$). The organic layer is isolated and the aqueous layer is optionally washed with additional organic solvent (such as DCM, $Et_2O$ or EtOAc). The combined organic layers are dried with a drying agent (such as $Na_2SO_4$ or $MgSO_4$), decanted or filtered and concentrated in vacuo. The crude material is purified by crystallization, precipitation, trituration or by chromatography to give the target compound.

Illustration of General Procedure AB

Example #AB.1.1

6-(4-(2,4-Difluorophenyl)-1-methyl-1H-imidazol-5-yl)-3-isopropyl-[1,2,4]triazolo[4,3-b]pyridazine

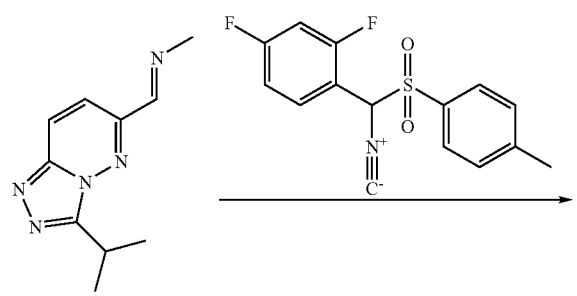

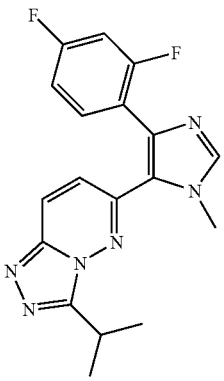

N-((3-Isopropyl-[1,2,4]triazolo[4,3-b]pyridazin-6-yl)methylene)methanamine (0.154 g, 0.758 mmol; Preparation #AP.1.1) and 2,4-difluoro-1-(isocyano(tosyl)methyl)benzene (0.233 g, 0.758 mmol, J. W. Pharmlab) were added to a 25 mL flask in DMF (4 mL). To the mixture was added $K_2CO_3$ (0.105 g, 0.758 mmol) and the mixture was heated to about 60° C. for about 17 h. The solvent was removed in vacuo and the material was washed with saturated aqueous $NaHCO_3$ (10 mL) and extracted with EtOAc (15 mL), dried over $MgSO_4$, filtered and concentrated to dryness. The residue was purified by flash chromatography (using MeOH/DCM 0-5% gradient) and then triturated with $Et_2O$ and dried in a vacuum oven overnight to afford the title compound as an off-white solid (0.062 g, 23%): LC/MS (Table 1, Method g) $R_t$=2.03 min; MS m/z: 355.2 $(M+1)^+$.

TABLE AB.2

Examples prepared from 2,5-difluoro-1-(isocyano(tosyl)methyl)benzene (Preparation #4) using General Procedure AB

| Imine | Product | Example # | $R_t$ min (method) | m/z ESI+ $(M + H)^+$ |
|---|---|---|---|---|
| N-((3-Isopropyl-[1,2,4]triazolo[4,3-b]pyridazin-6-yl)methylene)-2-methylpropan-2-amine [prepared using AP from Preparation #2 with tert-butylamine] | 6-(1-tert-Butyl-4-(2,5-difluorophenyl)-1H-imidazol-5-yl)-3-isopropyl-[1,2,4]triazolo[4,3-b]pyridazine | AB.2.1 | 2.34 (a) | 397.2 |

General Procedure AC: Formation of an Imidazo[1,2-a]imidazole

To a solution of a 6-aryl-5-heteroaryl-imidazo[2,1-b]oxazole (preferably 1 equiv) in an organic solvent (for example, THF, 1,4-dioxane, or DME, preferably 1,4-dioxane) is added a primary amine (5-50 equiv, preferably about 30 equiv) optionally in water. The mixture is heated in a microwave for about 30 min-4 h (preferably about 1 h) at about 100-150° C. (preferably about 120-130° C.). Alternatively the mixture is heated in a sealed tube for about 1-18 h (preferably about 12 h) at about 100-150° C. (preferably about 120-130° C.). The reaction is concentrated under reduced pressure then an organic acid (preferably HOAc) (5-50 equiv, preferably 30 equiv) is added and the mixture stirred at about 15-60° C. (preferably about 25° C.) for about 30 min-4 h (preferably about 1 h). Alternatively, the reaction mixture containing the 6-aryl-5-heteroaryl-imidazo[2,1-b]oxazole, primary amine and water can be directly subjected to the aforementioned heating conditions with the organic acid present to give the desired product. The reaction mixture is optionally concentrated in vacuo and partitioned between an organic solvent (such as DCM, Et$_2$O or EtOAc) and an aqueous base (such as saturated aqueous NaHCO$_3$). The organic layer is isolated and the aqueous layer is optionally washed with additional organic solvent (such as DCM, Et$_2$O or EtOAc). The combined organic layers are dried with a drying agent (such as Na$_2$SO$_4$ or MgSO$_4$), decanted or filtered and concentrated in vacuo. The crude material is purified by crystallization, precipitation, trituration, or chromatography to give the target compound.

Illustration of General Procedure AC

Example #AC.1.1

6-(6-(2,4-Difluorophenyl)-1-methyl-1H-imidazo[1,2-a]imidazol-5-yl)-3-isopropyl-[1,2,4]triazolo[4,3-b]pyridazine

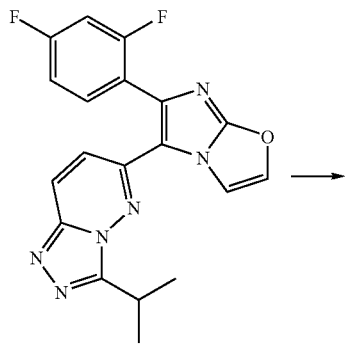

→

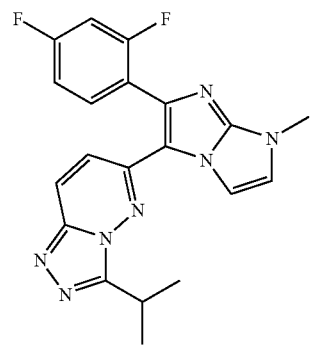

6-(2,4-Difluorophenyl)-5-(3-isopropyl-[1,2,4]triazolo[4,3-b]pyridazin-6-yl)imidazo[2,1-b]oxazole (0.200 g, 0.526 mmol, Example #8), 40% methylamine in water (1.50 mL, 15.4 mmol) and 1,4-dioxane (1 mL) were heated in a CEM® microwave at about 120° C. (250 psi maximum pressure, 10 min ramp, 300 max watts) for about 55 min. The mixture was concentrated under reduced pressure then treated with HOAc (1.5 mL). The solution was stirred at ambient temperature for about 1 h then the material was purified by RP-HPLC (Table 1, Method f). The desired fractions were collected and concentrated under reduced pressure to remove most of the ACN. The precipitate which formed was collected by filtration and washed with water (3 mL) then dried overnight under vacuum at about 70° C. to give the title compound (0.115 g, 56%): LC/MS (Table 1, Method g) R$_t$=1.88 min; MS m/z: 394.2 (M+H)$^+$.

TABLE AC.1

Examples prepared from 6-(2,4-difluorophenyl)-5-(3-isopropyl-[1,2,4]triazolo[4,3-b]pyridazin-6-yl)imidazo[2,1-b]oxazole (Example #8) using General Procedure AC

| Amine | Product | Example # | R$_t$ min (method) | m/z ESI+ (M + H)$^+$ |
|---|---|---|---|---|
| Ethylamine (70% solution in water) | 6-(6-(2,4-Difluorophenyl)-1-ethyl-1H-imidazo[1,2-a]imidazol-5-yl)-3-isopropyl-[1,2,4]triazolo[4,3-b]pyridazine | AC.1.2 | 2.01 (g) | 408.2 |
| N1,N1-Dimethylethane-1,2-diamine | 2-(6-(2,4-Difluorophenyl)-5-(3-isopropyl-[1,2,4]triazolo[4,3-b]pyridazin-6-yl)-1H-imidazo[1,2-a]imidazol-1-yl)-N,N-dimethylethanamine | AC.1.3 | 1.46 (g) | 451.4 |

General Procedure AD: Formation of a Tertiary Alcohol from a Ketone Using a Methyl Grignard A flask under an inert atmosphere is charged with a ketone (preferably 1 equiv) in an organic solvent (such as THF, 1,4-dioxane, Et$_2$O, or DME, preferably THF) and stirred at ambient temperature for about 0-30 min (preferably 15 min)

and then is cooled to about −78-0° C. (preferably about −40-−30° C.). A methyl Grignard (such as methylmagnesium chloride, methylmagnesium bromide, or methylmagnesium iodide, preferably methylmagnesium chloride, 1-10 equiv, preferably 3 equiv) is added over about 5-30 min (preferably about 10 min) to the reaction solution. The mixture is stirred at about −78-0° C. (preferably about −40-−30° C.) for about 10 min-3 h (preferably about 30 min). Optionally, a second portion of the methyl Grignard, preferably methylmagnesium chloride (0.5-5 equiv, preferably 1 equiv), is added and the reaction is continued at about −78-0° C. (preferably about −30-−40° C.) for about 10 min-1 h (preferably about 30 min). Upon consumption of the starting material ketone, the reaction mixture is cooled to −78-−30° C. (preferably −60-−30° C.) and a saturated solution of ammonium chloride is added slowly with stirring until gas evolution ceases and the reaction is warmed to ambient temperature. An organic solvent (such as DCM, EtOAc, Et$_2$O, or THF, preferably DCM) and water are added to the reaction mixture. The layers are separated and the aqueous layer is optionally extracted with additional organic solvent (such as DCM, EtOAc, Et$_2$O, or THF, preferably DCM) and combined with the original organic layer. The organic layer is optionally washed with brine, dried over a suitable drying agent (such as MgSO$_4$), filtered, and the solvents are removed under reduced pressure. The crude material can be further purified by trituration, crystallization, and/or chromatography to afford the target compound.

Illustration of General Procedure AD

Example #AD.1.1

2-(6-(2-(2,4-Difluorophenyl)-6,7-dihydro-5H-pyrrolo-[1,2-α]imidazol-3-yl)-[1,2,4]triazolo[4,3-b]pyridazin-3-yl)propan-2-ol

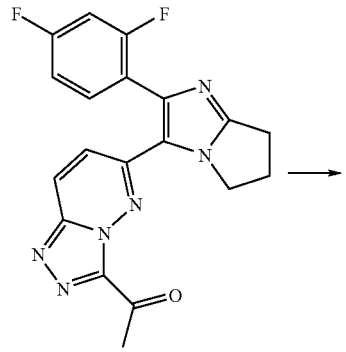

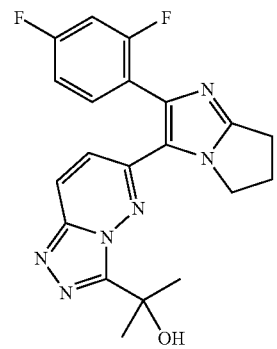

A 100 mL round bottom flask was charged with 1-(6-(2-(2,4-difluorophenyl)-6,7-dihydro-5H-pyrrolo[1,2-a]imidazol-3-yl)-[1,2,4]triazolo[4,3-b]pyridazin-3-yl)ethanone (2.74 g, 7.20 mmol, Example #35, Step G). THF (36.0 mL) was added and the mixture was stirred at ambient temperature for about 15 min. The slurry was cooled to about −40° C. and methylmagnesium chloride (3.0 M in THF, 6.00 mL, 18.0 mmol) was added slowly while keeping the internal temperature between about −40-−30° C. After about 15 min, the mixture was cooled to about −55° C. followed by the slow addition of a saturated solution of ammonium chloride (about 10 mL). The mixture was then warmed to ambient temperature and diluted with water (50 mL) and DCM (75 mL). The layers were separated. The aqueous layer was extracted with DCM (2×50 mL) then the combined organic extracts were dried over MgSO$_4$, filtered, and concentrated under reduced pressure to give a foam. The material was dissolved in 95:5 DCM/MeOH (about 20 mL) with warming and sonication and then loaded onto a 120 g silica column and eluted with 94:6 DCM/MeOH (about 1 L) followed by 92:8 DCM/MeOH (about 500 mL). Concentration of the fractions containing product under reduced pressure gave the title compound as a foam (2.88 g, 91%) that contained about 9 wt % DCM by $^1$H NMR. This material was combined with a second batch of the title compound (3.4 g, also contained about 9 wt % DCM). The combined material (5.7 g) was dissolved into ACN (150 mL), followed by a rapid precipitation of the title compound as an off-white powder. The material was collected by filtration and dried in a vacuum oven at 70° C. to give the title compound (4.69 g, 82% recovery): LC/MS (Table 1, Method g) R$_t$=1.58 min; MS m/z: 397.2 (M+H)$^+$.

TABLE AD.1

Examples prepared from a ketone and a methyl Grignard using General Procedure AD

| Ketone | Product | Example # | R$_t$ min (method) | m/z ESI+ (M + H)$^+$ |
|---|---|---|---|---|
| 1-(6-(6-(2,4-Difluorophenyl)-2,3-dihydroimidazo[2,1-b]oxazol-5-yl)-[1,2,4]triazolo[4,3-b]pyridazin-3-yl)ethanone [prepared using I.1 from Preparation #6 with Example #37, Step C, AF with methylmagnesium chloride (3.0 M in THF)] | 2-(6-(6-(2,4-Difluorophenyl)-2,3-dihydroimidazo[2,1-b]oxazol-5-yl)-[1,2,4]triazolo[4,3-b]pyridazin-3-yl)propan-2-ol | AD.1.2 | 1.67 (g) | 399.2 |
| 1-(6-(6-(2,4-Difluorophenyl)-2-methylimidazo[2,1-b]oxazol-5- | 2-(6-(6-(2,4-Difluorophenyl)-2- | AD.1.3 | 1.85 (g) | 410.9 |

TABLE AD.1-continued

Examples prepared from a ketone and a methyl Grignard using General Procedure AD

| Ketone | Product | Example # | R, min (method) | m/z ESI+ (M + H)+ |
|---|---|---|---|---|
| yl)-[1,2,4]triazolo[4,3-b]pyridazin-3-yl)ethanone [prepared using O.1 from 2-bromo-2',4'-difluoroacetophenone with Preparation #5, C.1 with NIS, I.1 with Example #37, Step C, AF with methylmagnesium bromide (1.4 M in toluene/THF (75:25))] | methylimidazo[2,1-b]oxazol-5-yl)-[1,2,4]triazolo[4,3-b]pyridazin-3-yl)propan-2-ol | | | |
| 1-(6-(2-(2,4-Difluorophenyl)-5,6,7,8-tetrahydroimidazo[1,2-a]pyridin-3-yl)-[1,2,4]triazolo[4,3-b]pyridazin-3-yl)ethanone [prepared using I.1 from Example #C.1.1 with Example #37, Step C, AF with methylmagnesium bromide (1.4 M in toluene/THF (75:25))] | 2-(6-(2-(2,4-Difluorophenyl)-5,6,7,8-tetrahydroimidazo[1,2-a]pyridin-3-yl)-[1,2,4]triazolo[4,3-b]pyridazin-3-yl)propan-2-ol | AC.1.4 | 1.74 (a) | 411.2 |

General Procedure AE: Alkylation of an Alcohol

To a solution or suspension of an alcohol (preferably 1 equiv) in an organic solvent or a mixture of organic solvents (for example, THF, 1,4-dioxane, DCM, toluene, $Et_2O$, acetone, DMF or DME, preferably a mixture of DMF and THF) is added a suitable base (for example $K_2CO_3$, $Cs_2CO_3$, $Na_2CO_3$, NaOH, KOH or NaH, preferably NaH, 1-5 equiv, preferably about 1-2 equiv) and an alkylating agent (for example primary alkyl halides, mesylates or tosylates, preferably an alkyl iodide, 1-8 equiv, preferably about 1-4 equiv). The reaction mixture is stirred about 30 min-18 h (preferably about 1-2 h) at about 0-100° C. (preferably about 50-75° C.). Optionally, additional alkylating agent and base is added as needed to consume the starting alcohol as monitored by LC-MS, HPLC or TLC during the course of the reaction. The reaction mixture is optionally concentrated in vacuo and partitioned between an organic solvent (such as DCM, $Et_2O$ or EtOAc) and an aqueous base (such as saturated aqueous $NaHCO_3$). The organic layer is isolated and the aqueous layer is optionally washed with additional organic solvent (such as DCM, $Et_2O$ or EtOAc). The combined organic layers are dried with a drying agent (such as $Na_2SO_4$ or $MgSO_4$), decanted or filtered and concentrated in vacuo. The crude material is purified by crystallization, precipitation, trituration or by chromatography to give the target compound.

Illustration of General Procedure AE

Example #AE.1.1

6-(2,4-Difluorophenyl)-5-(3-(2-(2-methoxyethoxy)propan-2-yl)-[1,2,4]triazolo[4,3-b]pyridazin-6-yl)imidazo[2,1-b]oxazole

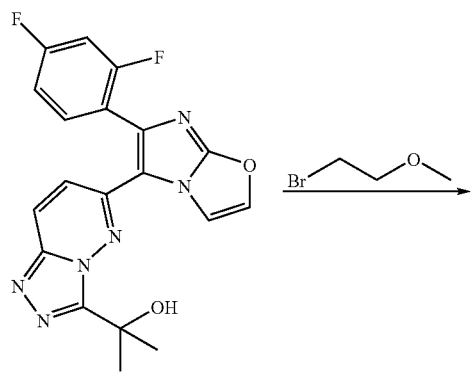

-continued

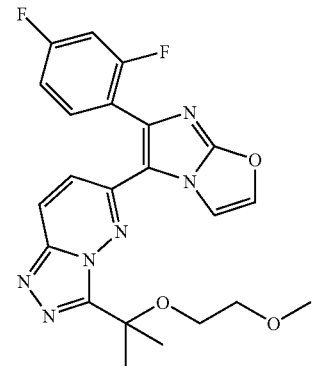

In a 10 mL pear flask, 2-(6-(6-(2,4-difluorophenyl)imidazo[2,1-b]oxazol-5-yl)-[1,2,4]triazolo[4,3-b]pyridazin-3-yl)propan-2-ol (0.100 g, 0.252 mmol, Example #37) and NaH (60% in mineral oil, 0.025 g, 0.631 mmol) in THF (5 mL) and DMF (1 mL) were added to give an off-white suspension. 1-Bromo-2-methoxyethane (0.140 g, 1.01 mmol) was then added and the suspension was stirred at about 70° C. for about 17 h. The mixture was concentrated under reduced pressure and was purified by flash chromatography on silica gel MeOH/DCM (gradient 1-5% over 14 min) and then further purified by RP-HPLC (Table 1, Method m) to afford the title compound (0.012 g, 11%) as a white fluffy solid: LC/MS (Table 1, Method g) $R_t$=2.02 min; MS m/z 455.2 $(M+H)^+$.

TABLE AE.1

Examples prepared from iodomethane using General Procedure AE

| Alcohol | Product | Example # | R$_t$ min (method) | m/z ESI+ (M + H)$^+$ |
|---|---|---|---|---|
| 2-(6-(6-(2,4-Difluorophenyl)imidazo[2,1-b]oxazol-5-yl)-[1,2,4]triazolo[4,3-b]pyridazin-3-yl)propan-2-ol (Example #37) | 6-(2,4-Difluorophenyl)-5-(3-(2-methoxypropan-2-yl)-[1,2,4]triazolo[4,3-b]pyridazin-6-yl)imidazo[2,1-b]oxazole | AE.1.2 | 2.00 (g) | 411.2 |
| 2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-ol (Example #35) | 6-(2-(2,4-Difluorophenyl)-6,7-dihydro-5H-pyrrolo[1,2-a]imidazol-3-yl)-3-(2-methoxypropan-2-yl)-[1,2,4]triazolo[4,3-b]pyridazine | AE.1.3 | 1.88 (g) | 411.2 |

General Procedure AF: Formation of a Ketone from an Ester Using a Methyl Grignard A flask charged with a ketone (preferably 1 equiv) in an organic solvent (such as THF, 1,4-dioxane, Et$_2$O, or DME, preferably THF) is cooled to about −78-0° C. (preferably about −30° C.). A methyl Grignard (such as methylmagnesium chloride, methylmagnesium bromide, or methylmagnesium iodide, preferably methylmagnesium chloride, 1-10 equiv, preferably 4 equiv) is added over about 5-30 min (preferably about 10 min) to the reaction solution. The mixture is stirred at about −78-0° C. (preferably about −30° C.) for about 10 min-3 h (preferably about 30 min). Optionally, a second portion of the methyl Grignard, (such as methylmagnesium chloride, methylmagnesium bromide, or methylmagnesium iodide, preferably methylmagnesium chloride, 0.5-5 equiv, preferably 1 equiv), is added and the reaction is continued at about −78-0° C. (preferably about −30° C.) for about 10 min-1 h (preferably about 30 min). Upon consumption of the starting material ketone, a saturated solution of ammonium chloride is added slowly to the cooled reaction flask (preferably at about −30° C.) with stirring until gas evolution ceases. An organic solvent (such as DCM, EtOAc, Et$_2$O, or THF, preferably DCM) and water are added to the reaction mixture. The layers are separated and the aqueous layer is optionally extracted with additional organic solvent (such as DCM, EtOAc, Et$_2$O, or THF, preferably DCM). The organic layers are combined and are optionally washed with water or brine, dried over a suitable drying agent (such as MgSO$_4$), filtered, and the solvents are removed under reduced pressure. The crude material can be further purified by trituration, crystallization, and/or chromatography to afford the target compound.

Illustration of General Procedure AF
Example #AF.1.1

1-(6-(6-(2,4-Difluorophenyl)imidazo[2,1-b]oxazol-5-yl)-[1,2,4]-triazolo[4,3-b]pyridazin-3-yl)ethanone In a 100 mL round-bottomed flask, ethyl 6-(6-(2,4-difluorophenyl)imidazo[2,1-b]oxazol-5-yl)-[1,2,4]triazolo[4,3-b]pyridazine-3-carboxylate (2.00 g, 4.87 mmol, Example #37, Step D) was suspended in THF (30 mL) and cooled to about −30° C. Methylmagnesium chloride (3.0 M in THF, 6.50 mL, 19.5 mmol) was added over about 10 min to the suspension. The mixture was stirred for about 25 min at about −30° C., followed by slow addition of a saturated solution of ammonium chloride (15 mL). The suspension was diluted with the addition of water (20 mL) and then DCM (20 mL). The layers were separated and the aqueous layer was extracted DCM (2×50 mL). The combined organic extracts were washed with water and brine, dried over MgSO$_4$, filtered, and the solvents were removed under reduced pressure to give a solid that was triturated with Et$_2$O (15 mL) and collected by vacuum filtration as a powder (1.50 g, 81%): LC/MS (Table 1, Method g) R$_t$=2.06 min; MS m/z: 380.9 (M+H)$^+$.

General Procedure AG: Formation of a 3-aminotriazolopyridizine

To a solution of a 3-hydrazinylpyridazine (preferably 1 equiv) in an organic solvent (for example, THF, 1,4-dioxane, DCM, toluene, Et$_2$O, acetone, DMF or DME, preferably DMF) is added a 1-(chloro(dialkylamino)methylene)dialkylaminium hexafluorophosphate(V) salt (1-1.5 equiv, preferably 1.1 equiv). The reaction mixture is stirred for about 1-30 min (preferably 5 min) at ambient temperature and then a suitable base (for example DIPEA, pyridine or TEA, preferably TEA, 1-4 equiv preferably about 2.2 equiv) is added. After about 30 min-18 h (preferably about 1-2 h) at about 0-100° C. (preferably about 60° C.), the reaction is concentrated under reduced pressure. The residue is partitioned between water and an organic solvent (such as EtOAc or DCM). The organic extract is dried over Na$_2$SO$_4$ or MgSO$_4$ and then filtered prior to concentrating under reduced pressure. The crude product is purified by crystallization or trituration from an appropriate solvent or solvents, aqueous work up, and/or by chromatography to give the target compound.

Illustration of General Procedure AG

Preparation #AG.1: 6-Iodo-N,N-dimethyl-[1,2,4]triazolo[4,3-b]pyridazin-3-amine

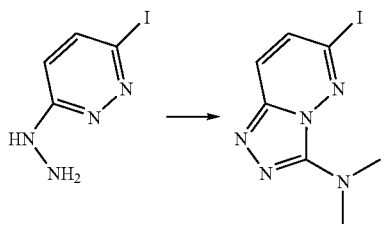

The 3-hydrazinyl-6-iodopyridazine (1.00 g, 4.24 mmol, prepared using General Procedure D from Example #9, Step A with hydrazine) was dissolved in DMF (10 mL) then N-(chloro(dimethylamino)methylene)-N-methylmethanaminium hexafluorophosphate(V) (1.31 g, 4.66 mmol, Fluka) was added. The solution was stirred for about 5 min and then TEA (1.30 mL, 9.32 mmol) was added. The mixture was stirred at ambient temperature for about 1 h then at about 60° C. for about 2 h. The reaction was concentrated under reduced pressure then the mixture was partitioned between DCM (20 mL) and saturated aqueous NaHCO$_3$. The layers were separated then the organic solution was dried over MgSO$_4$, filtered and concentrated under reduced pressure. The material was purified by flash chromatography on silica gel with DCM/MeOH (95:5) as an eluent. The fractions were collected then concentrated under reduced pressure and the residue was triturated with Et$_2$O (20 mL). The solid was collected by filtration and dried overnight under vacuum to give the title compound (1.01 g, 90%): LC/MS (Table 1, Method g) R$_t$=1.60 min; MS m/z: 289.8 (M+H)$^+$.

TABLE AG.1

Examples prepared from 2-(2,4-difluorophenyl)-3-(6-hydrazinylpyridazin-3-yl)-6,7-dihydro-5H-pyrrolo[1,2-a]imidazole (Example #35, Step E) using General Procedure AG

| 1-(Chloro(dialkylamino)methylene)-dialkylaminium hexafluorophosphate(V) salt | Product | Example # | R$_t$ min (method) | m/z ESI+ (M + H)$^+$ |
|---|---|---|---|---|
| (Chloro-dimethylamino-methylene)-dimethyl-ammonium hexafluorophosphate | 6-(2-(2,4-Difluorophenyl)-6,7-dihydro-5H-pyrrolo[1,2-a]imidazol-3-yl)-N,N-dimethyl-[1,2,4]triazolo[4,3-b]pyridazin-3-amine | AG.1.1 | 1.73 (g) | 381.9 |
| 1-(Chloro-1-pyrrolidinylmethylene)pyrrolidinium hexafluorophosphate | 6-(2-(2,4-Difluorophenyl)-6,7-dihydro-5H-pyrrolo[1,2-a]imidazol-3-yl)-3-(pyrrolidin-1-yl)-[1,2,4]triazolo[4,3-b]pyridazine | AG.1.2 | 1.77 (g) | 408.2 |

TABLE AG.2

Examples prepared from 6-(2,4-difluorophenyl)-5-(6-hydrazinylpyridazin-3-yl)imidazo[2,1-b]oxazole (prepared using I.1 from Preparation #C.1 with Example #9, Step A, D with hydrazine hydrate) using General Procedure AG

| 1-(Chloro(dialkylamino)methylene)-dialkylaminium hexafluorophosphate(V) salt | Product | Example # | R$_t$ min (method) | m/z ESI+ (M + H)$^+$ |
|---|---|---|---|---|
| 1-(Chloro-1-pyrrolidinylmethylene)pyrrolidinium hexafluorophosphate | 6-(2,4-Difluorophenyl)-5-(3-(pyrrolidin-1-yl)-[1,2,4]triazolo[4,3-b]pyridazin-6-yl)imidazo[2,1-b]oxazole | AG.2.1 | 1.98 (g) | 408.2 |

General Procedure AI.1 Dess-Martin Periodinane Oxidation of an Alcohol to an Aldehyde To a flask containing Dess-Martin periodinane (1-5 equiv, preferably 1.1 equiv) is added an appropriate solvent or solvents (preferably DCM). The reaction mixture is optionally cooled to about 0-25° C. (preferably 0-4° C.). A primary alcohol (1 equiv), optionally dissolved in an organic solvent (such as DCM), is added. The resulting mixture is stirred at about 0-30° C. (preferably about 23° C.) for about 1-24 h (preferably about 2-3 h). The reaction mixture is optionally filtered through a filter pad (such as Celite®, Florisil® or neutral alumina, preferably neutral alumina) that is rinsed with appropriate solvents (such as heptane, 1,4-dioxane, Et$_2$O, DCM, preferably DCM). The reaction mixture is optionally concentrated under reduced pressure, and then an appropriate solvent or solvents (such as heptane, 1,4-dioxane, Et$_2$O, preferably Et$_2$O) is added. The solids are filtered off and washed with an appropriate solvent or solvents (such as heptane, 1,4-dioxane, Et$_2$O, preferably Et$_2$O). The filtrate is concentrated and triturated with an appropriate solvent or solvents (such as heptane, 1,4-dioxane, Et$_2$O, DCM, preferably Et$_2$O).

Optionally, the filtrate is treated with solid Na$_2$CO$_3$ for about 15 min-24 h (preferably 30 min-2 h). The reaction mixture is filtered and washed with an appropriate solvent or solvents (such as heptane, 1,4-dioxane, Et$_2$O, DCM, preferably Et$_2$O). The filtrate is concentrated under reduced pressure to give the target compound. Optionally, the material can be purified by distillation or trituration from an appropriate solvent or solvents or by chromatography.

Illustration of General Procedure AI.1

Preparation #AI.1.1.1 Preparation of 1-formylcyclopropanecarbonitrile Using General Procedure A.I.1

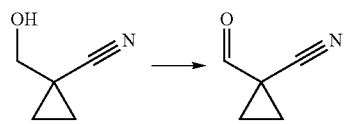

In a 200 mL round-bottomed flask, Dess-Martin periodinane (41.2 g, 97.0 mmol) was dissolved in DCM (236 mL). A solution of 1-(hydroxymethyl)cyclopropanecarbonitrile (8.58 g, 88.0 mmol, prepared using General Procedure AL from ethyl 1-cyanocyclopropanecarboxylate) in DCM (236 mL) was added portionwise and the reaction was stirred for about 2 h. The reaction mixture was filtered through neutral alumina which was washed with DCM (750 mL). The solvent was removed under reduced pressure to give a yellow solid. The residue was taken up in a minimal amount of DCM and filtered to give a yellow solid. The material was purified by chromatography on silica gel using EtOAc/DCM (0-30% gradient) to afford the title compound as a yellow oil (4.83 g, 52%): $^1$H NMR (CDCl$_3$) δ 9.33 (s, 1H), 1.87-1.50 (m, 4H).

General Procedure AI.2: Swern Oxidation of an Alcohol to an Aldehyde

To a solution of oxalyl chloride (1.0-1.5 equiv, preferably 1.25 equiv) in DCM at about −78° C. is added a solution of DMSO (2.0-4.0 equiv, preferably 2.5 equiv) in DCM. The reaction mixture is stirred about 5 min-30 min (preferably 15 min) at about −78° C. and then a solution of a primary alcohol (preferably 1.0 equiv) in DCM is added. The reaction mixture is stirred about 5 min-30 min (preferably 15 min) at about −78° C. and then a base (preferably TEA or DIPEA) (3-10.0 equiv, preferably 5.0 equiv) is added. The reaction mixture is stirred about 5 min-30 min, preferably 15 min) at about −78° C. and then warmed to ambient temperature. The reaction mixture is partitioned between water and an organic solvent (such as DCM or EtOAc) and the organic layer separated, dried over Na$_2$SO$_4$ or MgSO$_4$, filtered and concentrated under reduced pressure. The crude product is optionally purified by crystallization or trituration from an appropriate solvent or solvents, or by chromatography to give the target compound.

Illustration of General Procedure AI.2

Preparation #AI.2.1.1: 1-((tert-Butyldimethylsilyloxy)methyl)cyclobutanecarbaldehyde

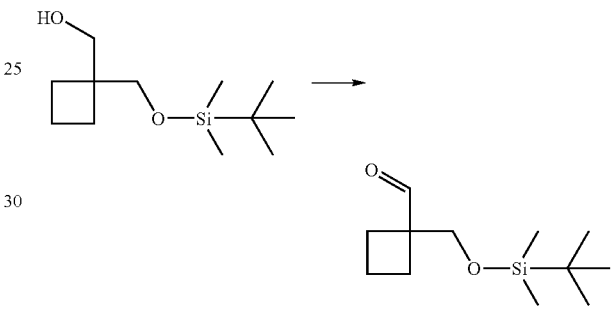

To a round bottom flask was added DCM (5.0 mL) and oxalyl chloride (2.0 M solution in DCM, 1.36 mL, 2.71 mmol). The reaction mixture was cooled to about −78° C. To the solution was added a solution of DMSO (0.385 mL, 5.42 mmol) in DCM (1.0 mL). The mixture was stirred for about 15 min at about −78° C. and then a solution of (1-((tert-butyldimethylsilyloxy)methyl)cyclobutyl)methanol (0.500 g, 2.17 mmol, prepared using General Procedure AL with diethyl cyclobutane-1,1-dicarboxylate [Fluka], General Procedure AK with tert-butylchlorodimethylsilane) in DCM (1.0 mL) was added. The reaction mixture was allowed to stir for about 15 min and then TEA (1.82 mL, 13.0 mmol) was added. The reaction mixture was allowed to stir for about 15 min and then warmed to ambient temperature. The reaction mixture was quenched with water (25 mL) and was extracted with DCM (3×25 mL). The organics were combined, dried with MgSO$_4$, filtered and concentrated in vacuo to give the title compound as a colorless oil (0.486 g, 98%): $^1$H-NMR (DMSO-d$_6$) δ 9.71 (s, 1H), 3.87 (s, 2H), 2.27 (m, 2H), 1.93 (m, 4H), 0.90 (s, 9H), 0.08 (s, 6H).

General Procedure AJ: Reaction of an Alcohol with DAST

A round bottom flask is charged with an alcohol (preferably 1 equiv) and a suitable organic solvent (such as DCM or DCE, preferably DCM) and the mixture is cooled to about −78-0° C. (preferably about −35° C.). To the reaction solution is slowly added DAST (1-5 equiv, preferably 2 equiv) and the mixture is stirred at about −40-0° C. (preferably about 0° C.) for about 15 min-6 h (preferably about 30 min-1 h). To the reaction mixture is added a saturated solution of aqueous NaHCO₃, followed by an organic solvent (such as DCM) and optionally additional water is added. The layers are separated and the organic solution is optionally washed with water and brine, dried over a suitable drying agent (such as Na₂SO₄ or MgSO₄), filtered, and the solvent is removed under reduced pressure. The crude material is then purified by trituration, crystallization, and/or chromatography to afford the target compound.

Illustration of General Procedure AJ

Example #AJ.1.1

6-(2-(2,4-Difluorophenyl)-6,7-dihydro-5H-pyrrolo[1,2-a]imidazol-3-yl)-3-(2-fluoropropan-2-yl)-[1,2,4]triazolo[4,3-b]pyridazine

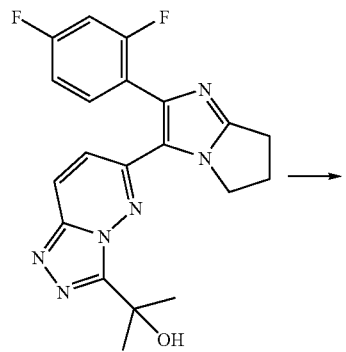

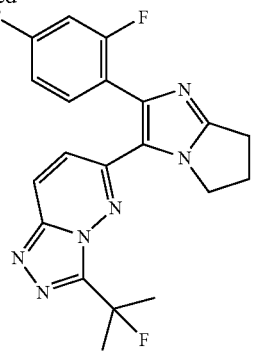

A 25 mL round-bottomed flask was charged with 2-(6-(2-(2,4-difluorophenyl)-6,7-dihydro-5H-pyrrolo[1,2-a]imidazol-3-yl)-[1,2,4]triazolo[4,3-b]pyridazin-3-yl)propan-2-ol (0.36 g, 0.91 mmol, Example #35) and DCM (6 mL). The resulting suspension was cooled to about −35° C., followed by the dropwise addition of DAST (0.240 mL, 1.82 mmol) to the suspension. The reaction mixture was slowly warmed to about 0° C. over about 30 min at which point a saturated solution of aqueous NaHCO₃ (about 5 mL) was added slowly. DCM (about 30 mL) and water (about 10 mL) were added and the layers were separated. The organic solution was dried over MgSO₄, filtered, and the solvent was removed under reduced pressure to give the crude title compound as a yellow foam. The product was purified by silica gel column chromatography using a stepwise gradient MeOH/DCM 1-2% as eluant. The fractions were combined and the solvents were removed under reduced pressure to give the product as a foam. Et₂O (about 4 mL) was added and the off-white powder that formed was collected by vacuum filtration (0.078 g). The material was dissolved into ACN (about 2 mL) and water (about 2 mL) was then added. The ACN was removed under reduced pressure at which point the aqueous solution became cloudy. The solution was then sonicated and the precipitate that was formed was collected by vacuum filtration and dried overnight at about 70° C. in a vacuum oven to give the title compound (0.050 g, 14%): LC/MS (Table 1, Method g) $R_t$=1.86 min; MS m/z: 399.2 (M+H)⁺.

TABLE AJ.1

Examples prepared from DAST using General Procedure AJ

| Alcohol | Product | Example # | $R_t$ min (method) | m/z ESI+ (M + H)⁺ |
|---|---|---|---|---|
| 2-(6-(6-(2,4-Difluorophenyl)imidazo[2,1-b]oxazol-5-yl)-[1,2,4]triazolo[4,3-b]pyridazin-3-yl)propan-2-ol [Example #37] | 6-(2,4-Difluorophenyl)-5-(3-(2-fluoropropan-2-yl)-[1,2,4]triazolo[4,3-b]pyridazin-6-yl)imidazo[2,1-b]oxazole | AJ.1.2 | 2.08 (g) | 399.1 |
| 2-(6-(6-(2,4-Difluorophenyl)-1-methyl-1H-imidazo[1,2-a]imidazol-5-yl)-[1,2,4]triazolo[4,3-b]pyridazin-3-yl)propan-2-ol [prepared using AC from from Example #37 with methylamine (40% solution in water)] | 6-(6-(2,4-Difluorophenyl)-1-methyl-1H-imidazo[1,2-a]imidazol-5-yl)-3-(2-fluoropropan-2-yl)-[1,2,4]triazolo[4,3-b]pyridazine | AJ.1.3 | 1.33 (i) | 412.1 |

TABLE AJ.1-continued

Examples prepared from DAST using General Procedure AJ

| Alcohol | Product | Example # | R, min (method) | m/z ESI+ (M + H)+ |
|---|---|---|---|---|
| 2-(6-(6-(2,4-Difluorophenyl)-2,3-dihydroimidazo[2,1-b]oxazol-5-yl)-[1,2,4]triazolo[4,3-b]pyridazin-3-yl)propan-2-ol [Example # AD.1.2] | 6-(2,4-Difluorophenyl)-5-(3-(2-fluoropropan-2-yl)-[1,2,4]triazolo[4,3-b]pyridazin-6-yl)-2,3-dihydroimidazo[2,1-b]oxazole | AJ.1.4 | 1.88 (i) | 401.2 |

General Procedure AK: Monosilylation of a Diol

A mixture of a diol (preferably 1 equiv) and a base (such as TEA, NaH or imidazole preferably NaH; 0.3-3 equiv, preferably 1 equiv) is stirred at about −10-10° C. (preferably about 0° C.) in an organic solvent (such as THF or Et$_2$O, preferably THF). Alternatively, if TEA is used, DMAP may be added (0.01-0.5 equiv, preferably 0.02 equiv) to the reaction mixture. To the reaction mixture is added a silylating agent (such as TBDMSCl, TMSCl, N,O-bis(trimethylsilyl)acetamide, TBDMSOTf preferably TBDMSCl; 0.1-1.0 equiv., preferably 1.0 equiv). After warming to ambient temperature for about 3 min-6 h (preferably 1 h), the solvent is optionally removed. The reaction mixture is partitioned between a suitable organic solvent (such as DCM, Et$_2$O or EtOAc, preferably EtOAc) and an aqueous base (such as saturated aqueous NaHCO$_3$). The organic layer is isolated and the aqueous layer is optionally washed with additional organic solvent (such as EtOAc, DCM or Et$_2$O, preferably EtOAc). The combined organic layers are dried with a drying agent (such as Na$_2$SO$_4$ or MgSO$_4$), filtered and concentrated in vacuo. The crude material is purified by crystallization, trituration, distillation or by chromatography to give the target compound.

Illustration of General Procedure AK

Preparation #AK.1.1 (1-((tert-Butyldimethylsilyloxy)methyl)cyclopropyl)methanol

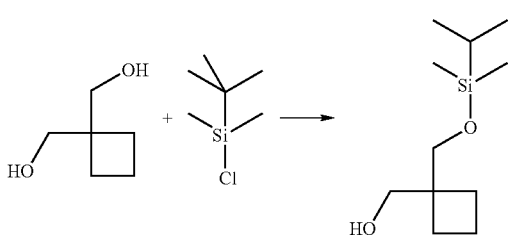

To a round bottom flask was added NaH (1.08 g, 27.0 mmol) and THF (35 mL). The reaction mixture was cooled to about 0° C. and a solution of cyclobutane-1,1-diyldimethanol (3.14 g, 27.0 mmol, prepared according to DE 19735574, Beispiel 8d) in THF (100 mL) was added dropwise. The reaction mixture was stirred for about 30 min and then a solution of tert-butylchlorodimethylsilane (4.07 g, 27.0 mmol) in THF (50 mL) was added dropwise. The reaction mixture was warmed to ambient temperature and the reaction mixture was stirred for about 1 h. The reaction mixture was quenched with the addition of saturated aqueous NaHCO$_3$ (200 mL) and the mixture was extracted with EtOAc (3×200 mL). The organics were combined and washed with brine (500 mL), dried with Na$_2$SO$_4$, filtered and concentrated in vacuo. The crude material was purified by flash chromatography (silica gel 120 g RediSep® column; heptane/EtOAc gradient from 1:0 to 0:1) to give the title compound (3.23 g, 52%). $^1$H NMR (CDCl$_3$) δ 3.72 (s, 2H), 3.70 (s, 2H), 1.97-1.68 (m, 6H), 0.91 (s, 9H), 0.91 (s, 3H), 0.09 (s, 3H).

General Procedure AL: Reduction of an Ester to an Alcohol

To a mixture of an ester (preferably 1 equiv) in a suitable solvent (for example, hexanes, THF, EtOH, MeOH, 1,4-dioxane, or heptane, preferably THF or hexanes) that is cooled to about −78-0° C. (preferably about −78° C.), is added a reducing agent (for example, DIBAL-H, LAH, NaBH$_4$, or LiBH$_4$, preferably, DIBAL-H or LiBH$_4$; 1-4 equiv, preferably 1-2 equiv). The reaction mixture is stirred at about −78-0° C. (preferably about −78° C.) for about 1 min-8 h (preferably about 10 min), then warmed to ambient temperature and is stirred for about 1-24 h (preferably about 1 h). Optionally the reaction mixture can be heated at about 40-100° C. (preferably about 60° C.), for about 1-24 h (preferably about 4 h). If the reaction mixture has been heated, it is cooled to about −10-25° C. (preferably about 0-20° C.). The reaction mixture is diluted with water or a saturated aqueous solution of sodium potassium tartrate and stirred about 0 min-4 h (preferably about 2 h). Optionally additional organic solvent (such as DCM, Et$_2$O or EtOAc) is added and the organic layer is separated. The organic layer may be optionally washed with water or brine, dried with a drying agent (such as Na$_2$SO$_4$ or MgSO$_4$), decanted or filtered, and concentrated to dryness under reduced pressure. The organic layer may optionally be filtered through Celite® prior to evaporation of the solvents. The crude product may be used without additional purification or can be purified by trituration, crystallization, distillation, or chromatography to give the target compound.

Illustration of General Procedure AL

Preparation #AL.1.1:
2-(tert-Butyldimethylsilyloxy)-2-methylpropan-1-ol

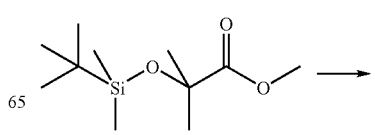

185
-continued

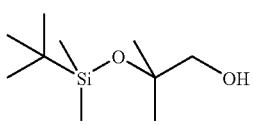

To a solution of methyl 2-(tert-butyldimethylsilyloxy)-2-methylpropanoate (1.00 g, 4.30 mmol) in hexanes (15 mL) at about −78° C. was added DIBAL-H (1.0 M in hexanes, 9.47 mL, 9.47 mmol) drop-wise over about 5 min. The solution was stirred at about −78° C. for about 5 min and the cooling bath was removed. The solution was warmed to ambient temperature and stirred for about 1 h. The reaction was then re-cooled to about 0° C. and was quenched with the slow addition of a saturated solution of sodium potassium tartrate (about 20 mL). The thick suspension was stirred at ambient temperature for about 2 h until the two layers were clear. The layers were separated and the aqueous layer was extracted with DCM (2×50 mL). The combined organic extracts were washed with water and brine, dried over MgSO$_4$, filtered, and the solvents were removed under reduced pressure to give as the title compound (0.73 g, 83%) as a colorless oil: $^1$H NMR (CDCl$_3$) δ 3.32 (s, 2H), 1.24 (s, 6H), 0.88 (d, J=2.9, 9H), 0.12 (d, J=3.2, 6H).

General Procedure AM: Deprotection of a Silyl Protected Alcohol

A silyl protected alcohol (preferably 1 equiv) is reacted with TBAF (1-5 equiv, preferably 1-1.5 equiv) or HCl (1-50 equiv, preferably 5-20 equiv) in a suitable organic solvent (such as THF, Et$_2$O, 1,4-dioxane, DCM, preferably THF) at ambient temperature for about 1-24 h (preferably about 4 h). The crude reaction mixture is partitioned between a suitable organic solvent (such as DCM, Et$_2$O or EtOAc, preferably DCM) and water. The organic layer is separated and dried over a drying agent (such as Na$_2$SO$_4$ or MgSO$_4$, preferably MgSO$_4$), filtered, and concentrated under reduced pressure. Optionally, the product can be purified by trituration, crystallization, distillation, and/or chromatography to give the target compound.

186
Illustration of General Procedure AM

Example #AM.1.1

2-(6-(2-(2,4-Difluorophenyl)-6,7-dihydro-5H-pyrrolo[1,2-a]imidazol-3-yl)-[1,2,4]triazolo[4,3-b]pyridazin-3-yl)-2-methylpropan-1-ol

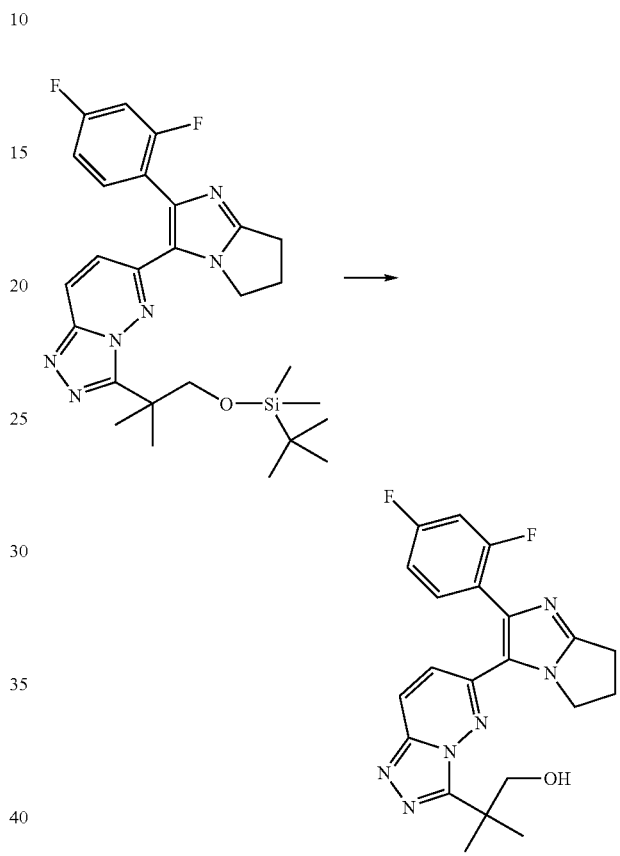

The 3-(1-(tert-butyldimethylsilyloxy)-2-methylpropan-2-yl)-6-(2-(2,4-difluorophenyl)-6,7-dihydro-5H-pyrrolo[1,2-a]imidazol-3-yl)-[1,2,4]triazolo[4,3-b]pyridazine (0.606 g, 1.16 mmol, Preparation #E.1.1.1) was dissolved in THF (15 mL) and reacted at about ambient temperature with TBAF (1.0 M in THF, 1.39 mL, 1.39 mmol) for about 4 h. The crude reaction mixture was partitioned between water and DCM. The organics were dried over MgSO$_4$, filtered and concentrated under reduced pressure. The resulting crude material was purified by chromatography on silica gel (DCM/MeOH gradient from 100:0-85:15) and triturated with a mixture of heptane/Et$_2$O (90:10) to give the title compound as a yellow solid (0.074 g, 16%): LC/MS (Table 1, Method g) R$_t$=1.64 min.; MS m/z: 411.98 (M+H)$^+$.

TABLE AM.1

Examples prepared from TBAF using General Procedure AM

| TBDMS protected alcohol | Product | Example # | R$_t$ min (method) | m/z ESI+ (M + H)$^+$ |
|---|---|---|---|---|
| 5-(3-(1-((tert-Butyldimethylsilyloxy)methyl)cyclobutyl)- | (1-(6-(6-(2,4-Difluorophenyl)imidazo[2,1- | AM.1.2 | 1.79 (g) | 423.2 |

TABLE AM.1-continued

Examples prepared from TBAF using General Procedure AM

| TBDMS protected alcohol | Product | Example # | R$_t$ min (method) | m/z ESI+ (M + H)$^+$ |
|---|---|---|---|---|
| [1,2,4]triazolo[4,3-b]pyridazin-6-yl)-6-(2,4-difluorophenyl)imidazo[2,1-b]oxazole (Preparation #E.1.4.1) | b]oxazol-5-yl)-[1,2,4]triazolo[4,3-b]pyridazin-3-yl)cyclobutyl)methanol | | | |
| 3-(1-(tert-Butyldimethylsilyloxy)cyclopropyl)-6-(2-(2,4-difluorophenyl)-6,7-dihydro-5H-pyrrolo[1,2-a]imidazol-3-yl)-[1,2,4]triazolo[4,3-b]pyridazine (Preparation #E.1.1.2) | 1-(6-(2-(2,4-Difluorophenyl)-6,7-dihydro-5H-pyrrolo[1,2-a]imidazol-3-yl)-[1,2,4]triazolo[4,3-b]pyridazin-3-yl)cyclopropanol | AM.1.3 | 1.65 (g) | 395.2 |
| 3-(1-((tert-Butyldimethylsilyloxy)methyl)cyclobutyl)-6-(2-(2,4-difluorophenyl)-6,7-dihydro-5H-pyrrolo[1,2-a]imidazol-3-yl)-[1,2,4]triazolo[4,3-b]pyridazine (Preparation #E.1.1.3) | (1-(6-(2-(2,4-Difluorophenyl)-6,7-dihydro-5H-pyrrolo[1,2-a]imidazol-3-yl)-[1,2,4]triazolo[4,3-b]pyridazin-3-yl)cyclobutyl)methanol | AM.1.4 | 1.62 (g) | 423.2 |

TABLE AM.2

Examples prepared from HCl using General Procedure AM

| TBDMS protected alcohol | Product | Example # | R$_t$ min (method) | m/z ESI+ (M + H)$^+$ |
|---|---|---|---|---|
| 5-(3-(1-(*tert*-Butyldimethylsilyloxy)cyclopropyl)-[1,2,4]triazolo[4,3-b]pyridazin-6-yl)-6-(2,4-difluorophenyl)imidazo[2,1-b]oxazole [prepared using D from Example #9, Step A with hydrazine hydrate, I.1 with Preparation # C.1, E.1 with 1-(*tert*-butyldimethylsilyloxy)cyclopropane carbaldehyde (*Bioorg. Med. Chem. Lett.* 2007, 17(22), 6290-6294)] | 1-(6-(6-(2,4-Difluorophenyl)imidazo[2,1-b]oxazol-5-yl)-[1,2,4]triazolo[4,3-b]pyridazin-3-yl)cyclopropanol | AM.2.1 | 1.72 (g) | 394.9 |

General Procedure AN: Cyclization of a Pyridazinylhydrazide

To a flask containing a pyridazinylhydrazide (preferably 1 equiv) in a suitable organic solvent (such as Et$_2$O, THF or 1,4-dioxane, preferably 1,4-dioxane) is added thionyl chloride or phosphorus oxychloride (1-50 equiv, preferably 7 equiv). The mixture is stirred for about 0.5-24 h (preferably about 4 h) at about 23-100° C. (preferably about 80° C.). The reaction is optionally quenched with a base (such as saturated aqueous Na$_2$CO$_3$ or saturated aqueous NaHCO$_3$) and then extracted with organic solvent (such as EtOAc, Et$_2$O, or DCM; preferably DCM). Alternatively, the reaction is concentrated under reduced pressure and dissolved in a suitable organic solvent (such as EtOAc, DCM or Et$_2$O, preferably DCM). In either case, the organic layers may be optionally washed with aqueous Na$_2$CO$_3$ or brine, dried over Na$_2$SO$_4$ or MgSO$_4$, and then decanted or filtered prior to concentrating under reduced pressure. The crude product is purified by crystallization or trituration from an appropriate solvent or solvents, or by chromatography to give the target compound.

Example #AN.1.1

6-(2-(2,4-Difluorophenyl)-6,7-dihydro-5H-pyrrolo[1,2-a]imidazol-3-yl)-3-(1-methylcyclopropyl)-[1,2,4]triazolo[4,3-b]pyridazine

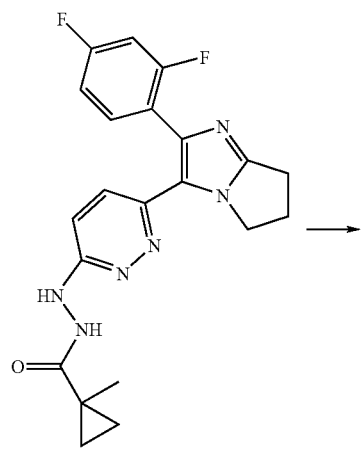

→

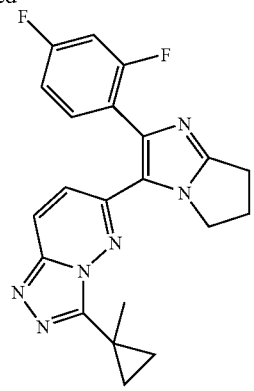

A 125 mL flask was charged with N'-(6-(2-(2,4-difluorophenyl)-6,7-dihydro-5H-pyrrolo[1,2-a]imidazol-3-yl)pyridazin-3-yl)-1-methylcyclopropanecarbohydrazide (0.458 g, 0.614 mmol, prepared using General Procedure AR from Example #35, Step E with 1-methylcyclopropanecarboxylic acid) and 1,4-dioxane (20 mL) to give a brown suspension. To the suspension, thionyl chloride (0.3 mL, 4.11 mmol) was added and the mixture was stirred at about 80° C. After about 4 h, the reaction was concentrated under reduced pressure. The residue was redissolved in DCM and washed with saturated aqueous $Na_2CO_3$. The organic solution was dried over $Na_2SO_4$ and concentrated in vacuo. The crude material was purified by silica gel chromatography using MeOH/DCM (gradient; 0:100 to 10:90) to give the title compound (0.140 g, 58% yield): LC/MS (Table 1, Method a) $R_f$=2.28 min; MS m/z: 393.3 (M+H)$^+$.

TABLE AN.1

Examples prepared with thionyl chloride using General Procedure AN

| Hydrazide | Product | Example # | $R_f$ min (method) | m/z ESI+ (M + H)$^+$ |
|---|---|---|---|---|
| N'-(6-(2-(2,4-Difluorophenyl)-6,7-dihydro-5H-pyrrolo[1,2-a]imidazol-3-yl)pyridazin-3-yl)morpholine-4-carbohydrazide [prepared using T.1 from Example #35, Step E with morpholine-4-carbonyl chloride] | 4-(6-(2-(2,4-Difluorophenyl)-6,7-dihydro-5H-pyrrolo[1,2-a]imidazol-3-yl)-[1,2,4]triazolo[4,3-b]pyridazin-3-yl)morpholine | AN.1.2 | 1.64 (g) | 424.2 |

General Procedure AO: Preparation of a Thiourea

To a suspension or solution of a functionalized secondary amine (preferably 1 equiv) in a suitable solvent (for example, THF, 1,4-dioxane, or DCE, preferably THF) is added 1,1-thiocarbonyldiimidazole (1-5 equiv, preferably 1.2 equiv). The reaction mixture is stirred at about 0-80° C. (preferably about 0-60° C.) for about 1-80 h (preferably about 8 h). Ammonia (1-25 equiv, preferably 12 equiv; for example, a solution of ammonia in MeOH, ammonia gas, or ammonium hydroxide, preferably 7 M ammonia in MeOH) is added and is stirred at about 40-80° C. (preferably about 40° C.) for about 2-24 h (preferably about 15 h). Optionally, a second portion of ammonia (1-25 equiv, preferably 12 equiv; for example, a solution of ammonia in MeOH, ammonia gas, or ammonium hydroxide, preferably 7 M ammonia in MeOH) is added and reaction is continued at about 40-80° C. (preferably about 40° C.) for about 2-24 h (preferably about 15 h). The reaction mixture is cooled to ambient temperature and solvent removed under reduced pressure. The crude material is purified by trituration with a suitable solvent (for example, Et$_2$O, DCM, ethyl acetate, MeOH, or heptanes, preferably Et$_2$O), and filtered to give the title compound.

Illustration of General Procedure AO:

Preparation #AO.1.1:
4-Isopropylpiperazine-1-carbothioamide

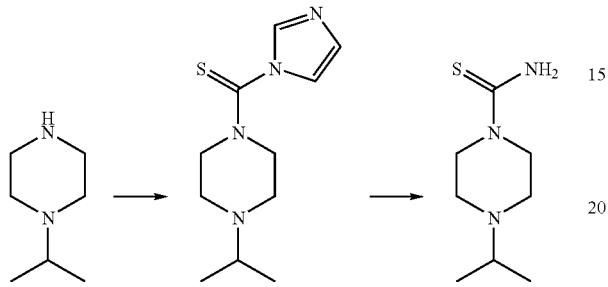

To a suspension of 1-isopropylpiperazine (1.5 g, 11.70 mmol) in THF (24 mL) was added 1,1-thiocarbonyldiimidazole (2.398 g, 13.45 mmol). The reaction mixture was stirred at ambient temperature for about 8 h. Upon addition of the 1,1-thiocarbonyldiimidazole, the reaction mixture slightly warmed. A solution of ammonia (7.0 M in MeOH, 20 mL) was added and the reaction mixture was stirred overnight at ambient temperature. Additional ammonia (7.0 M in MeOH, 20 mL) was added and the reaction mixture was stirred overnight at about 40° C. The reaction mixture was cooled to ambient temperature and solvent was removed under reduced pressure. The residue was triturated with Et$_2$O (15 mL) and filtered to give the title compound (2.5 g, 97%) as a yellow solid: LC/MS (Table 1, Method a) R$_t$=0.74 min; MS m/z: 188.1 (M+H)$^+$.

reduced pressure and then optionally purified by crystallization, trituration or by chromatography to give the target compound.

Illustration of General Procedure AP

Preparation #AP.1.1 N-((3-Isopropyl-[1,2,4]triazolo[4,3-b]pyridazin-6-yl)methylene)methanamine

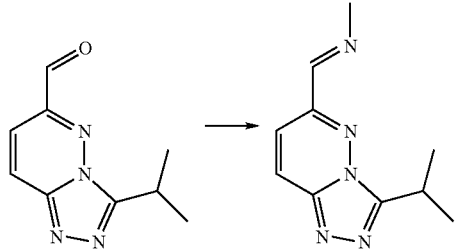

To a flask was added 3-isopropyl-[1,2,4]triazolo[4,3-b]pyridazine-6-carbaldehyde (0.420 g, 2.21 mmol, Preparation #2), and methylamine (40 wt % in water, 1.33 mL, 2.65 mmol) followed by MgSO$_4$ (0.399 g, 3.31 mmol) in DCM (2 mL) to give an orange suspension. The mixture was stirred at ambient temperature for about 17 h. The mixture was filtered and concentrated in vacuo to afford the title compound (0.300 g, 67%): $^1$H NMR (DMSO-d$_6$) δ 8.43 (s, 1H), 8.31 (d, 1H), 7.74 (d, 1H), 3.59 (m, 4H), 2.5 (s, 3H), 1.45 (d, 6H).

TABLE AO.1

Preparations prepared from thiocarbonyldiimidazole using General Procedure AO.

| Piperazine | Thioamide | Example # | R$_t$ min (method) | m/z ESI+ (M + H)$^+$ |
|---|---|---|---|---|
| 1-(Piperazin-1-yl)ethanone | 4-Acetylpiperazine-1-carbothioamide | AO.1.2 | 1.33 (a) | 188.1 |
| 1-tert-Butylpiperazine [Wako] | 4-tert-Butylpiperazine-1-carbothioamide | AO.1.3 | 0.87 (a) | 202.2 |
| 1-Cyclopropylpiperazine, 2 Hydrochloric Acid [CNH Technologies] | 4-Cyclopropylpiperazine-1-carbothioamide | AO.1.4 | 1.16 (a) | 186.1 |

General Procedure AP: Formation of an Imine

An aldehyde (preferably 1 equiv) and a primary amine (1-5 equiv, preferably about 1.2 equiv) are mixed in an organic solvent (such as DCM or toluene, preferably DCM) at ambient temperature. To the mixture is added a dehydrating agent (1-5 equiv, preferably about 1.5 equiv) such as MgSO$_4$ or Na$_2$SO$_4$ (preferably MgSO$_4$) and the mixture is stirred at ambient temperature for about 2-30 h (preferably 17 h). The mixture is filtered and optionally concentrated under General Procedure AQ: Cyclization of a Hydrazinylpyridazine with a Thioisocyanate A mixture of a hydrazine (preferably 1 equiv), and a thioisocyanate (1-3 equiv, preferably 1.6 equiv) is heated at about 20-100° C. (preferably about 75° C.) in an organic solvent (such as MeOH or EtOH, preferably EtOH) for about 0.5-10 h (preferably about 2 h). DMAP (0.5-3 equiv, preferably 1.1 equiv) is added and the reaction is heated in a microwave at about 70-180° C. (preferably about 150° C.) for about 2-30 min (preferably about 10 min). The solvent is removed and the residue is purified by crystallization, trituration or by chromatography to give the target compound.

Illustration of General Procedure AQ

Example #AQ.1.1

6-(2-(2,4-Difluorophenyl)-6,7-dihydro-5H-pyrrolo[1,2-a]imidazol-3-yl)-N-ethyl-[1,2,4]triazolo[4,3-b]pyridazin-3-amine

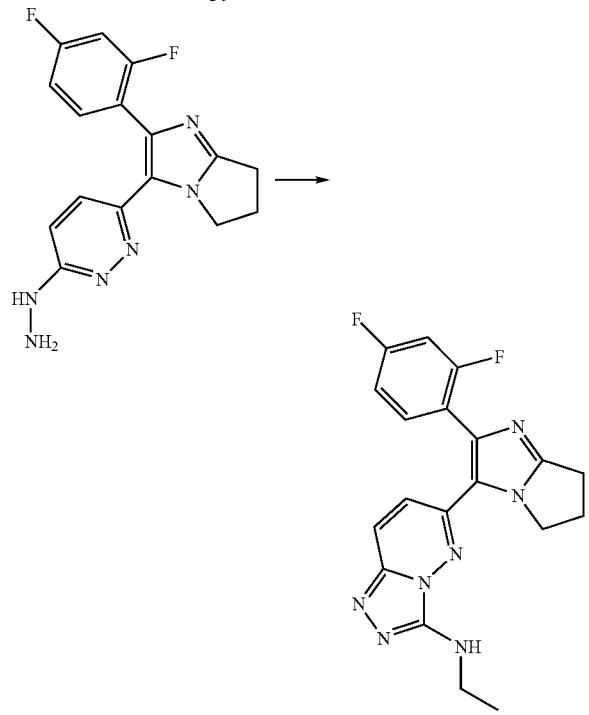

2-(2,4-Difluorophenyl)-3-(6-hydrazinylpyridazin-3-yl)-6,7-dihydro-5H-pyrrolo[1,2-a]imidazole (0.200 g, 0.609 mmol, Example #35, Step E) and isothiocyanatoethane (0.085 g, 0.975 mmol) were added to EtOH (3 mL). The suspension was heated to about 75° C. for about 3 h. DMAP (0.138 g, 0.670 mmol) was added and the solution was heated in a CEM® microwave at about 150° C. for about 10 min (250 psi maximum pressure, 10 min ramp, 300 max watts). Solvent was removed in vacuo and the material was purified by flash chromatography using MeOH/DCM (0-6% gradient) and then further purified by RP-HPLC (Table 1, Method m). The ACN was removed and the resulting precipitate was collected to afford the title compound (0.040 g, 17%): LC/MS (Table 1, Method g) $R_t$=1.77 min; MS m/z: 382.2 (M+1)$^+$.

General Procedure AR: Amide or Hydrazide Formation

An acid (preferably 1 equiv) is combined with a peptide coupling reagent (such as HBTU/HOBT, HATU, EDCI, BOP-Cl, TFFH or DCC/HOBT, preferably BOP-Cl (14 equiv, preferably 2 equiv)), an organic solvent (such as DMF, DCM, ethylene glycol dimethyl ether, EtOAc, or toluene (preferably DCM)), an amine (0.1-10 equiv, preferably 2.2 equiv) and optionally an organic base (such as DIPEA, NMM, TEA, or pyridine preferably DIPEA, 0.5-10 equiv (preferably 4 equiv)). The reaction is stirred at about 25-100° C. (preferably about 25° C.) for about 0.5-24 h (preferably about 1 h). Upon completion of the reaction, an organic solvent such as DCM or EtOAc and an aqueous acid (such as 1-6 N HCl, preferably 5 N HCl) is added. The organic phase is separated and dried with a drying agent (such as $Na_2SO_4$ or $MgSO_4$), filtered and concentrated under reduced pressure. Optionally, if the product is in the aqueous acid, it is neutralized with a base (such as 1-6 N aqueous NaOH, saturated $NaHCO_3$, saturated $Na_2CO_3$, solid $Na_2CO_3$, solid NOH or solid KOH, preferably 6 N aqueous NaOH) and then extracted with a suitable organic solvent (such as EtOAc, DCM or $Et_2O$, preferably DCM), dried with a suitable drying agent (such as $Na_2SO_4$ or $MgSO_4$), filtered and concentrated under reduced pressure. The crude product can be purified by trituration, crystallization, and/or chromatography to give the target compound.

Illustration of General Procedure AR

Example #AR.1.1

N-(2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-yl)acetamide

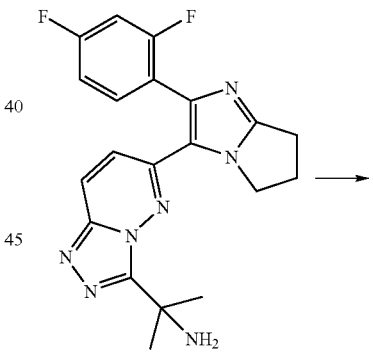

TABLE AQ.1

Examples prepared from 2-(2,4-difluorophenyl)-3-(6-hydrazinylpyridazin-3-yl)-6,7-dihydro-5H-pyrrolo[1,2-a]imidazole (Example #35, Step E) using General Procedure AQ

| Thioisocyanate | Product | Example # | $R_t$ min (method) | m/z ESI+ (M + H)$^+$ |
|---|---|---|---|---|
| Isothiocyanatomethane | 6-(2-(2,4-Difluorophenyl)-6,7-dihydro-5H-pyrrolo[1,2-a]imidazol-3-yl)-N-methyl-[1,2,4]triazolo[4,3-b]pyridazin-3-amine | AQ.1.2 | 1.63 (g) | 368.1 |

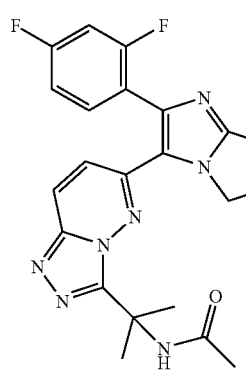

A flask was charged with 2-(6-(2-(2,4-difluorophenyl)-6,7-dihydro-5H-pyrrolo[1,2-a]imidazol-3-yl)-[1,2,4]triazolo[4,3-b]pyridazin-3-yl)propan-2-amine (0.125 g, 0.316 mmol, prepared using General Procedure I.1 from Example #6, Step B with Example #9, Step A, General Procedure D with hydrazine hydrate, General Procedure E.1 with tert-butyl 2-methyl-1-oxopropan-2-ylcarbamate (prepared using General Procedure A.I.1 from tert-butyl 1-hydroxy-2-methylpropan-2-ylcarbamate), General Procedure Q.1 with HCl) and DCM (2.0 mL) to give a brown solution. To the reaction flask were added DIPEA (0.166 mL, 0.948 mmol) and HOAC (0.022 mL, 0.38 mmol). BOP-Cl (0.161 g, 0.632 mmol, Lancaster) was added in one portion to the solution and the reaction mixture was stirred at ambient temperature for about 90 min. The mixture was poured into DCM (about 30 mL) and washed with 1N HCl (about 30 mL). The aqueous layer and the organic solution was then washed with 5 N HCl (about 2×30 mL). The aqueous solution was basified with 6N NaOH (about 20 mL). The cloudy solution was back-extracted with DCM (2×50 mL). The organic solution was dried over MgSO$_4$, filtered, and the solvent was removed under reduced pressure to give a yellow residue. The product was dissolved into hot ACN (about 4 mL) followed by the addition of water (about 2 mL). The mixture was concentrated under reduced pressure and then lyophilized to give the title compound (0.060 g, 43%): LC/MS (Table 1, Method g) R$_t$=1.67 min; MS m/z: 474.2 (M+H)$^+$.

Example #1

5-(2,4-Difluorophenyl)-4-(3-isopropyl-[1,2,4]triazolo[4,3-b]pyridazin-6-yl)isoxazole

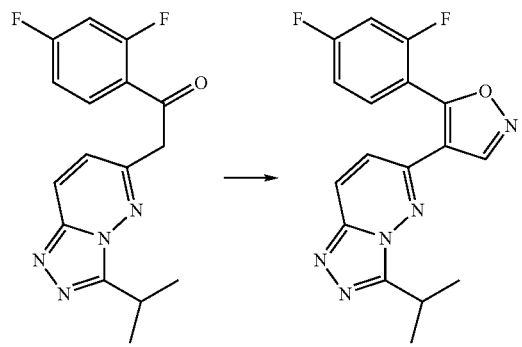

A solution of 1-(2,4-difluorophenyl)-2-(3-isopropyl-[1,2,4]triazolo[4,3-b]pyridazin-6-yl)ethanone (0.10 g, 0.316 mmol; Preparation #K.1), N,N-dimethylformamide dimethyl acetal (0.070 g, 0.57 mmol) and toluene (2 mL) was heated at about 110° C. in an oil bath for about 30 min. The reaction mixture was cooled and then concentrated under reduced pressure. The residue was dissolved in EtOH (2.0 mL) and then potassium acetate (0.12 g, 1.26 mmol) and hydroxylamine hydrochloride (0.090 g, 1.26 mmol) were added. The mixture was heated at about 95° C. in an oil bath for about 30 min. The mixture was concentrated under reduced pressure and then acetic acid was added and the material was purified by RP-HPLC (Table 1, Method d). The appropriate fractions were lyophilized to give the title compound (0.063 g, 58%): LC/MS (Table 1, Method a) R$_t$=2.11 min; MS m/z: 342.2 (M+H)$^+$.

Example #2

6-(3-(2,4-Difluorophenyl)-5-methyl-1H-pyrazol-4-yl)-3-isopropyl-[1,2,4]triazolo[4,3-b]pyridazine

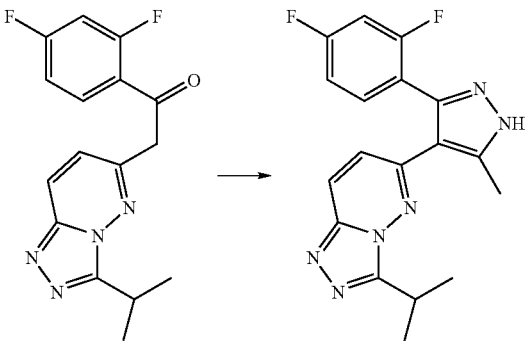

A solution of 1-(2,4-difluorophenyl)-2-(3-isopropyl-[1,2,4]triazolo[4,3-b]pyridazin-6-yl)ethanone (0.26 g, 0.82

TABLE AR.1

Examples prepared from 4-(2,4-difluorophenyl)-5-(3-isopropyl-[1,2,4]triazolo[4,3-b]pyridazin-6-yl)-2-(piperidin-4-yl)thiazole (Example #Q.1.1) using General Procedure AR

| Acid | Product | Example # | R$_t$ min (method) | m/z ESI+ (M + H)$^+$ |
|---|---|---|---|---|
| 2-Cyanoacetic acid | 3-(4-(4-(2,4-Difluorophenyl)-5-(3-isopropyl-[1,2,4]triazolo[4,3-b]pyridazin-6-yl)thiazol-2-yl)piperidin-1-yl)-3-oxopropanenitrile | AR.1.2 | 2.35 (a) | 508.3 | mmol; Preparation #K.1), N,N-dimethylacetamide dimethyl acetal (0.22 g, 1.64 mmol) and toluene (5 mL) was heated at about 110° C. in an oil bath for about 45 min. The reaction mixture was cooled and then concentrated under reduced pressure. 1,4-Dioxane (5.0 mL) and hydrazine (0.055 g, 1.64 mmol) were added to the mixture and it was then heated at about 95° C. in an oil bath for about 1 h. The mixture was concentrated under reduced pressure and then acetic acid was added and the material was purified by RP-HPLC (Table 1, Method d). The appropriate fractions were concentrated under reduced pressure to give a solid which was collected by filtration and dried to give the title compound (0.008 g, 3%): LC/MS (Table 1, Method a) $R_f$=1.99 min; MS m/z: 355.2 (M+H)⁺.

Example #3

6-(3-(2,4-Difluorophenyl)-1H-pyrazol-4-yl)-3-isobutyl-[1,2,4]triazolo[4,3-b]pyridazine Step A: 2-(6-Chloropyridazin-3-yl)-1-(2,4-difluorophenyl)ethanone

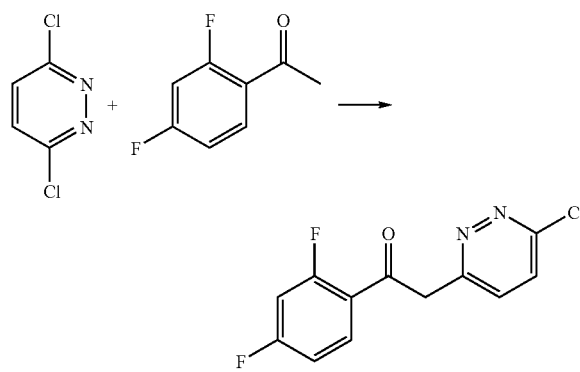

The 1-(2,4-difluorophenyl)ethanone (Apollo, 1.00 g, 6.40 mmol) and 3,6-dichloropyridazine (0.95 g, 6.4 mmol) in DME (10 mL) were treated with NaH (0.512 g, 12.8 mmol, 60% dispersion in oil) then warmed at about 50° C. in an oil bath. The mixture was stirred for about 4 h then sodium hydride (0.26 g, 6.4 mmol, 60% dispersion in oil) and 3,6-dichloropyridazine (0.48 g, 3.2 mmol) were added. The reaction was heated for about 0.5 h and then quenched with acetic acid and water. The mixture was extracted with EtOAc then purified by flash chromatography on silica with EtOAc as an eluent to give the title compound (0.98 g, 57%): LC/MS (Table 1, Method a) $R_f$=2.34 min; MS m/z: 269.1 (M+H)⁺.

Step B: 3-Chloro-6-(3-(2,4-difluorophenyl)-1H-pyrazol-4-yl)pyridazine

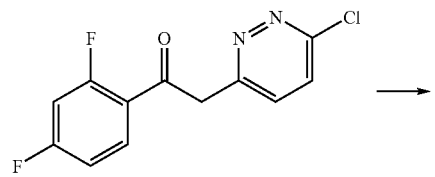

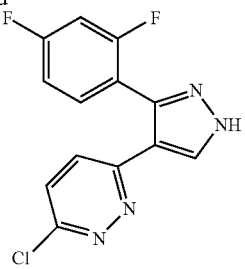

The title compound was prepared from 2-(6-chloropyridazin-3-yl)-1-(2,4-difluorophenyl)ethanone in a 25% yield according to General Procedure L: LC/MS (Table 1, Method a) $R_f$=2.13 min; MS m/z: 293.1 (M+H)⁺.

Step C: 6-(3-(2,4-Difluorophenyl)-1H-pyrazol-4-yl)-3-isobutyl-[1,2,4]triazolo[4,3-b]pyridazine

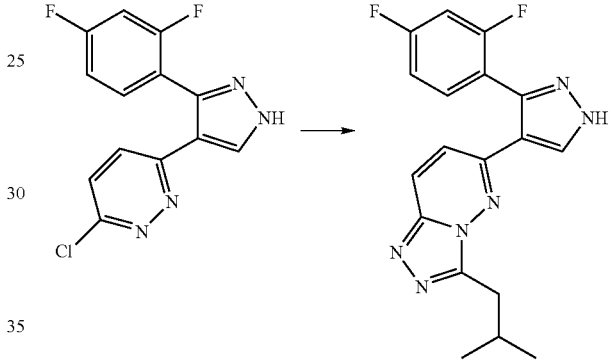

3-(3-(2,4-Difluorophenyl)-1H-pyrazol-4-yl)-6-hydrazinylpyridazine was prepared from 3-chloro-6-(3-(2,4-difluorophenyl)-1H-pyrazol-4-yl)pyridazine (0.26 g, 0.90 mmol) and hydrazine according to General Procedure D and then immediately cyclized with isovaleraldehyde according to General Procedure E to give the title compound (0.028 g, 8%) after purification by RP-HPLC (Table 1, Method d): LC/MS (Table 1, Method a) $R_f$=2.03 min; MS m/z: 355.2 (M+H)⁺.

Example #4

4-(2,4-Difluorophenyl)-5-(3-isopropyl-[1,2,4]triazolo[4,3-b]pyridazin-6-yl)-2-(piperidin-4-yl)thiazole

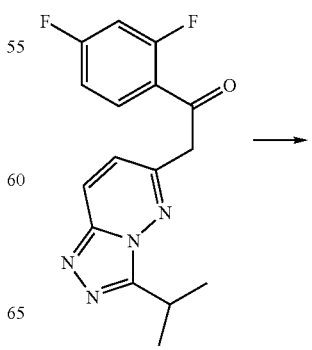

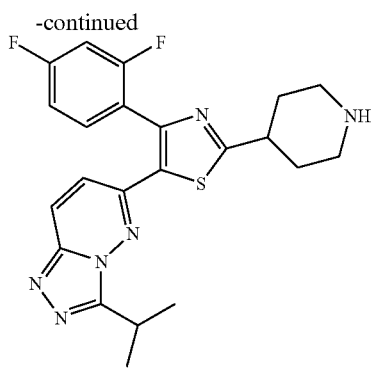

The 1-(2,4-difluorophenyl)-2-(3-isopropyl-[1,2,4]triazolo[4,3-b]pyridazin-6-yl)ethanone (0.250 g, 0.790 mmol, Preparation #K.1) was dissolved in THF (4 mL) then pyridinium tribromide (0.253 g, 0.790 mmol) was added in one portion. Within about 2-3 min, a solid started forming. The mixture was stirred at ambient temperature for about 1.5 h then DCM (20 mL) and water (10 mL) were added. The mixture was transferred to a separatory funnel and the layers were separated. The organic layer was dried over magnesium sulfate, filtered, and concentrated under reduced pressure. The residue was dissolved in DMF (4 mL) and then tert-butyl 4-carbamothioylpiperidine-1-carboxylate (0.290 g, 1.19 mmol) was added. The mixture was stirred overnight at ambient temperature, then concentrated under reduced pressure, and partitioned between EtOAc and water. The organic layer was concentrated under reduced pressure and then the residue was purified by flash chromatography with EtOAc as an eluent. Concentration of the desired fractions gave an oil which was dissolved in 1,4-dioxane (3 mL) and 6 N HCl (1 mL). The mixture was heated at about 60° C. in an oil bath for about 30 min then concentrated and purified by RP-HPLC (Table 1, Method d). Concentration of the appropriate fractions followed by basification with 1 N NaOH gave a turbid solution that was extracted with EtOAc (3×25 mL). The organic extracts were combined, dried over MgSO$_4$, and filtered. The filtrate was concentrated under reduced pressure. The residue was then suspended in water and lyophilized to give the title compound (0.125 g, 36% yield: LC/MS (Table 1, Method a) R$_t$=1.54 min; MS m/z: 441.2 (M+H)$^+$; $^1$H NMR (DMSO-d$_6$) δ 1.33 (d, 6H), 1.63 (m, 2H), 2.05 (m, 2H), 2.62 (m, 2H), 3.04 (m, 2H), 3.17 (m, 1H), 3.37 (m, 1H), 7.13 (m, 1H), 7.24 (m, 1H), 7.36 (m, 1H), 7.70 (m, 1H), 8.26 (d, 1H); Anal. calcd. for C$_{22}$H$_{22}$F$_2$N$_6$S: C, 59.98; H, 5.03; N, 19.08. found C, 59.66; H, 4.72; N, 19.05.

Example #5

4-(2,4-Difluorophenyl)-5-(3-isopropyl-[1,2,4]triazolo[4,3-b]pyridazin-6-yl)-2-(piperazin-1-yl)thiazole

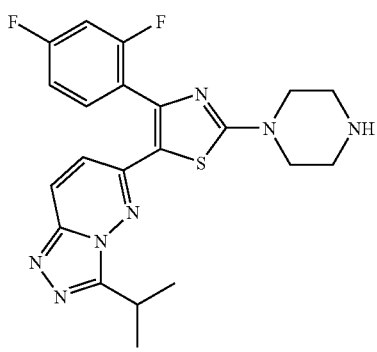

A mixture of 2-bromo-1-(2,4-difluorophenyl)-2-(3-isopropyl-[1,2,4]triazolo[4,3-b]pyridazin-6-yl)ethanone (0.61 g, 1.5 mmol; Preparation #A.2) and tert-butyl 4-carbamothioylpiperazine-1-carboxylate (Beta Pharma Inc, 0.341 g, 1.39 mmol) in EtOH (3 mL) was heated to reflux overnight. After cooling to ambient temperature, the crude mixture was partitioned between DCM and 1N aqueous HCl. The aqueous layer was basified with saturated aqueous Na$_2$CO$_3$ and extracted with DCM. The organics were dried over MgSO$_4$, filtered, concentrated under reduced pressure, and purified by silica gel chromatography using DCM/MeOH (linear gradient, 100:0 to 90:10) to give the title compound (0.061 g, 10%): LC/MS (Table 1, Method a) R$_t$=2.31 min; MS m/z: 442.8 (M+H)$^+$.

Example #6

6-(2-(2,4-Difluorophenyl)-6,7-dihydro-5H-pyrrolo[1,2-a]imidazol-3-yl)-3-isopropyl-[1,2,4]triazolo[4,3-b]pyridazine

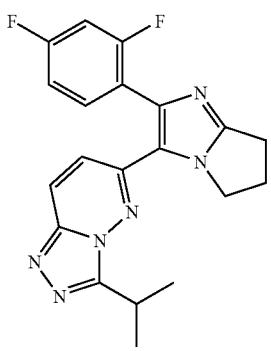

Step A: 2-(2,4-Difluorophenyl)-6,7-dihydro-5H-pyrrolo[1,2-a]imidazole

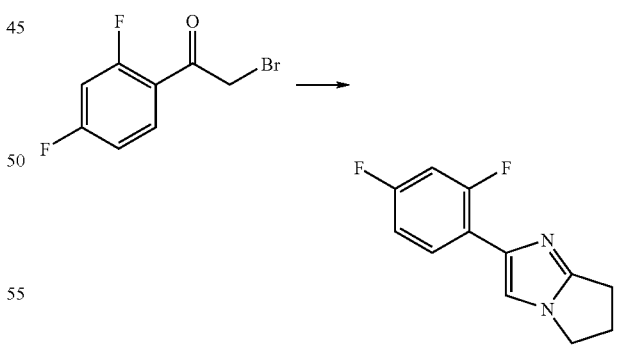

A mixture of 2-bromo-1-(2,4-difluorophenyl)ethanone (7.05 g, 30.0 mmol, prepared using General Procedure A.1 from 1-(2,4-difluorophenyl)ethanone), 2-imino-pyrrolidine hydrochloride (10.9 g, 90 mmol, prepared following the procedure in *J. Med. Chem.*, 2002, 45, 999-1001) and Na$_2$CO$_3$ (21.1 g, 199 mmol) in DMF (30 mL) was stirred overnight at about 80° C. The reaction mixture was cooled to ambient temperature, poured into water and extracted with EtOAc. The organics were dried over MgSO$_4$, filtered and concentrated under reduced pressure to give the crude title compound (6.61 g, 100%): LC/MS (Table 1, Method a) $R_t$=2.72 min; MS m/z: 221.0 (M+H)$^+$.

Step B: 2-(2,4-Difluorophenyl)-3-iodo-6,7-dihydro-5H-pyrrolo[1,2-a]imidazole

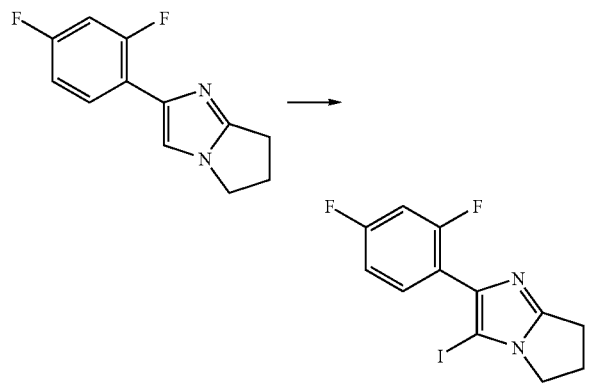

NIS (6.75 g, 30.0 mmol) was added to a solution of 2-(2,4-difluorophenyl)-6,7-dihydro-5H-pyrrolo[1,2-a]imidazole (6.61 g, 30.0 mmol) in DMF (50 mL). The reaction mixture was stirred at ambient temperature for about 35 min and then partitioned between DCM and water. The organics were dried over MgSO$_4$, filtered, concentrated under reduced pressure, and triturated with Et$_2$O to give the title compound (4.49 g, 43%): LC/MS (Table 1, Method a) $R_t$=3.18 min; MS m/z: 347.2 (M+H)$^+$.

Step C: 6-(2-(2,4-Difluorophenyl)-6,7-dihydro-5H-pyrrolo[1,2-a]imidazol-3-yl)-3-isopropyl-[1,2,4]triazolo[4,3-b]pyridazine

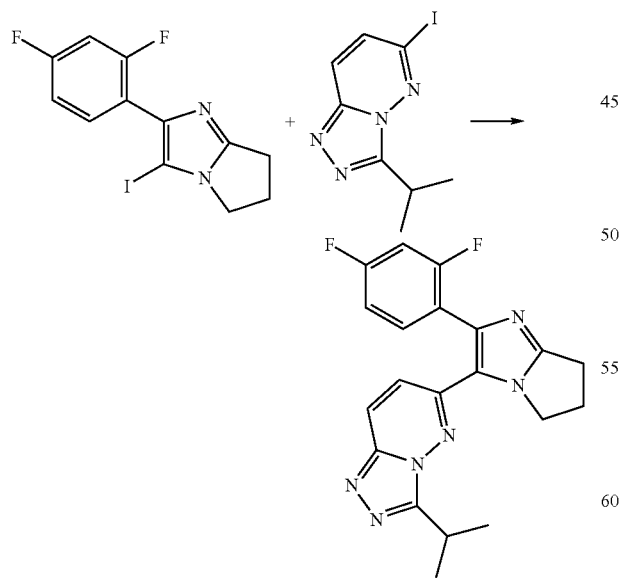

A 250 mL three-neck round bottom flask was charged with 2-(2,4-difluorophenyl)-3-iodo-6,7-dihydro-5H-pyrrolo[1,2-a]imidazole (5.00 g, 14.4 mmol) in THF (38 mL) to give a brown suspension. The suspension was cooled to about −30° C., followed by the drop-wise addition of a i-PrMgCl (2.0 M in THF, 8.70 mL, 17.3 mmol) over about 8 min. The reaction mixture was then stirred at about −20° C. for about 30 min. In a separate 50 mL round bottom flask were combined zinc chloride (2.56 g, 18.8 mmol) and THF (23 mL) with stirring. The clear, colorless solution was added drop-wise to the reaction mixture over about 10 min. The resulting suspension was stirred at about −20° C. for about 30 min. A third round bottom flask was charged with 6-iodo-3-isopropyl-[1,2,4]triazolo[4,3-b]pyridazine (4.16 g, 14.4 mmol, Preparation #H.1) and DMF (38 mL). The mixture was heated in order to fully dissolve the crystalline solid. The resulting yellow solution was rapidly added in one portion to the vigorously stirred reaction mixture, followed by the addition of Pd(PPh$_3$)$_4$ (0.67 g, 0.58 mmol) to the reaction mixture. Upon addition of this hot solution, the reaction mixture was immediately heated to about 80° C. Heating at about 80° C. was continued for about 30 min at which point the mixture was cooled to ambient temperature. The solvents were removed under reduced pressure to give a dark brown residue, which was then dissolved into a minimal volume of DCM (about 100 mL). The organic solution was washed with 1 N HCl (about 300 mL) and the remaining organic solution was then discarded. The aqueous solution containing the product was back-extracted once with DCM (about 75 mL) and then basified with solid Na$_2$CO$_3$. The yellow precipitate that formed was collected by vacuum filtration. The filtrate was then adjusted from pH ~6 to pH ~8 with additional solid Na$_2$CO$_3$, resulting in precipitation of additional solid that was also collected by vacuum filtration. The wet filter cake was partially dissolved into DCM and the solid that would not dissolve was removed by filtration and discarded. The organic solution was dried over MgSO$_4$, filtered, and concentrated to dryness to give a dark yellow oil that was purified by flash silica gel chromatography (stepwise gradient, DCM/MeOH/NH4OH 990:9:1 to 980:18:2 to 970:27:3). The product-containing fractions were combined and concentrated to dryness to give a viscous yellow oil. Et$_2$O was added to dissolve the oil and the resulting solution was re-concentrated to give the title compound as a yellow foam (1.4 g, 26%): LC/MS (Table 1, Method a) $R_t$=2.21 min; MS m/z 381.2 (M+H)$^+$; $^1$H NMR (400 MHz, DMSO-d$_6$) δ 8.20 (d, 1 H), 7.66 (m, 1 H), 7.34 (m, 1 H), 7.22 (m, 1 H), 6.96 (d, 1 H), 4.38 (m, 2 H), 3.55 (m, 1 H), 2.92 (m, 2 H), 2.64 (m, 2 H), 1.41 (d, 6 H).

Example #7

5-(3-Isopropyl-[1,2,4]triazolo[4,3-b]pyridazin-6-yl)-6-(2,4,5-trifluorophenyl)imidazo[2,1-b]oxazole

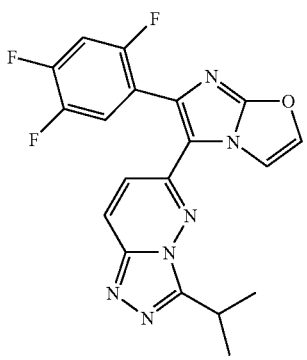

Step A: 2-Bromo-1-(2,4,5-trifluorophenyl)ethanone

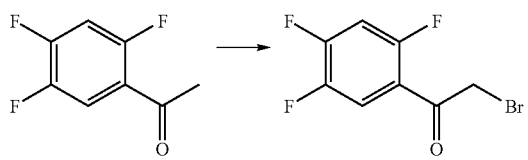

A 1 L 3-neck round bottom flask was charged with 1-(2,4,5-trifluorophenyl)ethanone (49.7 g, 285 mmol) and DCM (350 mL). The flask was equipped with a 250 mL dropping funnel that contained a solution of bromine (14.6 mL, 283 mmol) in DCM (125 mL). This solution was added to the reaction flask over about 1 h at about 23° C. Once addition of the solution was complete, the reaction mixture was stirred for about 1 h at about 23° C. Ice water was added to the reaction flask and the layers were stirred for about 15 min. The layers were separated and the organic solution was then washed with water and brine, dried over MgSO$_4$, filtered, and the solvent was removed under reduced pressure to give the title compound as a pale yellow solid (70.3 g, 97%): LC/MS (Table 1, Method b) R$_t$=2.20 min; MS m/z 251.0/253.0 (M+H)$^+$.

Step B: 6-(2,4,5-Trifluorophenyl)imidazo[2,1-b]oxazole

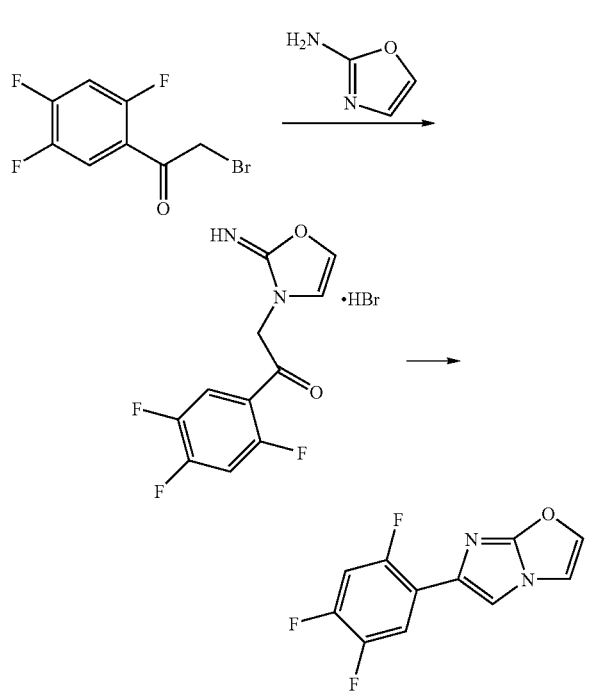

A round bottom flask was charged with 2-bromo-1-(2,4,5-trifluorophenyl)ethanone (50.0 g, 198 mmol), oxazol-2-amine (GL Synthesis, 11.1 g, 132 mmol), THF (200 mL), and ACN (330 mL). The resulting mixture was stirred at about 23° C. for about 20 h. The suspension was cooled to about −10° C. for about 15 min and the solid was collected by vacuum filtration, washed with additional ACN (150 mL), and dried under vacuum to give 2-(2-iminooxazol-3(2H)-yl)-1-(2,4,5-trifluorophenyl)ethanone hydrobromide (35.1 g, 79%) as a white solid. A portion of this material (20.0 g, 59.3 mmol) was suspended in toluene (140 mL) and the suspension was cooled to about 0° C. To the flask was added a 1.0 M solution of TiCl$_4$ in toluene (154 mL) over about 30 min. The mixture was stirred at about 0° C. for about 30 min and was then heated to about 100° C. for about 3 h. The mixture was cooled to ambient temperature, the toluene was decanted off, and ice was added to the remaining residue with stirring. The mixture was adjusted to about pH 8 with the addition of solid Na$_2$CO$_3$, followed by the addition of EtOAc. The mixture was stirred for about 1 h and then passed through a pad of Celite®. The layers were separated and the organic solution was dried over MgSO$_4$, filtered, and concentrated to dryness under reduced pressure to give the title compound as a white solid (11.7 g, 83%): LC/MS (Table 1, Method b) R$_t$=2.11 min; MS m/z 239.1 (M+H)$^+$.

Step C: 5-Iodo-6-(2,4,5-trifluorophenyl)imidazo[2,1-b]oxazole

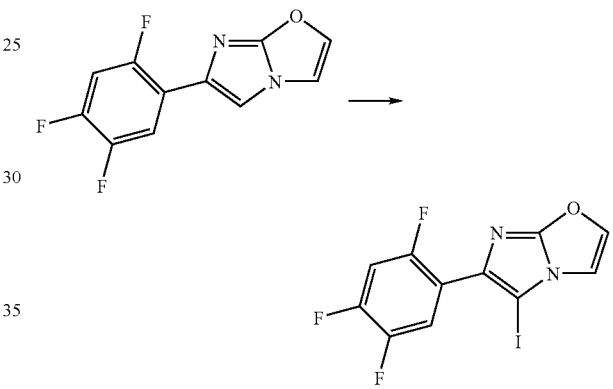

To a round bottom flask containing 6-(2,4,5-trifluorophenyl)imidazo[2,1-b]oxazole (11.7 g, 49.1 mmol) and DMF (120 mL) was added NIS (11.4 g, 50.6 mmol). The reaction mixture was stirred at ambient temperature for about 1 h. The reaction mixture was poured into water (300 mL) and the resulting precipitate was collected by vacuum filtration. The solid was dissolved into DCM (500 mL) and the organic suspension was washed sequentially with saturated NaHCO$_3$ solution, 5% sodium thiosulfate solution, and brine. The resulting solution was dried over MgSO$_4$, filtered, and concentrated to dryness under reduced pressure to give the title compound as a pale yellow solid (13.1 g, 73%): LC/MS (Table 1, Method b) R$_t$=2.17 min; MS m/z 365.0 (M+H)$^+$.

Step D: 5-(3-Isopropyl-[1,2,4]triazolo[4,3-b]pyridazin-6-yl)-6-(2,4,5-trifluorophenyl)imidazo[2,1-b]oxazole

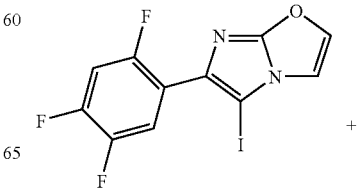

-continued

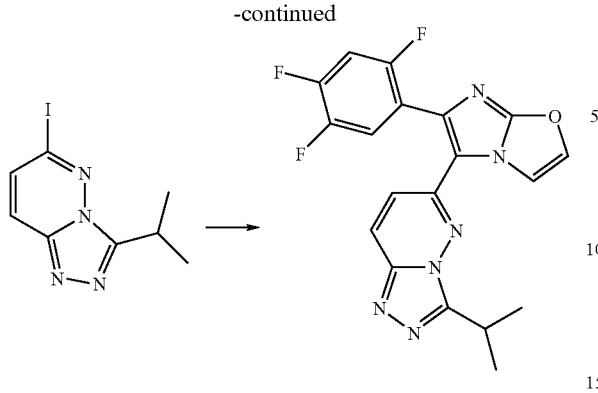

A 50-mL round bottom flask was charged with 5-iodo-6-(2,4,5-trifluorophenyl)imidazo[2,1-b]oxazole (0.65 g, 1.8 mmol) and THF (4.5 mL) to give a white suspension. The mixture was cooled to about −65° C. followed by the addition of a 2.0 M solution of i-PrMgCl (1.1 mL, 2.1 mmol). The resulting suspension was stirred at about −55° C. for about 30 min and at about −30° C. for about 1.75 h. To the reaction mixture was added dropwise a prepared solution of zinc chloride (0.32 g, 2.3 mmol) in THF (3.0 mL) and the resulting suspension was stirred at about −30° C. for about 30 min. In a separate flask were mixed 6-iodo-3-isopropyl-[1,2,4]triazolo[4,3-b]pyridazine (0.49 g, 1.7 mmol, Preparation #H.1), Pd(PPh₃)₄ (Strem, 0.073 g, 0.071 mmol), and DMF (5.0 mL). This solution was added to the reaction flask, which was immediately heated to about 80° C. in order to solubilize the resulting mixture. The mixture was heated at about 80° C. for about 1 h. The cooled reaction mixture was concentrated to dryness under reduced pressure and the residue was dissolved in DCM and washed with 1 N HCl, 5 N HCl, water, and brine. The solution was dried over MgSO₄, filtered, and concentrated to dryness under reduced pressure. The crude product was recrystallized from ACN to give a light yellow powder, followed by RP-HPLC (Table 1, Method l) purification to give the title compound as an off-white powder (0.025 g, 3.5%): LC/MS (Table 1, Method a) R$_f$=2.47 min; MS m/z 399.1 (M+H)$^+$; $^1$H NMR (400 MHz, DMSO-d₆) δ 8.28 (d, 1 H), 8.26 (d, 1 H), 8.22 (d, 1 H), 7.85-7.71 (m, 2 H), 7.07 (dd, 1 H), 3.73-3.66 (m, 1 H), 1.44 (d, 6 H).

Example #8

6-(2,4-Difluorophenyl)-5-(3-isopropyl-[1,2,4]triazolo[4,3-b]pyridazin-6-yl)imidazo[2,1-b]oxazole

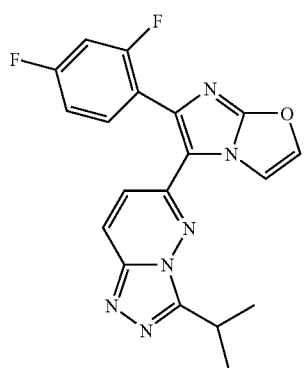

Step A: 2-Bromo-1-(2,4-difluorophenyl)ethanone

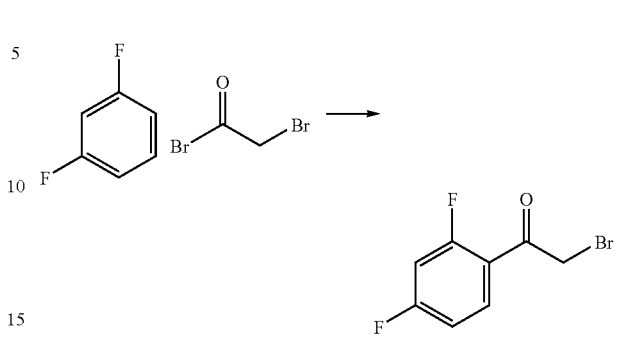

1,3-Difluorobenzene (100.0 g, 877 mmol) was added to a solution of bromoacetyl bromide (177.0 g, 870 mmol) and aluminum chloride (118.6 g, 890 mmol) in DCM (50 mL) at about 10-15° C. The reaction was then mixed at about 32° C. for about 2 h and then cooled and then added to 3N HCl (650 mL) at about 5-11° C. The solution was warmed to ambient temperature and the product was extracted with pentane (400 mL). The pentane was washed with pH 7 NaCl buffer, concentrated and filtered to afford the title compound (190.1 g, 91%). $^1$H NMR (DMSO-d₆) δ 8.01 (m, 1 H), 7.46 (m, 1 H), 7.27 (m, 1 H), 4.82 (s, 2 H).

Step B: 6-(2,4-Difluorophenyl)imidazo[2,1-b]oxazole

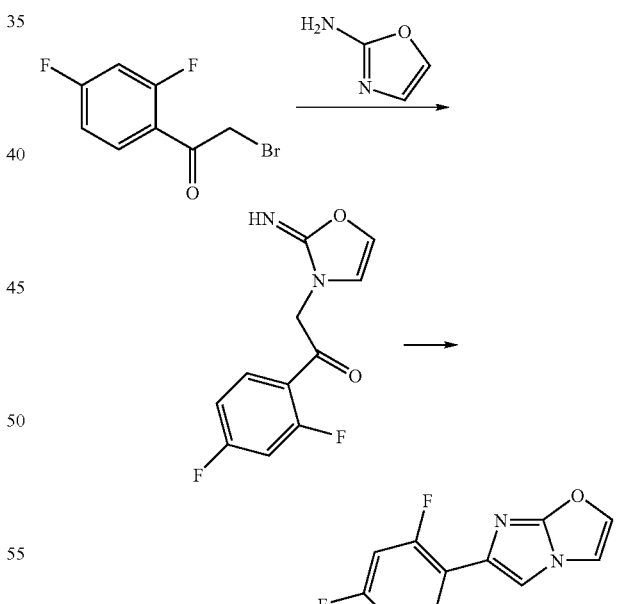

A round bottom flask was charged with 2-bromo-1-(2,4,-difluorophenyl)ethanone (74.8 g, 318 mmol), oxazol-2-amine (GL Synthesis, 22.3 g, 265 mmol), THF (400 mL), and ACN (660 mL). The resulting mixture was stirred at ambient temperature for about 20 h. The resulting suspension was filtered and the solids were washed with Et₂O (150 mL) and dried under reduced pressure to give 1-(2,4-difluorophenyl)-2-(2-iminooxazol-3(2H)-yl)ethanone hydrobromide (51.4 g, 61%). A portion of this material (19.8 g, 62.0 mmol) was added in 3 g portions over about 2 h to a flask charged with polyphosphoric acid (124.4 g) at about 80° C. The thick solution was mixed at about 80-90° C. for about 22 h. The reaction mixture was slowly transferred to a mixture of water (150 mL) and 30% aqueous NaOH (150 mL) at about 5-10° C. The pH of the resulting slurry was adjusted to about 5.4 by addition of 30% aqueous NaOH and the product was isolated by filtration. The wet cake was rinsed with warm water (3×150 mL) and dried under vacuum to give the title compound (9.5 g, 69%). MS m/z 221.1 (M+H)+ FIA(APCI)

Step C:
6-(2,4-Difluorophenyl)-5-iodoimidazo[2,1-b]oxazole

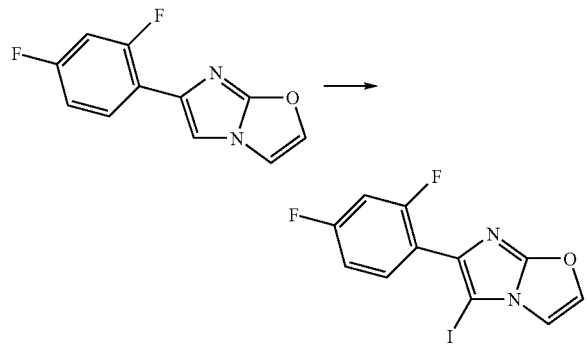

A solution of 6-(2,4-difluorophenyl)imidazo[2,1-b]oxazole (30.0 g, 136 mmol), NIS (31.6 g, 140 mmol), and DMF (350 mL) was stirred at ambient temperature. After about 1 h, the reaction was poured into water (2 L) and the resulting precipitate was filtered, washing with additional water. The brown solid was dissolved in DCM and washed with saturated aqueous NaHCO$_3$. The organic layer was dried over MgSO$_4$, filtered, and concentrated under reduced pressure to dryness. The solid was dissolved in DCM, filtered through Florosil® and then concentrated under reduced pressure to a volume of about 0.5 L. The organic layer was washed with 5% aqueous NaS$_2$O$_3$, dried over MgSO$_4$, filtered, and concentrated under reduced pressure to dryness to give the title compound as a yellow solid (34.5 g, 73%): LC/MS (Table 1, Method a) R$_f$=2.67 min; MS m/z: 346.9 (M+H)+.

Step D: 6-(2,4-Difluorophenyl)-5-(3-isopropyl-[1,2,4]triazolo[4,3-b]pyridazin-6-yl)imidazo[2,1-b]oxazole

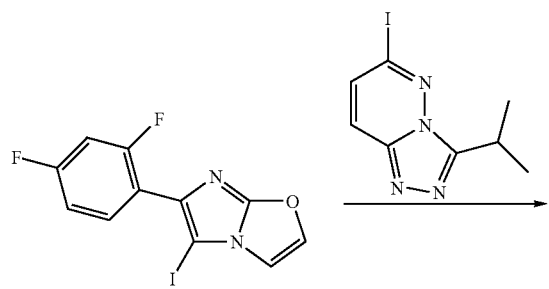

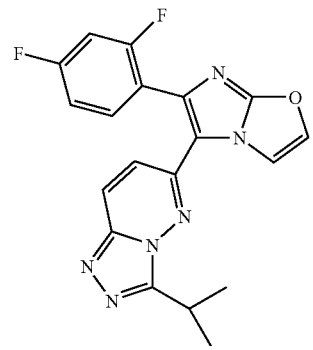

In a dry three-neck flask, 6-(2,4-difluorophenyl)-5-iodoimidazo[2,1-b]oxazole (9.61 g, 27.8 mmol, Preparation #C.1) was dissolved in THF (75 mL) under an atmosphere of nitrogen. The reaction mixture was cooled to about −30° C. and then i-PrMgCl (2.0 M in THF, 15.3 mL, 30.5 mmol) was added dropwise. The reaction mixture was stirred at about −30° C. for about 15 min. In a separate dry flask, zinc chloride (4.92 g, 36.1 mmol) was dissolved in THF (75 mL) and cooled to about 0° C. The zinc chloride solution was added dropwise to the heteroaryl Grignard mixture. The reaction mixture was stirred at about −15° C. for about 30 min. A flask containing 6-iodo-3-isopropyl-[1,2,4]triazolo[4,3-b]pyridazine (8.00 g, 27.8 mmol; Preparation #H.1) and Pd(Ph$_3$P)$_4$ (Strem, 1.28 g, 1.11 mmol) in DMF (75 mL) was stirred at about 80° C. until all of the solids were in solution. This solution was poured into the reaction mixture and the mixture was immediately heated to about 50° C. in an oil bath. After heating at about 50° C. for about 15 min, the mixture was cooled to ambient temperature. DMF was removed in vacuo and the residue was dissolved in DCM (50 mL) and was washed with 1N HCl (3×50 mL). The combined organic layers were washed with 6N HCl (1×50 mL) followed by a back extraction with DCM (50 mL). The aqueous layer was basified with solid Na$_2$CO$_3$ until the pH was about 9 and then extracted with DCM (3×70 mL). The combined organic layers were then washed with brine, dried over MgSO$_4$, filtered, and concentrated in vacuo. The residue was triturated with ACN. The resulting solid was filtered and then dissolved in 6N HCl (40 mL). The aqueous solution was extracted with DCM (2×40 mL). The product was recovered after basifying the aqueous portion with 1M aqueous Na$_2$CO$_3$ and a final extraction with DCM (3×40 mL). The combined organic layers were dried over MgSO$_4$, filtered, and concentrated in vacuo to afford the title compound (2.34 g, 22%). The mother liquor from the initial trituration was purified by silica gel flash chromatography using DCM/MeOH (gradient, 0-3% MeOH). A final recrystallization of the recovered material with ACN afforded an additional amount of the title compound (2.65 g, 25%) for a total recovered amount of 6-(2,4-difluorophenyl)-5-(3-isopropyl-[1,2,4]triazolo[4,3-b]pyridazin-6-yl)imidazo[2,1-b]oxazole (4.99 g, 47%) as a white solid: LC/MS (Table 1, Method a) R$_f$=2.16 min; MS m/z: 381.2 (M+H)+; $^1$H NMR (DMSO-d$_6$) δ 8.26 (m, 3H), 7.74 (m, 1H), 7.44 (m, 1H), 7.29 (m, 1H), 6.97 (m, 1H), 3.71 (m, 1H), 1.44 (m, 6H), Anal. calcd. for C$_{19}$H$_{14}$F$_2$N$_6$O: C, 60.00; H, 3.71; N, 22.09. found C, 59.76; H, 3.38; N, 22.08.

Example #9

3-tert-Butyl-6-(3-(2,4-difluorophenyl)-1H-pyrazol-4-yl)-[1,2,4]triazolo[4,3-b]pyridazine

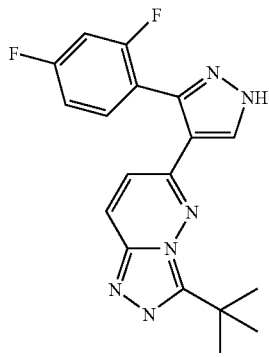

Step A: 3-Chloro-6-iodopyridazine

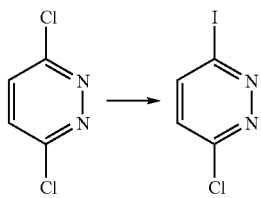

A mixture of 3,6-dichloropyridazine (10.0 g, 67.1 mmol) and sodium iodide (13.5 g, 90.0 mmol) in hydriodic acid (57 wt % in water, stabilized with <1.5% hypophosphorous acid; 50.0 mL, 379 mmol) was heated at about 40° C. for about 4 h. The reaction mixture was cooled to ambient temperature, poured slowly onto an ice/50% aqueous NaOH mixture (about 7:1, 400 mL) to basify to about pH 12 with stirring, and extracted with DCM (3×200 mL) after the ice melted. The combined organic extracts were washed with water (200 mL), dried over MgSO$_4$, filtered, concentrated under reduced pressure and dried in a vacuum oven overnight at about 50° C. to give the title compound (14.2 g, 88%): LC/MS (Table 1, Method b) R$_t$=1.57 min; MS m/z: 240.9 (M+H)$^+$.

Step B: 6-(2,4-Difluorophenyl)-5-iodoimidazo[2,1-b]oxazole

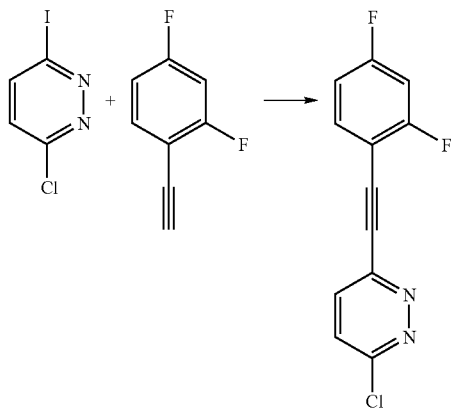

A solution of 3-chloro-6-iodopyridazine (10.0 g, 41.6 mmol, *Tetrahedron* 1999, 55(52), 15067-15070) in DMF (100 mL) was evacuated and purged with nitrogen 3 times. To the reaction mixture was added 1-ethynyl-2,4-difluorobenzene (7.47 g, 54.1 mmol), CuI (0.40 g, 2.08 mmol), TEA (11.0 mL, 79.0 mmol) and bis(triphenylphosphine)palladium(II) chloride (1.46 g, 2.08 mmol). The reaction mixture was heated to about 60° C. for about 2 h. The reaction mixture was then cooled to ambient temperature and concentrated in vacuo. The residue was taken up into DCM (200 mL) and the solid 1,2-bis(2,4-difluorophenyl)ethyne was filtered off. The filtrate was purified by silica gel flash chromatography using heptane/EtOAc (gradient, 4:1 to 1:1) to afford the title compound (7.85 g, 77%): LC/MS (Table 1, Method b) R$_t$=2.07 min; MS m/z: 251.0 (M+H)$^+$.

Step C: 3-((2,4-Difluorophenyl)ethynyl)-6-hydrazinylpyridazine

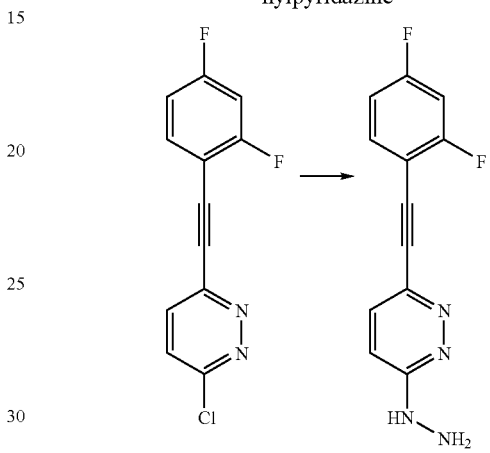

A flask was charged with 3-chloro-6-((2,4-difluorophenyl)ethynyl)pyridazine (1.60 g, 6.38 mmol) and 1,4-dioxane (15 mL) to give a tan solution. Anhydrous hydrazine (2.00 mL, 63.8 mmol) was added and the mixture was heated at about 80° C. for about 1 h. The mixture was cooled to ambient temperature and was concentrated in vacuo to about half the original volume. Water (20 mL) was added, followed by sonication, and filtration. The solids were collected and dried in a vacuum oven overnight at about 50° C. to afford the title compound (1.50 g, 95%): LC/MS (Table 1, Method b) R$_t$=1.72 min; MS m/z: 247.1 (M+H)$^+$.

Step D: 3-tert-Butyl-6-((2,4-difluorophenyl)ethynyl)-[1,2,4]triazolo[4,3-b]pyridazine

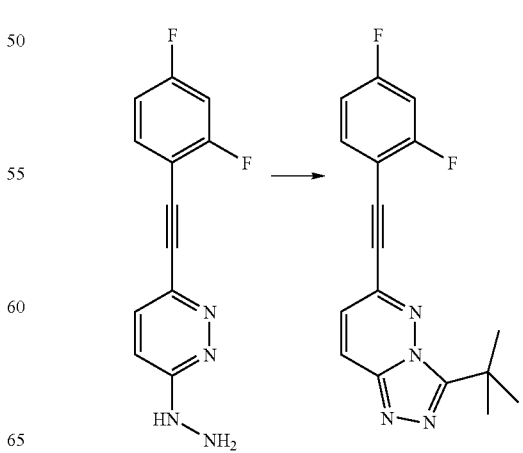

A mixture of 3-((2,4-difluorophenyl)ethynyl)-6-hydrazinylpyridazine (0.60 g, 2.4 mmol) and pivalaldehyde (0.31 g, 3.7 mmol) were dissolved in DCM (8 mL) and were stirred at ambient temperature for about 2 h. Iodobenzene diacetate (0.86 g, 2.7 mmol) was added and was stirred for about 2 h at ambient temperature. The reaction mixture was concentrated in vacuo and was purified by silica gel chromatography using DCM/MeOH (gradient, 0-2% MeOH) to afford the title compound (0.49 g, 64%): LC/MS (Table 1, Method a) $R_f$=2.50 min; MS m/z: 313.2 (M+H)$^+$.

Step E: 3-tert-Butyl-6-(3-(2,4-difluorophenyl)-1H-pyrazol-4-yl)-[1,2,4]triazolo[4,3-b]pyridazine

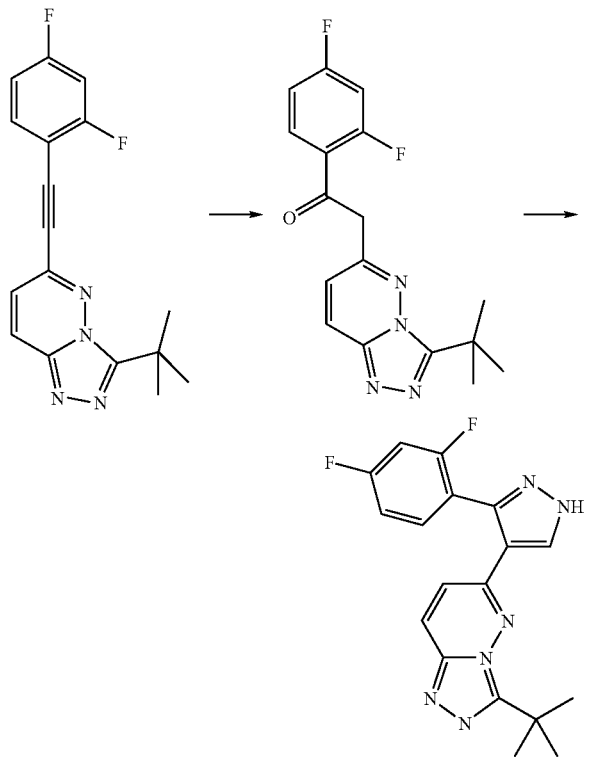

To a round bottom flask was added 3-tert-butyl-6-((2,4-difluorophenyl)ethynyl)-[1,2,4]triazolo[4,3-b]pyridazine (0.60 g, 1.92 mmol) and 60% aqueous H$_2$SO$_4$ (8.53 mL, 96 mmol). The reaction mixture was heated to about 90° C. for about 2 h. The reaction mixture was diluted with ice water (10 mL) and it was basified with 50% aqueous NaOH to a pH of about 9. The product was dried over MgSO$_4$, filtered, and concentrated in vacuo to afford 2-(3-tert-butyl-[1,2,4]triazolo[4,3-b]pyridazin-6-yl)-1-(2,4-difluorophenyl)ethanone which was carried forward without additional purification. To a mixture of 2-(3-tert-butyl-[1,2,4]triazolo[4,3-b]pyridazin-6-yl)-1-(2,4-difluorophenyl)ethanone in toluene (3 mL) was added 1,1-dimethoxy-N,N-dimethylethanamine (0.21 g, 1.73 mmol). The mixture was heated to about 100° C. for about 30 min. The toluene was removed in vacuo and the material was redissolved in 1,4-dioxane (3 mL). Anhydrous hydrazine (0.085 mL, 1.7 mmol) was added dropwise to the solution and it was heated to about 95° C. for about 30 min. The mixture was cooled to ambient temperature and the material was concentrated in vacuo. The material was purified by flash chromatography and eluted with DCM/MeOH (gradient, 1-4% MeOH) to afford the title compound (0.31 g, 46%): LC/MS (Table 1, Method a) $R_f$=1.82 min; MS m/z: 355.2 (M+H)$^+$; $^1$H NMR (DMSO-d$_6$) δ 1.17 (s, 9H), 7.19 (m, 1H), 7.32 (m, 1H), 7.56 (m, 1H), 7.63 (d, 1H), 8.28 (d, 1H), 8.66 (s (br), 1H), 13.66 (s (br), 1H).

Example #10

6-(4-(2,4-Difluorophenyl)-1H-1,2,3-triazol-5-yl)-3-isopropyl-[1,2,4]triazolo[4,3-b]pyridazine

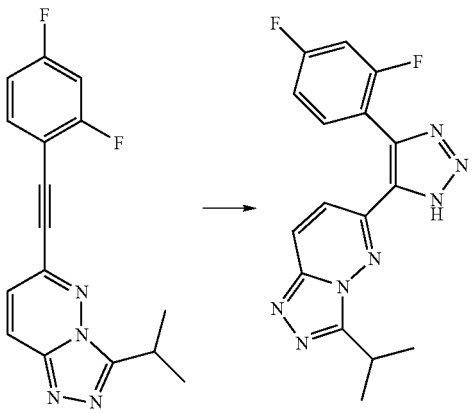

A 50 mL round-bottomed flask equipped with a condenser outfitted with a nitrogen inlet was charged with 6-((2,4-difluorophenyl)ethynyl)-3-isopropyl-[1,2,4]triazolo[4,3-b]pyridazine (0.500 g, 1.67 mmol, Preparation #J.1) in DMA (15 mL) to give a yellow solution. Sodium azide (0.327 g, 5.03 mmol) was added in one portion. The reaction mixture was heated at about 80° C. for about 16 h. The reaction mixture was partitioned between EtOAc and water. The layers were separated and the organic layer was washed with brine, dried over MgSO$_4$, filtered, and concentrated in vacuo. One-half of the aqueous mixture was purified via RP-HPLC (Table 1, Method f) to provide the title compound after lyophilization (0.080 g, 14%): LC/MS (Table 1, Method b) $R_f$=1.8 min; MS m/z: 342.2 (M+H)$^+$.

Example #11

6-(2-(2,4-Difluorophenyl)-4,5,6,7-tetrahydropyrazolo[1,5-a]pyrimidin-3-yl)-3-isopropyl-[1,2,4]triazolo[4,3-b]pyridazine

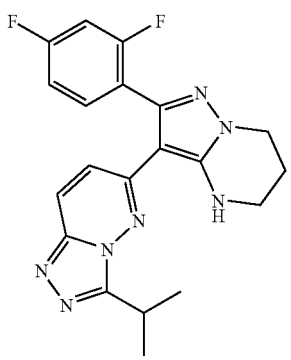

Step A: Azetidine-1-carbothiohydrazide

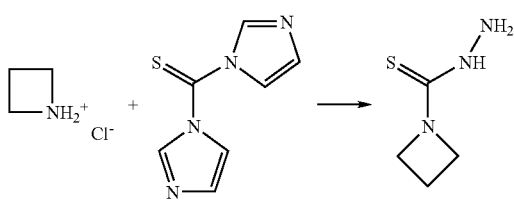

A mixture of azetidine hydrochloride (2.00 g, 21.4 mmol), TEA (4.47 mL, 32.1 mmol) and 1,1'-thiocarbonyldiimidazole (4.38 g, 24.6 mmol) in THF (20 mL) was stirred at ambient temperature overnight. The reaction mixture was filtered and the filtrate was concentrated under reduced pressure before addition of hydrazine (3.35 mL, 107 mmol). The resulting reaction mixture was stirred at ambient temperature for about 3 h and then partitioned between DCM and water. The organic layer was dried over $MgSO_4$, filtered, and concentrated under reduced pressure to give the title compound as a white sticky solid (2.80 g, 31%): $^1H$ NMR ($CDCl_3$) δ 2.25-2.43 (m, 2H), 4.02-4.21 (m, 4H), 6.35 (s, 1H).

Step B: 6-(2-(2,4-Difluorophenyl)-4,5,6,7-tetrahydropyrazolo[1,5-a]pyrimidin-3-yl)-3-isopropyl-[1,2,4]triazolo[4,3-b]pyridazine

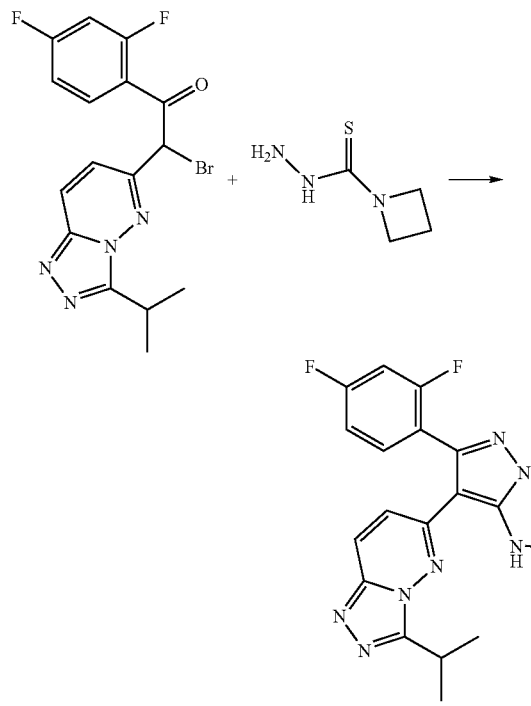

A mixture of 2-bromo-1-(2,4-difluorophenyl)-2-(3-isopropyl-[1,2,4]triazolo[4,3-b]pyridazin-6-yl)ethanone (0.61 g, 1.54 mmol; Preparation #A.2) and azetidine-1-carbothiohydrazide (0.29 g, 2.20 mmol) in HOAc (5 mL) was stirred at about 55° C. for about 1-2 h. The reaction mixture was cooled to ambient temperature overnight and partitioned between DCM and water. The aqueous layer was basified with a saturated aqueous solution of $Na_2CO_3$ and extracted with DCM. The combined organic layers were dried over $MgSO_4$, filtered, and concentrated under reduced pressure. The resulting crude material was purified by chromatography on silica gel using DCM/MeOH (gradient, 100:0 to 90:10), stirred overnight with $Et_2O$/DCM (100:10), and collected by vacuum filtration to give the title compound (0.16 g, 26%): LC/MS (Table 1, Method a) $R_t$=2.98 min; MS m/z: 396.2 $(M+H)^+$; $^1H$ NMR ($CDCl_3$) δ 7.76 (d, J=9.89 Hz, 1H), 7.56-7.51 (m, 1H), 7.11-6.99 (m, 1H), 6.98-6.87 (m, 1H), 6.73 (dd, J=9.89, 1.83 Hz, 1H), 6.44 (s, 1H, broad), 4.2 (t, J=6.08 Hz, 2H), 3.61-3.58 (m, 2H), 3.56-3.52 (m, 1H), 2.36-2.24 (m, 2H), 1.58 (d, J=6.99 Hz, 6H).

Example #12

6-(2,4-Difluorophenyl)-5-(3-isopropyl-[1,2,4]triazolo[4,3-b]pyridazin-6-yl)imidazo[2,1-b]thiazole

Step A: 6-(2,4-Difluorophenyl)imidazo[2,1-b]thiazole

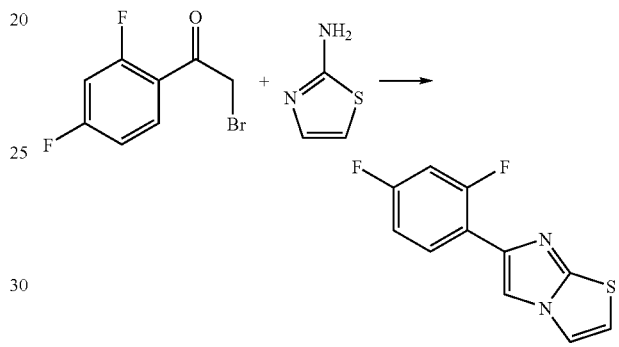

The 2-bromo-1-(2,4-difluorophenyl)ethanone (7.50 g, 31.9 mmol) and thiazol-2-amine (3.20 g, 31.9 mmol) were added to EtOH (85 mL) and then heated to about 85° C. in an oil bath for about 16 h. The mixture was cooled in ice water, filtered, and washed with EtOH. Drying under vacuum at about 60° C. provided the title compound (5.84 g, 77%): LC/MS (Table 1, Method a) $R_t$=2.68 min; MS m/z: 237.3 $(M+H)^+$.

Step B: 6-(2,4-Difluorophenyl)-5-iodoimidazo[2,1-b]thiazole

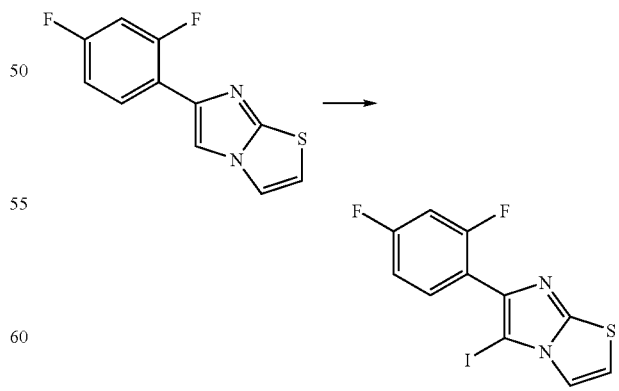

NIS (5.56 g, 24.7 mmol) was added to 6-(2,4-difluorophenyl)imidazo[2,1-b]thiazole (5.84 g, 24.72 mmol) in DMF (60 mL) then stirred at ambient temperature for about 30 min. The mixture was diluted with water (about 500 mL), filtered, and washed with ether to give the title compound (5.17 g, 58%): LC/MS (Table 1, Method a) $R_t$=2.13 min; MS m/z: 363.0 (M+H)$^+$.

Step C: 6-(2,4-Difluorophenyl)-5-(3-isopropyl-[1,2,4]triazolo[4,3-b]pyridazin-6-yl)imidazo[2,1-b]thiazole

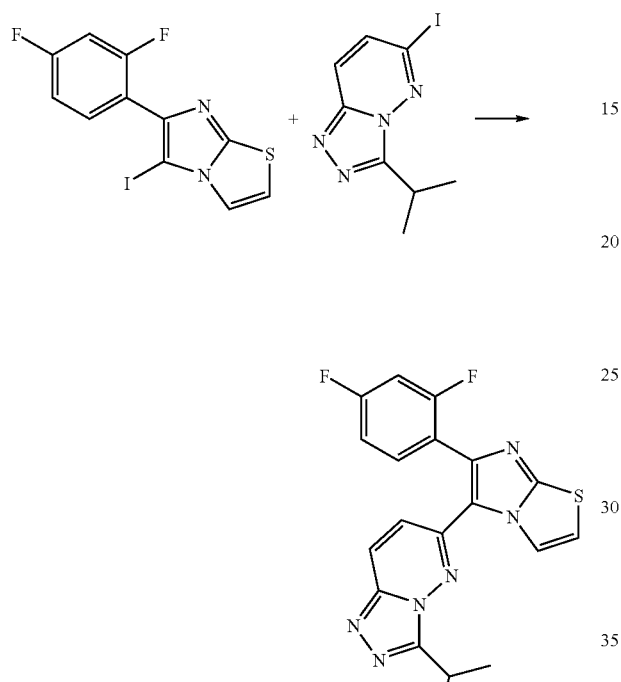

The 6-(2,4-difluorophenyl)-5-iodoimidazo[2,1-b]thiazole (1.00 g, 2.76 mmol) was suspended in THF (7.5 mL) then cooled to about −30° C. The i-PrMgCl (2 M in THF, 1.52 mL, 3.04 mmol) was added dropwise over about 15 min then stirred at about −30° C. for about 15 min. The ZnCl$_2$ (0.489 g, 3.59 mmol) was dissolved in THF (7.5 mL), cooled to about 0° C., and added dropwise to the Grignard solution. The reaction mixture was stirred for about 30 min at about −30° C. The 6-iodo-3-isopropyl-[1,2,4]triazolo[4,3-b]pyridazine (0.796 g, 2.76 mmol) was added to DMF (7.50 mL) and heated to about 80° C. to dissolve the material. Pd(Ph$_3$P)$_4$ (0.128 g, 0.110 mmol) was then added to the solution and the mixture was immediately added to the zincate suspension. The mixture was immediately heated to about 55° C. for about 45 min, then cooled, diluted with water and extracted with EtOAc. The organic solution was dried over MgSO$_4$, filtered, and concentrated under reduced pressure. Purification by flash chromatography on silica gel with DCM/MeOH (95:5) followed by trituration with MeOH (5 mL) gave a solid that was collected by filtration. The filtrate was concentrated under reduced pressure then purified by RP-HPLC using (Table 1, Method d). The desired fractions were concentrated under reduced pressure to give a solid that was collected by filtration. The two crops were combined to give the title compound (0.250 g, 23%): LC/MS (Table 1, Method a) $R_t$=2.46 min; MS m/z: 397.2 (M+H)$^+$.

Example #13

6-(2-(2,4-Difluorophenyl)-5,6-dihydro-4H-pyrrolo[1,2-b]pyrazol-3-yl)-3-isopropyl-[1,2,4]triazolo[4,3-b]pyridazine

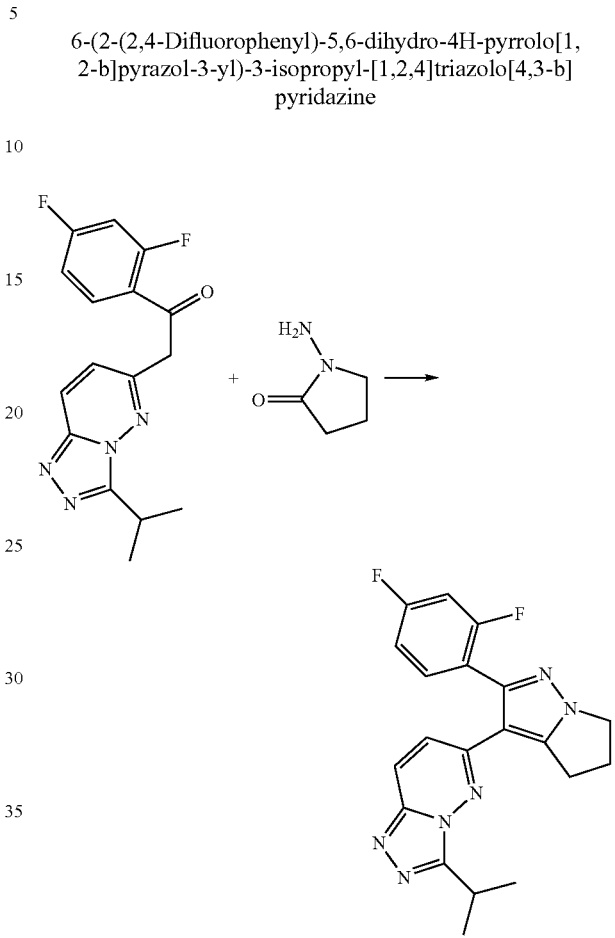

A mixture of 1-(2,4-difluorophenyl)-2-(3-isopropyl-[1,2,4]triazolo[4,3-b]pyridazin-6-yl)ethanone (0.20 g, 0.63 mmol, Preparation #K.1), 1-aminopyrrolidin-2-one hydrochloride (0.13 g, 0.95 mmol, prepared according to WO02/094833 Preparation #38), pyridine (0.15 mL, 1.9 mmol), and HOAc (1.2 mL) was sonicated to give a solution in a sealed vial. After stirring for about 16 h, additional 1-aminopyrrolidin-2-one hydrochloride (0.086 g, 0.632 mmol) was added and the resulting solution was stirred at ambient temperature for about 2 d. The reaction was then concentrated under reduced pressure and purified via silica gel chromatography eluting with a gradient of 0-5% MeOH in DCM to give impure 1-(1-(2,4-difluorophenyl)-2-(3-isopropyl-[1,2,4]triazolo[4,3-b]pyridazin-6-yl)ethylideneamino)pyrrolidin-2-one (0.16 g) as an oil that was carried on without further purification. A 10 mL round-bottomed flask equipped with reflux condenser and outfitted with a nitrogen inlet adapter was charged with 1-(1-(2,4-difluorophenyl)-2-(3-isopropyl-[1,2,4]triazolo[4,3-b]pyridazin-6-yl)ethylideneamino)pyrrolidin-2-one (0.060 g, 0.15 mmol) in toluene (1.5 L) to give a yellow solution. Sodium ethoxide (0.020 g, 0.30 mmol) was added in one portion to give a yellow suspension. The reaction mixture was heated to reflux for about 5 h. The reaction mixture was allowed to cool to ambient temperature and continued stirring for about 2 d. The reaction mixture was diluted with water (5 mL) adjusted to about pH 2 with 6 N HCl. The aqueous layer was extracted with EtOAc. The combined organic extracts were dried with MgSO$_4$, filtered, and concentrated under reduced pressure. The resulting residue was purified via silica gel chromatography eluting with a gradient of 0-10% MeOH in DCM. The product-containing fractions were concentrated under reduced pressure and the resulting material was crystallized from EtOAc/heptane to give the title compound (0.031 g, 54%) as orange needles: LC/MS (Table 1, Method b) R$_f$=2.44 min; MS m/z: 381.4 (M+H)$^+$.

Example #14

3-(2,4-Difluorophenyl)-4-(3-isopropyl-[1,2,4]triazolo[4,3-b]pyridazin-6-yl)-1,2,5-oxadiazole A 50 mL round bottomed flask was charged with 1-(2,4-difluorophenyl)-2-(3-isopropyl-[1,2,4]triazolo[4,3-b]pyridazin-6-yl)ethane-1,2-dione (0.300 g, 0.908 mmol, Preparation #M.1), hydroxylamine hydrochloride (0.631 g, 9.08 mmol) and EtOH (5 mL). The resulting mixture was treated with pyridine (3.67 mL, 45.4 mmol) and was then heated to about 90° C. for about 7 h. The mixture was cooled to ambient temperature, diluted with EtOAc (10 mL), washed with 1N HCl (10 mL) and water (10 mL). The organics were separated, dried over MgSO$_4$, filtered and concentrated in vacuo to afford a yellow residue. To the residue was added triphenylphosphine (0.328 g, 1.25 mmol) and toluene (5 mL). The mixture was cooled to about 0° C. and DIAD (0.243 mL, 1.25 mmol) was added to give a solution which was heated to about reflux for about 1 h. The solution was cooled to ambient temperature, diluted with EtOAc (10 mL) and washed with saturated aqueous NaHCO$_3$ (10 mL). The organics were separated, dried over MgSO$_4$, filtered and concentrated to dryness. The residue was purified by flash chromatography on silica gel with MeOH/DCM (0-5% gradient) followed by RP-HPLC (Table 1, Method n) to afford the title compound (0.056 g, 20%) as a yellow solid. LC/MS (Table 1, Method g) R$_f$=2.83 min; MS m/z 343 (M+H)$^+$.

Example #15

6-(2-(2,4-Difluorophenyl)-8-methylimidazo[1,2-a]pyrazin-3-yl)-3-isopropyl-[1,2,4]triazolo[4,3-b]pyridazine

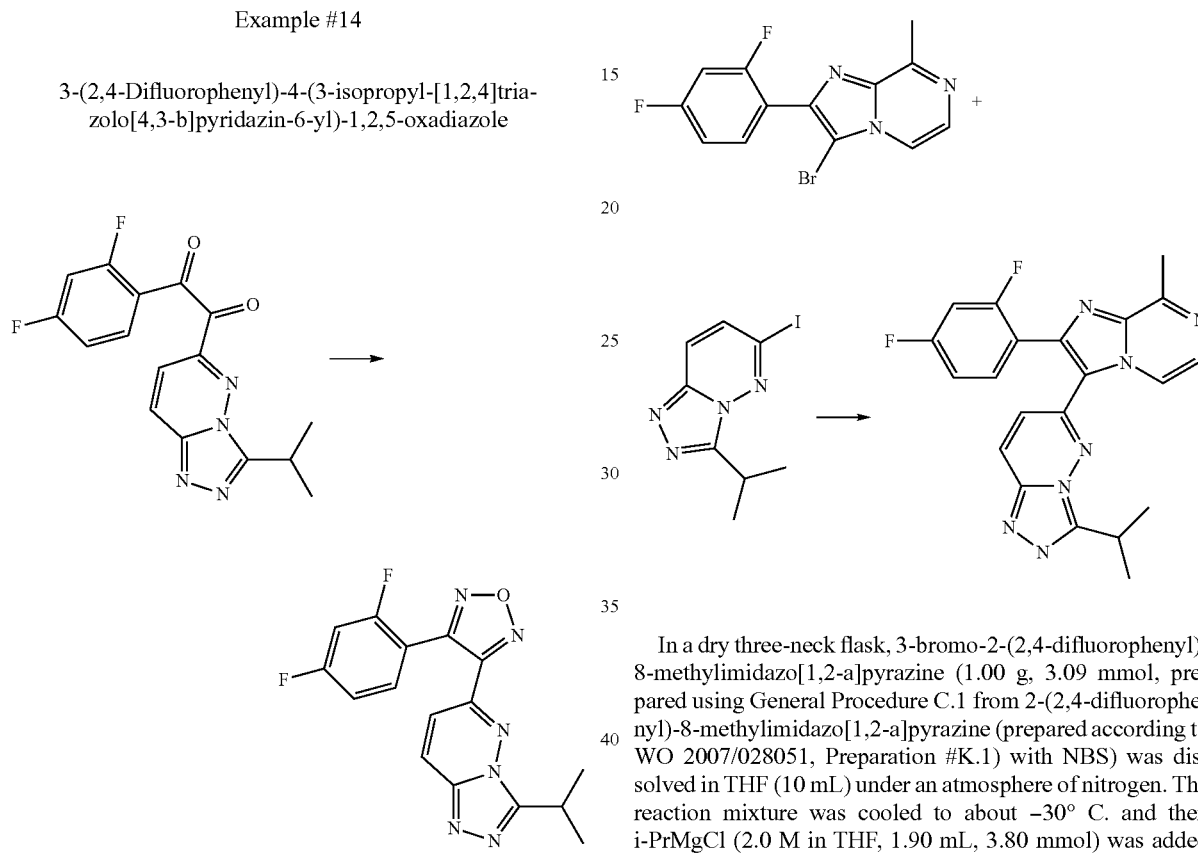

In a dry three-neck flask, 3-bromo-2-(2,4-difluorophenyl)-8-methylimidazo[1,2-a]pyrazine (1.00 g, 3.09 mmol, prepared using General Procedure C.1 from 2-(2,4-difluorophenyl)-8-methylimidazo[1,2-a]pyrazine (prepared according to WO 2007/028051, Preparation #K.1) with NBS) was dissolved in THF (10 mL) under an atmosphere of nitrogen. The reaction mixture was cooled to about −30° C. and then i-PrMgCl (2.0 M in THF, 1.90 mL, 3.80 mmol) was added drop-wise. The reaction mixture was stirred at about −30° C. for about 15 min. In a separate dry flask, zinc chloride (0.57 g, 4.2 mmol) was dissolved in THF (5 mL) and cooled to about 0° C. The zinc chloride solution was added dropwise to the heteroaryl Grignard mixture. The reaction mixture was stirred at about −15° C. for about 30 min. A flask containing 6-iodo-3-isopropyl-[1,2,4]triazolo[4,3-b]pyridazine (0.85 g, 2.9 mmol; Preparation #H.1) and Pd(Ph$_3$P)$_4$ (0.14 g, 0.12 mmol, Strem) in DMF (10 mL) was stirred at about 80° C. until all of the solids were in solution. This solution was poured into the zincate suspension and the mixture was immediately heated to about 50° C. in an oil bath. After heating at about 50° C. for about 18 h, the mixture was cooled to ambient temperature. The reaction mixture was concentrated under reduced pressure. The residue was dissolved in DCM (50 mL), washed with water (5×100 mL), washed with brine (100 mL), dried over MgSO$_4$, filtered, and concentrated in vacuo. The crude material was purified by silica gel flash chromatography using DCM/MeOH (gradient, 100:0 to 95:5) as eluent. The solid was then dissolved with heating in MeOH, sonicated, concentrated under reduced pressure to dryness under reduced pressure, then dried in a heated vacuum oven (about 60° C.) to afford a cream solid as the title compound (0.37 g, 29%): LC/MS (Table 1, Method a) $R_f$=2.85 min; MS m/z: 406.3 (M+H)$^+$.

Example #16

4-(2,4-Difluorophenyl)-5-(3-isopropyl-[1,2,4]triazolo[4,3-b]pyridazin-6-yl)-1,2,3-thiadiazole

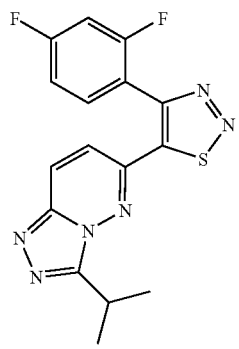

Step A: (E/Z)-Ethyl 2-(1-(2,4-difluorophenyl)-2-(3-isopropyl-[1,2,4]triazolo[4,3-b]pyridazin-6-yl)ethylidene)hydrazinecarboxylate

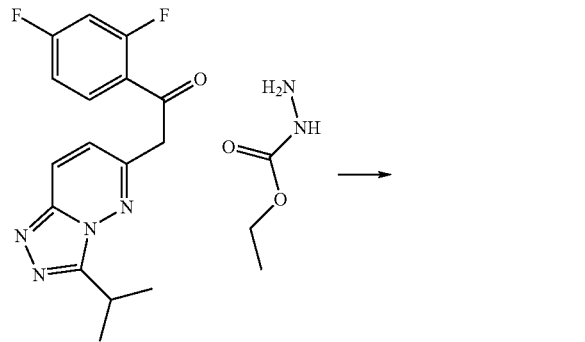

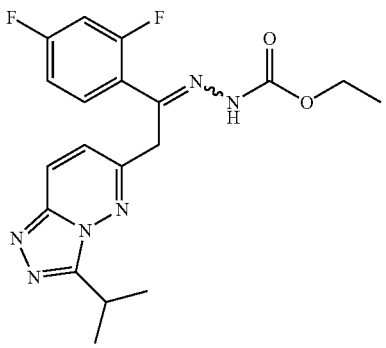

To a solution of 1-(2,4-difluorophenyl)-2-(3-isopropyl-[1,2,4]triazolo[4,3-b]pyridazin-6-yl)ethanone (0.60 g, 1.9 mmol, Preparation #K.1) in EtOH (30 mL) was added ethyl hydrazinecarboxylate (0.20 g, 1.9 mmol). The reaction mixture was stirred at about 45° C. for about 72 h. The solvent was removed under reduced pressure and the residue was dried overnight on a high vacuum pump to give the title compound (0.75 g, 93%): LC/MS (Table 1, Method a) $R_f$=2.25 min; MS m/z: 403.2 (M+H)$^+$.

Step B: 4-(2,4-Difluorophenyl)-5-(3-isopropyl-[1,2,4]triazolo[4,3-b]pyridazin-6-yl)-1,2,3-thiadiazole

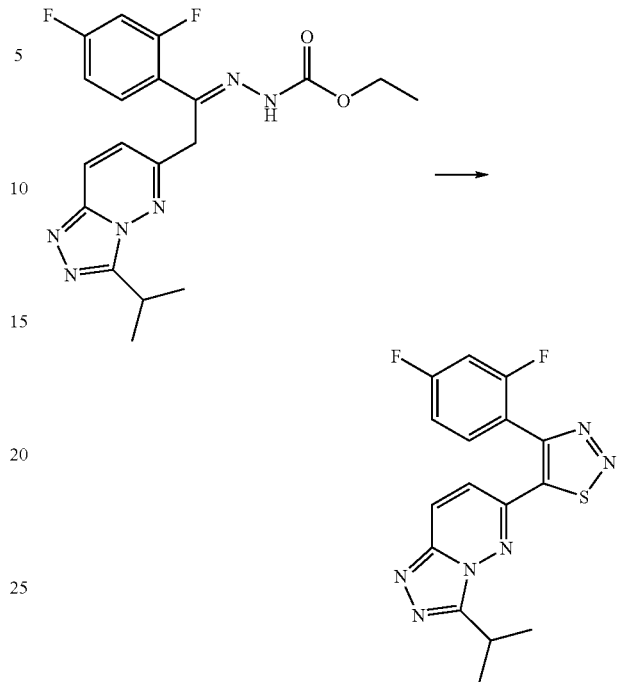

A 100 mL round-bottomed flask charged with (E/Z)-ethyl 2-(1-(2,4-difluorophenyl)-2-(3-isopropyl-[1,2,4]triazolo[4,3-b]pyridazin-6-yl)ethylidene)hydrazinecarboxylate (0.75 g, 1.9 mmol) was cooled to about 0° C. Thionyl chloride (10.0 mL, 137 mmol) was added and the mixture stirred at about 0° C. for about 15 min after which the reaction mixture was heated to about 50° C. for about 1.5 h. The solvent was removed under reduced pressure. The resulting residue was dissolved in EtOAc (50 mL) and washed with 1M aqueous Na$_2$CO$_3$ solution (200 mL) then water (100 mL). The organic layer was separated and dried over MgSO$_4$, filtered, and solvent removed under reduced pressure to give a brown solid. The crude material was purified by silica gel flash chromatography using DCM/MeOH (gradient, 100:0 to 95:5) to give the title compound (0.50 g, 75%) as a brown solid: LC/MS (Table 1, Method a) $R_f$=2.69 min; MS m/z: 359.2 (M+H)$^+$.

Example #17

4-(2,4-Difluorophenyl)-5-(3-isopropyl-[1,2,4]triazolo[4,3-b]pyridazin-6-yl)thiazole

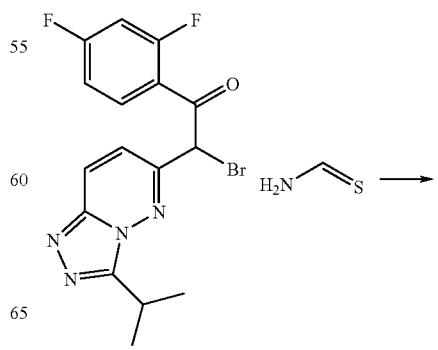

-continued

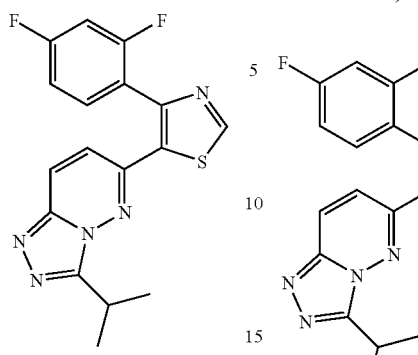

To a solution of 2-bromo-1-(2,4-difluorophenyl)-2-(3-isopropyl-[1,2,4]triazolo[4,3-b]pyridazin-6-yl)ethanone (0.60 g, 1.5 mmol, Preparation #A.2) in THF (25 mL) was added methanethioamide (0.19 g, 3.0 mmol, prepared according to *Euro. J. Med. Chem.,* 2004, 39, 867-872). The reaction mixture was stirred at ambient temperature for about 15 h. The solvent was removed under reduced pressure. The crude material was purified by silica gel flash chromatography using DCM/MeOH (gradient, 100:0 to 95:10). This residue was then repurified by silica gel flash chromatography using DCM/ACN (gradient, 90:10 to 0:100). The residue was dissolved in Et$_2$O and solvent removed under reduced pressure to give a yellow solid. The solid was dried overnight under high vacuum to afford the title compound (0.095 g, 17%) as a yellow solid: LC/MS (Table 1, Method a) R$_t$=2.39 min; MS m/z: 358.2 (M+H.

Example #18

4-(2,4-Difluorophenyl)-5-(3-isopropyl-[1,2,4]triazolo[4,3-b]pyridazin-6-yl)-1H-imidazol-2(3H)-one

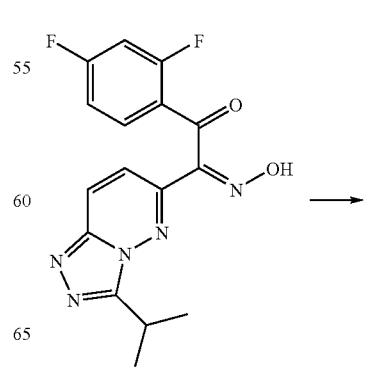

Step A: (E/Z)-1-(2,4-Difluorophenyl)-2-(hydroxyimino)-2-(3-isopropyl-[1,2,4]triazolo[4,3-b]pyridazin-6-yl)ethanone

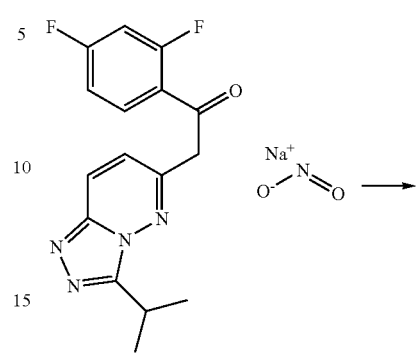

To a solution of 1-(2,4-difluorophenyl)-2-(3-isopropyl-[1,2,4]triazolo[4,3-b]pyridazin-6-yl)ethanone (2.50 g, 7.90 mmol, Preparation #K.1) in HOAc (50 mL) at about 10° C. was added a solution of sodium nitrite (1.39 g, 8.06 mmol) in water (50 mL). The reaction mixture was stirred for about 30 min at about 10° C. The reaction mixture was diluted with water (30 mL and stirred at ambient temperature for about 3 h. The solid was filtered and washed with water (100 mL). The solid was dried under vacuum for about 15 h to give the title compound (2.4 g, 80%): LC/MS (Table 1, Method a) R$_t$=2.81 min; MS m/z: 346.0 (M+H)$^+$.

Step B: 2-Amino-1-(2,4-difluorophenyl)-2-(3-isopropyl-[1,2,4]triazolo[4,3-b]pyridazin-6-yl)ethanone hydrochloride

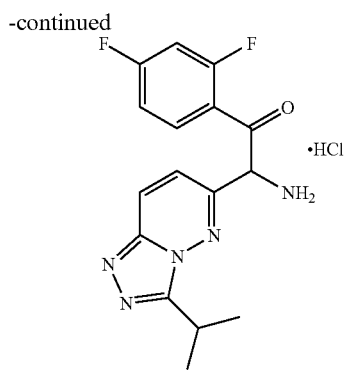

To a solution of (E/Z)-1-(2,4-difluorophenyl)-2-(hydroxy-imino)-2-(3-isopropyl-[1,2,4]triazolo[4,3-b]pyridazin-6-yl)ethanone (1.00 g, 2.90 mmol) in MeOH (50 mL) were added a solution of HCl (1.25 M in MeOH, 11.6 mL, 14.5 mmol) and 10% Pd/C (3.10 g, 2.90 mmol). The reaction mixture was stirred under a hydrogen atmosphere for about 3 h. The reaction mixture was filtered through Celite® and washed with MeOH (100 mL). Solvent was removed under reduced pressure to give the title compound (1.18 g, 100%) which was directly used in next reaction: LC/MS (Table 1, Method a) $R_t$=1.21 min; MS 1/z: 332.2 (M+H)$^+$.

Step C: 4-(2,4-Difluorophenyl)-5-(3-isopropyl-[1,2,4]triazolo[4,3-b]pyridazin-6-yl)-1H-imidazol-2(3H)-one

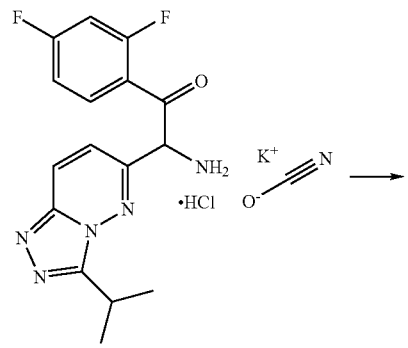

To a solution of 2-amino-1-(2,4-difluorophenyl)-2-(3-isopropyl-[1,2,4]triazolo[4,3-b]pyridazin-6-yl)ethanone hydrochloride (1.18 g, 3.21 mmol) in DMF (10 mL) was added potassium cyanate (0.65 g, 8.0 mmol). The reaction mixture was stirred at about 110° C. for about 2 h. The temperature was reduced to about 80° C. and stirring continued for about 15 h. The solvent was removed under reduced pressure. The crude material was purified by RP-HPLC (Table 1, Method f). The appropriate fractions were combined and solvent removed under reduced pressure. The sample was dissolved in DCM (20 mL) and washed with saturated NaHCO$_3$ solution (3×10 mL). The organic layer was dried over MgSO$_4$, filtered, and solvent removed under reduced pressure to afford a solid that was dried under vacuum to give the title compound (0.09 g, 8%): LC/MS (Table 1, Method a) $R_t$=2.25 min; MS m/z: 357.1 (M+H)$^+$.

Example #19

1-(2-(5-(2,4-Difluorophenyl)-4-(3-isopropyl-[1,2,4]triazolo[4,3-b]pyridazin-6-yl)-1H-pyrazol-1-yl)ethyl)-3-(2-phenylcyclopropyl)urea

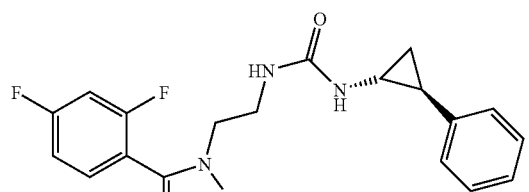

Step A: 2-(5-(2,4-Difluorophenyl)-4-(3-isopropyl-[1,2,4]triazolo[4,3-b]pyridazin-6-yl)-1H-pyrazol-1-yl)ethanamine

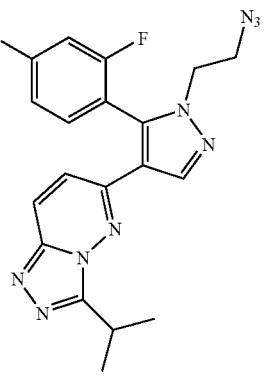

-continued

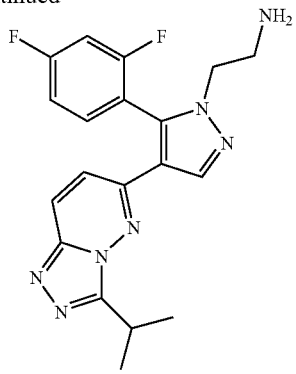

The 6-(1-(2-azidoethyl)-5-(2,4-difluorophenyl)-1H-pyrazol-4-yl)-3-isopropyl-[1,2,4]triazolo[4,3-b]pyridazine (0.485 g, 1.19 mmol; prepared using General Procedure L.1 from 1-(2,4-difluorophenyl)-2-(3-isopropyl-[1,2,4]triazolo[4,3-b]pyridazin-6-yl)ethanone (Preparation #K.1) with hydroxyethylhydrazine, General Procedure W with methanesulfonyl chloride, General Procedure X.1 with sodium azide) was dissolved in EtOH (20 mL) then platinum (IV) oxide (0.090 g, 0.40 mmol) was added. The mixture was hydrogenated at atmospheric pressure and ambient temperature for about 16 h then filtered through a pad of Celite®. The filtrate was concentrated under reduced pressure to give the title compound (0.447 g, 98%): LC/MS (Table 1, Method a) $R_t$=1.66 min; MS m/z: 384.3 (M+H)$^+$.

Step B: 1-(2-(5-(2,4-Difluorophenyl)-4-(3-isopropyl-[1,2,4]triazolo[4,3-b]pyridazin-6-yl)-1H-pyrazol-1-yl)ethyl)-3-(2-phenylcyclopropyl)urea

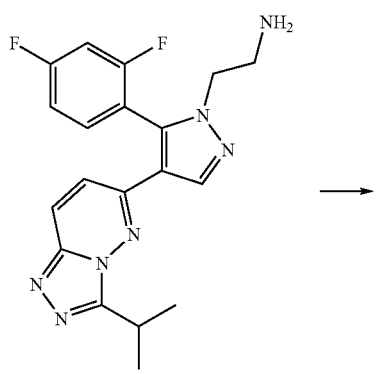

-continued

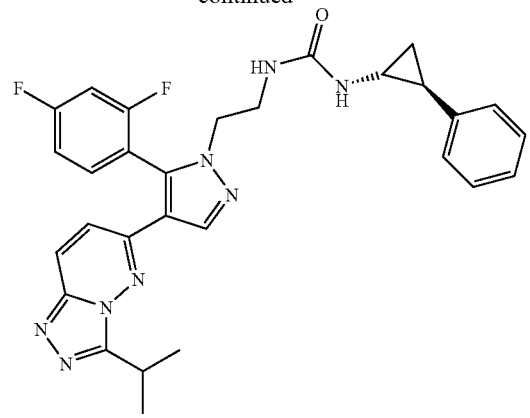

The 2-(5-(2,4-difluorophenyl)-4-(3-isopropyl-[1,2,4]triazolo[4,3-b]pyridazin-6-yl)-1H-pyrazol-1-yl)ethanamine (0.075 g, 0.20 mmol) was dissolved in DCM (4 mL) then trans-2-phenylcyclopropyl isocyanate (0.033 g, 0.21 mmol) was added. The mixture was stirred for about 10 min then concentrated under reduced pressure. The residue was purified by flash chromatography on silica gel with DCM/MeOH (9:1) as an eluent to give the title compound (0.065 g, 61%): LC/MS (Table 1, Method a) $R_t$=2.34 min; MS m/z: 543.3 (M+H)$^+$.

Example #20

6-(1-tert-Butyl-3-(2,4-difluorophenyl)-1H-pyrazol-4-yl)-3-isopropyl-[1,2,4]triazolo[4,3-b]pyridazine

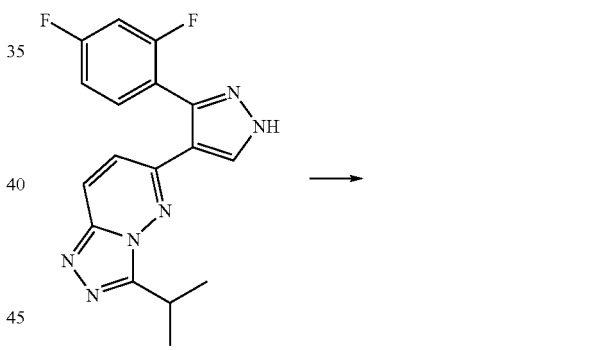

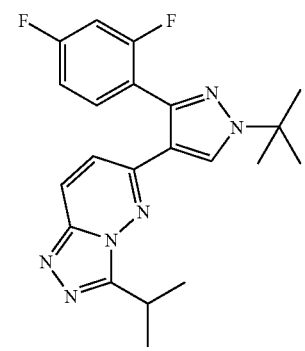

The 6-(3-(2,4-Difluorophenyl)-1H-pyrazol-4-yl)-3-isopropyl-[1,2,4]triazolo[4,3-b]pyridazine (0.300 g, 0.881 mmol, Example #L.1.1) was suspended in t-BuOH (3.0 mL) then sulfuric acid (0.15 g, 1.5 mmol) was added. The mixture was heated using a CEM® microwave at about 130° C. for about 10 min (250 psi maximum pressure, 10 min ramp, 300 max watts). The reaction mixture was concentrated under

Example #21

5-(2,4-Difluorophenyl)-4-(3-isopropyl-[1,2,4]triazolo[4,3-b]pyridazin-6-yl)-1H-pyrazol-3-amine

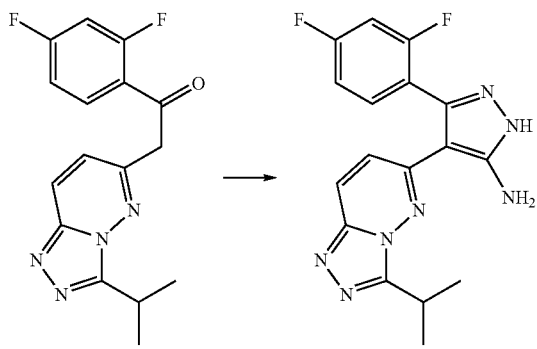

DMF (1.00 mL, 12.6 mmol) was cooled to about 5° C. then phosphorus oxychloride (0.44 mL, 4.7 mmol) was added dropwise. After about 15 min 1-(2,4-difluorophenyl)-2-(3-isopropyl-[1,2,4]triazolo[4,3-b]pyridazin-6-yl)ethanone (0.500 mg, 1.58 mmol, Preparation #K.1) in chloroform (10 mL) was added dropwise. The solution was heated to about 80° C. for about 15 min and then the mixture was cooled to about 5° C. then hydroxylamine hydrochloride (0.330 g, 4.7 mmol) and DMF (0.979 mL, 12.7 mmol) were added. The mixture was stirred at ambient temperature for about 3 h then DCM and saturated aqueous NaHCO₃ were added. The organic layer was dried over MgSO₄ then filtered and concentrated under reduced pressure. The resulting oil was dissolved in EtOH (4 mL) then hydrazine (0.15 mL, 4.7 mmol) was added. The mixture was refluxed for about 1 h then cooled, diluted with DCM and filtered to give the title compound (0.513 g, 91%): LC/MS (Table 1, Method a) R$_t$=2.38 min; MS m/z: 356.3 (M+H)⁺.

Example #22

6-(2-(2,4-Difluorophenyl)pyrazolo[1,5-a]pyrimidin-3-yl)-3-isopropyl-[1,2,4]triazolo[4,3-b]pyridazine

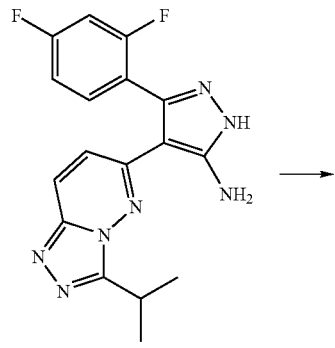

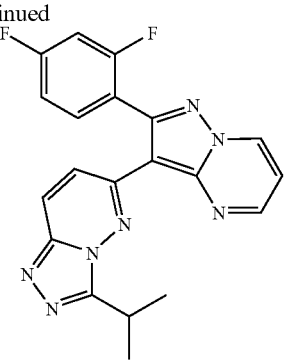

The 5-(2,4-difluorophenyl)-4-(3-isopropyl-[1,2,4]triazolo[4,3-b]pyridazin-6-yl)-1H-pyrazol-3-amine (0.200 g, 0.563 mmol, Example #23) and zinc chloride (0.038 g, 0.281 mmol) were added to EtOH (1 mL). Concentrated HCl (1.0 mL, 33 mmol) was added followed by malonaldehyde bis(dimethyl acetal) (0.111 g, 0.675 mmol). The mixture was heated to about 80° C. for about 15 min then the mixture was poured onto ice and basified with 50% aqueous NaOH. The mixture was extracted with EtOAc then the organic solution was dried over MgSO₄, filtered and concentrated under reduced pressure. The material was purified by flash chromatography on silica gel with DCM/MeOH (9:1) as an eluent to give the title compound (0.133 g, 60%): LC/MS (Table 1, Method a) R$_t$=3.05 min; MS m/z: 392.3 (M+H)⁺.

Example #23

6-(6-(2,4-Difluorophenyl)-2,3-dihydro-1H-imidazo[1,2-b]pyrazol-7-yl)-3-isopropyl-[1,2,4]triazolo[4,3-b]pyridazine

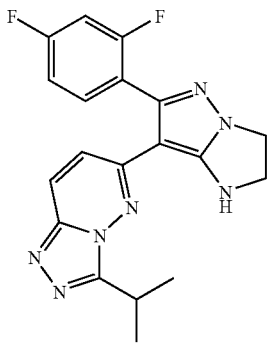

Step A: 2-(5-Amino-3-(2,4-difluorophenyl)-4-(3-isopropyl-[1,2,4]triazolo[4,3-b]pyridazin-6-yl)-1H-pyrazol-1-yl)ethanol

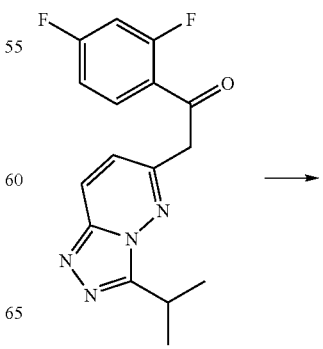

-continued

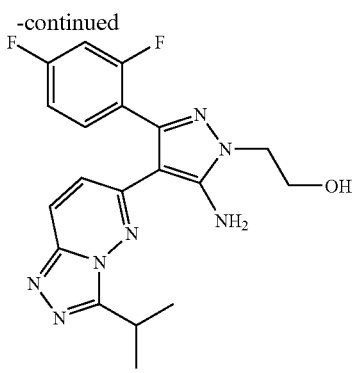

DMF (1.00 mL, 12.6 mmol) was cooled to about 5° C. then phosphorus oxychloride (0.44 mL, 4.7 mmol) was added dropwise. After about 15 min the 1-(2,4-difluorophenyl)-2-(3-isopropyl-[1,2,4]triazolo[4,3-b]pyridazin-6-yl)ethanone (0.500 g, 1.58 mmol, Preparation #K.1) in chloroform (10 mL) was added dropwise. The solution was heated to about 80° C. for about 15 min and then the mixture was cooled to about 5° C. then hydroxylamine hydrochloride (0.330 g, 4.74 mmol) and DMF (0.979 mL, 12.7 mmol) were added. The mixture was stirred at ambient temperature for about 3 h then DCM and saturated aqueous NaHCO₃ were added. The organic layer was dried over MgSO₄, filtered and concentrated under reduced pressure. The oil was dissolved in EtOH (4 mL) then 2-hydrazinylethanol (0.36 g, 4.7 mmol) was added. The mixture was refluxed for about 1 h then cooled, diluted with DCM and filtered to give the title compound (0.250 g, 40%): LC/MS (Table 1, Method a) $R_t$=2.09 min; MS m/z: 400.3 (M+H)⁺.

Step B: 6-(6-(2,4-Difluorophenyl)-2,3-dihydro-1H-imidazol-[1,2-b]pyrazol-7-yl)-3-isopropyl-[1,2,4]triazolo[4,3-b]pyridazine

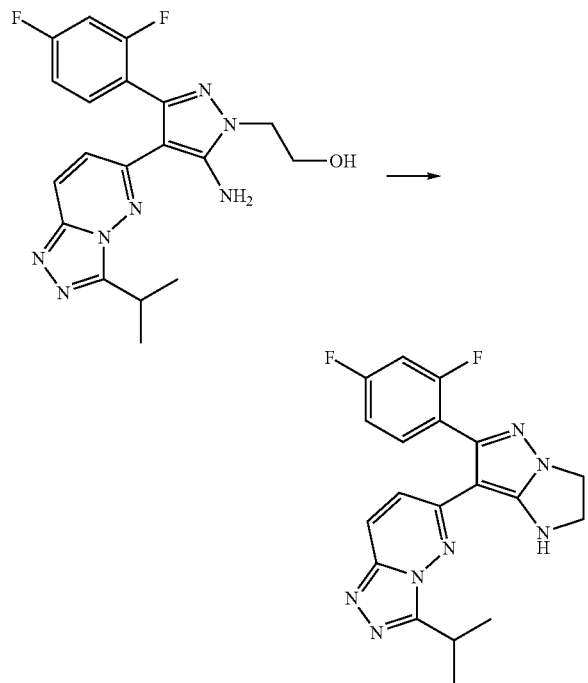

The 2-(5-amino-3-(2,4-difluorophenyl)-4-(3-isopropyl-[1,2,4]triazolo[4,3-b]pyridazin-6-yl)-1H-pyrazol-1-yl)etha-nol (0.205 g, 0.513 mmol) in DCM (4 mL) was treated with TEA (0.107 mL, 0.770 mmol) then methanesulfonyl chloride (0.042 mL, 0.54 mmol) was added. After about 30 min, TEA (0.107 mL, 0.770 mmol) and methanesulfonyl chloride (0.042 mL, 0.54 mmol) were added then the mixture was stirred for about 30 min. Additional TEA (0.107 mL, 0.770 mmol) and methanesulfonyl chloride (0.042 mL, 0.539 mmol) were added then the mixture was stirred for about 30 min. Water was added to the mixture, the layers were separated and the organic solution was dried over MgSO₄ then filtered and concentrated under reduced pressure. The material was dissolved in DMF (5 mL) then potassium carbonate (0.213 g, 1.54 mmol) was added and the mixture was heated to about 75° C. for about 16 h. The solvent was removed under reduced pressure then the residue was partitioned between EtOAc and water. The organic layer was dried over MgSO₄, filtered and concentrated under reduced pressure. The residue was purified by flash chromatography on silica gel using DCM/MeOH (95:5) as an eluent then trituration with Et₂O/EtOAc followed by RP-HPLC (Table 1, Method f) to give the title compound (0.016 g, 8%): LC/MS (Table 1, Method a) $R_t$=2.10 min; MS nm/z: 382.3 (M+H)⁺.

Example #24 trans-4-(4-(2,4-Difluorophenyl)-5-(3-isopropyl-[1,2,4]triazolo[4,3-b]pyridazin-6-yl)thiazol-2-yl)cyclohexanol

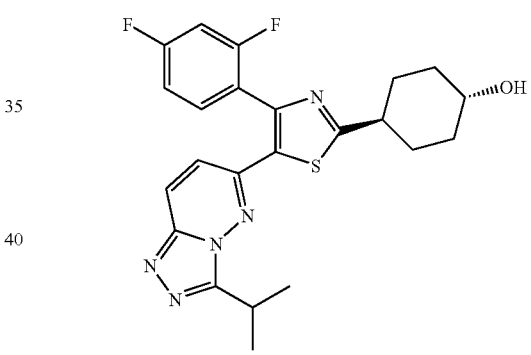

Step A: 1,4-Dioxaspiro[4.5]decane-8-carbothioamide

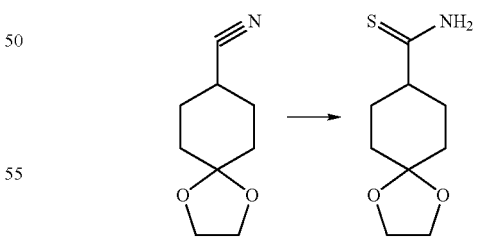

The 1,4-dioxaspiro[4.5]decane-8-carbonitrile (1.16 g, 6.94 mmol, *Tetrahedron,* 2002, 58(8), 1557), ammonium sulfide (20 wt. % in water, 2.84 mL, 8.33 mmol) and MeOH (14 mL) were heated in a CEM® microwave at about 130° C. for about (250 psi maximum pressure, 10 min ramp, 300 max watts). The mixture was concentrated under a stream of air and the resulting material was purified by flash chromatography on silica gel using EtOAc/heptane (7:3) as an eluent to give the title compound (0.317 g, 23%) as a light yellow solid: LC/MS (Table 1, Method a) R_t=1.68 min; MS m/z: 202.1 (M+H)+.

Step B: 4-(4-(2,4-Difluorophenyl)-5-(3-isopropyl-[1,2,4]triazolo[4,3-b]pyridazin-6-yl)thiazol-2-yl)cyclohexanone

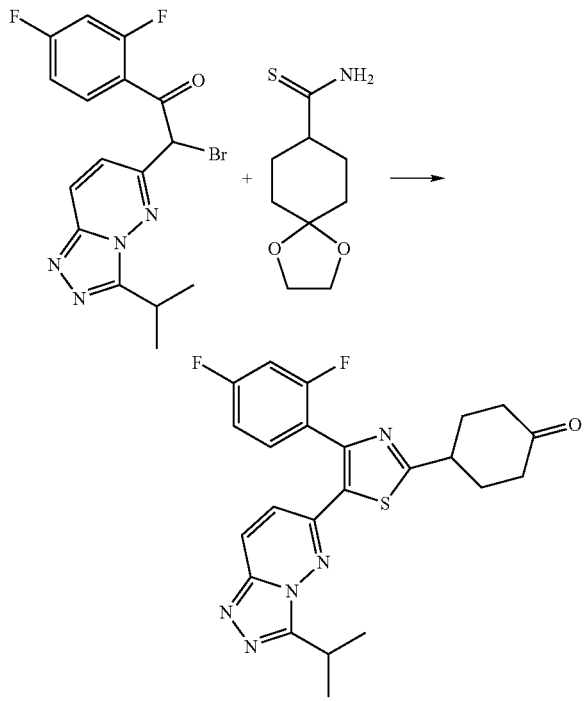

The 2-bromo-1-(2,4-difluorophenyl)-2-(3-isopropyl-[1,2,4]triazolo[4,3-b]pyridazin-6-yl)ethanone (0.622 g, 1.57 mmol, Preparation #A.2) and 1,4-dioxaspiro[4.5]decane-8-carbothioamide (0.317 g, 1.57 mmol) were dissolved in DMF (5 mL) then stirred at ambient temperature for about 12 h. The mixture was concentrated under reduced pressure then acetone (25 mL) and concentrated hydrochloric acid (2 µL, 10 mmol) were added. The mixture was heated to about 60° C. for about 1.5 h then concentrated under reduced pressure, basified with 50% NaOH and diluted with water. The mixture was extracted with ethyl acetate then organic solution was dried over MgSO_4, filtered and concentrated under reduced pressure. The material was purified by flash chromatography on silica gel using DCM/MeOH (95:5) as an eluent to give the title compound (0.495 g, 69%): LC/MS (Table 1, Method b) R_t=2.14 min; MS m/z: 454.2 (M+H)+.

Step C: trans-4-(4-(2,4-Difluorophenyl)-5-(3-isopropyl-[1,2,4]triazolo[4,3-b]pyridazin-6-yl)thiazol-2-yl)cyclohexanol

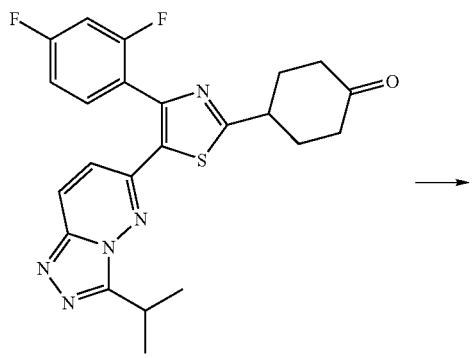

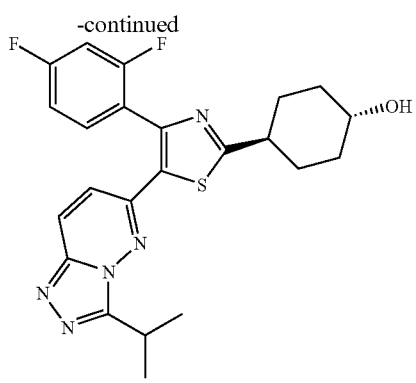

The 4-(4-(2,4-difluorophenyl)-5-(3-isopropyl-[1,2,4]triazolo[4,3-b]pyridazin-6-yl)thiazol-2-yl)cyclohexanone (0.495 g, 1.09 mmol) was dissolved in MeOH (5 mL) then cooled to about −5° C. Sodium borohydride (0.041 g, 1.09 mmol) was added and the mixture was stirred for about 5 min. Acetone was added, the solvents were concentrated under reduced pressure and the residue was purified by flash chromatography on silica gel with DCM/MeOH (95:5) as an eluent then by RP-HPLC (Table 1, Method f) to give the title compound (0.209 g, 42%): LC/MS (Table 1, Method a) R_t=2.29 min; MS m/z: 456.2 (M+H)+.

Example #25 cis-4-(4-(2,4-Difluorophenyl)-5-(3-isopropyl-[1,2,4]triazolo[4,3-b]pyridazin-6-yl)thiazol-2-yl)cyclohexanol

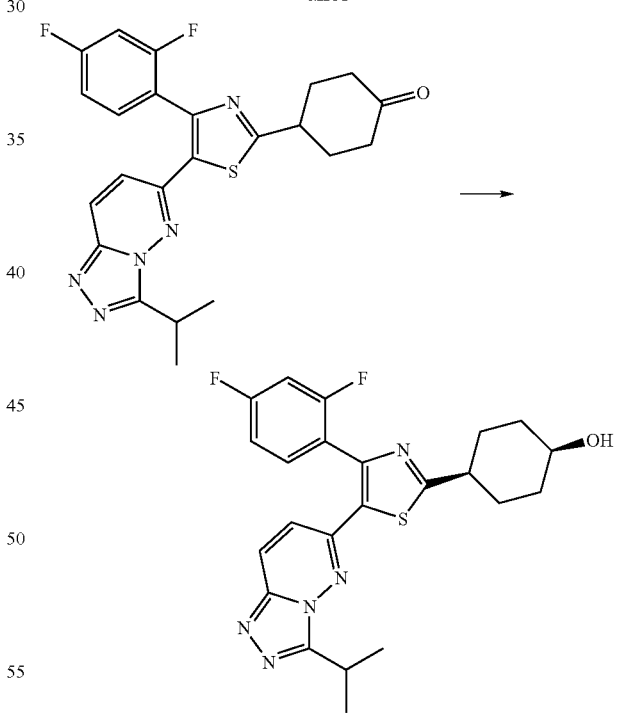

The 4-(4-(2,4-difluorophenyl)-5-(3-isopropyl-[1,2,4]triazolo[4,3-b]pyridazin-6-yl)thiazol-2-yl)cyclohexanone (0.495 g, 1.09 mmol, Example #26, Step B) was dissolved in MeOH (5 mL) then cooled to about −5° C. Sodium borohydride (0.0413 g, 1.09 mmol) was added and the mixture was stirred for about 5 min. Acetone was added then the solvents were concentrated under reduced pressure and the residue was purified by flash chromatography on silica gel with DCM/MeOH (95:5) as an eluent then by RP-HPLC (Table 1, Method f) to give the title compound: (0.029 g, 6%): LC/MS (Table 1, Method a) R_t=2.41 min; MS m/z: 456.2 (M+H)+.

Example #26

4-(2,4-Difluorophenyl)-5-(3-isopropyl-[1,2,4]triazolo[4,3-b]pyridazin-6-yl)oxazol-2-amine

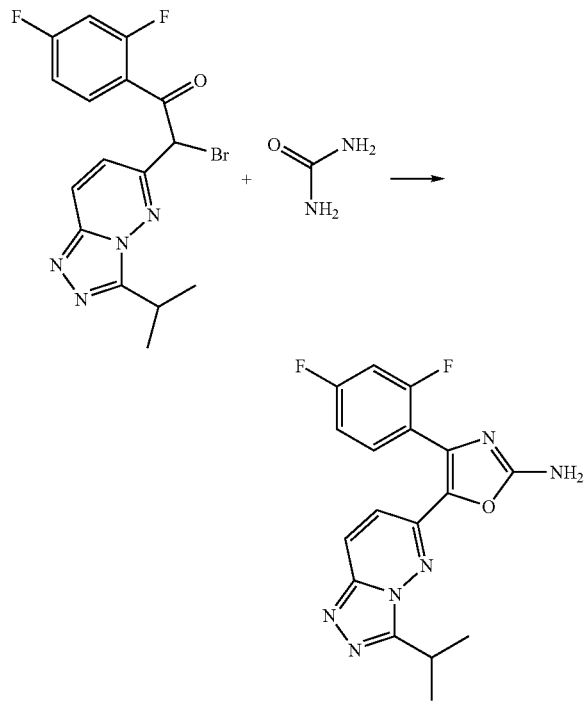

2-Bromo-1-(2,4-difluorophenyl)-2-(3-isopropyl-[1,2,4]triazolo[4,3-b]pyridazin-6-yl)ethanone (0.500 g, 1.26 mmol, Preparation #A.2) and urea (0.228 g, 3.80 mmol) were added to DMF (5 mL) then heated at about 100° C. for about 2 h. The mixture was cooled to ambient temperature then purified by RP-HPLC (Table 1, Method f). Concentration under reduced pressure of most of the organic solvent resulted in a precipitate which was collected by filtration and dried to give the title compound (0.018 g, 4%): LC/MS (Table 1, Method b) $R_t$=1.96 min; MS m/z: 357.2 (M+H)$^+$.

Example #27

2-(1-tert-Butylpiperidin-4-yl)-4-(2,4-difluorophenyl)-5-(3-isopropyl-[1,2,4]triazolo[4,3-b]pyridazin-6-yl)thiazole

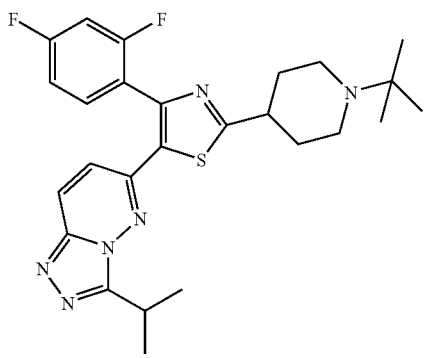

Step A: 1-tert-Butylpiperidine-4-carbothioamide

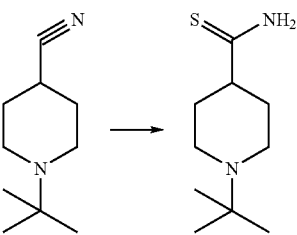

The 1-tert-butylpiperidine-4-carbonitrile (0.900 g, 5.41 mmol, (prepared as described in WO2008/1017461, Compound XXIV), ammonium sulfide (20 wt % in water, 3.69 mL, 10.8 mmol) and MeOH (9.0 mL) were heated in a CEM® microwave at about 120° C. for about 2 h (250 psi maximum pressure, 10 min ramp, 300 max watts). The mixture was concentrated under a stream of air and the resulting material was purified by flash chromatography on silica gel using DCM/MeOH with 3% NH$_4$OH (8:2) as an eluent to give the title compound (0.140 g, 13%): LC/MS (Table 1, Method a) $R_t$=0.44 min; MS m/z: 201.1 (M+H)$^+$.

Step B: 2-(1-tert-Butylpiperidin-4-yl)-4-(2,4-difluorophenyl)-5-(3-isopropyl-[1,2,4]triazolo[4,3-b]pyridazin-6-yl)thiazole

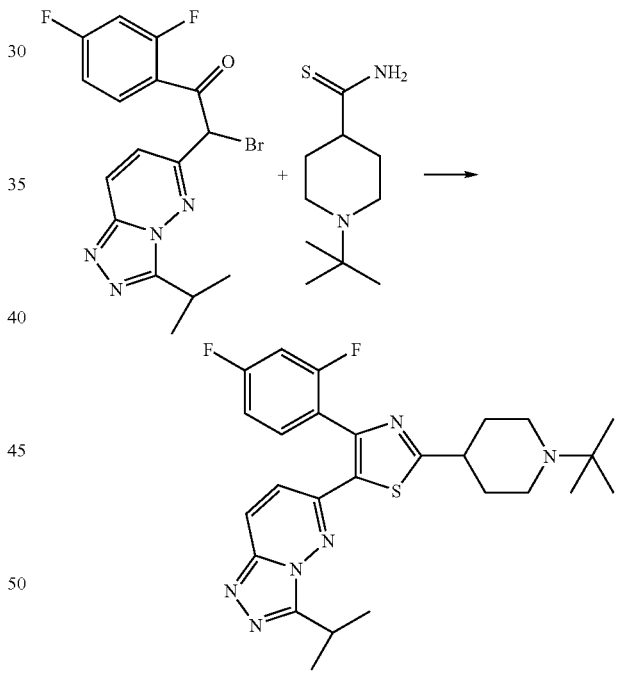

The 2-bromo-1-(2,4-difluorophenyl)-2-(3-isopropyl-[1,2,4]triazolo[4,3-b]pyridazin-6-yl)ethanone (0.276 g, 0.699 mmol, Preparation #A.2), 1-tert-butylpiperidine-4-carbothioamide (0.140 g, 0.699 mmol) and HOAc (0.080 mL, 1.40 mmol) were added to DMF (4 mL). The mixture was stirred at ambient temperature for about 1 h then at about 85° C. for about 1.5 h. The reaction was cooled to ambient temperature and then concentrated under reduced pressure. The residue was partitioned between EtOAc and 1 N aqueous NaOH. The organic solution was dried over MgSO$_4$, filtered and concentrated under reduced pressure to an oil which was then purified by flash chromatography on silica gel using DCM/MeOH with 3% NH$_4$OH (95:5) as an eluent to give the title compound: (0.077 g, 22%): LC/MS (Table 1, Method a) R$_t$=1.66 min; MS m/z: 497.2 (M+H)$^+$.

Example #28

2-(6-(6-(2,4-Difluorophenyl)imidazo[2,1-b]oxazol-5-yl)-[1,2,4]-triazolo[4,3-b]pyridazin-3-yl)propan-2-yl acetate

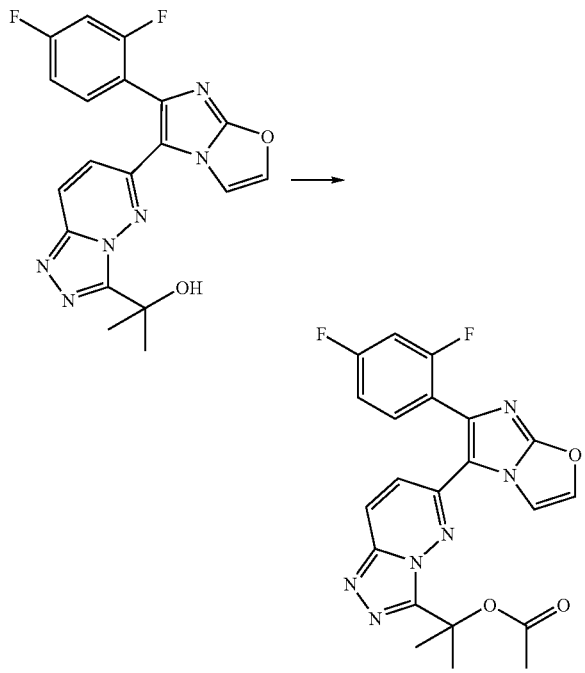

2-(6-(6-(2,4-Difluorophenyl)imidazo[2,1-b]oxazol-5-yl)-[1,2,4]triazolo[4,3-b]pyridazin-3-yl)propan-2-ol (0.125 g, 0.315 mmol, Example #37) was added to DCM (2 mL). Pyridine (0.077 mL, 0.95 mmol) and acetic anhydride (0.045 mL, 0.47 mmol) were added and the suspension was stirred at ambient temperature for about 15 min. Acetyl chloride (0.027 mL, 0.38 mmol) was added and the mixture was stirred at ambient temperature for about 30 min. DMF (1 mL), pyridine (0.077 mL, 0.95 mmol) and acetyl chloride (0.027 mL, 0.38 mmol) were added then the mixture was heated at about 85° C. for about 90 min. The mixture was cooled to ambient temperature, concentrated under reduced pressure then purified by RP-HPLC (Table 1, Method f). Concentration under reduced pressure resulted in a precipitate that was collected by filtration and dried to give the title compound (0.075 g, 54%): LC/MS (Table 1, Method g) R$_t$=1.96 min; MS m/z: 438.9 (M+H)$^+$.

Example #29

3-(2,4-Difluorophenyl)-4-(3-isopropyl-[1,2,4]triazolo[4,3-b]pyridazin-6-yl)-5-methylisoxazole

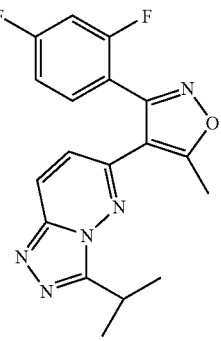

Step A: (E)-1-(2,4-Difluorophenyl)but-2-yn-1-one O-methyl Oxime

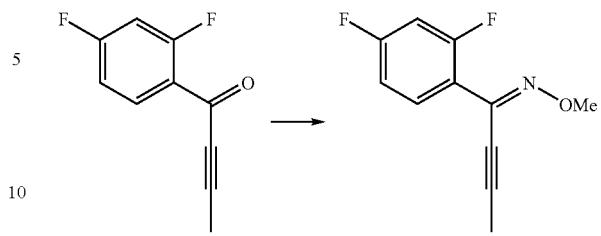

1-(2,4-Difluorophenyl)but-2-yn-1-one (3.95 g, 21.93 mmol, prepared as described in WO 2000008002, Intermediate #39) was dissolved in MeOH (60 mL) then pyridine (6 mL) and O-methylhydroxylamine hydrochloride (3.66 g, 43.9 mmol) were added. The mixture was stirred for about 2 min until a solution was obtained then sodium sulfate (6.23 g, 43.9 mmol) was added. The mixture was stirred overnight at ambient temperature then the mixture was diluted with water (150 mL) and extracted with ethyl acetate (3×50 mL). The combined organic solutions were extracted with brine (50 mL), dried over MgSO$_4$, filtered and concentrated under reduced pressure to an oil. The material was purified by flash chromatography silica gel with heptane/ethyl acetate (85:15) as an eluent to give the title compound: (2.29 g, 50%): LC/MS (Table 1, Method g) R$_t$=2.58 min; MS m/z: 210.0 (M+H)$^+$.

Step B: 3-(2,4-Difluorophenyl)-4-iodo-5-methylisoxazole

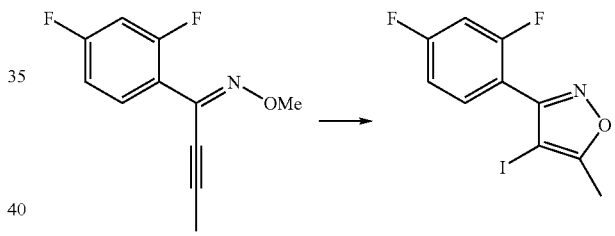

Iodine monochloride (2.13 g, 13.1 mmol) was dissolved in DCM (15 mL) then the solution was added over about 10 min to the (E)-1-(2,4-difluorophenyl)but-2-yn-1-one O-methyl oxime (2.29 g, 10.9 mmol) in DCM (100 mL). The mixture was stirred for about 1 h then saturated aqueous sodium thiosulfate (50 mL) was added. The mixture was stirred for about 10 min then the layers were separated. The aqueous layer was extracted with DCM (25 mL) then the combined organics were dried over MgSO$_4$, filtered and concentrated under reduced pressure. The material was purified by flash chromatography on silica gel with heptane/EtOAc (95:5) as an eluent to give the title compound (1.64 g, 47%): LC/MS (Table 1, Method g) R$_t$=2.65 min; MS m/z: 322.0 (M+H)$^+$.

Step C: 3-(2,4-Difluorophenyl-4-(3-isopropyl-[1,2,4]triazolo[4,3-b]pyridazin-6-yl)-5-methylisoxazole

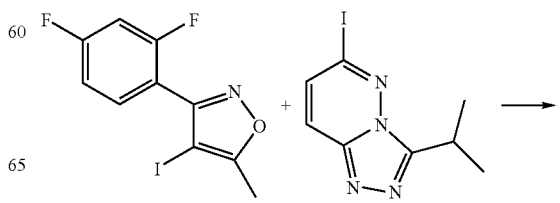

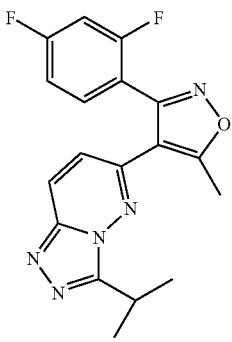

6-Iodo-3-isopropyl-[1,2,4]triazolo[4,3-b]pyridazine (0.400 g, 1.25 mmol, Preparation #H.1) and 3-(2,4-difluorophenyl)-4-iodo-5-methylisoxazole (0.360 g, 1.25 mmol) were coupled using General Procedure I.1 to provide the title compound (0.098 g, 22%): LC/MS (Table 1, Method g) $R_t$=2.16 min; MS m/z: 356.0 (M+H)$^+$.

Example #30

3-(2,4-Difluorophenyl)-4-(3-isopropyl-[1,2,4]triazolo[4,3-b]pyridazin-6-yl)isoxazol-5-amine

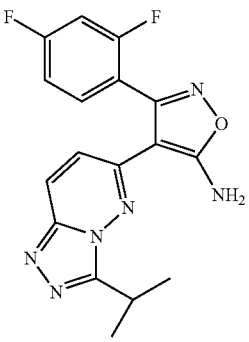

Step A: Ethyl 2-cyano-2-(3-isopropyl-[1,2,4]triazolo[4,3-b]pyridazin-6-yl)acetate

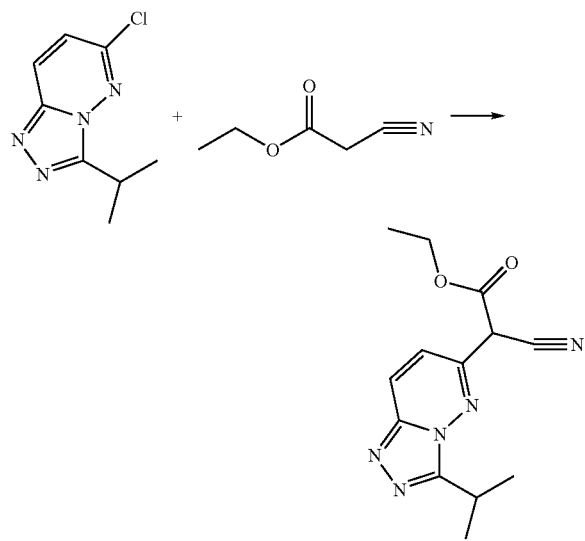

6-Chloro-3-isopropyl-[1,2,4]triazolo[4,3-b]pyridazine (5.00 g, 25.4 mmol, Preparation #G.1) and ethyl 2-cyanoacetate (3.16 g, 28.0 mmol) were added to DMF (50 mL) then the solution was cooled to about 0° C. Sodium hydride (60% in oil, 1.22 g, 30.5 mmol) was added then the mixture was stirred for about 5 min at ambient temperature and at about 60° C. for about 14 h. The mixture was cooled to ambient temperature then concentrated under reduced pressure. The residue was stirred with EtOAc (100 mL) and 2N HCl (50 mL) for about 10 min and the insoluble material was collected by filtration and dried to give the title compound (1.16 g, 17%): LC/MS (Table 1, Method g) $R_t$=1.53 min; MS m/z: 273.9 (M+H)$^+$.

Step B: 2-(3-Isopropyl-[1,2,4]triazolo[4,3-b]pyridazin-6-yl)acetonitrile

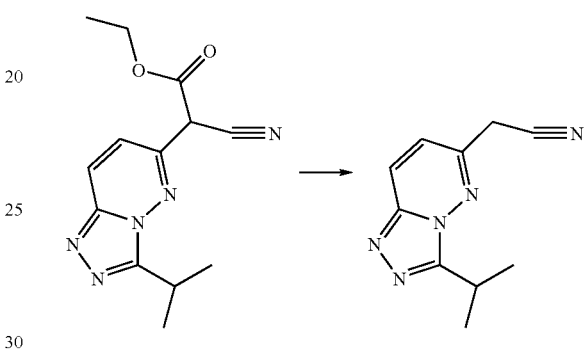

Ethyl 2-cyano-2-(3-isopropyl-[1,2,4]triazolo[4,3-b]pyridazin-6-yl)acetate (1.16 g, 4.24 mmol) was suspended in 5N HCl (15 mL, 75 mmol) then heated at about 105° C. for about 20 min. The mixture was cooled to ambient temperature then concentrated under reduced pressure. The residue was partitioned between saturated aqueous NaHCO$_3$ (25 mL) and EtOAc (50 mL). The aqueous layer was extracted with EtOAc (25 mL), the combined organics were dried over MgSO$_4$, filtered and concentrated under reduced pressure. The oil was purified by flash chromatography on silica gel using DCM/MeOH (95:5) as an eluent to give the title compound (0.493 g, 58%): LC/MS (Table 1, Method g) $R_t$=1.41 min; MS m/z: 202.1 (M+H)$^+$.

Step C: (E)-2,4-Difluorobenzaldehyde Oxime

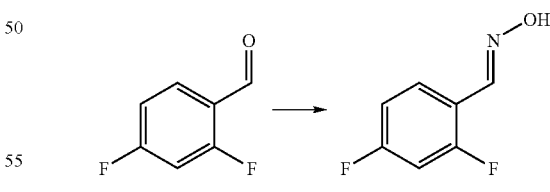

2,4-Difluorobenzaldehyde (2.27 g, 16.0 mmol) and hydroxylamine hydrochloride (6.67 g, 96.0 mmol) were added to EtOH (25 mL) and water (25 mL) along with about 40 g of ice. The mixture was stirred and 50% aqueous NaOH (7.68 g, 96 mmol) was added dropwise. The mixture was stirred at ambient temperature for about 15 min then the solid was collected by filtration, washed with water (10 mL) and dried to give the title compound (1.25 g, 50%): $^1$H NMR (DMSO-d$_6$) δ 11.58 (d, 1H), 8.18 (s, 1H), 7.78 (m, 1H), 7.33 (m, 1H), 7.14 (m, 1H).

Step D: 3-(2,4-Difluorophenyl)-4-(3-isopropyl-[1,2,4]triazolo[4,3-b]pyridazin-6-yl)isoxazol-5-amine

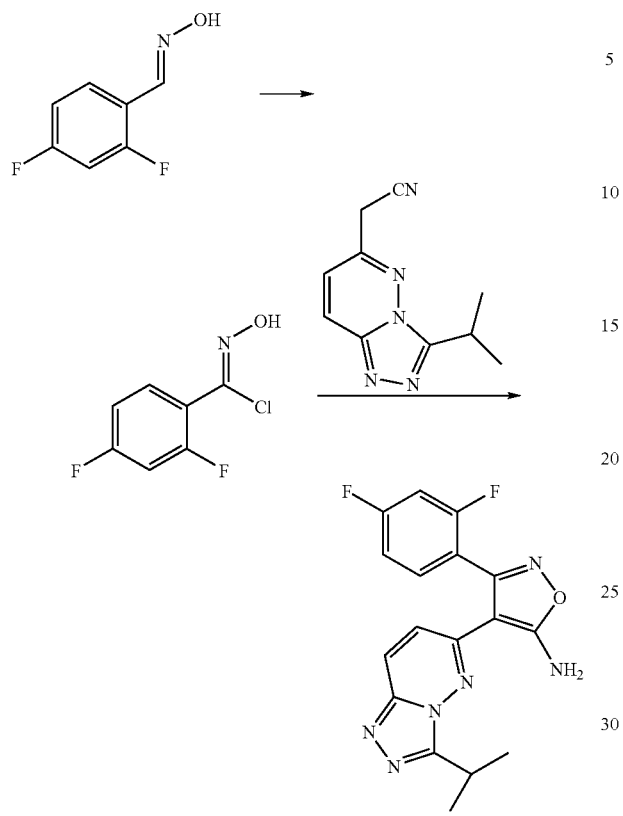

(E)-2,4-Difluorobenzaldehyde oxime (1.25 g, 7.96 mmol) was dissolved in DMF (5 mL) then NCS (1.10 g, 8.27 mmol) was added. The mixture was stirred for about 30 min then water (75 mL) was added and the mixture was extracted with Et$_2$O (100 mL). The organic solution was extracted with brine (25 mL), dried over Na$_2$SO$_4$, filtered and concentrated under reduced pressure to give a solid (1.44 g). A portion of the solid (0.428 g, 2.24 mmol) was dissolved in EtOH (2 mL) then the solution was added to a mixture of 2-(3-isopropyl-[1,2,4]triazolo[4,3-b]pyridazin-6-yl)acetonitrile (0.450 g, 2.23 mmol) and sodium methoxide (0.120 g, 2.24 mmol) in EtOH (4 mL) and THF (4 mL) over about 10 min while keeping the temperature of the mixture at about 0° C. The mixture was allowed to warm to ambient temperature then stirred for about 16 h. Potassium tert-butoxide (0.188 g, 1.68 mmol) was added then the mixture was stirred for about 1.5 h. The solvents were removed under reduced pressure and the residue was then triturated with water (25 mL) and DCM (20 µL) then the solid was collected by filtration then further triturated with 9:1 DCM/MeOH (10 mL), filtered and washed with 9:1 DCM/MeOH (5 mL). The material was dried under vacuum at about 70° C. to give the title compound (0.462 g, 58%) as an off white solid. An analytically pure sample was obtained as follows. A portion of the solid (0.150 g) was suspended in water (5 mL) and MeOH (1 mL) then filtered and washed with water (3 mL). The material was dried under vacuum at about 70° C. to give 0.140 g of solid. The material was suspended in MeOH (4 mL) and heated to about 60° C. with stirring then cooled slightly and the solid collected by filtration. The solid was dissolved in hot DMF (3.3 mL), cooled and the solid collected by filtration then washed with Et$_2$O and dried to give the title compound (0.107 g): LC/MS (Table 1, Method g) R$_f$=1.94 min; MS m/z: 357.0 (M+H)$^+$.

Example #31

6-(2,4-Difluorophenyl)-5-(3-isopropyl-[1,2,4]triazolo[4,3-a]pyrazin-6-yl)imidazo[2,1-b]oxazole

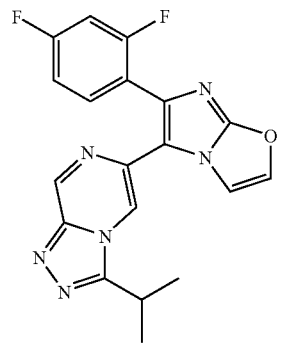

Step A: 2-Chloro-5-hydrazinylpyrazine

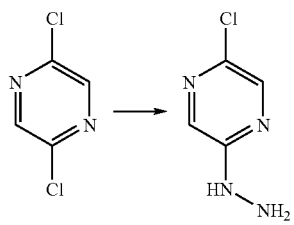

To a mixture of 2,5-dichloropyrazine (CombiPhos, 2.00 g, 13.42 mmol), ammonium hydroxide (5.05 mL, 38.9 mmol), and water (10.0 mL) was added hydrazine hydrate (1.57 mL, 32.2 mmol). The mixture was heated at reflux for about 17 h, cooled in an ice bath for about 15 min, filtered, washed with ice cold water (3×25 mL), and dried in a vacuum oven at about 70° C. to give the title compound (1.60 g, 78%): LC/MS (Table 1, Method h) R$_f$=1.07 min; MS m/z: 145.0 (M+H)$^+$.

Step B: 6-Chloro-3-isopropyl-[1,2,4]triazolo[4,3-a]pyrazine

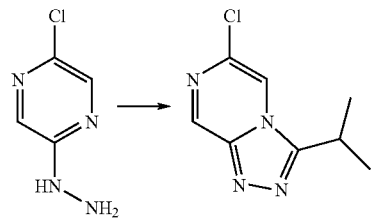

The 2-chloro-5-hydrazinylpyrazine (0.325 g, 2.248 mmol) was suspended in DCM (4 mL) then the isobutyraldehyde (0.195 g, 2.70 mmol) was added. The mixture was stirred for about 30 min, the solvent was concentrated under reduced pressure and the solid was dissolved in DCM (4 mL). Iodobenzene diacetate (0.724 g, 2.24 mmol) was added and the solution was stirred at ambient temperature for about 2 h. The mixture was diluted with DCM (20 mL), extracted with saturated aqueous NaHCO$_3$, dried over MgSO$_4$, filtered and concentrated under reduced pressure. The material was purified by flash chromatography on silica gel using DCM/EtOAc (1:1) as an eluent to give the title compound (0.278 g, 63%): LC/MS (Table 1, Method g) R$_t$=1.74 min; MS m/z: 197.1 (M+H)$^+$.

Step C: 6-(2,4-Difluorophenyl)-5-(3-isopropyl-[1,2,4]triazolo[4,3-a]pyrazin-6-yl)imidazo[2,1-b]oxazole

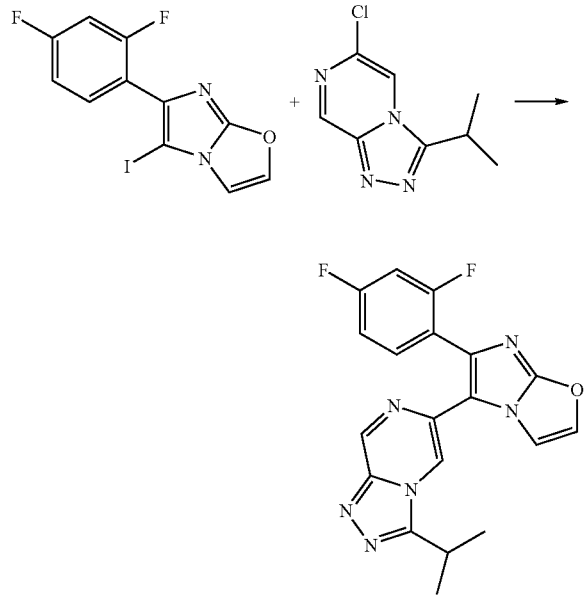

A 25 mL 3 necked round bottom flask with stir bar, nitrogen line, thermometer and septum was charged with 6-(2,4-difluorophenyl)-5-iodoimidazo[2,1-b]oxazole (0.458 g, 1.322 mmol, Preparation #C.1) and THF (6 mL). The solution was cooled to about −35° C. then i-PrMgCl (2.0 M in THF, 0.730 mL, 1.45 mmol) was added dropwise. After about 10 min zinc chloride (0.225 g, 1.653 mmol) in THF (2 mL) was added while maintaining the temperature of the mixture at about −30° C. The suspension was stirred at about −25 to −30° C. for about 15 min then a solution of 6-chloro-3-isopropyl-[1,2,4]triazolo[4,3-a]pyrazine (0.260 g, 1.32 mmol) and Pd(Ph$_3$P)$_4$ (0.076 g, 0.066 mmol) in DMF (2 mL) was added. The mixture was immediately heated in an oil bath preheated to about 85° C. for about 45 min. The reaction mixture was cooled to ambient temperature, concentrated under reduced pressure then dissolved in HOAc (approx. 0.5 mL) and DMF (such that volume was about 9 mL). The material was purified in three equal portions by RP-HPLC (Table 1, method p). The fractions containing product were combined then most of the ACN was removed under reduced pressure. The solution was basified with 2 N aqueous NaOH then extracted with DCM (25 mL then 10 mL). The organic solutions were combined and dried over MgSO$_4$, filtered and concentrated under reduced pressure. The material was purified by flash chromatography on silica gel using DCM/MeOH (95:5) as an eluent. The fractions with product were combined then concentrated under reduced pressure. The light yellow solid was dissolved in hot ACN (about 1 mL) then added dropwise to rapidly stirring water (10 mL). The solid was collected by filtration then dried under vacuum at about 80° C. to give the title compound (0.009 g, 2%): LC/MS (Table 1, Method g) R$_t$=1.83 min; MS m/z: 381.1 (M+H)$^+$.

Example #32

6-(6-(2,4-Difluorophenyl)imidazo[2,1-b]oxazol-5-yl)-[1,2,4]triazolo[4,3-b]pyridazin-3-amine

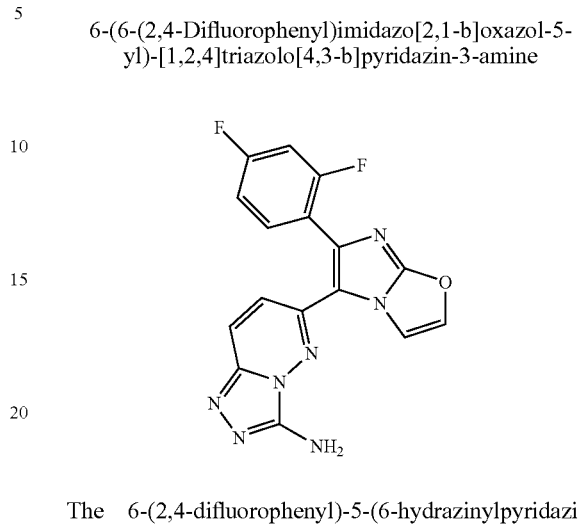

The 6-(2,4-difluorophenyl)-5-(6-hydrazinylpyridazin-3-yl)imidazo[2,1-b]oxazole (0.300 g, 0.914 mmol, Example #40, Step B, was dissolved in MeOH (15 mL) at about ambient temperature before addition of Na$_2$CO$_3$ (0.112 g, 1.371 mmol). Cyanogen bromide (3M in DCM, 0.305 mL, 0.914 mmol) was added and the resulting mixture was stirred at about ambient temperature for about 1 h. The crude mixture was partitioned between water and DCM. The organics were dried over MgSO$_4$, filtered, concentrated under reduced pressure to give a yellow solid that was triturated with Et$_2$O and filtered to give the title compound (0.185 g, 57%): LC/MS (Table 1, Method g) R$_t$=1.65 min.; MS m/z: 354.07 (M+H)$^+$.

Example #33

2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-ol

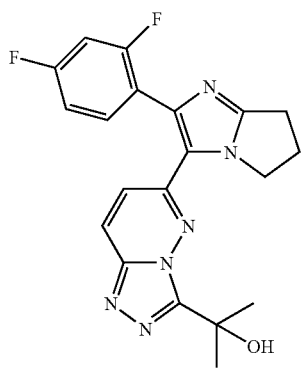

Step A: Pyrrolidin-2-imine Hydrochloride

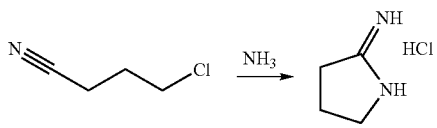

In a 250 mL round bottomed flask, ammonia was bubbled through EtOH (80 mL) that was cooled to about −50--−40° C. After about 45 min, the solution had reached saturation and ammonia (about 59.2 g, about 3480 mmol) had been dissolved. This solution was added to a Parr Autoclave that contained the 4-chlorobutanenitrile (60 g, 580 mmol). The reaction mixture was stirred and heated at about 120° C. for about 18 h. The reaction mixture was cooled and transferred to a round bottom flask and the solvent was concentrated under reduced pressure to give a pale yellow solid. The solid was triturated with petroleum ether (b.p 36-60° C., 100 mL). Toluene (2×60 mL) was added and was azeotroped to remove the solvent under reduced pressure. The solid was collected, washed with Et$_2$O (3×70 mL) and dried in a vacuum oven at about 60° C. overnight to yield the title compound as an off-white solid (69.1 g, 99%): $^1$H NMR (DMSO-d$_6$) δ 9.60 (s (br), 1 H), 9.18 (s (br), 1 H), 8.88 (s (br), 1 H), 3.52 (m, 2 H), 2.76 (m, 2 H), 2.03 (m, 2 H).

Step B, Procedure 1:
2-(2,4-Difluorophenyl)-6,7-dihydro-5 H-pyrrolo[1,2-a]imidazole

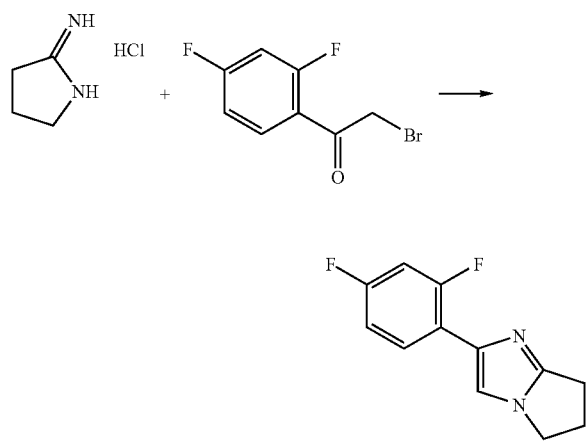

A mixture of 2-bromo-1-(2,4-difluorophenyl)ethanone (150 g, 640 mmol, Example #8, Step A), pyrrolidin-2-imine hydrochloride (108 g, 894 mmol) and Na$_2$CO$_3$ (134 mL, 3190 mmol) in DMF (650 mL) was stirred and heated at about 80° C. in a 3 L 3 necked flask for about 24 h. The mixture was cooled to ambient temperature and poured into water (about 5 L). The product was partitioned between EtOAc (800 mL) and the basic aqueous phase. The aqueous layer was extracted with additional EtOAc (3×800 mL). The combined organic extracts were washed with water (4×800 mL), dried over MgSO$_4$ and filtered through a pad of Florisil® (2" depth×3" diameter). The pad was washed with EtOAc (4×250 mL) and the filtrate was concentrated to dryness under reduced pressure to yield the title compound as a solid (98.6 g, 70%): LC/MS (Table 1, Method a) R$_t$=2.72 min; MS m/z: 221.0 (M+H)$^+$.

Alternatively, 2-(2,4-Difluorophenyl)-6,7-dihydro-5H-pyrrolo[1,2-a]imidazole can be prepared using the following procedure:

A mixture of 2-bromo-1-(2,4-difluorophenyl)ethanone (7.05 g, 30.0 mmol, Example #8, Step A), 2-pyrrolidin-2-imine hydrochloride (10.9 g, 90 mmol, prepared according to J. Med. Chem., 2002, 45, 999-1001) and Na$_2$CO$_3$ (21.1 g, 199 mmol) in DMF (30 mL) was stirred overnight at about 80° C. The reaction mixture was cooled to ambient temperature, poured into water and extracted with EtOAc. The organic layers were dried over MgSO$_4$, filtered and concentrated under reduced pressure to give the title compound (6.61 g, 100%): LC/MS (Table 1, Method a) R$_t$=2.72 min; MS m/z: 221.0 (M+H)$^+$.

Step C: 2-(2,4-Difluorophenyl)-3-iodo-6,7-dihydro-5H-pyrrolo[1,2-a]imidazole

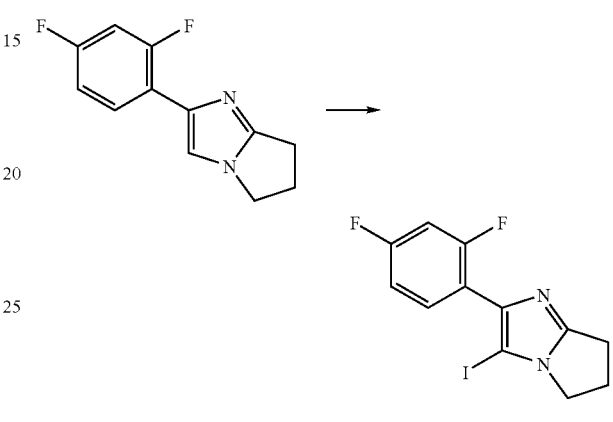

To a stirred solution of 2-(2,4-difluorophenyl)-6,7-dihydro-5H-pyrrolo[1,2-a]imidazole (93.5 g, 425 mmol) in DMF (550 mL), NIS (105 g, 467 mmol) was added portionwise over about 1 h, maintaining the temperature at about 20-25° C. with an ice-water bath. After the final addition, the reaction suspension was stirred for about 2 h. After a total of about 3 h from the start of addition of the NIS, the reaction mixture was poured into ice water (4 L) and was stirred at about 15-20° C. for about 15 min before the addition of a 10% solution of Na$_2$S$_2$O$_3$ (500 mL). The resulting solution was stirred for about 1 h. The tan colored solid was collected by vacuum filtration, washed with water (5×200 mL), and dried overnight at room temperature. The solid was stirred with ether (300 mL), filtered, and washed with additional portions of ether (3×30 mL). This ether trituration process was repeated before the solid was dried in a vacuum oven at about 50-60° C. to give the title compound as a powdery solid (91.4 g, 52%): LC/MS (Table 1, Method h) R$_t$=1.40 min; MS m/z: 347.0 (M+H)$^+$.

Alternatively, the title compound can be isolated from the reaction of 2-(2,4-difluorophenyl)-6,7-dihydro-5H-pyrrolo[1,2-a]imidazole (98.1 g, 445 mmol) in DMF (500 mL) with NIS (108 g, 480 mmol) overnight at ambient temperature. The reaction was cooled to about −5° C. and the crude product was collected by vacuum filtration and the filter cake washed with DMF (50 mL) that was pre-cooled to about −5° C. followed by Et$_2$O (2×50 mL). This material was dissolved into DMF (475 mL) and heated to about 105° C., cooled to room temperature and stirred for about 30 min. The material was then cooled to about 0° C. for about 30 min and collected by vacuum filtration. The filter cake was washed with Et$_2$O (2×50 mL, 1×25 mL) and dried in a vacuum oven at about 60° C. for about 2 h to give the title compound (95.5 g, 61.9%). LC/MS (Table 1, Method g) R$_t$=2.12 min; MS m/z: 347.0 (M+H)$^+$.

245

Step D: 3-(6-Chloropyridazin-3-yl)-2-(2,4-difluorophenyl)-6,7-dihydro-5H-pyrrolo[1,2-a]imidazole

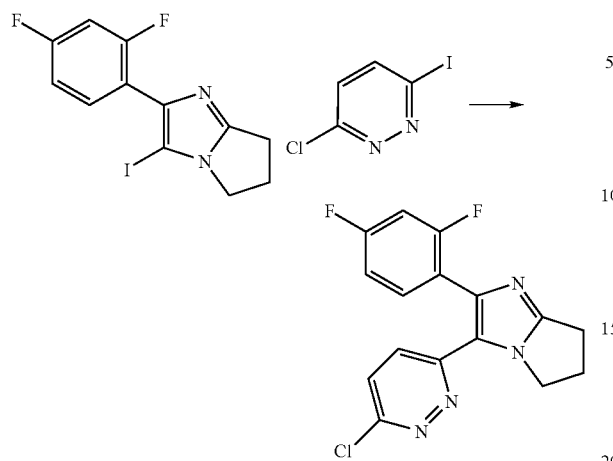

A 500 mL 3-neck flask was charged with 2-(2,4-difluorophenyl)-3-iodo-6,7-dihydro-5H-pyrrolo[1,2-a]imidazole (15.9 g, 45.9 mmol) and THF (119 mL). The reaction mixture was stirred at ambient temperature for about 5 min and then cooled to about −30° C., followed by the dropwise addition of a solution of i-PrMgCl (2.0 M in THF, 25.3 mL, 50.5 mmol) over about 15 min. Stirring was continued at about −30° C. for about 15 min, and consumption of starting material was confirmed by LC/MS. A separate round bottom flask was charged with zinc chloride (8.14 g, 59.7 mmol) and THF (47.5 mL). The resulting solution was added dropwise to the reaction mixture over about 10 min, and stirring was continued for about 45 min at about −30° C. A separate flask was charged with 3-chloro-6-iodopyridazine (12.1 g, 50.5 mmol, Example #9, Step A) in DMF (47.5 mL). The mixture was stirred at ambient temperature until a solution was formed. Pd(PPh$_3$)$_4$ (2.12 g, 1.84 mmol, Strem) was added to the flask and the solution was immediately poured into the reaction mixture and allowed to stir for about 5 min at ambient temperature. The mixture was heated to about 80° C. for about 15 min. The reaction mixture was cooled to ambient temperature and the solvents were removed under reduced pressure. 1-Propanol (about 30 mL) was added and the resulting suspension was sonicated and then cooled in the refrigerator for about 30 min, and a dry ice/acetone bath for about 5 min. The beige precipitate was collected by vacuum filtration and was washed with ice-cold 1-propanol (about 30 mL).

The filtrate was concentrated under reduced pressure and DCM was added to the resulting residue. The suspension in DCM was washed with ammonium hydroxide, resulting in the formation of an emulsion that was subsequently filtered to remove undissolved particulates. The layers were then separated and the organic solution was dried over MgSO$_4$ and concentrated under reduced pressure to about 16 mL that was loaded onto a silica column (120 g) and eluted with a gradient from 0-20% EtOAc/DCM. The product that eluted was concentrated to dryness and triturated with cold MeOH to give an additional 2 g of a solid that was combined with the initial crop of material that was isolated from 1-propanol.

The combined solids were added to 6N HCl (500 mL). Any solids that would not dissolve were separated by filtration and discarded. The acidic solution was washed once with DCM (about 50 mL) and then was cooled to 0° C. and gradually basified with saturated aqueous Na$_2$CO$_3$ while maintaining a temperature of <10° C. to give a solid that was collected by filtration. The solid was dried overnight in a vacuum oven at about 60° C. to give the title compound as a light yellow solid (12.5 g, 82%): LC/MS (Table 1, Method h) R$_t$=1.35 min; MS m/z: 333.1 (M+H)$^+$.

Step E: 2-(2,4-Difluorophenyl)-3-(6-hydrazinylpyridazin-3-yl)-6,7-dihydro-5H-pyrrolo[1,2-a]imidazole

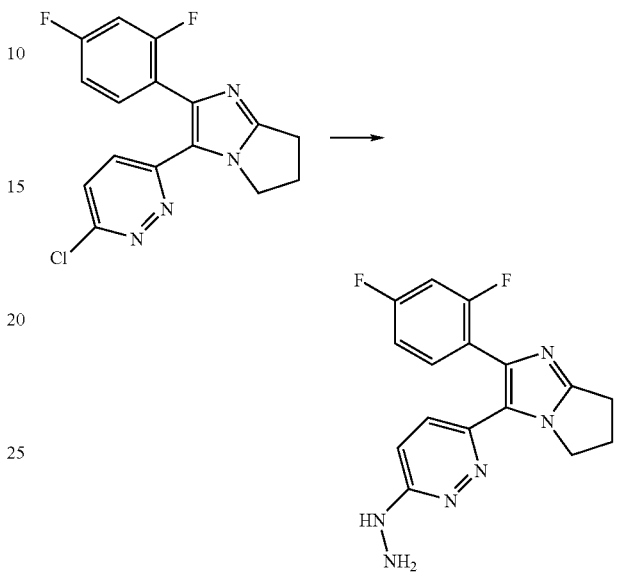

A 500 mL round bottom flask was charged with 3-(6-chloropyridazin-3-yl)-2-(2,4-difluorophenyl)-6,7-dihydro-5H-pyrrolo[1,2-a]imidazole (7.50 g, 22.5 mmol), 1-propanol (225 mL) and hydrazine hydrate (11.3 g, 225 mmol). The mixture was then heated at about 105° C. for about 10 h. The reaction mixture was cooled to ambient temperature and stirred overnight. The mixture was concentrated under reduced pressure to remove about ¾ of the volume. The remaining mixture was stirred with DCM (250 mL) and saturated aqueous NaHCO$_3$ (200 mL). The layers were partitioned, the aqueous layer was diluted with water (100 mL) and extracted with DCM (2×200 mL). The combined organic extracts were washed with brine (100 mL), dried over MgSO$_4$, filtered, and concentrated under reduced pressure. The resulting residue was triturated with Et$_2$O (50 mL) and the solid was collected by vacuum filtration. The filter cake was washed with additional Et$_2$O (10 mL) and then dried in a vacuum oven for about 1 h at about 60° C. to give the title compound (4.59 g, 62%): LC/MS (Table 1, Method g) R$_t$=1.41 min; MS m/z: 329.1 (M+H)$^+$.

Step F: Ethyl 6-(2-(2,4-difluorophenyl)-6,7-dihydro-5H-pyrrolo[1,2-a]imidazol-3-yl)-[1,2,4]triazolo[4,3-b]pyridazine-3-carboxylate

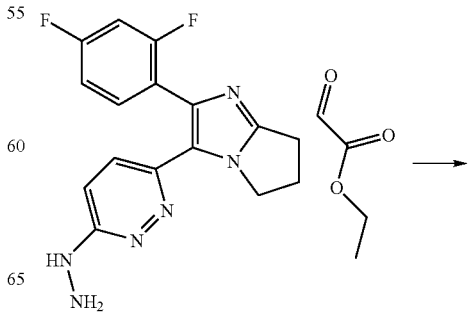

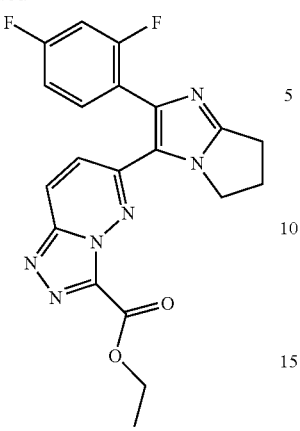

A 250 mL pear flask was charged with 2-(2,4-difluorophenyl)-3-(6-hydrazinylpyridazin-3-yl)-6,7-dihydro-5H-pyrrolo[1,2-a]imidazole (7.90 g, 24.1 mmol) and MeOH (70 mL). To the flask was added ethyl 2-oxoacetate (Fluka, 5.72 mL, 28.9 mmol) and the mixture was heated to about 70° C. for about 1 h, at which point the starting material was consumed. The suspension was cooled to ambient temperature and the MeOH was removed under reduced pressure to give a brown solid. To the flask was added DCM (70 mL) and iodobenzene diacetate (10.1 g, 31.3 mmol) resulting in the formation of a dark solution. After about 1 h, the solution was poured into additional DCM (100 mL) and washed with water and brine. The layers were separated and the organic solution was dried over MgSO$_4$, filtered, and concentrated to give a dark brown solid. The solid was triturated with Et$_2$O (about 30 mL) and a brown solid was collected by vacuum filtration. A second trituration was carried out with Et$_2$O/MeOH (9:1, 45 mL) to give the title compound as a light brown solid (7.25 g, 73%): LC/MS (Table 1, Method h) R$_t$=1.27 min; MS m/z: 411.1 (M+H)$^+$.

Step G: 1-(6-(2-(2,4-difluorophenyl)-6,7-dihydro-5H-pyrrolo[1,2-a]imidazol-3-yl)-[1,2,4]triazolo[4,3-b]pyridazin-3-yl)ethanone

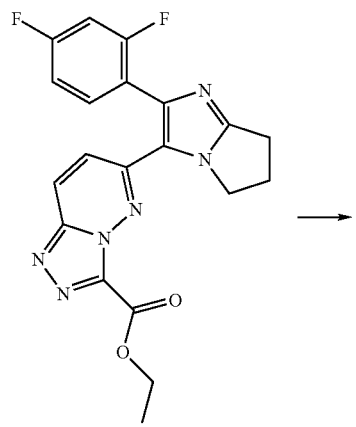

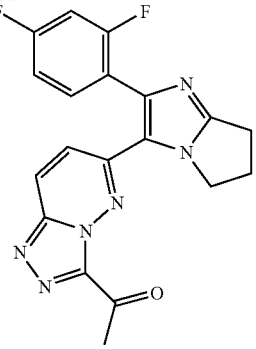

A 100 mL round bottom flask was charged with ethyl 6-(2-(2,4-difluorophenyl)-6,7-dihydro-5H-pyrrolo[1,2-a]imidazol-3-yl)-[1,2,4]triazolo[4,3-b]pyridazine-3-carboxylate (3.04 g, 7.41 mmol). THF (37.0 mL) was added and the mixture was stirred at ambient temperature for about 15 min. The slurry was cooled to about −40° C. and a solution of methylmagnesium chloride (3 M in THF, 9.88 mL, 29.6 mmol) was added slowly while keeping the internal temperature between about −30° C. and −40° C. After about 15 min the mixture was cooled to about −55° C. followed by the slow addition of saturated ammonium chloride solution (about 10 mL). The mixture was then warmed to ambient temperature and diluted with water (50 mL), DCM (75 mL), and saturated aqueous ammonium chloride solution (50 mL). The layers were separated and the aqueous solution was extracted with DCM (2×100 mL). The combined organic extracts were dried over MgSO$_4$, filtered, and concentrated under reduced pressure to give the title compound (2.74 g, 97%): LC/MS (Table 1, Method h) R$_t$=1.22 min; MS m/z: 381.1 (M+H)$^+$.

Step H: 2-(6-(2-(2,4-Difluorophenyl)-6,7-dihydro-5H-pyrrolo[1,2-a]imidazol-3-yl)-[1,2,4]triazolo[4,3-b]pyridazin-3-yl)propan-2-ol

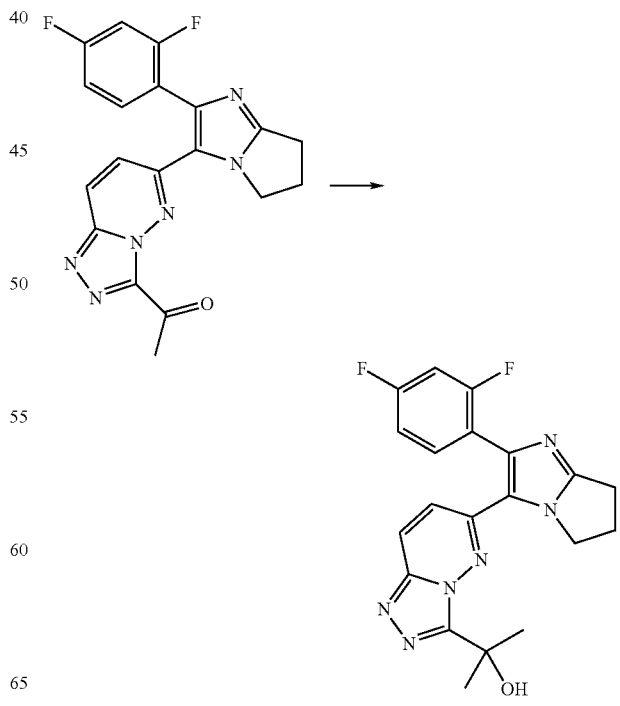

A 100 mL round bottom flask was charged with 1-(6-(2-(2,4-difluorophenyl)-6,7-dihydro-5H-pyrrolo[1,2-a]imidazol-3-yl)-[1,2,4]triazolo[4,3-b]pyridazin-3-yl)ethanone (2.74 g, 7.20 mmol). THF (36.0 mL) was added and the mixture was stirred at ambient temperature for about 15 min. The slurry was cooled to about −40° C. and a solution of methylmagnesium chloride (3 M in THF, 6.00 mL, 18.0 mmol) was added slowly while keeping the internal temperature between about −30° C. and −40° C. After about 15 min, the mixture was cooled to about −55° C. followed by the slow addition of a saturated ammonium chloride solution (about 10 mL). The mixture was then warmed to ambient temperature and diluted with water (50 mL), DCM (75 mL) and the layers were separated. The aqueous layer was extracted with DCM (2×50 mL) then the combined organic extracts were dried over MgSO$_4$, filtered, and concentrated under reduced pressure to give a foam. The material was dissolved in 95:5 DCM/MeOH (about 20 mL) with warming and sonication and then loaded onto a 120 g silica column and eluted with 94:6 DCM/MeOH (about 1 L) followed by 92:8 DCM/MeOH (about 500 mL). Evaporation of the fractions gave the title compound as a yellow foam (2.88 g, 91%) that contained about 9 wt % DCM by $^1$H NMR. This material was combined with a second batch of the title compound (3.4 g that also contained about 9 wt % DCM). The combined material (5.7 g) was dissolved into ACN (150 mL), followed by a rapid precipitation of the title compound as an off-white powder (4.69 g, 82% recovery): LC/MS (Table 1, Method g) R$_t$=1.58 min; MS m/z: 397.2 (M+H)$^+$; $^1$H NMR (DMSO-d$_6$) δ 8.18 (d, 1H), 7.65 (m, 1H), 7.29 (m, 1H), 7.19 (m, 1H), 6.93 (m, 1H), 5.46 (s, 1H), 4.36 (t, 2H), 2.90 (t, 2H), 2.68-2.54 (m, 2H), 1.70 (s, 6H); mp 221.6-222.7° C.; Anal. calcd. for C$_{20}$H$_{18}$F$_2$N$_6$O: C, 60.60; H, 4.58; N, 21.20; F, 9.59. found C, 60.43; H, 4.46; N, 21.38; F, 9.56.

Example #34

3-Cyclopropyl-6-(2-(2,4-difluorophenyl)-6,7-dihydro-5H-pyrrolo[1,2-a]imidazol-3-yl)-[1,2,4]triazolo[4,3-b]pyridazine

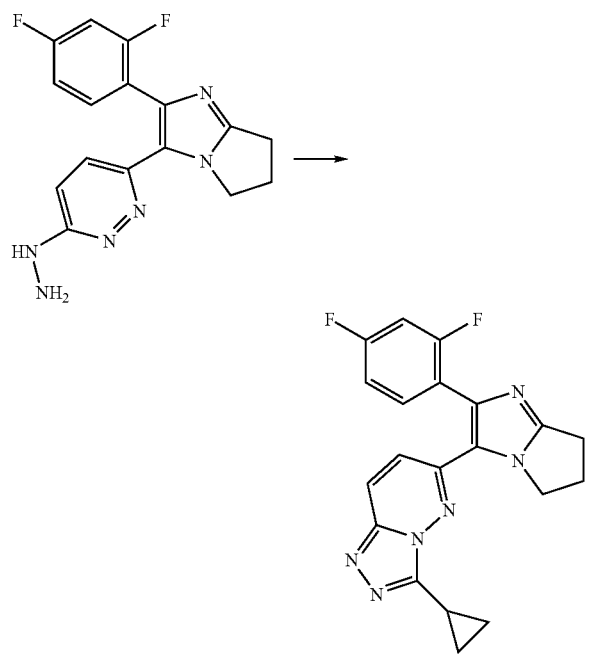

The 2-(2,4-difluorophenyl)-3-(6-hydrazinylpyridazin-3-yl)-6,7-dihydro-5H-pyrrolo[1,2-a]imidazole (5.00 g, 15.2 mmol, Example #35, Step E) was reacted with cyclopropanecarbaldehyde (1.60 g, 22.8 mmol) overnight at ambient temperature in DCM (300 mL). The reaction mixture was cooled to about 0-4° C. Iodobenzene diacetate (5.4 g, 16.75 mmol) was added and the reaction mixture stirred at about 0-4° C. for about 30 min and then at ambient temperature for about 3 h. The reaction mixture was partitioned between DCM and a saturated aqueous Na$_2$CO$_3$ solution. The aqueous phase was back-extracted with of DCM (2×50 mL). The combined organics were dried over MgSO$_4$, filtered, concentrated and purified by chromatography on silica gel using DCM/MeOH (gradient, 100:0 to 95:5) and subsequently triturated with a 90:10 mixture of DCM/Et$_2$O to give the title compound (3.7 g, 64%): LC/MS (Table 1, Method a) R$_t$=2.22 min; MS m/z: 379.3 (M+H)$^+$; $^1$H NMR (CDCl$_3$) δ 7.84 (d, 1H), 7.66 (m, 1H), 7.08-7.00 (m, 1H), 6.95-6.85 (m, 2H), 4.55-4.45 (m, 2H), 3.12-3.01 (m, 2H), 2.78 (m, 2H), 2.53-2.42 (m, 1H), 1.45-1.38 (m, 2H), 1.28-1.19 (m, 2H).

Example #35

2-(6-(6-(2,4-Difluorophenyl)imidazo[2,1-b]oxazol-5-yl)-[1,2,4]triazolo[4,3-b]pyridazin-3-yl)propan-2-ol

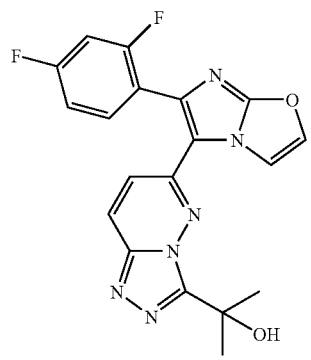

Step A: 3-Chloro-6-iodopyridazine

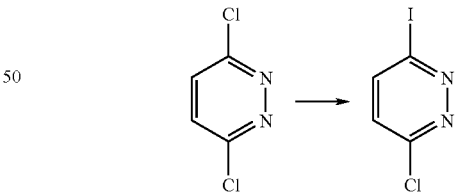

A mixture of 3,6-dichloropyridazine (10.0 g, 67.1 mmol) and sodium iodide (13.5 g, 90.0 mmol) in hydriodic acid (57 wt % in water, stabilized with <1.5% hypophosphorous acid; 50.0 mL, 379 mmol) was heated at about 40° C. for about 4 h. The reaction mixture was cooled to ambient temperature, poured slowly onto an ice/50% aqueous NaOH mixture (about 7:1, 400 mL) to basify to about pH 12 with stirring, and extracted with DCM (3×200 mL) after the ice melted. The combined organic extracts were washed with water (200 mL), dried over MgSO$_4$, filtered, concentrated under reduced pressure and dried in a vacuum oven overnight at about 50° C. to give the title compound (14.2 g, 88%): LC/MS (Table 1, Method b) $R_t$=1.57 min; MS m/z: 240.9 (M+H)$^+$.

Step B: 3-Chloro-6-iodopyridazine

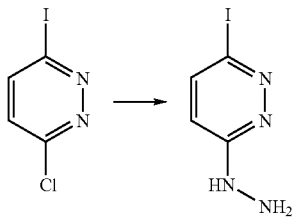

A 200 mL flask was charged with 3-chloro-6-iodopyridazine (10.0 g, 41.6 mmol) and ammonium hydroxide (15.6 mL, 400 mmol) in water (50 mL) to give a tan suspension. Hydrazine (2.2 mL, 79 mmol) was added in one portion to the suspension and the reaction mixture was heated at reflux for about 4 h. The reaction solution was cooled to about 0° C. and the precipitate that formed was collected by vacuum filtration, washed with water, and dried for about 1 h on a Buchner funnel to give the title compound (7.9 g, 68%). By $^1$H NMR, the material contained about 15% of 3-chloro-6-hydrazinylpyridazine. LC/MS (Table 1, Method b) $R_t$=0.76 min; MS m/z: 237.0 (M+H)$^+$.

Step C: Ethyl 6-iodo-[1,2,4]triazolo[4,3-b]pyridazine-3-carboxylate

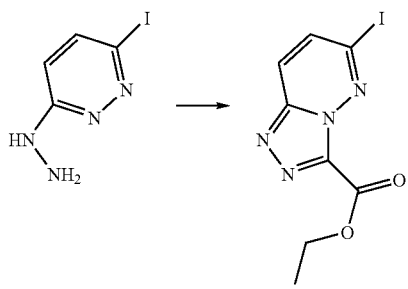

In a 1 L round-bottomed flask was added 3-hydrazinyl-6-iodopyridazine (60.6 g, 257 mmol, prepared using General Procedure D from 3-chloro-6-iodopyridazine [Example #9 Step A] with hydrazine hydrate) and MeOH (600 mL) to give a tan suspension. A solution of glyoxylic acid ethyl ester (50 wt % in toluene, 54.9 mL, 270 mmol, Fluka) was added. The mixture was heated at about 40° C. for about 2 h. The reaction mixture was cooled to ambient temperature and the solvent was removed in vacuo. The residue was dissolved in DCM (600 mL) and iodobenzene diacetate (99.0 g, 308 mmol) was added and the mixture was stirred overnight. The reaction mixture was diluted with additional DCM (600 mL) and extracted with water (600 mL). The organic layer was dried over MgSO$_4$ and concentrated in vacuo. The solid was triturated with EtOAc (500 mL) and then collected by filtration. The solid was washed with additional EtOAc (250 mL) and then dried in vacuo to give title compound (53.9 g, 65%).

LC/MS (Table 1, Method g) $R_t$=1.18 min; MS m/z: 319.0 (M+H)$^+$. $^1$H NMR (DMSO-d$_6$) δ 8.29 (m, 1H), 7.84 (m, 1H), 4.48 (m, 2H), 1.39 (t, 3H).

Step D: Ethyl 6-(6-(2,4-difluorophenyl)imidazo[2,1-b]oxazol-5-yl)-[1,2,4]triazolo[4,3-b]pyridazine-3-carboxylate

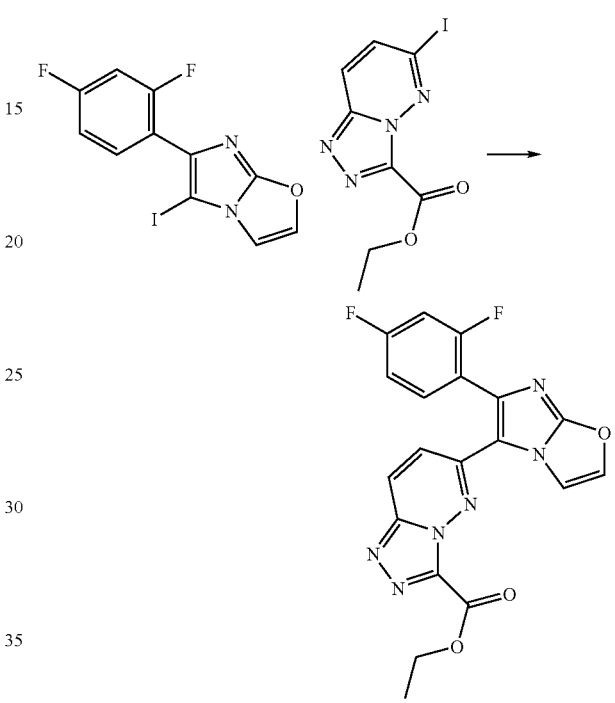

A 100 mL 3-neck flask and a stir bar were dried in oven overnight and then cooled under nitrogen. The reaction was kept under a nitrogen atmosphere through its entirety. 6-(2,4-difluorophenyl)-5-iodoimidazo[2,1-b]oxazole (10.0 g, 28.9 mmol, Preparation #C.1) was added to the 3-neck flask and dissolved in THF (90 mL). The reaction mixture was cooled to about −30° C. and then a solution of i-PrMgCl (2.0 M in THF, 15.9 mL, 31.8 mmol) was added dropwise. The reaction mixture continued stirring at about −30° C. for about 15 min. In a separate flask, zinc chloride (4.73 g, 34.7 mmol) was dissolved in THF (40 mL) and cooled to about 0° C. The zinc chloride solution was added dropwise (over about 30 min) to the reaction mixture to form a dark yellow suspension. The reaction mixture was stirred at about −30° C. for about 45 min. A third flask was charged with ethyl 6-iodo-[1,2,4]triazolo[4,3-b]pyridazine-3-carboxylate (9.19 g, 28.9 mmol) and DMF (80 mL). To the suspension was added Pd(PPh$_3$)$_4$ (2.00 g, 1.73 mmol) and the suspension was immediately poured into the reaction mixture. The reaction mixture was heated to about 80° C. for 15 min. The mixture was cooled and the DMF was removed under vacuum. The resulting solid was triturated with 1-propanol (20 mL) and filtered to afford a white solid. The material was taken up in DCM (250 mL) and washed with dilute aqueous NaHCO$_3$ (250 mL). The organics were dried and solvent was removed in vacuo to afford the title compound (6.90 g, 16.8 mmol, 58%). LC/MS (Table 1, Method b) $R_t$=1.72 min; MS m/z: 411.2 (M+1)$^+$. $^1$H NMR (DMSO-d$_6$) δ 8.60 (m, 1H), 8.42 (m, 1H), 8.33 (m, 1H), 7.75 (m, 1H), 7.54-7.46 (m, 1H), 7.31 (m, 1H), 7.08 (m, 1H), 4.55 (q, 2H), 1.43 (t, 3H).

Step E: 1-(6-(6-(2,4-Difluorophenyl)imidazo[2,1-b]oxazol-5-yl)-[1,2,4]triazolo[4,3-b]pyridazin-3-yl)ethanone

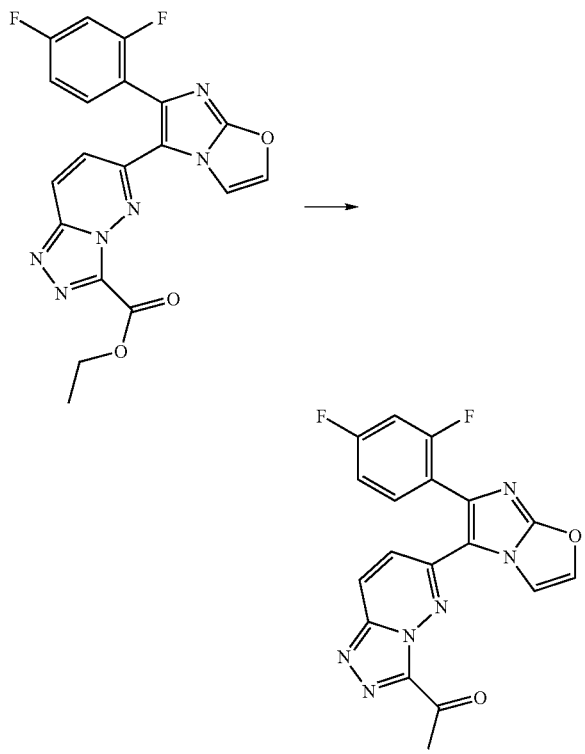

In a 100 mL round-bottomed flask, ethyl 6-(6-(2,4-difluorophenyl)imidazo[2,1-b]oxazol-5-yl)-[1,2,4]triazolo[4,3-b]pyridazine-3-carboxylate (2.00 g, 4.87 mmol) was suspended in THF (30 mL) and cooled to about −30° C. A solution of methylmagnesium chloride (3 M in THF, 6.50 mL, 19.5 mmol) was added over about 10 min to the suspension. The mixture was stirred for about 25 min at about −30° C., followed by slow addition of a saturated solution of ammonium chloride (15 mL). The suspension was diluted with the addition of water (20 mL) and then DCM (20 mL). The layers were separated and the aqueous layer was extracted with DCM (2×50 mL). The combined organic extracts were washed with water and brine, dried over MgSO$_4$, filtered, and the solvents were removed under reduced pressure to give a solid that was triturated with Et$_2$O (15 mL) and collected by vacuum filtration as a slightly off-white powder (1.50 g, 81%): LC/MS (Table 1, Method g) R$_t$=2.06 min; MS m/z: 380.9 (M+H)$^+$.

Step F: 2-(6-(6-(2,4-Difluorophenyl)imidazo[2,1-b]oxazol-5-yl)-[1,2,4]triazolo[4,3-b]pyridazin-3-yl)propan-2-ol

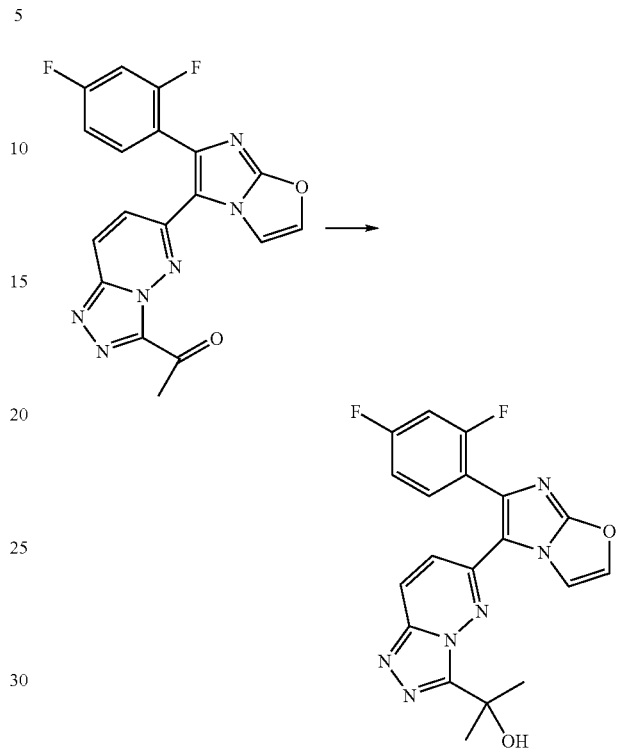

Into a 100 mL round-bottomed flask was added 1-(6-(6-(2,4-difluorophenyl)imidazo[2,1-b]oxazol-5-yl)-[1,2,4]triazolo[4,3-b]pyridazin-3-yl)ethanone (1.04 g, 2.73 mmol) and THF (20 mL) to give an off-white suspension. The reaction suspension was cooled to about −30° C. Then methylmagnesium chloride (3 M in THF, 3.65 mL, 10.9 mmol) was added over about 5 min. The reaction was stirred at about −30° C. for about 30 min. A saturated solution of NH$_4$Cl (50 mL) was slowly added to the reaction suspension, followed by the addition of DCM (50 mL). The layers were partitioned and the aqueous solution was extracted with DCM (2×50 mL). The combined organic extracts were washed with brine, dried over MgSO$_4$, filtered, and the solvents removed under reduced pressure to give the title compound (0.86 g, 79%). The product was combined with other product from additional reactions (7.5 g total) and the material was purified by flash chromatography (40 g RediSep® silica gel; DCM/MeOH 1:0 to 9:1) to give an off-white solid. The material was dissolved in DMSO (35 mL) at about 80° C. and then cooled to about 0° C. Then water (200 mL) was added to form a precipitate that was collected by filtration. The filter pad was washed with water and then triturated with 1-propanol using sonication and the solid collected by filtration. The solid was further triturated with 1-propanol using sonication and the solid collected by filtration and then dried in a vacuum oven at about 80° C. to give the title compound (5.05 g, 67% recovery). LC/MS (Table 1, Method g) R$_t$=1.78 min; MS m/z: 398.2 (M+M)$^+$. $^1$H NMR (DMSO-d$_6$) δ 8.53 (d,), 8.26 (m, 2H), 7.76 (m, 1H), 7.55-7.24 (m, 2H), 6.93 (m, 1H), 5.77 (s, 1H), 2.58-2.50 (m, 4H), 1.79 (s, 6H). mp 258-260° C.; Anal. calcd. for C$_{19}$H$_{14}$F$_2$N$_6$O$_2$: C, 57.58; H, 3.56; N, 21.20; F, 9.59. found C, 57.42; H, 3.36; N, 21.22; F, 9.28.

Example #36

6-(2,4-Difluorophenyl)-5-(3-isopropyl-[1,2,4]triazolo[3,4-b][1,3,4]thiadiazol-6-yl)imidazo[2,1-b]oxazole

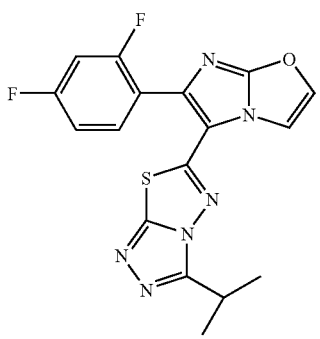

Step A: 6-(2,4-Difluorophenyl)imidazo[2,1-b]oxazole-5-carboxylic Acid

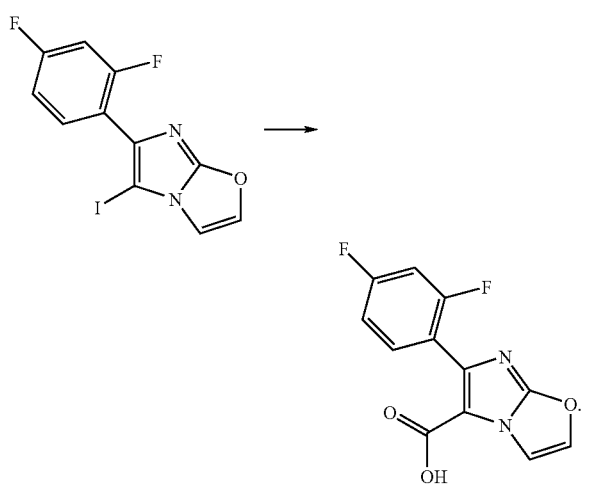

A 50 mL 3-neck flask and a stir bar were dried in an oven overnight, cooled under vacuum, and then flushed with nitrogen. 6-(2,4-Difluorophenyl)-5-iodoimidazo[2,1-b]oxazole (0.320 g, 0.925 mmol, Preparation #C.1) was added to the 3-neck flask and dissolved in THF (6 mL). The reaction mixture was cooled to about 0° C. and i-PrMgCl (2 M in THF, 0.51 mL, 1.0 mmol) was added dropwise. The reaction mixture was stirred at about 0° C. for about 15 min then $CO_2$ gas was bubbled into the mixture for about 5 min. The gas addition was followed by the addition of solid $CO_2$ (dry ice). The mixture was quenched with HOAc, the solvent was concentrated under reduced pressure, and the resulting residue was triturated with $Et_2O$ to give a solid. The solid was dried under vacuum to give the crude title compound (0.31 g, 125% yield, 53% purity by ELSD) which was used as is in the next step: LC/MS (Table 1, Method b) $R_t$=1.53 min; MS m/z 265.1 (M+H)$^+$.

Step B: 6-(2,4-Difluorophenyl)-5-(3-isopropyl-[1,2,4]triazolo[3,4-b][1,3,4]thiadiazol-6-yl)imidazo[2,1-b]oxazole

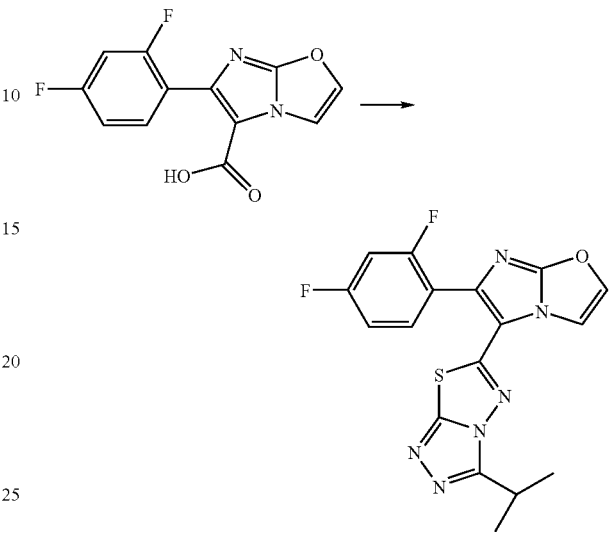

A 5 mL round-bottomed flask equipped with a reflux condenser outfitted with a nitrogen inlet adapter was charged with 4-amino-5-isopropyl-4H-1,2,4-triazole-3-thiol (0.15 g, 0.95 mmol, Enamine) and 6-(2,4-difluorophenyl)imidazo[2,1-b]oxazole-5-carboxylic acid (0.25 g, 0.95 mmol) in $POCl_3$ (3.5 mL, 38 mmol) to give a tan suspension. The reaction mixture was heated at about reflux for about 18 h, allowed to cool, and then poured over stirring ice water. The mixture was diluted with DCM and the layers were separated. The organic layer was concentrated under reduced pressure. The resulting residue was purified via silica gel chromatography eluting with a gradient of 0-5% MeOH in DCM to provide a white solid (0.055 g) which was dissolved in a minimal amount of hot ACN and left to cool to ambient temperature for about 2 h. The resulting crystals were isolated by filtration, washed with ACN, and dried under vacuum to give the title compound (0.020 g, 5%): LC/MS (Table 1, Method b) $R_t$=1.95 min; MS m/z: 387.2 (M+H)$^+$.

Example #37

6-(2,4-Difluorophenyl)-5-(3-isopropyl-[1,2,4]triazolo[4,3-a]pyrimidin-6-yl)imidazo[2,1-b]oxazole

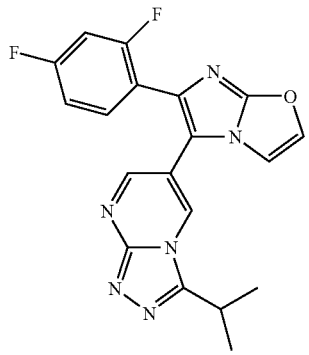

Step A: 6-(2,4-Difluorophenyl)-5-(2-(methylthio)pyrimidin-5-yl)imidazo[2,1-b]oxazole

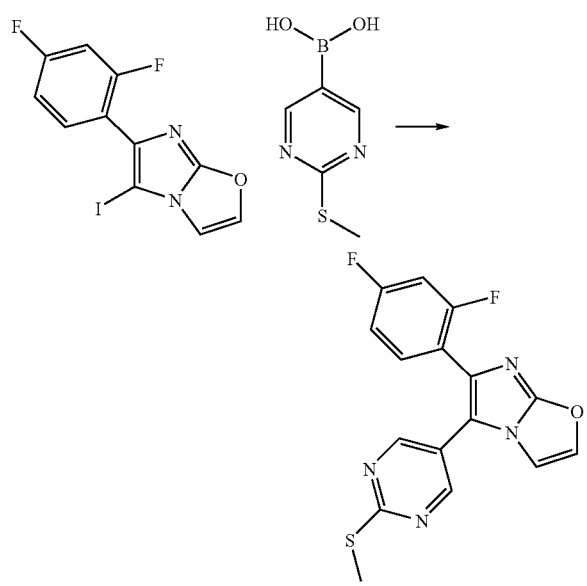

A round bottom flask was charged with 6-(2,4-difluorophenyl)-5-iodoimidazo[2,1-b]oxazole (0.25 g, 0.72 mmol; Example #8, step C) and 2-(methylthio)pyrimidin-5-ylboronic acid (0.184 g, 1.08 mmol, Indofine), bis(triphenylphosphine)palladium (II) chloride (0.051 g, 0.072 mmol) and cesium carbonate (0.588 g, 1.81 mmol). The reaction mixture was diluted with 1,4-dioxane (10 mL) and water (2 mL). The reaction mixture was degassed under vacuum and purged with nitrogen 3 times and then stirred at about 90° C. for about 4 h. The reaction mixture was cooled to ambient temperature and then diluted with $H_2O$. The mixture was extracted with EtOAc (2×200 mL). The organic layers were combined and concentrated under reduced pressure. The product was purified by silica gel flash chromatography using a gradient of 0-10% EtOAc in DCM to give the title compound as yellow solid (0.17 g, 64%); $^1H$ NMR (DMSO-$d_6$) δ 8.62 (s, 2H), 8.34 (d, J=1.8, 1H), 8.12 (d, J=1.8, 1H), 7.68 (m, 1H), 7.33-7.25 (m, 1H), 7.20 (m, 1H), 2.54 (s, 3H).

Step B: 6-(2,4-Difluorophenyl)-5-(2-(methylsulfinyl)pyrimidin-4-yl)imidazo[2,1-b]oxazole

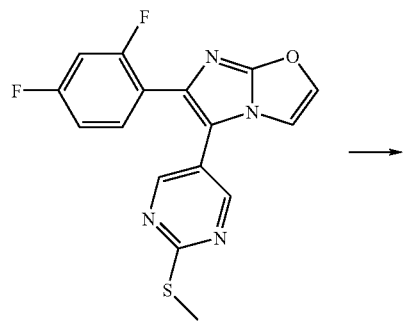

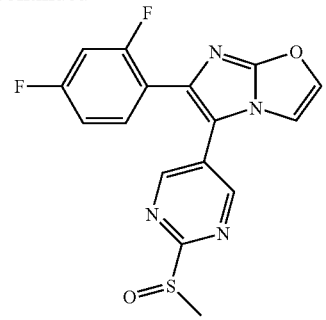

A round bottom flask was charged with 6-(2,4-difluorophenyl)-5-(2-(methylthio)pyrimidin-4-yl)imidazo[2,1-b]oxazole (0.16 g, 0.47 mmol) and OXONE® (0.312 g, 0.508 mmol). The reaction mixture was diluted with MeOH (10.0 mL), DCM (10.0 mL) and water (2.0 mL). The reaction mixture was stirred at ambient temperature for about 8 h. The reaction mixture was quenched with water (100 mL) and extracted with DCM (2×200 mL). The organic phase was washed with $H_2O$ (100 mL) then dried over $Na_2SO_4$, filtered and concentrated under reduced pressure. The crude product was purified by silica gel flash chromatography using a gradient of 10-100% EtOAc in heptane and then a gradient of 0-20% MeOH in DCM to give the title compound (0.16 g, 96%). LC/MS (Table 1, Method o) $R_t$=2.63 min; MS m/z 361.1.

Step C: 6-(2,4-difluorophenyl)-5-(2-hydrazinylpyrimidin-5-yl)imidazo[2,1-b]oxazole

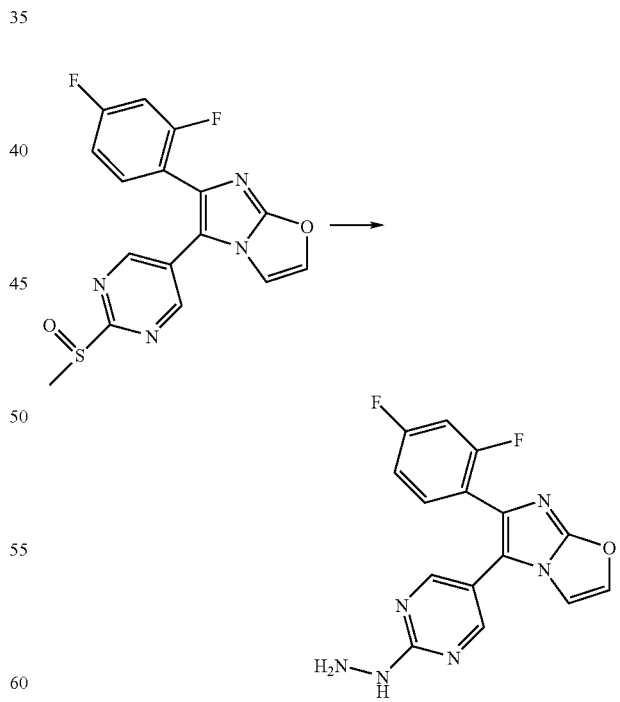

A round bottomed flask was charged with 6-(2,4-difluorophenyl)-5-(2-(methylsulfinyl)pyrimidin-5-yl)imidazo[2,1-b]oxazole (0.16 g, 0.44 mmol), ACN (20 mL) and hydrazine (0.10 mL, 3.2 mmol). The reaction mixture was stirred at about 80° C. for about 2 h. The reaction mixture was concentrated to dryness and then triturated with Et₂O to give the title compound (0.13 g, 89%). LC/MS (Table 1, Method o) R_t=2.56 min; MS m/z 329.1.

Step D: 6-(2,4-Difluorophenyl)-5-(3-isopropyl-[1,2,4]triazolo[4,3-a]pyrimidin-6-yl)imidazo[2,1-b]oxazole

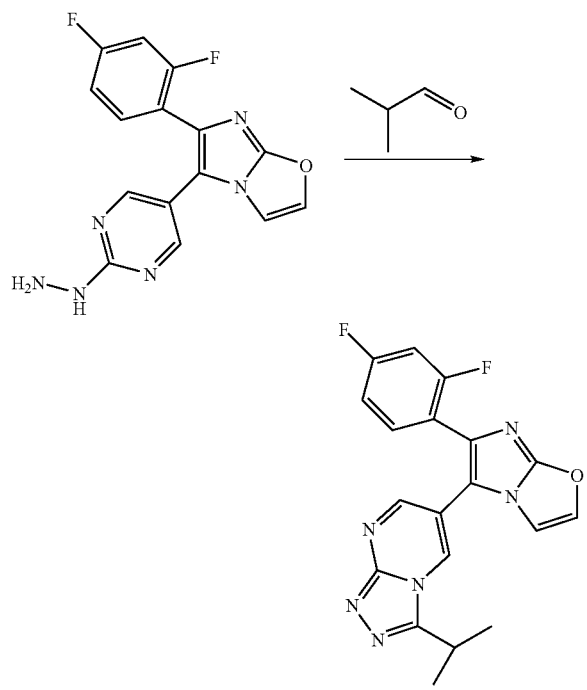

To a flask was added 6-(2,4-difluorophenyl)-5-(2-hydrazinylpyrimidin-5-yl)imidazo[2,1-b]oxazole (0.120 g, 0.366 mmol) and DCM (8 mL). Isobutyraldehyde (0.026 g, 0.366 mmol) and HOAc (0.000021 mL, 0.000366 mmol) were added. The reaction mixture was stirred at ambient temperature for about 2 h. Then iodobenzene diacetate (0.124 g, 0.384 mmol) was added. The reaction mixture was stirred at ambient temperature for about 2 h. The crude material was purified by silica gel flash chromatography using a gradient of 0-20% MeOH in DCM to give the title compound (0.085 g, 61%): LC/MS (Table 1, Method a) R_t=2.62 min; MS m/z: 381.2 (M+H)⁺.

Example #38

1-(6-(6-(2,4-Difluorophenyl)imidazo[2,1-b]oxazol-5-yl)-[1,2,4]triazolo[4,3-b]pyridazin-3-yl)-2-methylpropan-2-ol

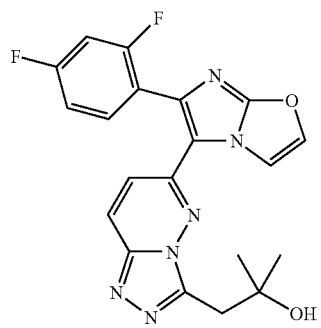

Step A: 5-(6-Chloropyridazin-3-yl)-6-(2,4-difluorophenyl)imidazo[2,1-b]oxazole

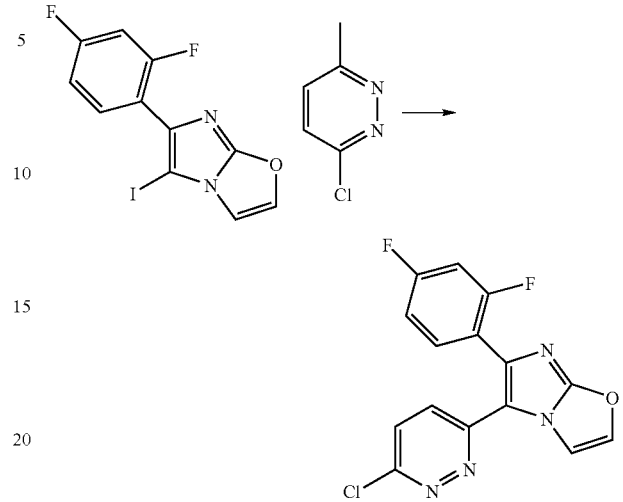

To a flask was added 6-(2,4-difluorophenyl)-5-iodoimidazo[2,1-b]oxazole (10.0 g, 28.9 mmol, Preparation #C.1) and THF (50 mL). The mixture was cooled to about −30° C. and then a solution of iPrMgCl (2.0 M in THF, 15.2 mL, 30.3 mmol) was added dropwise. The reaction mixture was stirred about 15 min at about 0° C. and then a solution of zinc chloride (4.73 g, 34.7 mmol) in THF (50 mL) was added dropwise. The reaction mixture was stirred at about 0° C. for about 30 min. To a second flask was added 3-chloro-6-iodopyridazine (6.67 g, 27.7 mmol, Example #9, Step A) and DMF (20 mL) and the mixture was stirred at ambient temperature until all solids were in solution. To this flask was added Pd(PPh₃)₄ (1.336 g, 1.156 mmol, Strem) and then the entire contents were poured in to the first reaction flask. The reaction mixture was heated to about 80° C. and stirred for about 1 h. The reaction mixture was cooled to ambient temperature and the solids were filtered. The solid was triturated with 1-propanol (25 mL) to give a solid. The solid was portioned between 1N aqueous HCl (250 mL) and DCM (250 mL). The organic layer was isolated and then extracted with 6N aqueous HCl. The acid layer was then basified with solid Na₂CO₃ and the precipitate filtered and dried under vacuum to give the title compound (3.26 g, 34%). LC/MS (Table 1, Method a) R_t=2.69 min; MS m/z: 333.1 (M+H)⁺

Step B: 6-(2,4-difluorophenyl)-5-(6-hydrazinylpyridazin-3-yl)imidazo[2,1-b]oxazole

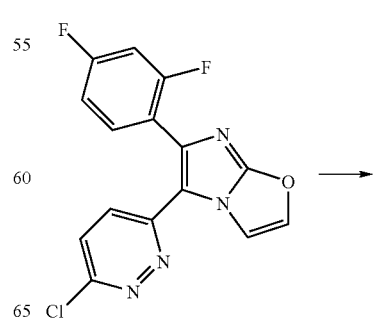

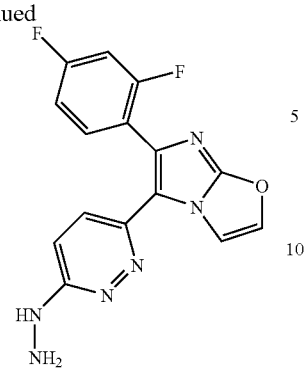

To a flask was added 5-(6-chloropyridazin-3-yl)-6-(2,4-difluorophenyl)imidazo[2,1-b]oxazole (4.00 g, 12.0 mmol), 1-propanol (80 mL) and hydrazine hydrate (5.89 mL, 120 mmol). The reaction mixture was heated at about 100° C. for about 20 h. The reaction mixture was cooled to ambient temperature and then diluted with DCM (100 mL). The organic layer was washed with saturated aqueous NaHCO$_3$ (80 mL), dried with MgSO$_4$, filtered and concentrated under reduced pressure to give the title compound (3.04 g, 77%) as a solid. LC/MS (Table 1, Method g) R$_t$=1.58 min; MS m/z: 329.1 (M+H)$^+$.

Step C: 3-Hydroxy-3-methylbutanal

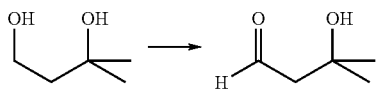

In a 25 mL round-bottomed flask 3-methylbutane-1,3-diol (1.2 g, 11.52 mmol, TCI), Dess-Martin periodinane (5.86 g, 13.83 mmol, Alfa) and DCM (40 mL) were added to give a white suspension. The reaction mixture was stirred at about ambient temperature for about 1.5 h. The reaction mixture was diluted with ether and the solids were filtered off. The filtrate was concentrated to about 20 mL, filtered and washed with ether. The filtrate is treated with solid Na$_2$CO$_3$, filtered and washed with ether. The filtrate was concentrated to about 20 mL and treated with solid Na$_2$CO$_3$ in Et$_2$O (10 mL) at about ambient temperature for about 2 h. The resulting mixture was filtered and washed with ether. The filtrate is concentrated under reduced pressure to give the target compound as oil (1.2 g, 69%). $^1$H NMR (CDCl$_3$) δ 9.88 (t1H), 2.63 (d, 2H), 1.34 (s, 6H).

Step D: 1-(6-(6-(2,4-Difluorophenyl)imidazo[2,1-b]oxazol-5-yl)-[1,2,4]triazolo[4,3-b]pyridazin-3-yl)-2-methylpropan-2-ol

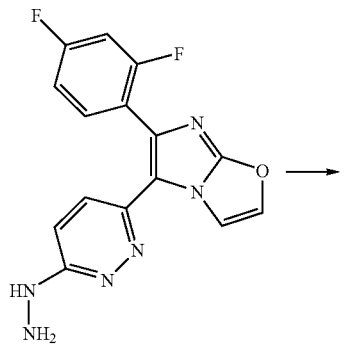

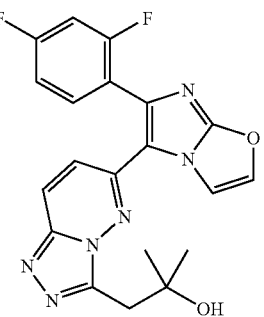

To round bottom flask, 3-hydroxy-3-methylbutanal (0.178 g, 1.185 mmol) and 6-(2,4-difluorophenyl)-5-(6-hydrazinylpyridazin-3-yl)imidazo[2,1-b]oxazole (0.3 g, 0.859 mmol) and DCM 5 mL were added. The reaction mixture was stirred at about ambient temperature for about 1 h. Iodobenzene diacetate (0.38 g, 1.18 mmol) was added and was stirred at ambient temperature for overnight. The reaction mixture was quenched with water. The aqueous phase was extracted with DCM and the organic layer was concentrated under reduced pressure. The crude material was purified by silica gel chromatography using DCM/MeOH (90:10). After concentration of the fractions with product, the resulting solid was triturated with ether. The solid was collected by filtration then dried under vacuum at about 60° C. for about 2 days to give the title compound (0.118 g, 33.5%): LC/MS (Table 1, Method g) R$_t$=1.78 min; MS m/z: 411.2 (M+H)$^+$. $^1$H NMR (DMSO-d$_6$) δ 8.52 (d, 1H), 8.27 (d, 1H), 8.21 (d, 1H), 7.75 (m, 1H), 7.50-7.40 (m, 1H), 7.34-7.25 (m, 1H), 6.90 (m, 1H), 4.71 (s, 1H), 3.33 (s, 2H), 1.27 (s, 6H)

Example #39

2-(6-(6-(2,4-Difluorophenyl)-1-methyl-1H-imidazo[1,2-a]imidazol-5-yl)-[1,2,4]triazolo[4,3-b]pyridazin-3-yl)propan-2-ol

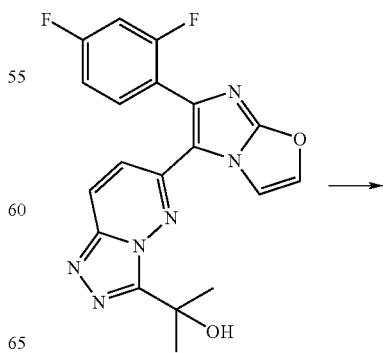

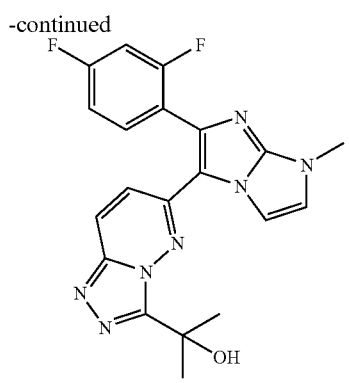

The 2-(6-(6-(2,4-difluorophenyl)imidazo[2,1-b]oxazol-5-yl)-[1,2,4]triazolo[4,3-b]pyridazin-3-yl)propan-2-ol (0.200 g, 0.505 mmol, Example #35) in 1,4-dioxane (1 mL) and 40% methylamine in water (1.5 mL, 17 mmol) was heated in a CEM microwave at about 120° C. for about 55 minutes, (100 psi maximum pressure, 5 min ramp, 300 max watts). The mixture was evaporated and then dissolved in HOAc (2 mL). The solution was stirred at room temperature for about 1 hour then the material was purified by RP-HPLC (Table 1, Method f). The combined fractions were concentrated under reduced pressure to remove the acetonitrile then the solution was basified with saturated aqueous NaHCO$_3$ solution gave an oil. The mixture was extracted with 20% EtOAc in DCM (25 mL) then EtOAc (approx. 15 mL). The combined organics solutions were dried over MgSO$_4$ then filtered and evaporated. The solid was triturated with about 10 mL water then collected by filtration. The material was dissolved in hot acetonitrile (1 mL) then added dropwise to about 10 mL water. The solution was allowed to stand at ambient temperature until a solid formed then the mixture was diluted with water (5 mL). The solid was collected by filtration then dried under vacuum at about 80° C. to give the title compound (0.040 g, 20%); $^1$H NMR (DMSO-d$_6$) δ 8.15 (d, 1H), 8.10 (d, 1H), 7.76-7.67 (m, 1H), 7.46 (m, 2H), 7.31-7.23 (m, 1H), 6.85-6.80 (m, 1H), 5.66 (s, 1H), 3.72 (s, 3H), 1.78 (s, 6H); LC/MS (Table 1, Method g) R$_t$=1.65 min; MS m/z: 410.2 (M+H)$^+$.

What is claimed:

1. A compound of formula (I)

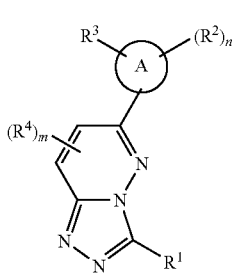

Formula (I)

pharmaceutically acceptable salts thereof or isomers thereof wherein

A is heteroaryl or heterocyclyl;

R$^1$ is —C(O)—(C$_1$-C$_6$) optionally substituted alkyl, —C(O)—O—(C$_1$-C$_6$) optionally substituted alkyl, —NR$^a$R$^b$, —(C$_1$-C$_6$)alkyl —NR$^a$—S(O)$_2$—(C$_1$-C$_6$) alkyl or —(C$_1$-C$_6$)alkyl —NR$^a$—C(O)—(C$_1$-C$_6$)alkyl; or R$^1$ is optionally substituted (C$_1$-C$_6$)alkyl, optionally substituted (C$_2$-C$_6$)alkenyl, optionally substituted (C$_3$-C$_6$) cycloalkyl, optionally substituted aryl or optionally substituted heterocyclyl;

R$^2$ for each occurrence is independently H, OH, oxo, —(CR$^a$R$^b$)$_x$—NR$^a$—C(O)—NR$^a$—(C$_3$-C$_6$)cycloalkylphenyl or —(CR$^a$R$^b$)$_x$—NR$^a$R$^b$; or R$^2$ for each occurrence is independently optionally substituted (C$_1$-C$_6$)alkyl, —(CH$_2$)$_x$— optionally substituted aryl, —(CH$_2$)$_x$—(C$_3$-C$_6$) optionally substituted cycloalkyl, —(CH$_2$)$_x$— optionally substituted heteroaryl, or —(CH$_2$)$_x$— optionally substituted heterocyclyl;

wherein R$^2$ can replace hydrogen on either nitrogen or carbon;

R$^3$ is aryl optionally substituted with one or more substituents;

R$^4$ for each occurrence is independently H, OH, halo or optionally substituted (C$_1$-C$_4$)alkyl;

R$^a$ and R$^b$ are independently H or optionally substituted (C$_1$-C$_6$)alkyl;

m is 1 or 2;

n is 0, 1 or 2; and x for each occurrence is independently 0, 1 or 2;

provided that the compound is not

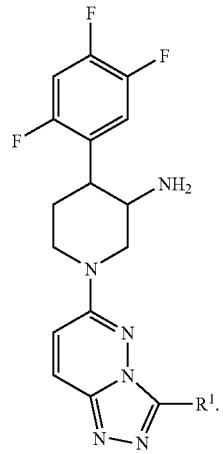

wherein R$^1$ is methyl, ethyl, propyl, isopropyl, t-butyl, cyclopropyl, cyclohexyl, C$_2$F$_5$, CF$_3$, or 4-fluorophenyl;

provided that the compound is not

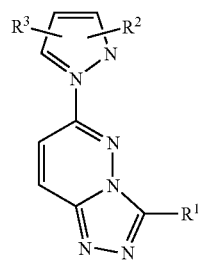

wherein R$^1$ is CF$_3$, CH$_3$, NH$_2$ or phenyl optionally substituted with Br or F;

R$^2$ is H or CH$_3$; and

R$^3$ is phenyl optionally substituted with F;

provided the compound is not

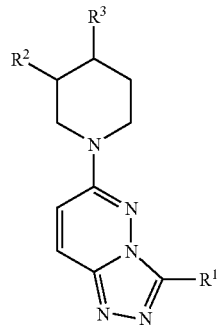

wherein R¹ is phenyl substituted with F;
R² is CN or NH₂; and
R³ is phenyl optionally substituted with three F;
provided that the compound is not

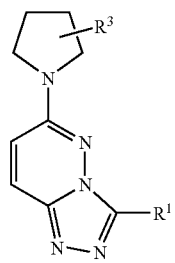

wherein R¹ is CF₃, CH₃ or phenyl optionally substituted with F; and
R³ is phenyl optionally substituted with CH₃, F or two OCH₃;
provided that the compound is not

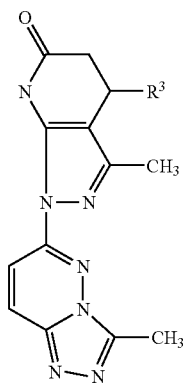

wherein R₃ is phenyl substituted with three OCH₃ or phenyl substituted with two OCH₃ and one OH;
provided that the compound is not

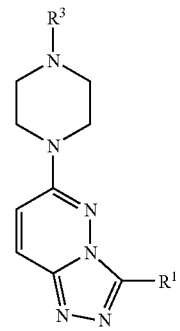

wherein R¹ is CH₃, CF₃, —CH₂CH₂OH or phenyl optionally substituted with B, Cl or F; and
R³ is phenyl optionally substituted with OCH₃, CF₃, F, isopropyl, Cl or one or two CH₃; or R¹ is phenyl substituted with four F and one CF₃; and
provided the compound is not

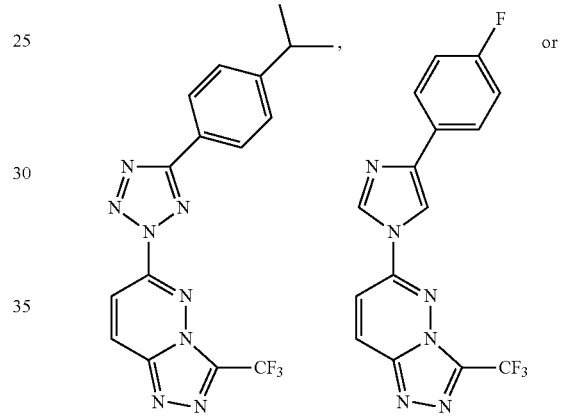

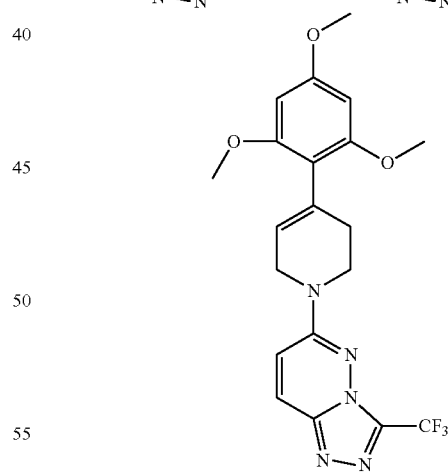

2. The compound according to claim 1 wherein A is

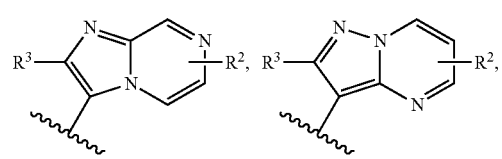

-continued

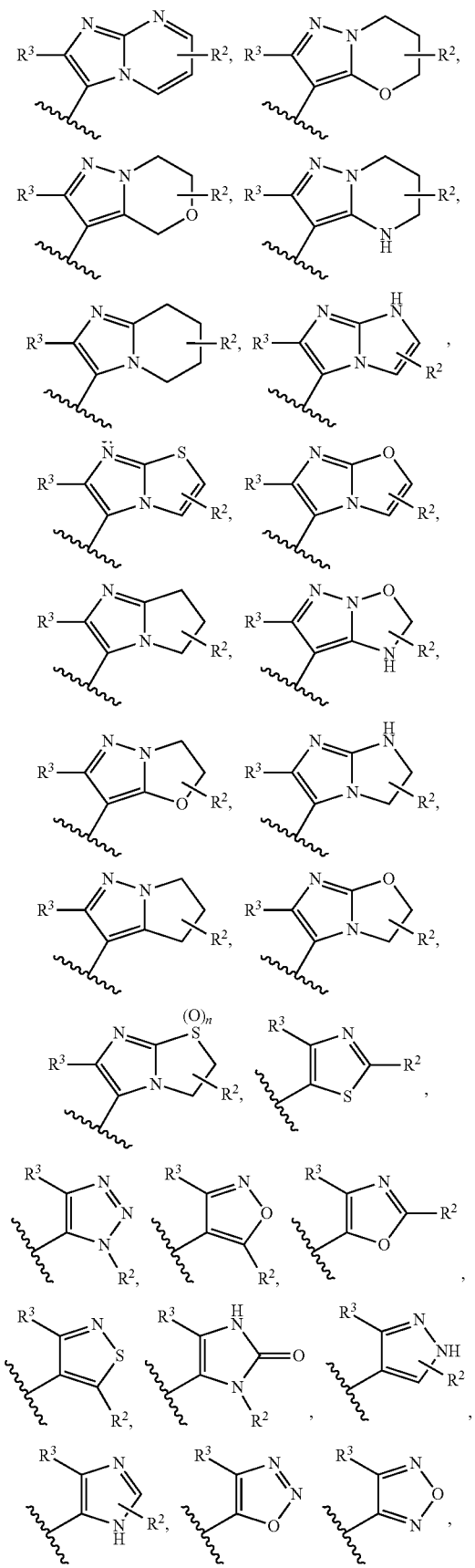

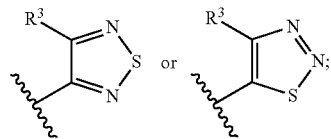

wherein R² can replace hydrogen on either nitrogen or carbon.

3. The compound according to claim 2 wherein R¹ is N(CH₃)₂, optionally substituted (C₁-C₆)alkyl, optionally substituted (C₂-C₆)alkenyl, optionally substituted (C₃-C₆)cycloalkyl, optionally substituted phenyl, optionally substituted piperidinyl, optionally substituted pyrrolidinyl or tetrahydropyranyl.

4. The compound according to claim 3 wherein R³ is phenyl optionally substituted with one or more substituents.

5. The compound according to claim 4 wherein R² for each occurrence is independently H and —(CH₂)ₓ—NRᵃRᵇ or R² is independently optionally substituted (C₁-C₆)alkyl, —(CH₂)ₓ— optionally substituted phenyl, —(CH₂)ₓ— optionally substituted imidazolyl, —(CH₂)ₓ— optionally substituted morpholinyl, —(CH₂)ₓ— optionally substituted piperidinyl, —(CH₂)ₓ— optionally substituted piperazinyl or —(CH₂)ₓ— optionally substituted tetrahydropyranyl.

6. The compound according to claim 5 wherein R¹ is N(CH₃)₂, optionally substituted (C₃-C₄)alkyl, optionally substituted cyclopropyl, optionally substituted cyclobutyl, optionally substituted phenyl or optionally substituted pyrrolidinyl.

7. The compound according to claim 6 wherein A is

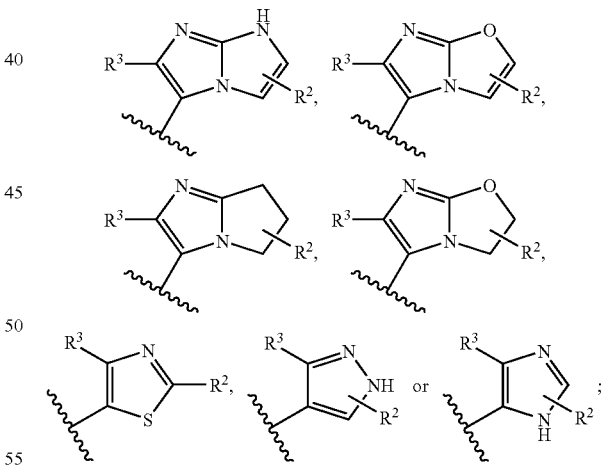

wherein R² can replace hydrogen on either nitrogen or carbon.

8. The compound according to claim 7 wherein R² is H, NH², optionally substituted (C₁-C₄)alkyl, optionally substituted phenyl or optionally substituted piperidinyl.

9. The compound according to claim 8 wherein R³ is substituted phenyl and the substituents are independently halogen or optionally substituted (C₁-C₄)alkyl.

10. The compound according to claim 9 wherein R⁴ is H.

11. The compound according to claim 10 wherein the compound is

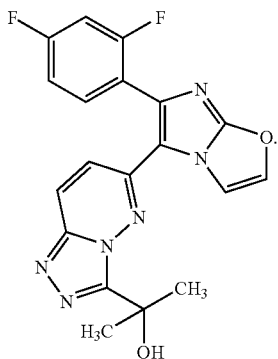

12. The compound according to claim 10 wherein the compound is

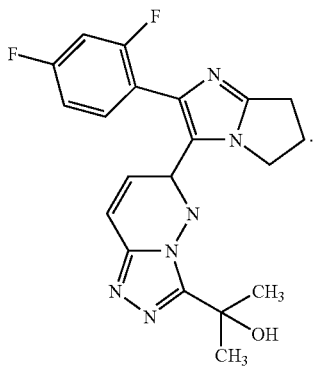

13. The compound according to claim 10 wherein $R^1$ is isopropyl.
14. The compound according to claim 13 wherein $R^2$ is H.
15. The compound according to claim 14 wherein A is

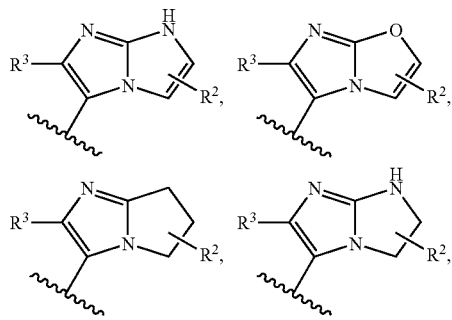

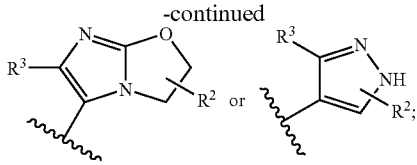

wherein $R^2$ can replace hydrogen on either nitrogen or carbon.

16. The compound according to claim 15 wherein the compound is

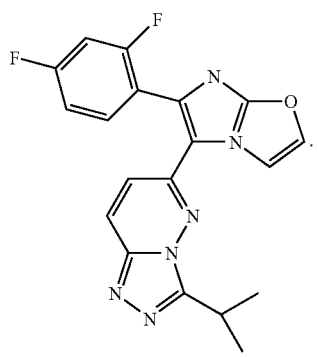

17. A method of treating a condition in a patient comprising administering a therapeutically effective amount of a compound of claim 1 or a physiologically acceptable salt thereof to said patient, wherein said condition is selected from rheumatoid arthritis.

18. A pharmaceutical composition comprising

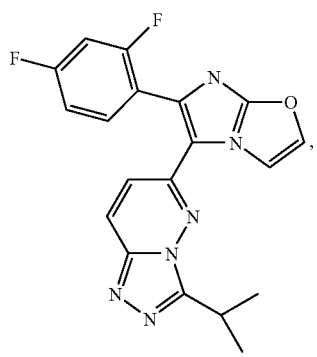

a pharmaceutically acceptable salt thereof and a pharmaceutically-acceptable carrier or excipient.

* * * * *

UNITED STATES PATENT AND TRADEMARK OFFICE
CERTIFICATE OF CORRECTION

| | | |
|---|---|---|
| PATENT NO. | : 8,188,083 B2 | Page 1 of 1 |
| APPLICATION NO. | : 12/215338 | |
| DATED | : May 29, 2012 | |
| INVENTOR(S) | : David J. Calderwood et al. | |

It is certified that error appears in the above-identified patent and that said Letters Patent is hereby corrected as shown below:

Claim 1, Column 267 line 25 delete " 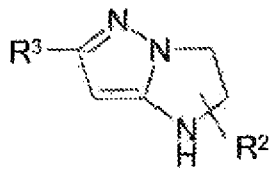 " and insert -- 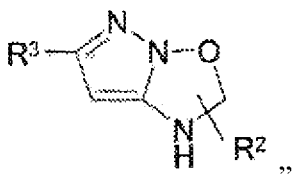 --

Signed and Sealed this

Twenty-seventh Day of November, 2012

David J. Kappos
*Director of the United States Patent and Trademark Office*